(12) United States Patent
Ruttenberg

(10) Patent No.: US 12,208,213 B2
(45) Date of Patent: Jan. 28, 2025

(54) MULTI-SENSORY, ASSISTIVE WEARABLE TECHNOLOGY, AND METHOD OF PROVIDING SENSORY RELIEF USING SAME

(71) Applicant: PHOEB-X, INC., Boca Raton, FL (US)

(72) Inventor: David Ruttenberg, Boca Raton, FL (US)

(73) Assignee: PHOEB-X, INC., Boca Raton, FL (US)

( * ) Notice: Subject to any disclaimer, the term of this patent is extended or adjusted under 35 U.S.C. 154(b) by 0 days.

(21) Appl. No.: 18/211,992

(22) Filed: Jun. 20, 2023

(65) Prior Publication Data
US 2023/0338698 A1    Oct. 26, 2023

Related U.S. Application Data

(63) Continuation of application No. 17/899,562, filed on Aug. 30, 2022, which is a continuation-in-part of
(Continued)

(51) Int. Cl.
*G02C 7/02* (2006.01)
*A61B 5/00* (2006.01)
(Continued)

(52) U.S. Cl.
CPC ........ *A61M 21/0094* (2013.01); *G16H 10/60* (2018.01); *G16H 40/63* (2018.01);
(Continued)

(58) Field of Classification Search
CPC ............ A61M 21/00; A61M 2021/005; A61M 2021/0027; A61M 2021/0044
See application file for complete search history.

(56) References Cited

U.S. PATENT DOCUMENTS 6,702,767 B1    3/2004  Douglas et al.
9,940,844 B2    4/2018  Gazzaley
(Continued)

FOREIGN PATENT DOCUMENTS

EP        3879853 A1      9/2021
WO   WO-2019165698 A1 *  9/2019   ......... G05B 19/4183
(Continued)

OTHER PUBLICATIONS

Ruttenberg, David, Porayska-Pomsta, K, White, Sarah and Homes, J., "Refining the ML/DL Argument for the SensorAble Project", 4 pages (2020).
(Continued)

*Primary Examiner* — Thaddeus B Cox
*Assistant Examiner* — Joshua Daryl D Lannu
(74) *Attorney, Agent, or Firm* — SHEPPARD, MULLIN, RICHTER & HAMPTON LLP

(57) ABSTRACT

A system and method for providing sensory relief from distractibility, inattention, anxiety, fatigue, and/or sensory issues to a user in need. The user can be autistic/neurodiverse, or neurotypical. The system can be configured to obtain user sensory sensitivity data indicating a user's visual, sonic, or interoceptive, sensitivities; determine, using at least the user sensory sensitivity data, sensory thresholds specific to the user and mediation data corresponding to mediations specific to the user; store the sensory thresholds and mediation data; record, using one or more sensors, a sensory input stimulus to the user; compare the sensory input stimulus with the sensory thresholds; in response to comparing the sensory input stimulus with the sensory thresholds, determine, based at least on the mediation data, a mediation to be provided to the user, the mediation configured to provide the user relief from distractibility, inattention, anxiety, fatigue, or sensory issues.

28 Claims, 73 Drawing Sheets

Related U.S. Application Data application No. 17/882,517, filed on Aug. 5, 2022, now Pat. No. 11,779,275.

(60) Provisional application No. 63/238,490, filed on Aug. 30, 2021, provisional application No. 63/229,963, filed on Aug. 5, 2021.

(51) Int. Cl.
    *A61B 5/16*     (2006.01)
    *A61M 21/00*     (2006.01)
    *G02C 11/00*     (2006.01)
    *G16H 10/60*     (2018.01)
    *G16H 40/63*     (2018.01)

(52) U.S. Cl.
CPC .............. *A61M 2021/0027* (2013.01); *A61M 2021/0044* (2013.01); *A61M 2205/3306* (2013.01); *A61M 2205/3375* (2013.01); *A61M 2205/3561* (2013.01); *A61M 2205/3584* (2013.01); *A61M 2205/502* (2013.01); *A61M 2210/0612* (2013.01); *A61M 2210/0662* (2013.01)

(56) References Cited

U.S. PATENT DOCUMENTS

| | | | |
|---|---|---|---|
| 10,235,128 | B2 | 3/2019 | Vaughn et al. |
| 10,405,786 | B2 | 9/2019 | Sahin |
| 10,524,715 | B2 * | 1/2020 | Sahin ..................... A61B 5/165 |
| 10,559,221 | B2 | 2/2020 | Martucci et al. |
| 10,593,221 | B1 | 3/2020 | Johnson et al. |
| 10,772,178 | B2 | 9/2020 | Van Der Zwaag et al. |
| 10,783,800 | B1 | 9/2020 | Dieker et al. |
| 10,839,201 | B2 | 11/2020 | Johnson et al. |
| 10,974,020 | B2 | 4/2021 | Rabin et al. |
| 10,976,806 | B1 | 4/2021 | Vancamberg et al. |
| 11,122,998 | B2 | 9/2021 | Martucci et al. |
| 11,176,753 | B1 | 11/2021 | Chakravarthi et al. |
| 11,260,198 | B2 | 3/2022 | Rabin et al. |
| 2001/0049480 | A1 | 12/2001 | John et al. |
| 2011/0080273 | A1 | 4/2011 | Kawai et al. |
| 2016/0220198 | A1 | 8/2016 | Proud |
| 2017/0039045 | A1 | 2/2017 | Abrahami et al. |
| 2018/0177451 | A1 | 6/2018 | Sahin |
| 2019/0053766 | A1 | 2/2019 | Mijovic et al. |
| 2020/0012872 | A1 | 1/2020 | Autran |
| 2020/0215298 | A1 * | 7/2020 | Rabin ..................... G16H 10/60 |
| 2020/0258316 | A1 | 8/2020 | Lee |
| 2020/0302825 | A1 * | 9/2020 | Sachs ..................... G09B 5/02 |
| 2020/0337631 | A1 | 10/2020 | Sahin |
| 2021/0303070 | A1 | 9/2021 | Croxford et al. |
| 2021/0398357 | A1 | 12/2021 | Samec et al. |
| 2021/0401338 | A1 | 12/2021 | Flickinger |
| 2021/0407532 | A1 | 12/2021 | Salahuddin et al. |
| 2022/0105944 | A1 | 4/2022 | Ghannam et al. |

FOREIGN PATENT DOCUMENTS

| | | | | |
|---|---|---|---|---|
| WO | WO-2020146749 | A1 * | 7/2020 | ............. G05B 17/02 |
| WO | 2022/069269 | A1 | 4/2022 | |

OTHER PUBLICATIONS

Holmes, Joni & White, Sarah, Porayska-Pomsta, Kaska and Ruttenberg, David., "Sound Impairment Effect on Cognitive Skill Performance", 5 pages (2020).

White, Sarah & Holmes, Joni, Porayska-Pomsta, Kaska and Ruttenberg, David., "PPI Questionnaire on Adaptive Wearable Appropriateness as an Autistic Intervention," 9 pages (2020).

Holmes, Joni & White, Sarah, Porayska-Pomsta, Kaska and Ruttenberg, David., "In Defence of ML/CNN for the SensorAble Research Project", 9 pages (2020).

Abdus-Sabur, Rafiq, Keshav, Neha U., Liu, Runpeng, Salisbury, Joseph P., Vahabzadeh, Arshya, "Case Study of a Digital Augmented Reality Intervention for Autism in School Classrooms: Associated With Improved Social Communication, Cognition, and Motivation via Educator and Parent Assessment", Frontiers in Education, Technology Report, vol. 3, retrieved at https://www.frontiersin.org/articles/10.3389/feduc.2018.00057, 21 pages (2018).

Hackl, A. and Hlavacs, H., "Diminishing Reality", 17th International Conference on Entertainment Computing (ICEC), Poznan, Poland. pp. 28-39 (Sep. 2018).

Murph, I., McDonald, M., Richardson, K., Wilkinson, M., Robertson, S., Karunakaran, A., Coleman, M., Byrne, V. and McLaughlin, A., "Diminishing Reality: Potential Benefits and Risks", Proceedings of the Human Factors and Ergonomics Society Annual Meeting, vol. 65, pp. 164-168, (2021).

Yantac, E., Corlu, D., Fjeld, M. and Kunz, A., "Exploring Diminished Reality (DR) Spaces to Augment the Attention of Individuals with Autism", 6 pages (2015).

Ruttenberg, D., Blog—SensorAble, Aspiring to lessen distraction, anxiety and improve attention/focus for individuals diagnosed or identifying with autism spectrum condition (ASC), retrieved at http://davidruttenberg.com/SensorAble/index.php/blog/, 24 pages (2021).

Ruttenberg, D. P., Ph.D/DPhil Research Proposal, Doctor of Philosophy—Autism Research, A novel, wearable, and multi-sensory feedback device that filters distractions and increases focus for individuals with Autism Spectrum Disorder, 17 pages (2018).

Huang, W., Feng, J., Wang, H. and Le Sun, L., "A New Architecture of Densely Connected Convolutional Networks for Pan-Sharpening", ISPRS International Journal of Geo-Information, vol. 9, No. 4, 20 pages (2020).

Huang, Y., Yang, X., Gao, J.,Sang, J. and Xu, C., "Knowledge-driven Egocentric Multimodal Activity Recognition", ACM Transactions on Multimedia Computing, Communications, and Applications, vol. 16, No. 4, Art. 133, 21 pages (2020).

Kaur, M. and Singh, D., "Fusion of medical images using deep belief networks", Cluster Computing, vol. 23, pp. 1439-1453 (2019).

Kazanidis, I., Pellas, N. and Christopoulos, A., "A Learning Analytics Conceptual Framework for Augmented Reality-Supported Educational Case Studies", Multimodal Technologies and Interaction, vol. 5, No. 9, 16 pages (2021).

Rajawat, A., Bedi, P., Goyal, S. B., Alharbi, A., Aljaedi, A., Jamal, S. S. and Shukla, P., "Fog Big Data Analysis for IoT Sensor Application Using Fusion Deep Learning", Mathematical Problems in Engineering, vol. 2021, Art. 6876688,16 pages (2021).

Rivera-Pelayo, V., Zacharias, V. and Braun, S., "Applying quantified self approaches to support reflective learning", 4 pages, (2012).

Tobón, D. P., Hossain, M. S., Muhammad, G., Bilbao, J. and Saddik, A. E., "Deep learning in multimedia healthcare applications: a review", Multimedia systems, Advance online publication, 15 pages (2022).

Wang, R., Liu, Y., Zhang, P., Li, X, and Kang, X., "Edge and Cloud Collaborative Entity Recommendation Method towards the IoT Search", Sensors, vol. 20, No. 7: 1918, 22 pages (2020).

Ruttenberg, D., K. Porayska-Pomsta, Sarah White, and J. Holmes, "PPI Questionnaire on Adaptive Wearable Appropriateness as an Autistic Intervention", OSF.

Schallmo, M.-P. and Murray, S., "People with Autism May See Motion Faster", vol. 19, (2016).

American Psychological Association, "The State-Trait Anxiety Inventory (STAI)2", American Psychological Association, https://www.apa.org/pi/about/publications/caregivers/practice-settings/assessment/tools/trait-state, (2011).

Anwyl-Irvine, A.L., Massonié J., Flitton, A., Kirkham, N.Z., Evershed, J.K., "Gorilla in our midst: an online behavioural experiment builder", Behavior Research Methods (2019).

Bernsen, N. O., Dybkjær, H. and Dybkjær, L., "Wizard of oz prototyping: How and when. Proc. CCI Working Papers Cognit. Sci./HCI", Roskilde, Denmark, (1994).

Burchi, E., & Hollander, E. Anxiety in Autism Spectrum Disorder. Retrieved Dec. 11, 2020, from https://adaa.org/learn-from-us/from-the-experts/blog-posts/consumer/anxiety-autism-spectrum-disorder, (2019).

(56) References Cited

OTHER PUBLICATIONS

Faul, F., Erdfelder, E., Lang. A .- G., & Buchner, A. (2007). G*Power 3: A flexible statistical power analysis program for the social, behavioral, and biomedical sciences. Behavior Research Methods, vol. 39, 175-191.

Fiedler, A., Gabsdil, M., and Horacek, H., A tool for supporting progressive refinement of wizard-of-oz experiments in natural language. In International conference on intelligent tutoring systems Springer, Berlin, Heidelberg, pp. 325-335 (2004).

Forbes-Riley, K. and Litman, D., "Designing and evaluating a wizarded uncertainty-adaptive spoken dialogue tutoring system", Computer Speech & Language vol. 25, pp. 105-126 (2011).

Goldman, N., Lin, I.-F., Weinstein, M. and Lin, Y.-H. 2003. Evaluating the quality of self-reports of hyperthension and diabetes. Journal of Clinical Epidemiology 56, 148-154.

Li, X., Improving the Reliability and Validity of Wizard-of-Oz Methods. University of Huddersfield (2012).

Maulsby, D., Greenberg, S., and Mander, R., "Prototyping an intelligent agent through Wizard of Oz", In Proceedings of the Interact'93 and CHI'93 conference on Human factors in computing systems, pp. 277-284, (1993).

Neels, B., "Polly", Retrieved Dec. 17, 2020, from https://aws.amazon.com/polly/ (2008).

Robertson, I. H., Manly, T., Andrade, J., Baddeley, B. T., and Ylend, J., "Oops!: Performance correlates of everyday attentional failures in traumatic brain injured and normal subjects", Neuropsychologia, vol. 35, No. 6, pp. 747-758, (1997).

Robertson, I. H., Ward, T., Ridgeway, V., & Nimmo-Smith, I, "The structure of normal human attention: The Test of Everyday Attention", Journal of the International Neuropsychological Society, vol. 2, No. 6, pp. 525-534 (1996).

Johnston, V., Black, M., Wallace, J., Mulvenna, M. and Bond, R., "A Framework for the Development of a Dynamic Adaptive Intelligent User Interface to Enhance the User Experience", ECCE 2019: Proceedings of the 31st European Conference on Cognitive Ergonomics, Belfast United Kingdom, pp. 32-35 (2019).

Rajawat, A. S., & Jain, S., "Fusion deep learning based on back propagation neural network for personalization.", In 2nd International Conference on Data, Engineering and Applications (IDEA) IEEE, pp. 1-7 (2020).

Bull, S. and Kay, J., "SMILI: A Framework for Interfaces to Learning Data in Open Learner Models, Learning Analytics and Related Fields", International Journal of Artificial Intelligence in Education, vol. 26, 39 pages (2016).

Non-Final Office Action mailed Jan. 20, 2023 for U.S. Appl. No. 17/882,517, 23 pages.

International Search Report and Written Opinion mailed Nov. 4, 2022 for International Application No. PCT/US2022/039643, filed Aug. 5, 2022.

International Search Report and Written Opinion mailed Dec. 2, 2022 for International Application No. PCT/US2022/042100, filed Aug. 30, 2022.

\* cited by examiner

<<Haptic alert for large butterflies>>
<<Tone alert for flying objects>>
<<Verbal Guidance for specific colors>>
<<Eraser effect: applied to certain objects>>

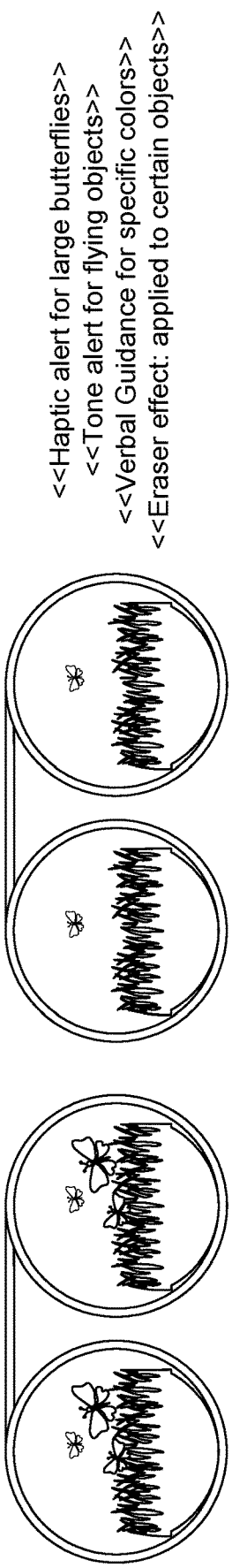

FIG. 24A

<<Text alert: don't look at clock>>
<<Blur effect: applied to bulletin board>>
<<Cover-Up: to be applied to either if alerts or effect not heeded>>

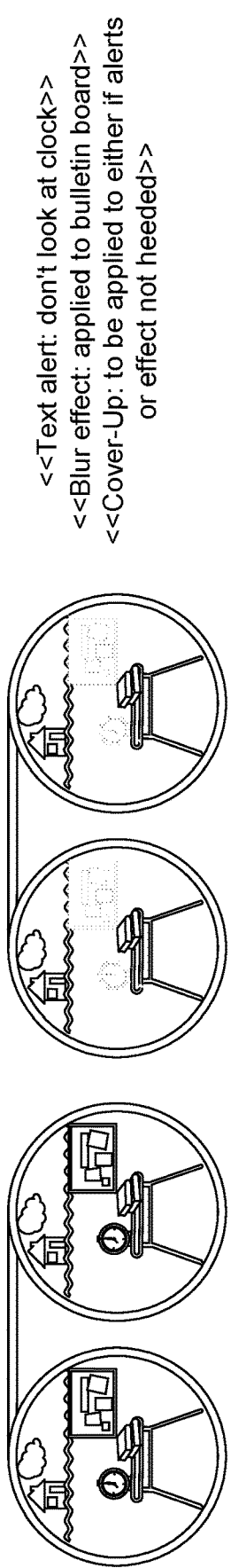

FIG. 24B

<<Color balance adjusted for stop sign>>
<<Contrast adjusted for roadway>>
<<Enhancement for stop sign safety>>

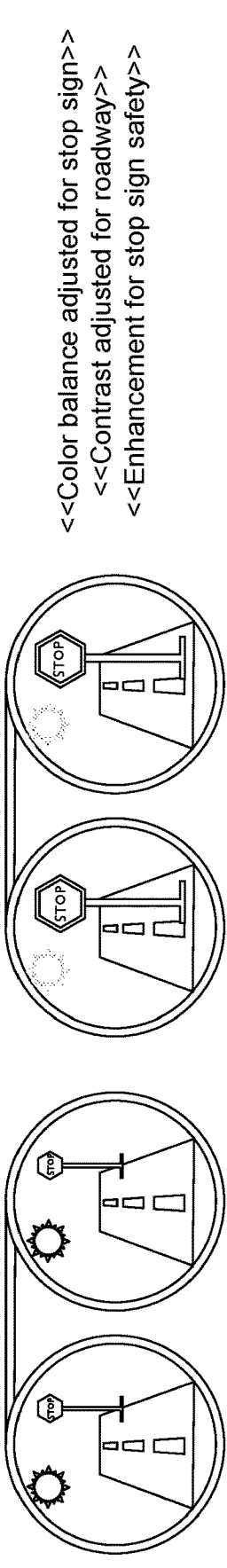

FIG. 24C

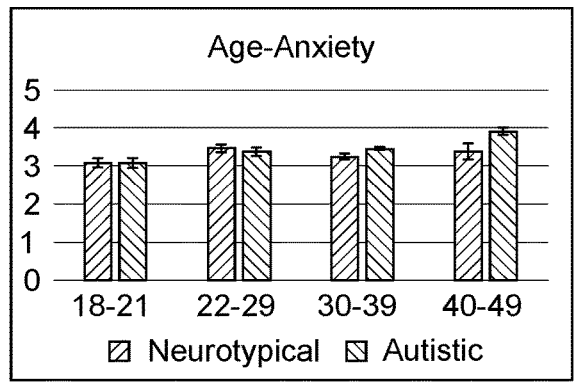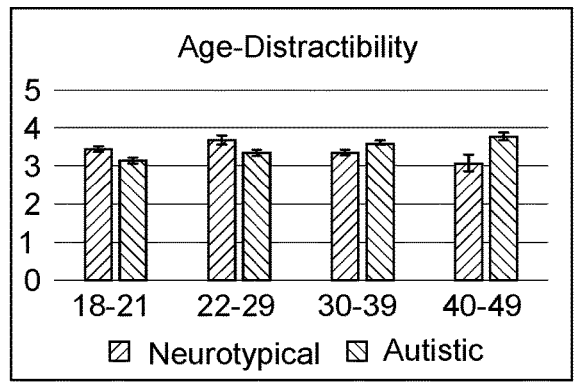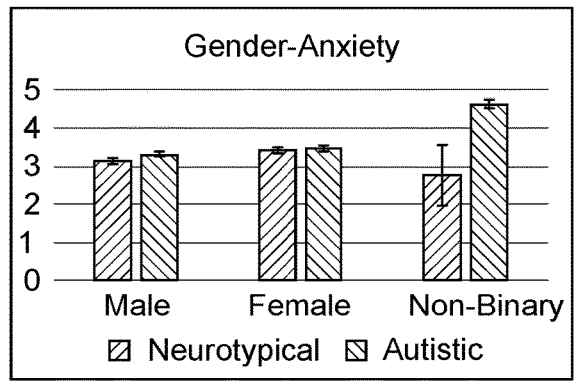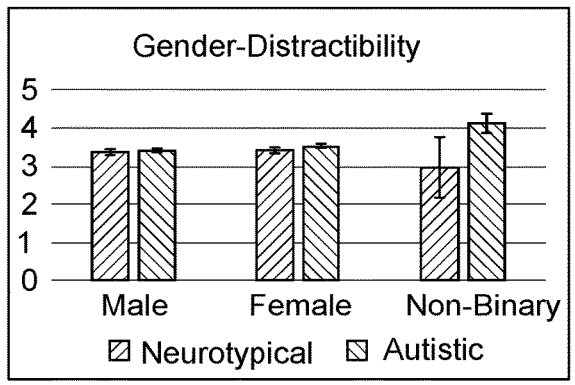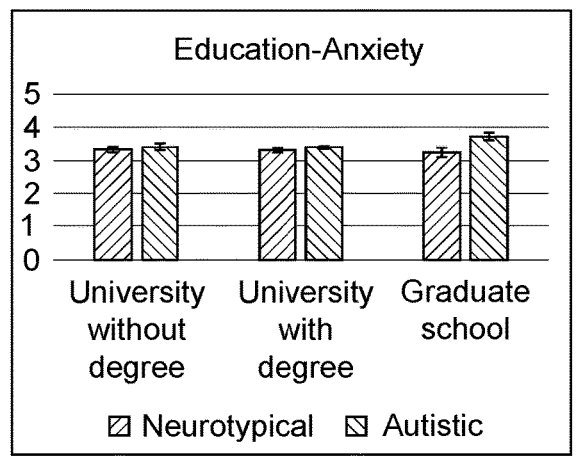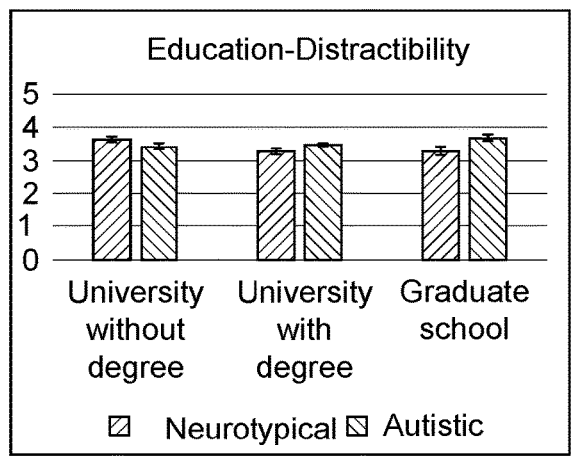
FIG. 29

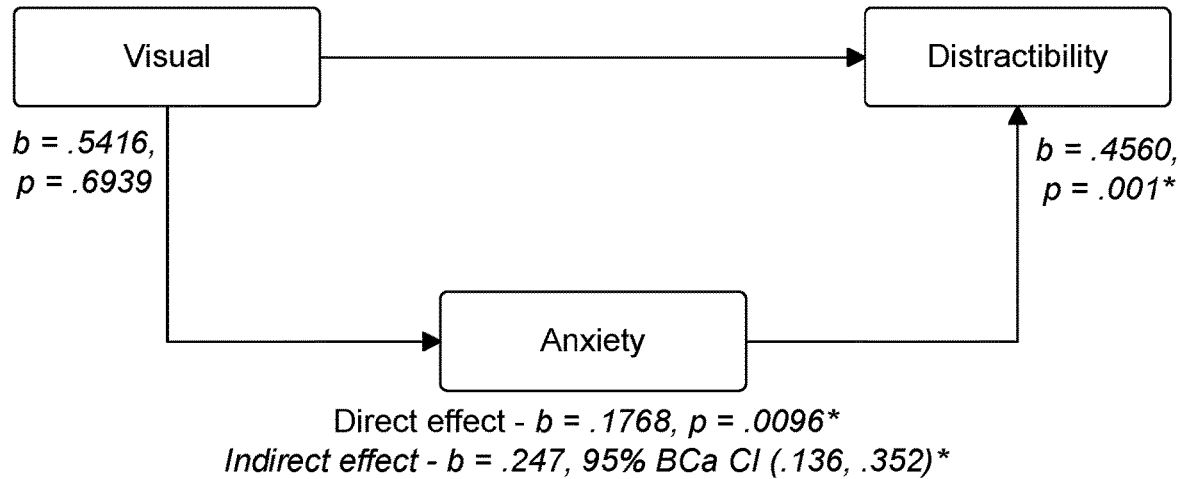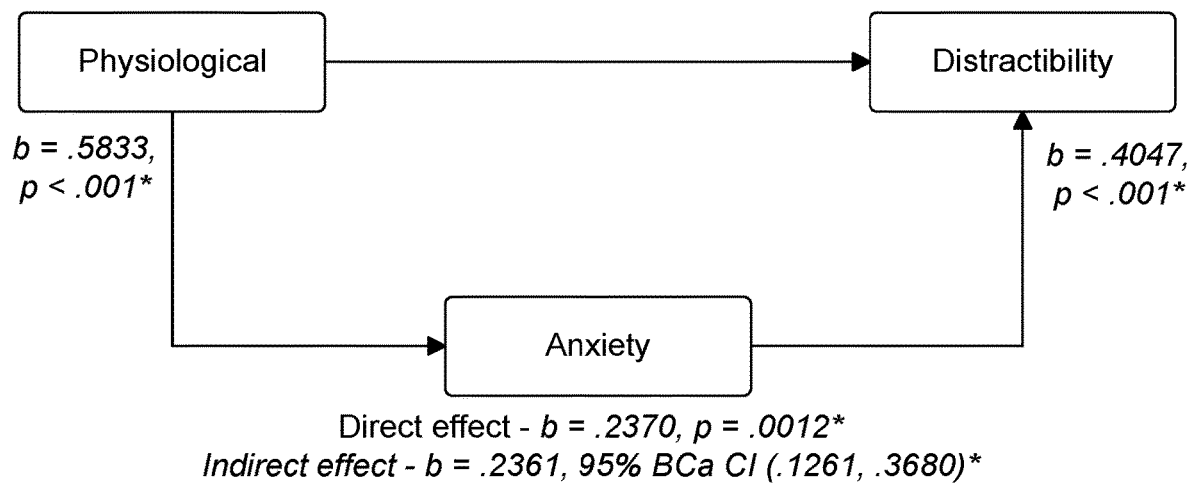
FIG. 30

PPI Study Summary Results

| DEMOGRAPHICS | Autistic | Non-autistic |
|---|---|---|
| Age | Anxiety increases as age increases | No effect |
| Age | Older are more distracted | No effect |
| Sex | Non-binary more anxious & distracted than Females or Males | Females more anxious than males |
| Education | High schoolers more anxious than college grads | College degreed are less distracted than those without degrees |

| GROUP DIFFERENCES | Autistic | Non-autistic |
|---|---|---|
| More sensitive to VISUAL stimuli | ✔ | |
| More sensitive to PHYSICAL stimuli | ✔ | |
| More ALERT (less fatigued) | ✔ | |

| CORRELATIONS | Autistic | Non-autistic |
|---|---|---|
| Visual | ✔ | ✔ |
| Auditory | No association | ✔ |
| Physiology | ✔ | ✔ |
| Distractibility | ✔ | ✔ |
| Anxiety | ✔ | ✔ |
| Fatigue | ✔ | ✔ |

FIG. 34A

PPI Study Summary Results

| MEDIATION ANALYSIS | Autistic | | Non-autistic | |
|---|---|---|---|---|
| | Direct effect | indirect effect | Direct effect | Indirect effect |
| Anxiety between Visual & Distraction | – | ✔ | ✔ | ✔ |
| Anxiety between Auditory & Distraction | – | ✔ | – | – |
| Anxiety between Physical & Distraction | ✔ | ✔ | ✔ | ✔ |
| Fatigue between Visual & Distraction | – | – | – | – |
| Fatigue between Auditory & Distraction | ✔ | ✔ | – | – |
| Fatigue between Physical & Distraction | ✔ | ✔ | – | – |

FIG. 34B

SART/WOz Clinical Trial Summary Results

| Improving Anxiety | Autistic | Non-autistic |
|---|---|---|
| Alert efficacy | 7.516% | 2.915% |
| Filters efficacy | 14.706% | 18.076%* |
| Guidance efficacy | 9.510% | 8.455% |
| Combination efficacy | 16.340% | 18.076%* |
| Customized Mediation Efficacy | 23.856%* | 23.615%* |

Note, N=38; *p < 0.05 (two-tailed); **p < 0.01 (two tailed).

| Improving Fatigue | Autistic | Non-autistic |
|---|---|---|
| Alert efficacy | 2.247% | 0.000% |
| Filters efficacy | 8.614% | 4.764% |
| Guidance efficacy | -10.112% | -1.695% |
| Combination efficacy | 7.491% | 11.186%* |
| Customized Mediation Efficacy | 14.607%* | 14.576%* |

Note, N=38; *p < 0.05 (two-tailed).

| Overall Helpfulness | All Users | Autistic | Non-autistic |
|---|---|---|---|
| Helped performance and comfort | 56% | 56% | 57% |
| Worked well | 80% | 78% | 81% |
| Well suited | 64% | 61% | 67% |
| Well tolerated & would use in future | 95% | 94% | 95% |

FIG. 35A

SART/WOz Clinical Trial Summary Results

| Improved Performance | Baseline to Distraction | Baseline to Mediation | Distraction to Mediation |
|---|---|---|---|
| Reduction in Errors Committed (EoC) | -16.268%* | 20.734% | 31.824% |
| Reduction in Errors Omitted (EoO) | -3.095%* | 46.422% | 48.030% |
| Better Reaction Time (RT) for EoC | 11.274% | 101.534% | 81.115% |
| Response Time for EoO | 3.542% | 27.471% | 23.110% |

\* Represents an increase in errors from baseline (no distracting cues present), and then added in follow one distraction trial. Performance was improved for all users when mediations were personalized - regardless of baseline to mediation or distraction to mediation phase.

| CORRELATIONS | Autistic | Non-autistic |
|---|---|---|
| Fatigue and anxiety correlated | ✔ | — |
| Fewer EoC correlated to more EoO | ✔ | — |
| Fewer RTs correlated to more EoC | — | ✔ |
| Faster RTEoO correlate to slower RTEoC | — | ✔ |
| Fewer EoC correlate to reduced fatigue | — | ✔ |

| REGRESSION ANALYSIS | Autistic | Non-autistic |
|---|---|---|
| Predictions on Errors of Commission | ☀ 🐾 ⚲ ⚥ ♡ ☺ ☻ ⚥ 📜 👤 | ☀ 🐾 ⚲ ⚥ ♡ ☺ ☻ ⚥ 📜 👤 |
| Predictions on Performance | ☀ 🐾 ⚲ ⚥ ♡ ☺ ☻ ⚥ 📜 👤 | ☀ 🐾 ⚲ ⚥ ♡ ☺ ☻ ⚥ 📜 👤 |
| Predictions on Best Mediation | 📜 👤 | 📜 👤 |

Key: ☀ (alert) 🐾(filter) ⚲(guidance) ⚥(combination) ♡(anxiety) ☺(fatigue) ☻ (age) ⚥ (sex) 📜 (education) 👤 (diagnosis)

FIG. 35B

| Purpose Element | Properties | Description (text) | Accuracy | Right to access | Control-trust | Interface agents | Reflection | Plan monitor | Positive affective states | Collaboration competition | Navigation | Multiple sources | Assessment |
|---|---|---|---|---|---|---|---|---|---|---|---|---|---|
| WHAT is available? | | | | | | | | | | | | | |
| 1. Extent of model accessible | Complete | Multimodal system providing ecological & physiological sensing, alert, filtering, and guidance for sensory, attention and mental health issues | xx | xx | xx | xx | x | | x | xx | x | x | |
| | Partial | | | | | | | xx | | | | | x |
| | Competencies | | | xx | xx | x | | x | x | x | x | | |
| 2. Match underlying representation | Similar | Including sounds, visuals, and guidance | x | x | xx | xx | x | x | x | x | x | x | x |
| | Different | | x | x | xx | xx | x | x | x | x | x | x | x |
| 3. Access to uncertainty | Compete | | x | x | xx | x | xx | | x | xx | x | x | |
| | Partial | | | | | | | x | | | | | x |
| 4. Role of time | Previous | | | | | | | | | | | | |
| | Current | | x | x | xx | x | x | | x | x | x | x | x |
| | Future | | x | x | xx | x | x | | x | x | x | x | x |

Key = x: important  xx: especially critical  =: contentious  "blank": not relevant

| Purpose Element | Properties | Description (text) | Accuracy | Right to access | Control-trust | Interface agents | Reflection | Plan monitor | Positive affective states | Collaboration-competition | Navigation | Multiple sources | Assessment |
|---|---|---|---|---|---|---|---|---|---|---|---|---|---|
| WHAT is available? | | | | | | | | | | | | | |
| 1. Extent of model accessible | Complete | Multimodal system providing ecological & physiological sensing, alert, filtering, and guidance for sensory, attention and mental health issues | xx | | xx | xx | x | | x | xx | x | x | |
| | Partial | | | | | | | xx | | | | | | x |
| | Competencies | | | xx | x | x | | x | x | x | x | | x |
| 2. Match underlying representation | Similar | Including sounds, visuals, and guidance | x | x | xx | xx | x | x | x | x | x | x | x |
| | Different | | x | x | xx | xx | xx | x | x | x | x | x | x |
| 3. Access to uncertainty | Compete | | x | x | xx | xx | x | xx | x | xx | x | x | x |
| | Partial | | | | | | | x | | | | | x |
| 4. Role of time | Previous | | | | | | | | | | | | |
| | Current | | x | x | xx | x | x | x | x | x | x | x | x |
| | Future | | x | x | xx | x | x | x | x | x | x | x | x |

FIG. 42

| 5. Access to sources of input | | | | | | | | | |
|---|---|---|---|---|---|---|---|---|---|
| Complete | x | | x | | x | | | | |
| Partial | = | xx | = | | | | | | |
| System | x | = | x | | | xx | x | x | x |
| Peer | = | = | = | | | | | | |
| Instructor | | | x | x | = | x | x | x | x |
| Other | xx | xx | xx | xx | xx | xx | xx | xx | xx |
| Researcher, healthcare worker, parent/caregiver, physician | xx | xx | x | | x | x | x | x | x |

6. Access to model effect on personalizatio

Key = x: important   xx: especially critical   =: contentious   "blank": not relevant FIG. 42 (Continued)

| Purpose Element | Properties | Description (text) | Accuracy | Right to access | Control-trust | Interface agents | Reflection | Plan monitor | Positive affective states | Collaboration-competition | Navigation | Multiple sources | Assessment |
|---|---|---|---|---|---|---|---|---|---|---|---|---|---|
| WHO controls access? | | | | | | | | | | | | | |
| 10. Access initiative comes from | System | | x | | | | | | = | | x | | x |
| | User | | x | x | = | xx | x | = | x | x | x | x | x |
| | Peer | | = | = | = | = | = | x | = | x | = | = | = |
| | Instructor | | | x | = | x | x | x | x | x | x | x | x |
| | Other | Researcher, healthcare worker, parent/ caregiver, physician | xx | xx | xx | xx | xx | xx | xx | xx | xx | xx | xx |
| 11. Control over accessibility to others | Partial | | x | x | xx | x | x | x | x | | x | x | x |
| | System | | | | | | | | | x | | | |
| | Peer | | x | = | = | = | = | = | = | x | x | = | x |
| | Instructor | | = | = | = | = | = | = | = | x | = | = | = |
| | Other | Researcher, healthcare worker, parent/ caregiver, physician | xx | xx | xx | xx | xx | xx | xx | xx | xx | xx | xx |

Key: = x: important  xx: especially critical  =: contentious  "blank": not relevant

FIG. 44

MULTI-SENSORY, ASSISTIVE WEARABLE TECHNOLOGY, AND METHOD OF PROVIDING SENSORY RELIEF USING SAME

CROSS-REFERENCE TO RELATED APPLICATIONS

This application is a continuation of and claims priority to U.S. patent application Ser. No. 17/899,562, titled "MULTI-SENSORY, ASSISTIVE WEARABLE TECHNOLOGY, AND METHOD OF PROVIDING SENSORY RELIEF USING SAME" filed Aug. 30, 2022, which is a continuation-in-part of and claims priority to U.S. patent application Ser. No. 17/882,517, titled "MULTI-SENSORY, ASSISTIVE WEARABLE TECHNOLOGY, AND METHOD OF PROVIDING SENSORY RELIEF USING SAME" filed Aug. 5, 2022, which claims priority to U.S. Provisional Patent Application No. 63/229,963, titled "MULTI-SENSORY, ASSISTIVE WEARABLE TECHNOLOGY, AND METHOD OF PROVIDING SENSORY RELIEF USING SAME" filed Aug. 5, 2021, and U.S. Provisional Patent Application No. 63/238,490, titled "MULTI-SENSORY, ASSISTIVE WEARABLE TECHNOLOGY, AND METHOD OF PROVIDING SENSORY RELIEF USING SAME" filed Aug. 30, 2021. The aforementioned applications are incorporated herein by reference in their entirety.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

A significantly high percentage (about 90%) of autistic adults report that sensory issues cause significant barriers at school and/or work. (Leekam, S. R., Nieto, C., Libby, S. J., Wing, L., & Gould, J. (2007). Describing the Sensory Abnormalities of Children and Adults with Autism. Journal of Autism and Developmental Disorders, 37(5), 894-910). Additionally, 87% of autistic employees feel environmental adjustments would make critical differences to their performance. (Maltz, S. (2019). Autistica Action Briefing: Employment-Harper G, Smith E, Heasman B, Remington A, Girdler S, Appleton V J, Cameron C, Fell C). These numbers make a compelling case for addressing the sensory issues that affect an autistic adult's ability to function successfully. Environmental factors are also known to trigger persistent sensory and cognitive challenges (e.g., sensory overload) leading to mental health challenges. Mental health is the number one autistic priority and primary barrier to schooling/employment (Cusack, J., & Sterry, R. (2019, December). Autistica's top 10 research priorities), and it contributes substantially to autism's societal expenditures, which in the UK exceeds £27.5 billion per annum—surpassing cancer, heart, stroke, and lung diseases combined. (Knapp, M., Romeo, R., & Beecham, J. (2009). Economic cost of autism in the UK. Autism, 13(3), 317-336); (London School of Economics (2014). Autism is the most costly medical condition in the UK).

SUMMARY

This application addresses the above-described challenges, by providing a wearable technology that offers ground-breaking opportunities to: (i) monitor environments and adjust user-experiences; (ii) lessen sensory-load and enable greater participation; and (iii) improve mental health with efficacious interventions. The wearable technology described herein increases attentional focus, reduces sensory distraction, and improves quality-of-life/lessens anxiety and fatigue.

It should be understood that the various individual aspects and features of the present invention described herein can be combined with any one or more individual aspect or feature, in any number, to form embodiments of the present invention that are specifically contemplated and encompassed by the present invention.

One embodiment of the application is directed to a system, comprising: a wearable device comprising one or more sensors; one or more processors; and one or more non-transitory computer-readable media having executable instructions stored thereon that, when executed by the one or more processors, cause the system to perform operations comprising: obtaining user sensory sensitivity data corresponding to user input indicating whether a user of the wearable device is visually sensitive, sonically sensitive, or interoceptively sensitive; determining, using at least the user sensory sensitivity data, one or more sensory thresholds specific to the user and mediation data corresponding to one or more mediations specific to the user, the one or more sensory threshold selected from auditory, visual, or physiological sensory thresholds; storing the one or more sensory thresholds and the mediation data; recording, using the one or more sensors, a sensory input stimulus to the user; comparing the sensory input stimulus with the one or more sensory thresholds specific to the user; in response to comparing the sensory input stimulus with the one or more sensory thresholds, determining, based at least on the mediation data, a mediation to be provided to the user, the mediation configured to provide the user relief from distractibility, inattention, anxiety, fatigue, or sensory issues; and providing the mediation to the user, the mediation comprising an alert mediation, a guidance mediation, or a filter mediation.

In some implementations, the operations further comprise: storing a first identifier that indicates whether the user is neurodiverse or neurotypical; and determining the one or more sensory thresholds specific to the user and the mediation data corresponding to one or more mediations specific to the user, comprises: determining, using at least the first identifier and the user sensory sensitivity data, the one or more sensory thresholds and the mediation data.

In some implementations, the operations further comprise: receiving user demographic data corresponding to user input indicating an age, education level, or gender of the user; and determining the one or more sensory thresholds specific to the user and the mediation data corresponding to one or more mediations specific to the user, comprises: determining, using at least the first identifier, the user sensory sensitivity data, and the user demographic data, the one or more sensory thresholds and the mediation data.

In some implementations, the first identifier indicates whether or not the user is autistic.

In some implementations, the first identifier indicates that the user is autistic.

In some implementations, the mediation is configured to provide the user relief from fatigue; the mediation comprises the filter mediation; and the filter mediation comprises filtering, in real-time, an audio signal presented to the user or an optical signal presented to the user.

In some implementations, the mediation is configured to provide the user relief from a distraction by increasing a response time of the user to the distraction.

In some implementations, obtaining the user sensory sensitivity data comprises receiving, at a graphical user interface, one or more first responses by the user to one or more first prompts indicating whether the user is visually sensitive, sonically sensitive, or interoceptively sensitive; and the operations further comprise deriving the first identifier indicating that the user is autistic by: receiving, at the graphical user interface, one or more second responses by the user to one or more second prompts indicating an anxiety level of the user; deriving, based on the sensory sensitivity data, one or more sensory sensitivity scores comprising a visual sensitivity score, a sonic sensitivity score, or an interoceptive sensitivity score; deriving, based on the one or more second responses, an anxiety score; and predicting, using a model that predicts a probability of autism based at least on an anxiety level and one or more sensory sensitivity levels, based at least on the anxiety score and the one or more sensory sensitivity scores, that the user is autistic.

In some implementations, obtaining the user sensory sensitivity data comprises receiving, at a graphical user interface, one or more first responses by the user to one or more first prompts indicating whether the user is visually sensitive, sonically sensitive, or interoceptively sensitive; and the operations further comprise deriving the first identifier indicating that the user is autistic by: receiving, at the graphical user interface, one or more second responses by the user to one or more second prompts indicating a fatigue level of the user; deriving, based on the sensory sensitivity data, one or more sensory sensitivity scores comprising a visual sensitivity score, a sonic sensitivity score, or an interoceptive sensitivity score; deriving, based on the one or more second responses, a fatigue score; and predicting, using a model that predicts a probability of autism based at least on a fatigue level and one or more sensory sensitivity levels, based at least on the fatigue score and the one or more sensory sensitivity scores, that the user is autistic.

In some implementations, obtaining the user sensory sensitivity data further comprises: recording, using at least the one or more sensors, a response by the user to a visual stimulus, a sonic stimulus, or a physiological stimulus.

In some implementations, the mediation comprises a combination mediation of at least two mediations selected from the alert mediation, the guidance mediation, and the filter mediation.

In some implementations, the combination mediation comprises the alert mediation followed by the filter mediation.

In some implementations, the alert mediation comprises alerting the user about a distraction that is visual or auditory; and the filter mediation comprises: comprising filtering, in real-time, an audio or optical signal presented to the user, the audio or optical signal associated with the distraction.

In some implementations, the system further comprises one or more fog nodes configured to locally store sensor data collected by the one or more sensors, the sensor data including first sensor data associated with the sensory input stimulus.

In some implementations, storing the one or more sensory thresholds and the mediation data, comprises: locally storing, using the one or more fog nodes, the one or more sensory thresholds and the mediation data; and comparing the sensory input stimulus with the one or more sensory thresholds, comprises: comparing, using the one or more fog nodes, the sensory input stimulus with the one or more sensory thresholds.

In some implementations, the system further comprises one or more edge nodes configured to communicatively couple to the one or more fog nodes and a cloud server remotely located from the wearable device.

In some implementations, the one or more edge nodes are configured to: encrypt the first sensor data associated with the sensory input stimulus to obtain encrypted data; transmit the encrypted data to the cloud server; and receive a response from the cloud server.

In some implementations, the one or more fog nodes and the one or more edge nodes reside on a local area network (LAN) containing the wearable device, an ad-hoc network containing the wearable device, a LAN of a mobile device directly coupled to the wearable device, or an ad-hoc network of the mobile device.

In some implementations, the sensor data comprises second sensor data that does not trigger a mediation; and the system is configured such that the second sensor data that does not trigger a mediation is not made available to any cloud server remotely located from the wearable device.

In some implementations, the mediation comprises the filter mediation that comprises filtering, in real-time, an optical signal presented to the user; the first sensor data associated with the sensory input stimulus comprises first image data; the one or more edge nodes or the one or more fog nodes are configured to determine whether the first image data is sufficiently similar to second image data stored at the cloud server; and determining the mediation to be provided to the user comprises in response to determining that the first image data is sufficiently similar to the second image data, determining the filter mediation.

In some implementations, the mediation comprises the filter mediation that comprises filtering, in real-time, an audio signal presented to the user; the first sensor data associated with the sensory input stimulus comprises first audio data; the one or more edge nodes or the one or more fog nodes are configured to determine whether the first audio data is sufficiently similar to second audio data stored at the cloud server; and determining the mediation to be provided to the user comprises in response to determining that the first audio data is sufficiently similar to the second audio data, determining the filter mediation.

In some implementations, the operations further comprise: presenting to the user, on a graphical user interface, one or more access controls for controlling user data that is made available to one or more other users, the user data comprising sensor data collected by the one or more sensors, the one or more sensory thresholds, the mediation data, or a record of mediations presented to the user; and receiving data corresponding to user input selecting the one or more access controls. For example, the one or more access controls may be configured such that only sensor data that triggered a mediation is accessible to one or more other users (e.g., a general practitioner, a therapist, a family member, etc.). As another example, the one or more access controls can be configured such that certain types of sensor data (e.g., image or audio data of the environment) are not made available to other users. As a further example, the one or more access controls can be configured such that there are different hierarchies of data access, where some users have more access to certain types of data than other users.

In some implementations, the operations further comprise: presenting to the user, on a graphical user interface, one or more access controls that grant or deny access to one or more other users to influence mediations that are presented to the user; and receiving data corresponding to user input actuating the one or more access controls. For example, a wearer user can grant a therapist user access to modify the user's preferences to optimize the mediation that is presented to the user. In some implementations, certain types of mediations can be disabled or enabled.

In some implementations, the operations further comprise: presenting to the user, on a graphical user interface, a graphical summary of progress of the user from using the wearable device, the graphical summary including a moving average or change of time between mediations. As another example, the graphical summary of progress of the user can indicate a change in the sensory thresholds and/or mediations over time, a change/moving average of the user's average response time to distracting stimuli, a change/moving average of the number of mediations required in some time frame (e.g., during the day) and/or some event (e.g., while in the workplace or classroom), etc.

In some implementations, the one or more sensors comprise multiple sensors of different types, the multiple sensors comprising: an auditory sensor, a galvanic skin sensor, a pupillary sensor, a body temperature sensor, a head sway sensor, or an inertial movement unit; recording the sensory input stimulus to the user comprises obtaining first sensory data corresponding to a first sensory input stimulus from a first sensor of the multiple sensors, and second sensory data corresponding to a second sensory input stimulus from a second sensor of the multiple sensors; and determining the mediation to be provided to the user, comprises: inputting at least the first sensory data and the second sensory data into a fusion-based deep learning (FBDL) model that outputs an identification of the mediation to be provided to the user.

In some implementations, determining the mediation to be provided to the user, comprises: inputting at least the first sensory data, the second sensory data, and the mediation data into the FBDL model that outputs the identification of the mediation to be provided to the user.

One embodiment of the application is directed to a method, comprising: obtaining, at a wearable device system, user sensory sensitivity data corresponding to user input indicating whether a user of a wearable device of the wearable device system is visually sensitive, sonically sensitive, or interoceptively sensitive; determining, at the wearable device system, using at least the user sensory sensitivity data, one or more sensory thresholds specific to the user and mediation data corresponding to one or more mediations specific to the user, the one or more sensory threshold selected from auditory, visual, or physiological sensory thresholds; storing, at a storage of the wearable device system, the one or more sensory thresholds and the mediation data; recording, using one or more sensors of the wearable device system, a sensory input stimulus to the user; comparing, at the wearable device system, the sensory input stimulus with the one or more sensory thresholds specific to the user; in response to comparing the sensory input stimulus with the one or more sensory thresholds, determining, based at least on the mediation data, a mediation to be provided to the user, the mediation configured to provide the user relief from distractibility, inattention, anxiety, fatigue, or sensory issues; and providing, using at least the wearable device, the mediation to the user, the mediation comprising an alert mediation, a guidance mediation, or a filter mediation.

One embodiment of the application is directed to a system, comprising: a wearable device comprising one or more sensors; one or more processors; and one or more non-transitory computer-readable media having executable instructions stored thereon that, when executed by the one or more processors, cause the system to perform operations comprising: connecting to a datastore that stores one or more sensory thresholds specific to a user of the wearable device, the one or more sensory thresholds selected from auditory, visual or physiological sensory thresholds; recording, using the one or more sensors, a sensory input stimulus to the user; comparing the sensory input stimulus with the one or more sensory thresholds specific to the user to determine an intervention to be provided to the user, the intervention configured to provide the user relief from distractibility, inattention, anxiety, fatigue, or sensory issues; and providing the intervention to the user, the intervention comprising filtering, in real-time, an audio signal presented to the user or an optical signal presented to the user. The physiological sensory thresholds can be physiological/psychophysiological sensory thresholds.

In some implementations, the operations further comprise: communicatively coupling the system to an Internet of Things (IoT) device, the sensory input stimulus generated at least in part due to sound emitted by a speaker of the IoT device or light emitted by a light emitting device of the IoT device; and providing the intervention to the user, comprises: controlling the IoT device to filter, in real-time, the audio signal or the optical signal.

In some implementations, the IoT device comprises the light emitting device; controlling the IoT device to filter, in real-time, the audio signal or the optical signal, comprises controlling the IoT device to filter, in real-time, the optical signal; and filtering the optical signal adjusts a brightness or color of light output by the lighting device.

In some implementations, the IoT device comprises the speaker; controlling the IoT device to filter, in real-time, the audio signal or the optical signal, comprises controlling the IoT device to filter, in real-time, the audio signal; and filtering the audio signal adjusts a frequency of sound output by the speaker.

In some implementations, the wearable device further comprises a bone conduction transducer or a hearing device; and providing the intervention to the user comprises: filtering, at the wearable device, in real-time, the audio signal in a frequency domain; and after filtering the audio signal, presenting the audio signal to the user by outputting, using the bone conduction transducer or the hearing device, a vibration or sound wave corresponding to the audio signal.

In some implementations, the wearable device further comprises a head mounted display (HMD) that presents the optical signal to the user, the HMD worn by the user; and providing the intervention to the user further comprises filtering, in real-time, the optical signal by modifying a real-time image of the real-world environment presented to the user via the HMD.

In some implementations, comparing the sensory input stimulus with the one or more sensory thresholds specific to the user to determine the intervention to be provided to the user, comprises: determining, based on the same sensor data recorded by the one or more sensors, to filter the audio signal and to filter the optical signal.

In some implementations, the wearable device further comprises a HMD that presents the optical signal to the user, the HMD worn by the user; and providing the intervention to the user includes filtering, in real-time, the optical signal by modifying a real-time image of the real-world environment presented to the user via the HMD.

In some implementations, modifying the real-time image comprises inserting a virtual object into the real-time image or modifying the appearance of an object of the real-world environment in the real-time image.

In some implementations, comparing the sensory input stimulus with the one or more sensory thresholds specific to the user to determine the intervention to be provided to the user, comprises: inputting the sensory input stimulus and the one or more user-specific sensory thresholds into a trained model to automatically determine, based on an output of the trained model, a visual intervention to be provided to the user.

In some implementations, the one or more sensors comprise multiple sensors of different types, the multiple sensors comprising: an auditory sensor, a galvanic skin sensor, a pupillary sensor, a body temperature sensor, a head sway sensor, or an inertial movement unit; recording the sensory input stimulus to the user comprises recording a first sensory input stimulus from a first sensor of the multiple sensors, and a second sensory input stimulus from a second sensor of the multiple sensors; and inputting the sensory input stimulus into the trained model comprises inputting the first sensory input stimulus and the second sensory input stimulus into the trained model.

In some implementations, the visual intervention comprises: presenting an alert to the user of a visually distracting object; and after it is determined that the user does not sufficiently respond to the alert within a period of time, filtering, in real-time, the optical signal presented to the user.

In some implementations, the visual intervention comprises: filtering, in real-time, the optical signal to hide a visually distracting object without providing a prior alert to the user that the visually distracting object is present.

In some implementations, the operations further comprise determining the one or more sensory thresholds specific to the user and one or more interventions specific to the user by: presenting multiple selectable templates to the user, each of the templates providing an indication of whether the user is visually sensitive, sonically sensitive, or interoceptively sensitive, and each of the templates associated with corresponding one or more sensory thresholds and one or more interventions; and receiving data corresponding to input by the user selecting one of the templates.

In some implementations, determining the one or more sensory thresholds specific to the user and the one or more interventions specific to the user further comprises: receiving additional data corresponding to additional user input selecting preferences, the preferences comprising audio preferences, visual preferences, physiological preferences, alert preferences, guidance preferences, or intervention preferences; and in response to receiving the additional data, modifying the one or more thresholds and the one or more interventions of the selected template to derive the one or more sensory thresholds specific to the user and the one or more interventions specific to the user. In some implementations, the physiological preferences are psychophysiological preferences.

In some implementations, comparing the sensory input stimulus with the one or more sensory thresholds specific to the user to determine the intervention to be provided to the user, comprises: inputting the sensory input stimulus and the one or more user-specific sensory thresholds into a trained model to automatically determine, based on an output of the trained model, the intervention to be provided to the user.

In some implementations, the user is neurodiverse. In some implementations, the user can be autistic.

In some implementations, the intervention further comprises an alert intervention; and with the alert intervention, a response time for the user increases by at least 3% and accuracy increases by at least about 26% from baseline for errors of commission, the errors of commission being a measure of a failure of the user to inhibit a response when prompted by a feedback device.

In some implementations, the intervention further comprises a guidance intervention; and with the guidance intervention, a response time for the user increases by at least about 20% and accuracy increases by at least about 10% from baseline for errors of commission, the errors of commission being a measure of a failure of the user to inhibit a response when prompted by a feedback device.

In some implementations, the intervention further comprises a guidance intervention; and with the guidance intervention, a response time for the user increases by at least about 2% and accuracy increases by at least about 30% from baseline for errors of omission, the errors of omission being a measure of a failure of the user to take appropriate action when a prompt is not received from a feedback device.

In some implementations, with the intervention to filter, a response time for the user increases by at least about 10% from baseline for errors of omission, the errors of omission being a measure of a failure of the user to take appropriate action when a prompt is not received from a feedback device.

In some implementations, with the intervention to filter, a response time for the user is at least about 15% faster than would be a response time for a neurotypical user using the system for errors of omission, the errors of omission being a measure of a failure of the user to take appropriate action when a prompt is not received from a feedback device.

In some implementations, the intervention further comprises a guidance intervention; and with the guidance intervention, a response time for the user is at least about 20% faster and accuracy is about 8% higher than would be a response time and accuracy of a neurotypical user using the system for errors of commission, the errors of commission being a measure of a failure of the user to inhibit a response when prompted by a feedback device.

In some implementations, the intervention further comprises an alert intervention; and with the alert intervention, accuracy for the user is at least about 25% higher than would be an accuracy of a neurotypical user using the system for errors of commission, the errors of commission being a measure of a failure of the user to inhibit a response when prompted by a feedback device.

One embodiment of the application is directed to a method, comprising: connecting a wearable device system to a datastore that stores one or more sensory thresholds specific to a user of a wearable device of the wearable device system, the one or more sensory thresholds selected from auditory, visual or physiological sensory thresholds; recording, using one or more sensors of the wearable device, a sensory input stimulus to the user; comparing, using the wearable device system, the sensory input stimulus with the one or more sensory thresholds specific to the user to determine an intervention to be provided to the user, the intervention configured to provide the user relief from distractibility, inattention, anxiety, fatigue, or sensory issues; and providing, using the wearable device system, the intervention to the user, the intervention comprising filtering, in real-time, an audio signal presented to the user or an optical signal presented to the user. In some implementations, the physiological preferences are psychophysiological preferences.

In some implementations, the method further comprises communicatively coupling the wearable device system to an IoT device; providing the intervention to the user comprises controlling the IoT device to filter, in real-time, the audio signal or the optical signal; and the sensory input stimulus generated at least in part due to sound emitted by a speaker of the IoT device or light emitted by a light emitting device of the IoT device.

In some implementations, the IoT device comprises the light emitting device; controlling the IoT device to filter, in real-time, the audio signal or the optical signal, comprises controlling the IoT device to filter, in real-time, the optical signal; and filtering the optical signal adjusts a brightness or color of light output by the lighting device.

In some implementations, the IoT device comprises the speaker; controlling the IoT device to filter, in real-time, the audio signal or the optical signal, comprises controlling the IoT device to filter, in real-time, the audio signal; and filtering the audio signal adjusts a frequency of sound output by the speaker.

In some implementations, the wearable device further comprises a bone conduction transducer or a hearing device; and providing the intervention to the user comprises: filtering, at the wearable device, in real-time, the audio signal in a frequency domain; and after filtering the audio signal, presenting the audio signal to the user by outputting, using the bone conduction transducer or the hearing device, a vibration or sound wave corresponding to the audio signal.

One embodiment of this application is directed to a system for providing sensory relief from distractibility, inattention, anxiety, fatigue, sensory issues, or combinations thereof, to a user in need thereof, the system comprising: (i.) a wearable device; (ii) a database of one or more user-specific sensory thresholds selected from auditory, visual, and physiological sensory thresholds, one or more user-specific sensory resolutions selected from auditory, visual and physiological sensory resolutions, or combinations thereof; (iii) an activation means for connecting the wearable device and the database; (iv) one or more sensors for recording a sensory input stimulus to the user; (v) a comparing means for comparing the sensory input stimulus recorded by the one or more sensors with the database of one or more user-specific sensory thresholds to obtain a sensory resolution for the user; (vi) one or more feedback devices for transmitting the sensory resolution to the user; and (vii) a user-specific intervention means for providing relief to the user from the distractibility, inattention, anxiety, fatigue, sensory issues, or combinations thereof. The user-specific intervention means is selected from an alert intervention, a filter intervention, a guidance intervention, or a combination thereof, and the user can be a neurodiverse user or a neurotypical user. In a preferred embodiment, the neurodiverse user can be an autistic user. In some implementations, the physiological sensory thresholds are psychophysiological sensory thresholds, and the physiological sensory resolutions are psychophysiological sensory resolutions.

In some implementations, the wearable device is an eyeglass frame comprising the one or more sensors and the one or more feedback devices.

In some implementations, the one or more sensors are selected from one or more infrared sensors, one or more auditory sensors, one or more galvanic skin sensors, one or more inertial movement units, or combinations thereof.

In some implementations, the one or more feedback devices are selected from one or more haptic drivers, one or more bone conduction transducers, or combinations thereof.

In some implementations, the system further comprises a wireless or wired hearing device.

In some implementations, the sensory input stimulus is selected from an ecological auditory input, an ecological visual input, a egocentric physiological/psychophysiological input, or combinations thereof.

In some implementations, the sensory input stimulus is measured by evaluating one or more parameters selected from eye tracking, pupillometry, auditory cues, interoceptive awareness, physical movement, variations in body temperature or ambient temperatures, pulse rate, respiration, or combinations thereof.

In some implementations, the sensory resolution is provided by one or more alerts selected from a visual alert, an auditory alert, a physiological/psychophysiological alert, a verbal alert, or combinations thereof.

In some implementations, the activation means is a power switch located on the wearable device.

In some implementations, the power switch is located at a left side of the wearable device.

In some implementations, the power switch is located at a right side of the wearable device.

In some implementations, the power switch is a recessed power switch.

In some implementations, the database is stored in a storage device.

In some implementations, the storage device is selected from a fixed or movable computer system, a portable wireless device, a smartphone, a tablet, or combinations thereof.

In some implementations, with an alert intervention, a response time for autistic users increases by at least about 3% and accuracy increases by at least about 26% from baseline for errors of commission, wherein the errors of commission are a measure of the user's failure to inhibit a response when prompted by the feedback device.

In some implementations, with an alert intervention, a response time for neurotypical users increases by at least about 18% and accuracy increases by at least about 2.0% from baseline for errors of commission, wherein the errors of commission are a measure of the user's failure to inhibit a response when prompted by the feedback device.

In some implementations, with a guidance intervention, a response time for autistic users increases by at least about 20% and accuracy increases by at least about 10% from baseline for errors of commission, wherein the errors of commission are a measure of the user's failure to inhibit a response when prompted by the feedback device.

In some implementations, with guidance intervention, a response time for autistic users increases by at least about 2% and accuracy increases by at least about 30% from baseline for errors of omission, wherein the errors of omission is a measure of the user's failure to take appropriate action when a prompt is not received from the feedback device.

In some implementations, with a filter intervention, a response time for autistic users increases by at least about 10% from baseline for errors of omission, wherein the errors of omission is a measure of the user's failure to take appropriate action when a prompt is not received from the feedback device.

In some implementations, with a filter intervention, a response time for autistic users is at least about 15% faster than neurotypical users for errors of omission, wherein the errors of omission are a measure of the user's failure to take appropriate action when a prompt is not received from the feedback device.

In some implementations, with a guidance intervention, a response time for autistic users is at least about 20% faster and accuracy is about 8% higher than neurotypical users for errors of commission, wherein the errors of commission are a measure of the user's failure to inhibit a response when prompted by the feedback device.

In some implementations, with an alert intervention, accuracy for autistic users is at least about 25% higher than neurotypical users for errors of commission, wherein the errors of commission are a measure of the user's failure to inhibit a response when prompted by the feedback device.

In one embodiment, a method of providing sensory relief from distractibility, inattention, anxiety, fatigue, sensory issues, or combinations thereof, to a user in need thereof, comprises: creating a database of one or more user-specific sensory thresholds selected from auditory, visual and physiological/psychophysiological sensory thresholds, one or more user-specific sensory resolutions selected from auditory, visual and physiological/psychophysiological sensory resolution, or combinations thereof; attaching a wearable device to the user, wherein the wearable device comprises one or more sensors and one or more feedback devices; activating and connecting the wearable device to the database; recording a sensory input stimulus to the user via the one or more sensors; comparing the sensory input stimulus with the database of one or more user-specific sensory thresholds; selecting an appropriate user-specific sensory resolution from the database; delivering the user-specific sensory resolution to the user via the one or more feedback devices; and providing a user-specific intervention (a/k/a digital mediation) to provide relief to the user from the distractibility, inattention, anxiety, fatigue, sensory issues, or combinations thereof, wherein the user-specific intervention is selected from an alert intervention, a filter intervention, a guidance intervention, or a combination thereof, and wherein the user is an autistic user, a neurotypical user, or a neurodiverse user.

In some implementations, the one or more sensors are selected from one or more infrared sensors, one or more microphones, one or more galvanic skin sensors, one or more inertial movement units, or combinations thereof.

In some implementations, the one or more feedback devices is selected from one or more haptic drivers, one or more bone conduction transducers, or combinations thereof.

In some implementations, the sensory input stimulus is selected from an auditory input, a visual input, a physiological/psychophysiological input or combinations thereof.

In some implementations, the sensory input stimulus is measured by one or more parameters selected from eye tracking, pupillometry, auditory cues, interoceptive awareness, physical movement, variations in body or ambient temperatures, pulse rate, respiration, or combinations thereof.

In some implementations, the user-specific sensory resolution is provided by one or more alerts selected from a visual alert, an auditory alert, a physiological/psychophysiological alert, a verbal alert or combinations thereof.

In some implementations, the activation and connection of the wearable device to the database is through a power switch located on the wearable device.

In some implementations, the power switch is located at a left side of the wearable device or a right side of the wearable device In some implementations, the power switch is a recessed power switch.

In some implementations, the wearable device is an eyeglass frame.

In some implementations, the database is stored in a storage device.

In some implementations, the storage device is selected from a fixed or movable computer system, a portable wireless device, a smartphone, a tablet, or combinations thereof.

In some implementations, with an alert intervention, a response time for autistic users increases by at least about 3% and accuracy increases by at least about 26% from baseline for errors of commission, wherein the errors of commission are a measure of the user's failure to inhibit a response when prompted by the feedback device.

In some implementations, with an alert intervention, a response time for neurotypical users increases by at least about 18% and accuracy increases by at least about 2.0% from baseline for errors of commission, wherein the errors of commission are a measure of the user's failure to inhibit a response when prompted by the feedback device.

In some implementations, with a guidance intervention, a response time for autistic users increases by at least about 20% and accuracy increases by at least about 10% from baseline for errors of commission, wherein the errors of commission are a measure of the user's failure to inhibit a response when prompted by the feedback device.

In some implementations, with a guidance intervention, a response time for autistic users increases by at least about 2% and accuracy increases by at least about 30% from baseline for errors of omission, wherein the errors of omission are a measure of the user's failure to take appropriate action when a prompt is not received from the feedback device.

In some implementations, with a filter intervention, a response time for autistic users increases by at least about 10% from baseline for errors of omission, wherein the errors of omission are a measure of the user's failure to take appropriate action when a prompt is not received from the feedback device.

In some implementations, with a filter intervention, a response time for autistic users is at least about 15% faster than neurotypical users for errors of omission, wherein the errors of omission are a measure of the user's failure to take appropriate action when a prompt is not received from the feedback device.

In some implementations, with a guidance intervention, a response time for autistic users is at least about 20% faster and accuracy is about 8% higher than neurotypical users for errors of commission, wherein the errors of commission are a measure of the user's failure to inhibit a response when prompted by the feedback device.

In some implementations, with an alert intervention, accuracy for autistic users is at least about 25% higher than neurotypical users for errors of commission, wherein the errors of commission are a measure of the user's failure to inhibit a response when prompted by the feedback device.

In one embodiment, a wearable device comprises one or more sensors and one or more feedback devices, wherein a combination of the one or more sensors and the one or more feedback devices provides sensory relief from distractibility, inattention, anxiety, fatigue, sensory issues, or combinations thereof, to a user/wearer in need thereof.

In some implementations, the wearable device is an eyeglass frame.

In some implementations, the one or more sensors are connected to the eyeglass frame.

In some implementations, the one or more feedback devices are connected to the eyeglass frame.

In some implementations, the eyeglass frame comprises a rim, two earpieces and hinges connecting the earpieces to the rim.

In some implementations, the one or more sensors are selected from the group consisting of one or more infrared sensors, one or more auditory transducers, one or more galvanic skin sensors, one or more inertial movement units, or combinations thereof.

In some implementations, the infrared sensor is surface-mounted on an inner side of the wearable device.

In some implementations, the infrared sensor is arranged to be incident on a right eye, a left eye or both eyes of a user.

In some implementations, the auditory transducer is a subminiature microphone.

In some implementations, the subminiature microphone is surface-mounted on an outer side of the wearable device.

In some implementations, the wearable device comprises at least two auditory transducers, wherein a first auditory transducer is arranged at an angle of about 110° to a second auditory transducer.

In some implementations, the galvanic skin sensor is surface-mounted on an inner side of the wearable device, and wherein the galvanic skin sensor is in direct contact with skin of a user.

In some implementations, the inertial movement unit is internally-mounted on an inner-side of the wearable device.

In some implementations, the one or more feedback devices are selected from one or more haptic drivers, one or more bone conduction transducers, or combinations thereof.

In some implementations, the haptic drive is internally mounted on an inner side of the wearable device.

In some implementations, the haptic drive is internally mounted on an inner side of the wearable device and behind the inertial movement unit.

In some implementations, the haptic drive provides a vibration pattern in response to a sensory input stimulus selected from eye tracking, pupillometry, auditory cues, interoceptive awareness, physical movement, variations in body or ambient temperature, pulse rate, respiration, or combinations thereof.

In some implementations, the stereophonic bone conduction transducer is surface-mounted on an inner side of the wearable device, and the stereophonic bone conduction transducer is in direct contact with a user's skull.

In some implementations, the stereophonic bone conduction transducer provides an auditory tone, a pre-recorded auditory guidance, real-time filtering, or combinations thereof, in response to a sensory input stimulus selected from eye tracking, pupillometry, auditory cues, interoceptive awareness, physical movement, variations in body or ambient temperature, pulse rate, respiration, or combinations thereof.

In some implementations, the wearable device further comprises an optional wireless or wired hearing device.

In some implementations, the wearable device further comprises an intervention means to providing relief to a user from the distractibility, inattention, anxiety, fatigue, sensory issues, or combinations thereof, the intervention means selected from an alert intervention, a filter intervention, a guidance intervention, or a combination thereof.

In some implementations, the wearable device further comprises a power switch. The power switch can be located at a left side of the wearable device or a right side of the wearable device. The power switch can be a recessed power switch.

In one embodiment, a non-transitory computer-readable medium has executable instructions stored thereon that, when executed by a processor, cause a wearable device to perform operations comprising: connecting the wearable device to a datastore that stores one or more sensory thresholds and one or more sensory resolutions specific to a user, the one or more sensory thresholds selected from auditory, visual or physiological/psychophysiological sensory thresholds, and the one or more sensory resolutions selected from auditory, visual, or physiological/psychophysiological sensory resolutions; recording, via one or more sensors, a sensory input stimulus to the user; comparing the sensory input stimulus recorded by the one or more sensors with one or more sensory thresholds to obtain a sensory resolution for the user; and transmitting the sensory resolution to the user.

In some implementations, the operations further comprise: communicatively coupling to an IoT device providing the sensory input stimulus to the user; and transmitting the sensory resolution to the user, comprises: after communicatively coupling to the IoT device, controlling the IoT device to transmit the sensory resolution.

In some implementations, the IoT device comprises a networked lighting device; and controlling the IoT device to transmit the sensory resolution, comprises: controlling a brightness or color output of the networked lighting device.

In some implementations, the IoT device comprises a networked speaker; and controlling the IoT device to transmit the sensory resolution, comprises: controlling a volume, an equalization setting, or a channel balance of the networked speaker.

In some implementations, comparing the sensory input stimulus recorded by the one or more sensors with the one or more user-specific sensory thresholds to obtain the sensory resolution for the user, comprises: inputting the sensory input stimulus and the one or more user-specific sensory thresholds into a trained model to automatically determine the sensory resolution for the user.

In some implementations, the operations further comprise determining the one or more sensory thresholds and the one or more sensory resolutions by: presenting multiple selectable templates to the user, each of the templates providing an indication of whether the user is visually sensitive, sonically sensitive, or interoceptively sensitive, and each of the templates associated with corresponding one or more thresholds and one or more sensory resolutions; and receiving data corresponding to input by the user selecting one of the templates.

In some implementations, determining the one or more user-specific sensory thresholds and the one or more user-specific sensory resolutions further comprises: receiving additional data corresponding to additional user input selecting preferences, the preferences comprising audio preferences, visual preferences, physiological/psychophysiological preferences, alert preferences, guidance preferences, or intervention preferences; and in response to receiving the additional data, modifying the one or more thresholds and one or more sensory resolutions of the selected template to derive the one or more user-specific sensory thresholds and the one or more user-specific sensory resolutions.

Other features and aspects of the disclosed method will become apparent from the following detailed description, taken in conjunction with the accompanying drawings, which illustrate, by way of example, the features in accordance with embodiments of the disclosure. The summary is not intended to limit the scope of the claimed disclosure, which is defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments of the disclosure.

FIG. 8A shows the EOC from baseline to baseline. FIG. 8B shows the EOC intervention effect. FIG. 8C shows the lasting effect of EOC.

FIG. 9A shows the EOC vs RT from starting baseline to final baseline. FIG. 9B shows the EOC vs RT intervention effect. FIG. 9C shows the lasting effect of EOC vs RT.

FIG. 12A shows the EOO from starting baseline to final baseline. FIG. 12B shows the EOO intervention effect. FIG. 12C shows the lasting effect of EOO.

FIG. 13A shows the EOO vs RT from starting baseline to final baseline. FIG. 13B shows the EOO vs RT intervention effect. FIG. 13C shows the lasting effect of EOO vs RT.

FIG. 24A depicts interventions that can be delivered using a real-time optical enhancement algorithm, the interventions including haptic alerts, tone alerts guidance, and an eraser effect, in accordance with some implementations of the disclosure.

FIG. 24B depicts interventions that can be delivered using a real-time optical enhancement algorithm, the interventions including a text alert, a blur effect, and a cover-up effect, in accordance with some implementations of the disclosure.

FIG. 24C depicts interventions that can be delivered using a real-time optical enhancement algorithm, the interventions including color balance, a contrast effect, and an enhancement effect, in accordance with some implementations of the disclosure.

FIG. 29 depicts the mean distribution of anxiety and distractibility scores for diagnostic groups across demographic variable for the PPI study described herein.

FIG. 30 depicts non-autistic mediation models, in accordance with some implementations of the disclosure.

FIG. 34A shows summary results of the PPI study described herein.

FIG. 34B shows summary results of the PPI study described herein.

FIG. 35A shows summary results of the SART/WOz clinical study described herein.

FIG. 35B shows summary results of the SART/WOz clinical study described herein.

FIG. 40 depicts a table of the OLM described herein, the table describing what is available.

FIG. 42 depicts a table of the OLM described herein, the table describing how the model is presented to stakeholders.

FIG. 44 depicts a table of the OLM described herein, the table describing who controls access over others.

Figure 1:
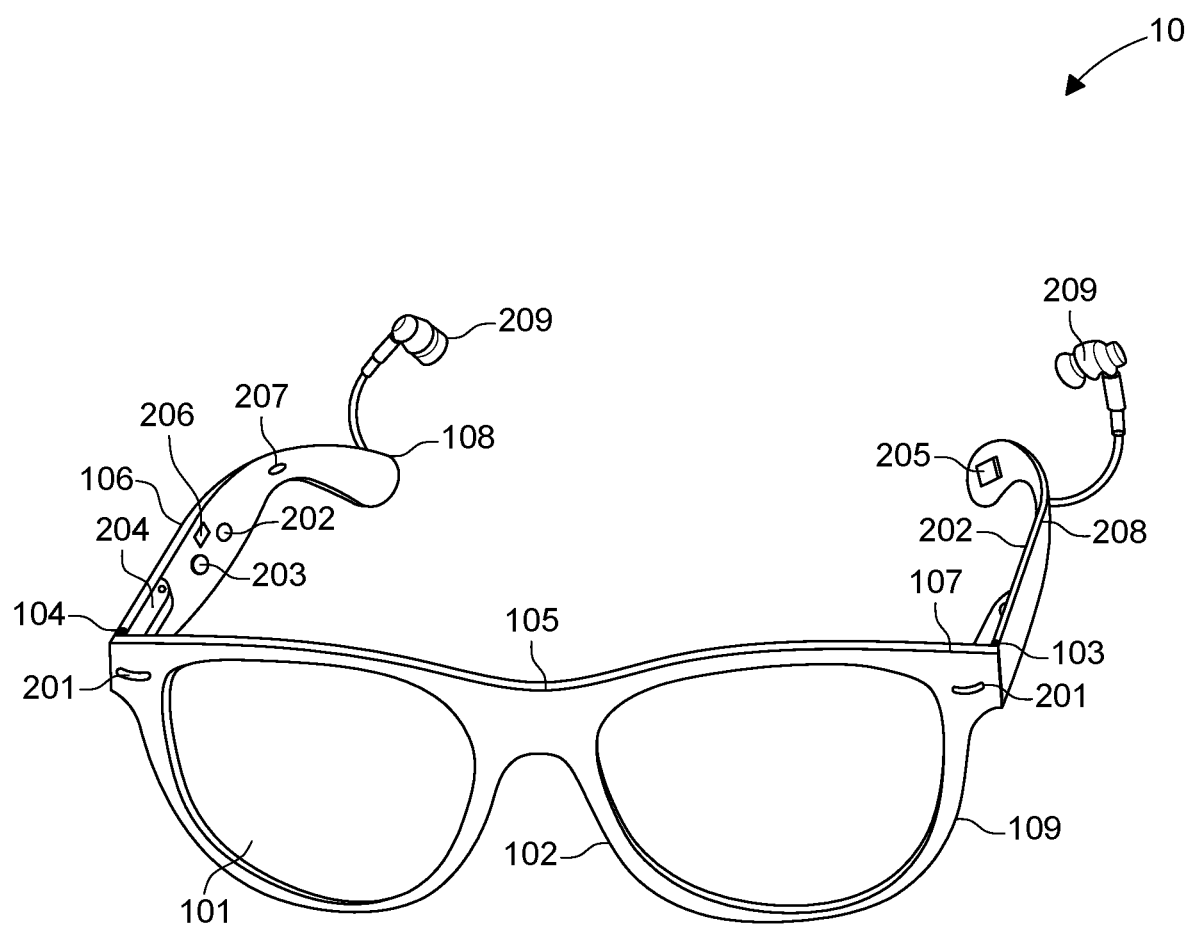
FIG. 1 is a schematic representation of a wearable device, in accordance with some implementations of the disclosure.

The figures are not exhaustive and do not limit the disclosure to the precise form disclosed.

DETAILED DESCRIPTION

Further aspects, features and advantages of this invention will become apparent from the detailed description which follows.

As used herein, the singular forms "a", "an" and "the" are intended to include the plural forms as well, unless the context clearly indicates otherwise. Additionally, the use of "or" is intended to include "and/or", unless the context clearly indicates otherwise.

As used herein, "about" is a term of approximation and is intended to include minor variations in the literally stated amounts, as would be understood by those skilled in the art. Such variations include, for example, standard deviations associated with conventional measurement techniques or specific measurement techniques described herein. All of the values characterized by the above-described modifier "about," are also intended to include the exact numerical values disclosed herein. Moreover, all ranges include the upper and lower limits.

Any apparatus, device or product described herein is intended to encompass apparatus, device or products which consist of, consist essentially of, as well as comprise, the various constituents/components identified herein, unless explicitly indicated to the contrary.

As used herein, the recitation of a numerical range for a variable is intended to convey that the variable can be equal to any value(s) within that range, as well as any and all sub-ranges encompassed by the broader range. Thus, the variable can be equal to any integer value or values within the numerical range, including the end-points of the range. As an example, a variable which is described as having values between 0 and 10, can be 0, 4, 2-6, 2.75, 3.19-4.47, etc.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Unless indicated otherwise, each of the individual features or embodiments of the present specification are combinable with any other individual features or embodiments that are described herein, without limitation. Such combinations are specifically contemplated as being within the scope of the present invention, regardless of whether they are explicitly described as a combination herein.

Technical and scientific terms used herein have the meaning commonly understood by one of skill in the art to which the present description pertains, unless otherwise defined. Reference is made herein to various methodologies and materials known to those of skill in the art.

As used herein, the term "alert intervention" can include: in the event of an ecological and/or physiological (e.g., psychophysiological) threshold's activation that corresponds to a wearer's preferences, a signal is delivered to: (i) a haptic driver that provides a gentle, tactile vibration pattern to convey information to the wearer that focus, anxiety, fatigue or related characteristics require their attention; and/or (ii) a bone conduction transducer that delivers an auditory/sonic message (e.g., pre-recorded text-to-speech, beep tone, etc.) reinforcing the haptic with an aural intervention and set of instructions.

As used herein, the term "filter intervention" can include: in the event of an ecological and/or physiological (e.g., psychophysiological) threshold's activation that corresponds to a wearer's preferences and requires auditory or optical filtering, performing audio signal processing or optical signal processing. Digital audio signal processing can deliver real-time and low-latency audio signals that include corrected amplitude (compression, expansion), frequency (dynamic, shelving, low/hi-cut, and parametric equalization), spatial realignment (reposition, stereo to mono) and/or phase correction (time delay, comb filtering, linear phase alignment). In an embodiment, the filter invention can be delivered to a bone conduction transducer. In other embodiments, the filter invention can be delivered to optional wireless or wired hearing devices, including but not limited to earbuds, earphones, headphones, and the like.

As used herein, the term "guidance intervention" can include an intervention similar to an alert intervention, where the guidance can be provided by way of step-by-step instructions for re-alignment of focus, head sway, pupillary activity, pulse, temperature, respiration, anxiety, and fatigue coaching. These pre-recorded, text-to-speech audio streams can be delivered to bone conduction systems, which provide step-by-step instructional intervention both privately and unobtrusively.

As used herein, the term "combination intervention" can include as follows: an intervention that can be selected by the wearer, which can be a combination of alert, filter and guidance interventions, and which are provided depending upon the triggering mechanism. For example, only sonic disturbances can be addressed through filter intervention, while all other issues (attentional-focus, anxiety, fatigue, and the like) can be intervened through haptic, text-to-speech alerts, long-form step-by-step guidance, and the like.

As used herein, the terms "user" and "wearer" are used interchangeably.

As used herein, the terms "intervention" and "mediation" are used interchangeably.

As used herein, the term "errors of commission" are a measure of the user's failure to inhibit a response when prompted by the feedback device As used herein, the term "errors of omission" are a measure of the user's failure to take appropriate action when a prompt is not received from the feedback device As used herein, the term "response time" is intended to include the time taken by a participant to respond to a sensory cue and/or an alert, filter and/or guidance intervention. Response Time may also be interchangeably referred to as Reaction Time and is defined as the amount of time between when a participant perceives a sensory cue and when the participant responds to said sensory cue. Response Time or Reaction Time is the ability to detect, process, and respond to a stimulus.

As used herein to refer to processing such as, for example, any processing that can include filtering of an audio signal and/or an optical signal that is presented to a user, the term "real-time" is intended to refer to processing and/or filtering the signal with a minimal latency after the original audio signal and/or optical signal occurs. For example, the latency can be a non-zero value of about 500 milliseconds (ms) or less, about 250 ms or less, about 200 ms or less, about 150 ms or less, about 100 ms or less, about 90 ms or less, about 80 ms or less, about 70 ms or less, about 60 ms or less, about 50 ms or less, about 40 ms or less, about 30 ms or less, about 20 ms or less, or about 10 ms or less, ranges and/or combinations thereof and the like. The minimum latency can be subject to system and hardware and software limitations, including communication protocol latency, digital signal processing latency, electrical signal processing latency, combinations thereof and the like. In some instances, real-time filtering of an audio signal and/or an optical signal can be perceived by a user as being immediate, instantaneous or nearly immediate and/or instantaneous.

Autism Spectrum Condition (ASC) is a life-long diagnosis, which has a subset of features including hyper-, seeking- and/or hypo-reactivity to sensory inputs or unusual interests. These qualities are evident across environmental (e.g., response to specific sounds, visual fascination with lights or movements) and physiological/psychophysiological domains (e.g., anxiety, respiration or euthermia). Scholars report that ninety (90%) of autistic adults experience sensory issues causing significant barriers at school/work (Leekam et al., 2007). Individuals with ASC often exhibit persistent deficits in social communication and interaction across multiple contexts. An additional hallmark includes restricted, repetitive patterns of behavior and interests (RRBI). Importantly, RRBIs include hyper-, seeking- and/or hypo-reactivity to sensory input along with attainably unusual interests in sensory aspects of the environment and physiological/psychophysiological responses to visuals, textures, smells, touch, and sounds. As the diagnosis of ASC populations increases exponentially over time, an ever-expanding social policy chasm proliferates, whereby an autistic individual's smooth transition into the fabric of daily life is often compromised. Experts identify this as a gap stemming from either: (i) stunted public/government support for neurodiverse individuals; ii) tensions between the autism community and society; and iii) limited support for later-life educational/vocational pathways. The negative effects of policy-related factors are a consequence resulting in societal costs that have a potential to become still more significant and possibly irremediable.

This application provides various interventions to alter, redirect and/or attenuate disruptive stimuli. Namely, described herein are systems, devices and methods to determine whether distractions exist, which can be exacerbated at school and at work, and provide interventions to compensate for such distractions, thereby lessening anxiety for neurotypical and neurodiverse individuals, and providing sensory relief. This application aspires to help individuals learn, adapt, and internalize how best to respond to encroaching ecological stimuli and resulting physiological/psychophysiological responses. Wearables, as described herein, may, through repetitive processes observed and experienced by users, pave the way for a call and response process that may eventually transfer directly from a machine or system to the person, thus embedding guidance for similarly reoccurring/future scenarios. An autistic individual, for example, might watch, experience, and learn precisely how an Artificial Intelligence/Cognitive Enhancement system detects, filters and coaches herself when confronted with an undesirable sensory stimulus.

One embodiment is directed to a system for providing sensory relief from distractibility, inattention, anxiety, fatigue, sensory issues, or combinations thereof, to a user in need thereof, the system comprising: (i.) a wearable device; (ii) a database of one or more user-specific sensory thresholds selected from auditory, visual and physiological/psychophysiological sensory thresholds, one or more user-specific sensory resolutions selected from auditory, visual and physiological/psychophysiological sensory resolutions, or combinations thereof; (iii) an activation means for connecting the wearable device and the database; (iv) one or more sensors for recording a sensory input stimulus to the user; (v) a comparing means for comparing the sensory input stimulus recorded by the one or more sensors with the database of one or more user-specific sensory thresholds to obtain a sensory resolution for the user; (vi) one or more feedback devices for transmitting the sensory resolution to the user; and (vii) a user-specific intervention means for providing relief to the user from the distractibility, inattention, anxiety, fatigue, sensory issues, or combinations thereof. The user-specific intervention means can be selected from an alert intervention, a filter intervention, a guidance intervention, or a combination thereof. The user can be an autistic user, a neurodiverse user or a neurotypical user.

Another embodiment is directed to a method of providing sensory relief from distractibility, inattention, anxiety, fatigue, sensory issues, or combinations thereof, to a user in need thereof, the method comprising: (i) creating a database of one or more user-specific sensory thresholds selected from auditory, visual and physiological/psychophysiological sensory thresholds, one or more user-specific sensory resolutions selected from auditory, visual and physiological/psychophysiological sensory resolution, or combinations thereof; (ii) attaching a wearable device to the user, wherein the wearable device comprises one or more sensors and one or more feedback devices; (iii) activating and connecting the wearable device to the database; (iv) recording a sensory input stimulus to the user via the one or more sensors; (v) comparing the sensory input stimulus with the database of one or more user-specific sensory thresholds; (vi) selecting an appropriate user-specific sensory resolution from the database; (vi) delivering the user-specific sensory resolution to the user via the one or more feedback devices; and (vii) providing a user-specific intervention to provide relief to the user from the distractibility, inattention, anxiety, fatigue, sensory issues, or combinations thereof.

Another embodiment is directed to a wearable device comprising one or more sensors and one or more feedback devices. According to further embodiments, the wearable device can be an eyeglass frame. One or more sensors and/or one or more feedback devices can be connected to the eyeglass frame. The eyeglass frame may comprise a rim, two earpieces and hinges connecting the earpieces to the rim. In alternate embodiments, the wearable device may include jewelry, smart clothing, and accessories, including but not limited to rings, sensor woven fabrics, wristbands, watches, pins, hearing aid, assistive devices, medical devices, virtual, augmented, and mixed reality (VR/AR/MR) headsets, and the like. The wearable device may have the ability to coordinate with mobile and/or network devices for alert, filter, and guidance interventions, and may include sensors and feedback devices in various combinations.

According to further embodiments, the one or more sensors can be selected from one or more infrared sensors, one or more auditory sensors, one or more galvanic skin sensors, one or more inertial movement units, or combinations thereof. The infrared sensor can be surface-mounted on an inner side of the wearable device. The infrared sensor can be arranged to be incident on a right eye, a left eye or both eyes of a user.

According to further embodiments, the one or more feedback devices can be selected from one or more haptic drivers, one or more bone conduction transducers, or combinations thereof.

According to further embodiments, the wearable device may further comprise a wireless or wired hearing device.

According to further embodiments, the sensory input stimulus can be selected from an auditory input, a visual input, a physiological/psychophysiological input or combinations thereof. The sensory input stimulus can be measured by evaluating one or more parameters selected from eye tracking, pupillometry, auditory cues, interoceptive awareness, physical movement, variations in body or ambient temperature, pulse rate, respiration, or combinations thereof. The sensory resolution can be provided by one or more alerts selected from a visual alert, an auditory alert, a physiological/psychophysiological alert, a verbal alert or combinations thereof.

According to further embodiments, the activation means can be a power switch located on the wearable device. The power switch can be located at a left side of the wearable device and/or at a right side of the wearable device. The power switch can be a recessed power switch. In another embodiment, power may be supplied when in stand-by mode from a user interface component, including but not limited to mobile phones, laptops, tablets, desktop computers, and the like, and any user interface known in the field can be used without limitation. In another embodiment, the activation means may include a power switch or power source that can be activated remotely (i.e., when not in proximity of a user).

In another embodiment, the activation means may be triggered by the wearable's accelerometer, pupillary and head sway sensors, and the like. For example, when an accelerometer is selected as an activation means, the accelerometer senses when the wearer (and wearable) is idle. In this instance, the unit can be in a low-power or power-off mode, and when the wearable is engaged (e.g., the wearable is lifted from a surface, move or agitated), such engagement is recognized by the accelerometer, which switches the wearable into a power-on mode. Similarly, for example, when pupillary or head sway sensors are used as an activation means, the power management system includes the ability to place the unit into a battery conservation mode (e.g., low-power mode). If, for example, a wearer was to shut their eyes whilst resting with a wearable "in place", the sensors would react to a novel movement and immediately return the system into a powered-on state when/if the user was to eventually arise from a period of rest, and the like.

In another embodiment, an activation means may include a power-on activity programmed from a biopotential analogue front end (AFE), which includes galvanic skin sensor response applications including perspiration, heart rate, blood pressure, temperature, and the like, all of which can trigger an activation of the wearable device.

In another embodiment, the wearable device's activation can be fully accessed by any type of network device/protocol because of its IoT connectivity, which enables communication, activation, and the like, of the wearable device.

According to further embodiments, a database can be stored in a storage device. The storage device can be selected from a fixed or movable computer system, a portable wireless device, a smartphone, a tablet, or combinations thereof. In an alternate embodiment, the database can be stored locally on or in the wearable device. In another alternate embodiment, the databased can be stored remotely, including but not limited to cloud-based systems, secured datacenters behind DMZ, and the like, and the database can be in encrypted and decrypted communication with the secured wearable device and its data.

Based on any of the exemplary embodiments described herein, a response time for autistic users increases by at least about 0.5% to about 5%, about 1% to about 4.5%, about 1.5% to about 4%, about 2% to about 3.5%, and preferably about 3% after alert intervention and accuracy increases by at least about 10% to about 50%, about 15% to about 40%, about 20% to about 30%, and preferably about 26% from baseline for errors of commission, wherein the errors of commission are a measure of the user's failure to inhibit a response when prompted by the feedback device. A numerical value within these ranges can be equal to any integer value or values within any of these ranges, including the end-points of these ranges.

Based on the exemplary embodiments described herein, a response time for neurotypical users increases by at least about 0.5% to about 50%, about 5% to about 40%, about 10% to about 30%, about 15% to about 20%, and preferably about 18% after alert intervention and accuracy increases by at least about 0.01% to about 5%, about 0.05% to about 4%, about 1% to about 3%, and preferably about 2.0% from baseline for errors of commission, wherein the errors of commission are a measure of the user's failure to inhibit a response when prompted by the feedback device. A numerical value within these ranges can be equal to any integer value or values within any of these ranges, including the end-points of these ranges.

Based on the exemplary embodiments described herein, a response time for autistic users increases by at least about 0.5% to about 50%, about 1% to about 40%, about 10% to about 30%, and preferably about 20% after guidance intervention and accuracy increases by at least about 0.5% to about 30%, about 1.0% to about 20%, about 5% to about 15%, and preferably about 10% from baseline for errors of commission, wherein the errors of commission are a measure of the user's failure to inhibit a response when prompted by the feedback device. A numerical value within these ranges can be equal to any integer value or values within any of these ranges, including the end-points of these ranges.

Based on the exemplary embodiments described herein, a response time for autistic users increases by at least about 0.01% to about 5%, about 0.05% to about 4%, about 1% to about 3%, and preferably about 2% after guidance intervention and accuracy increases by at least about 10% to about 50%, about 15% to about 45%, about 20% to about 40%, and preferably about 30% from baseline for errors of omission, wherein the errors of omission is a measure of the user's failure to take appropriate action when a prompt is not received from the feedback device. A numerical value within these ranges can be equal to any integer value or values within any of these ranges, including the end-points of these ranges.

Based on the exemplary embodiments described herein, a response time for autistic users increases by at least about 0.5% to about 30%, about 1.0% to about 20%, about 5% to about 15%, and preferably about 10% from baseline after filter intervention for errors of omission, wherein the errors of omission is a measure of the user's failure to take appropriate action when a prompt is not received from the feedback device. A numerical value within these ranges can be equal to any integer value or values within any of these ranges, including the end-points of these ranges.

Based on the exemplary embodiments described herein, a response time for autistic users is at least about 0.5% to about 30%, about 1.0% to about 25%, about 5% to about 20%, and preferably about 15% faster than neurotypical users after filter intervention for errors of omission, wherein the errors of omission are a measure of the user's failure to take appropriate action when a prompt is not received from the feedback device. A numerical value within these ranges can be equal to any integer value or values within any of these ranges, including the end-points of these ranges.

Based on the exemplary embodiments described herein, a response time for autistic users is at least about 0.5% to about 50%, about 1% to about 40%, about 10% to about 30%, and preferably about 20% faster after guidance intervention and accuracy is at least about 0.5% to about 30%, about 1.0% to about 20%, about 5% to about 15%, and preferably about 8% higher than neurotypical users for errors of commission, wherein the errors of commission are a measure of the user's failure to inhibit a response when prompted by the feedback device. A numerical value within these ranges can be equal to any integer value or values within any of these ranges, including the end-points of these ranges.

Based on the exemplary embodiments described herein, accuracy for autistic users is at least about 0.5% to about 50%, about 1% to about 4%, about 10% to about 30%, and preferably about 25% higher than neurotypical users after alert intervention for errors of commission, wherein the errors of commission are a measure of the user's failure to inhibit a response when prompted by the feedback device. A numerical value within these ranges can be equal to any integer value or values within any of these ranges, including the end-points of these ranges.

According to further embodiments, an auditory transducer can be a subminiature microphone. The subminiature microphone may preferably be surface-mounted on an outer side of the wearable device.

According to further embodiments, a wearable device may include at least two auditory transducers, and the arrangement of the first and second auditory transducers can be one that is known in the art, including but not limited to the first and second auditory transducers being arranged at an angle ranging from about 45° to about 135°, about 55° to about 130°, about 65° to about 125°, about 75° to about 120°, about 85° to about 120°, about 95° to about 115°, about 100°, about 110°, and the like. The numerical value of any specific angle within these ranges can be equal to any integer value or values within any of these ranges, including the end-points of these ranges can be.

According to further embodiments, a galvanic skin sensor can be surface-mounted on an inner side of the wearable device, and the galvanic skin sensor can be in direct contact with skin of a user. The inner side of the wearable device can be a side facing the skin or substantially facing the skin.

According to further embodiments, an inertial movement unit may preferably be internally-mounted on an inner-side of the wearable device.

According to further embodiments, the one or more feedback devices can be selected from one or more haptic drivers, one or more bone conduction transducers, or combinations thereof. The haptic drive can be internally mounted on an inner side of the wearable device. The haptic drive can be internally mounted on an inner side of the wearable device and behind the inertial movement unit. The haptic drive provides a vibration pattern in response to a sensory input stimulus selected from eye tracking, pupillometry, auditory cues, interoceptive awareness, physical movement, variations in body or ambient temperature, pulse rate, respiration, or combinations thereof. In another exemplary embodiment, the feedback device may also include a heads-up visual component, or other feedback devices that provide pupillary projection, distracting visual blurring, removal, squelching, recoloring, or combinations thereof.

According to further embodiments, the stereophonic bone conduction transducer can be surface-mounted on an inner side of the wearable device, and the stereophonic bone conduction transducer can be in direct contact with a user's skull. The stereophonic bone conduction transducer provides an auditory tone, a pre-recorded auditory guidance, real-time filtering, or combinations thereof, in response to a sensory input stimulus selected from eye tracking, pupillometry, auditory cues, interoceptive awareness, physical movement, variations in body and ambient temperature, pulse rate, respiration, or combinations thereof.

According to further embodiments, the wearable device may further include an intervention means to providing relief to a user from the distractibility, inattention, anxiety, fatigue, sensory issues, or combinations thereof, wherein the intervention means is selected from an alert intervention, a filter intervention, a guidance intervention, or a combination thereof. In exemplary embodiments, the intervention means and the feedback means can be the same or different.

Figure 16:
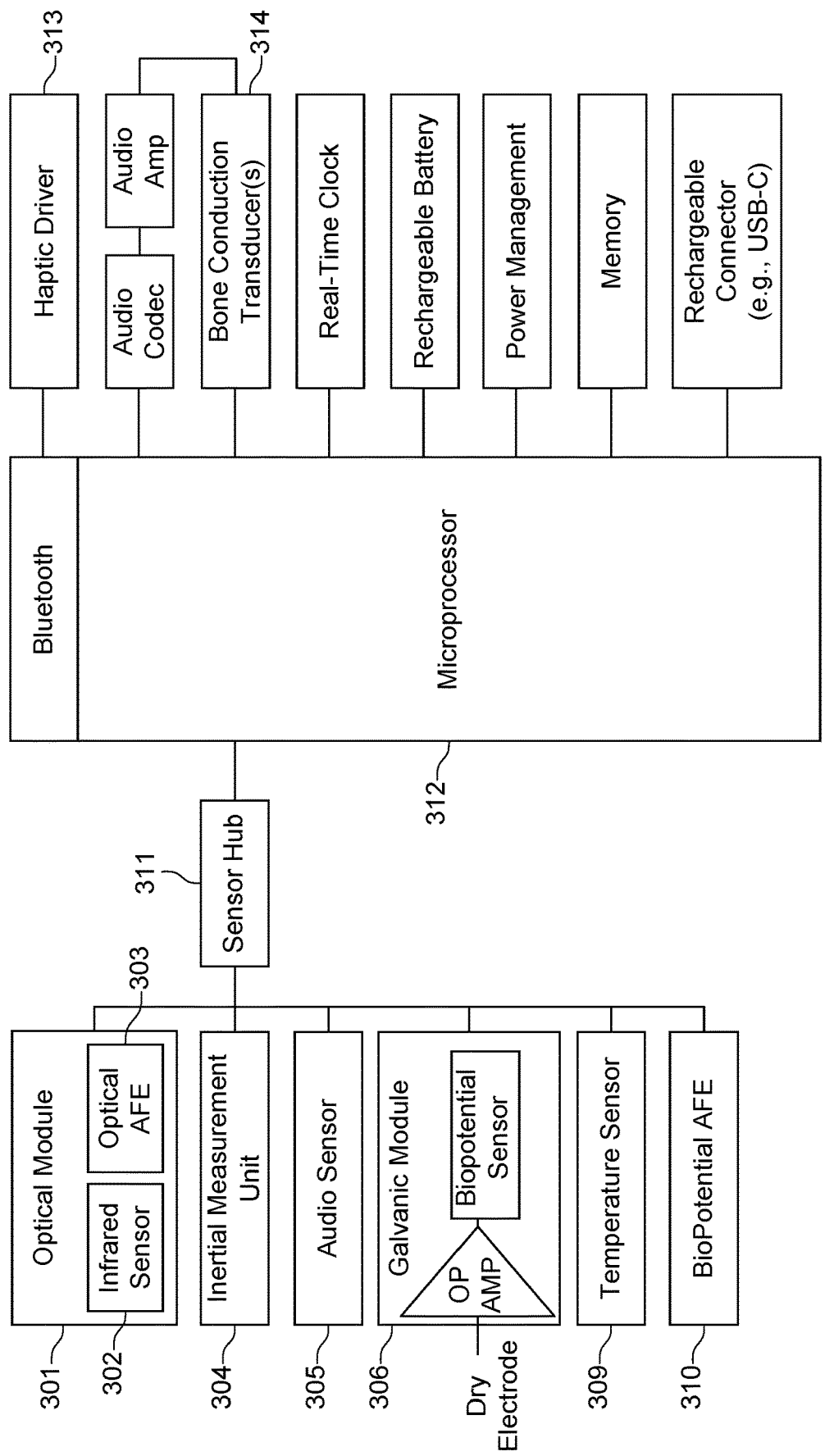
FIG. 16 is a block diagram of components of a wearable device, in accordance with some implementations of the disclosure.

Various possible intervention means available to the user and delivered by the wearable device are illustrated in the block diagram of FIG. 16. As illustrated in FIG. 16, following sensor(s) data stream delivery and microprocessor 312 comparison between ecological/environmental and physiological/psychophysiological thresholds to real-time data, those events deemed subject for interventional processing can be delivered to one of two discrete (or simultaneous)

components: a haptic driver 313 or a bone conduction transducer 314. Pending a wearer's previously defined preferences (stored in the microprocessor), one of four interventional strategies can be invoked: alert, filter, guidance, or combination.

Alert intervention: In the event of an ecological and/or physiological/psychophysiological threshold's activation that corresponds to a wearer's preferences, a signal is delivered to: (i) the haptic driver that provides a gentle, tactile vibration pattern to convey information to the wearer that focus, anxiety, fatigue or related characteristics require their attention; and/or (ii) the bone conduction transducer(s) that deliver an auditory/sonic message (e.g., pre-recorded text-to-speech, beep tone, etc.) reinforcing the haptic with an aural intervention and set of instructions.

Filter intervention: In the event of an ecological and/or physiological/psychophysiological threshold's activation that corresponds to a wearer's preferences and requires auditory filtering, digital audio signal processing delivers real-time and low-latency audio signals that include corrected amplitude (compression, expansion), frequency (dynamic, shelving, low/hi-cut, and parametric equalisation), spatial realignment (reposition, stereo to mono) and/or phase correction (time delay, comb filtering, linear phase alignment). Though typically delivered to bone conduction transducers, these can be delivered to optional wireless or wired hearing devices, including but not limited to earbuds, earphones, headphones, and the like.

Guidance intervention: Similar to alert intervention, the guidance by way of step-by-step instructions for re-alignment in focus, head sway, pupillary activity, anxiety, and fatigue coaching is provided to a wearer. These pre-recorded, text-to-speech audio streams are delivered to the bone conduction systems, which provide step-by-step instructional intervention both privately and unobtrusively.

Combination intervention: Selectable by the wearer, a combination of alert, filter and guidance interventions are provided depending upon the triggering mechanism. For example, only sonic disturbances are addressed through filter intervention, while all other issues (attentional-focus, anxiety, etc.) can be intervened through haptic, text-to-speech alerts and long-form step-by-step guidance.

According to further embodiments, the wearable device may further include a power switch. The power switch can be located at a left side of the wearable device and/or a right side of the wearable device. The power switch can be a recessed power switch.

In an embodiment, the wearable device may have a structure illustrated in FIG. 1. As illustrated in FIG. 1, the wearable device 10 can be in the form of an eyeglass frame including a rim 109, left and right earpieces, each having a temple portion 106 and temple tip 108 and screws 103 and hinges 104 connecting the earpieces to the rim 109. The frame may further include lenses 101, a nose pad 102, end pieces 107, and a bridge 105 connecting left- and right-sides of the frame. The wearable device may have one or more sensors connected to the frame, including infrared pupillometry sensors 204, galvanic skin sensors 205, inertial movement units 206, wireless transceiver and A/D multiplexers 208, microphones 201, and the like. The wearable device 10 may also include one or more feedback devices connected to the frame, including haptic drivers 203, bone conduction transducers 202, and the like. The wearable device 10 may further include an optional wireless or wired hearing device 209, and a power switch (not shown) and/or a rechargeable power source 207.

Although the wearable device is depicted as an eyeglass frame in FIG. 1, it should be appreciated that the wearable device can be implemented using a different type of head mount such as a visor or helmet. Other exemplary embodiments of the wearable device can include, but are not limited to, wrist worn devices, bone conduction devices, and the like, and any wearable device known in the field and adaptable to the method described herein can be used, and any of which may work in conjunction with a user interface described herein. In some cases, the wearable device can be implemented as a combination of devices (e.g., wearable eyeglasses, ring, wrist-worn, clothing/textile, and watch).

Figure 19:
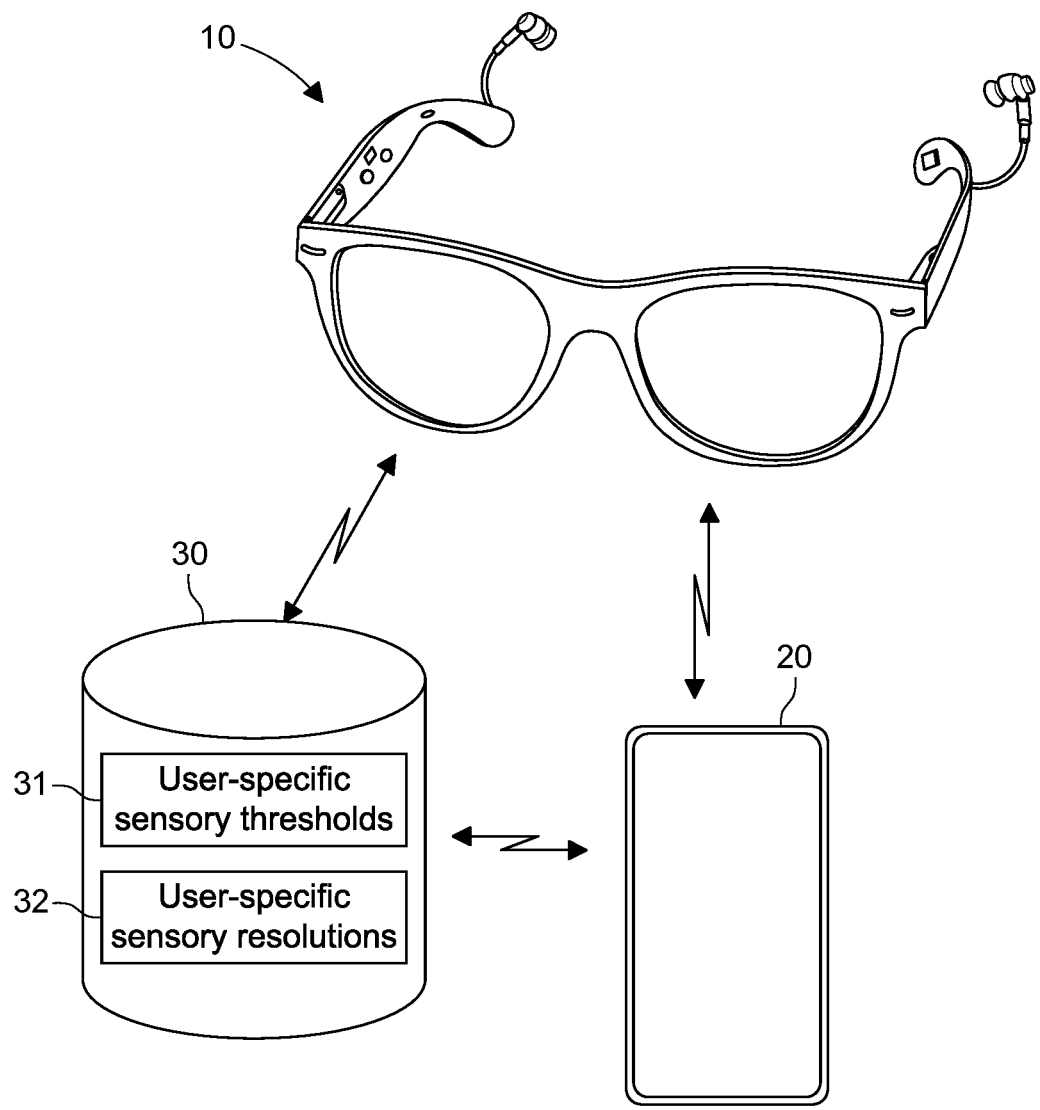
FIG. 19 depicts a wearable device system including a wearable device in communication with a mobile device and a datastore, in accordance with some implementations of the disclosure.

In some implementations, the wearable device can be communicatively coupled to a mobile device (e.g., smartphone and/or other smart device) that controls operations of, works in concert with, and/or provides a user interface for change settings of the wearable device. For example, FIG. 19 depicts a wearable device system including a wearable device 10 in communication with a mobile device 20, and a datastore 30. In this example system, the wearable device 10 communicates with mobile device 20 over a wireless communication network. The wireless communication network can be any suitable network that enables communications between the devices. The wireless communication network can be an ad-hoc network such as a WiFi network, a Bluetooth network, and/or a network using some other communication protocol. In some implementations, the wearable device 10 can be tethered to mobile device 20. In some implementations, the mobile device 20 processes sensor data collected by one or more sensors of wearable device 10. For example, the mobile device 20 can determine, based on the processed sensor data, one or more interventions to be applied using the wearable device 10 and/or some other device. The determination can be based on one or more sensory thresholds 31 specific to a user wearing the wearable device 10. The interventions that are applied can be based on one or more user-specific sensory resolutions 32 specific to the user. Although the datastore storing thresholds 31 and resolutions 32 is illustrated in this example as being separate from wearable device 10 and mobile device 20, in other implementations the datastore 30 can be incorporated within wearable device 10 and/or mobile device 20.

Prior to use, the user can initiate personalization of the wearable device by identifying individual sound, visual and physiological/psychophysiological thresholds using software integrated in the wearable device. Personalization can identify unique sensory, attentional-focus and anxiety/fatigue producing cues that a user finds distracting particularly in educational, employment, social, and typical daily activities, and can be derived from the Participant Public Information (PPI) study described herein. The user-specific thresholds are used to customize subsequent alerts, filters, and guidance experienced by the user when wearing the wearable device. Upon completion of the personalization process, the thresholds are transmitted to the wearable device. The personalization thresholds may be updated over time (e.g., periodically or dynamically) as the user adapts to stimuli or is presented with new stimuli.

In some implementations, the device may be configured via a mobile application (app), web-based application or other web-based interface (e.g., website). During the personalization process, the user can be presented with a graphical user interface or other user interface via the wearable device or via a smartphone or other device communicatively coupled to the wearable device. For example, the wearable device or other device can include a processor that executes instructions that cause the device to present (e.g., display) selectable controls or choices to the user that are used to refine a set of thresholds, alerts, filters, and/or guidance in discrete or combined formats. In some implementations, the personalization process can be conducted by the wearer of the device, a healthcare provider, or a caretaker of the user. For example, the personalization process can be conducted by running an application instance on the wearable device or other device and receiving data corresponding to input from the wearer, health provider, or caretaker making selections (e.g., telemetry/biotelemetry). In some cases, different user interfaces and options can be presented depending on whether personalization is conducted by the wearer, healthcare provider, or caretaker.

In some implementations of the personalization process, a datastore associated with the wearable device may pre-store initialization templates that correspond to a particular set of thresholds (e.g., sound, visual, and/or physiological/psychophysiological) and/or alerts, filters, and/or guidance. For example, templates corresponding to predominantly sonically sensitive wearers, predominantly visually sensitive wearers, predominantly interoceptive sensitive wears, combination wearers, and the like can be preconfigured and stored by the system. During device initialization, the wearer can select one of the templates (e.g., the user is predominantly visually sensitive), and the configured parameters (e.g., thresholds, alerts, filters, and/or guidance) for the selected template can be further customized in response to additional user input. The additional user input can include responses to questions, or a selection of preferences as further discussed below.

In some implementations, each of the templates can be associated with a trained model that given a set of inputs (e.g., sensor readings from the wearable device, user thresholds, etc.) generates one or more outputs (e.g., alerts, filters, guidance, sonic feedback, visual feedback, haptic feedback) experienced by the user. The model can be trained and tested with anonymized historical data associated with users to predict appropriate outputs given sensory inputs and thresholds. Supervised learning, semi-supervised learning, or unsupervised learning can be utilized to build the model. During a personalization process, further discussed below, parameters of the model (e.g., weights of input variables) can be adjusted depending on the user's sensitivities and/or selections.

In some implementations of the personalization process, the user can be presented with selectable preferences and/or answers to questions. For example, the personalization process may present the user with selectable choices relating to demographics (e.g., gender, age, education level, handedness, etc.) and sensitivities (e.g., audio preferences, visual preferences, physiological/psychophysiological preferences, alert preferences, guidance preferences, intervention ranking preferences, and the like). Depending on the user's selections, a particular set of thresholds (e.g., sound, visual, and/or physiological/psychophysiological), alerts, filters, and/or guidance may be customized for the user and stored. For instance, based on the user's selection of audio preferences, the system can be configured to perform digital signal processing of audio signals before audio is played to the user to adjust the energy of different frequency ranges (e.g., bass, mid-range, treble, etc.) within the audible frequency band (e.g., 20 Hz to 20,000 Hz), the audio channels that emit sound, or other characteristics of audio. During configuration, the user can specify a preference for filtering (e.g., enhancing, removing, or otherwise altering) low-range sounds, mid-range sounds, high-range sounds, soft sounds, loud sounds, reverberant sounds, surround sounds, etc. As another example, a user can specify a preference for receiving alerts of sounds having particular sonic characteristics (e.g., alert for loud, echoing, and/or surround sounds before they occur). As a further example, a user can prefer that guided sounds have particular characteristics (e.g., soft-spoken words, gentle sounds) when the user becomes anxious, unfocused, or sensitive.

In some implementations, the user's selected preferences and/or answers during personalization can be used to build a model that given a set of inputs (e.g., sensor readings from the wearable device, user thresholds, etc.) generates one or more outputs (e.g., alerts, filters, guidance, sonic feedback, visual feedback, haptic feedback) experienced by the user. For example, a website or mobile app configurator accessed via a user login can generate one or more tolerance scores based on the user's answers to questions pertaining to visual, auditory, or physiological/psychophysiological stimuli. The one or more tolerance scores can be used to initialize the model. The model can also be initialized, modified and/or monitored by a specialist, healthcare provider, or caretaker.

During personalization, a user can rank the types of interventions. For example, a user can rank and/or specify a preferred type of alert (e.g., beep, haptic, voice, or some combination thereof), a preferred audio filter (e.g., volume (compression, limiting), equalization (tone, EQ), noise reduction, imaging (panning, phase), reverberation (echo), imaging (panning, phase), or some combination thereof), a preferred type of guidance (e.g., encouragement), and the like.

In some implementations, one or more sensors of the wearable device can be calibrated during initialization of the device. A user can be presented with an interface for calibrating sensors and/or adjusting sensor parameters. For example, the user can specify whether all or only some sensors are active and/or gather data, adjust sensor sensitivity, or adjust a sensor threshold (e.g., brightness for an optical sensor, loudness for an audio sensor) and what order of implementation they are desired (e.g., alerts first, followed by guidance, followed by filters, etc.).

In some implementations, after an initial set of user-specific thresholds and alerts, filters, and guidance are set up for a user, validation of the configuration can be conducted by presenting the user with external stimuli, and providing alerts, filters, and/or guidance in accordance with the user-configured thresholds. Depending on the user's response, additional configuration can be conducted. This validation process can also adjust sensor settings such as sensor sensitivity.

In implementations where a trained model is used to provide alerts, filters, and/or guidance, the model can be retrained over time based on collected environmental and/or physiological/psychophysiological data. To save on computational resources and/or device battery life, retraining can be performed at night and/or when the system is not in use.

Figure 20:
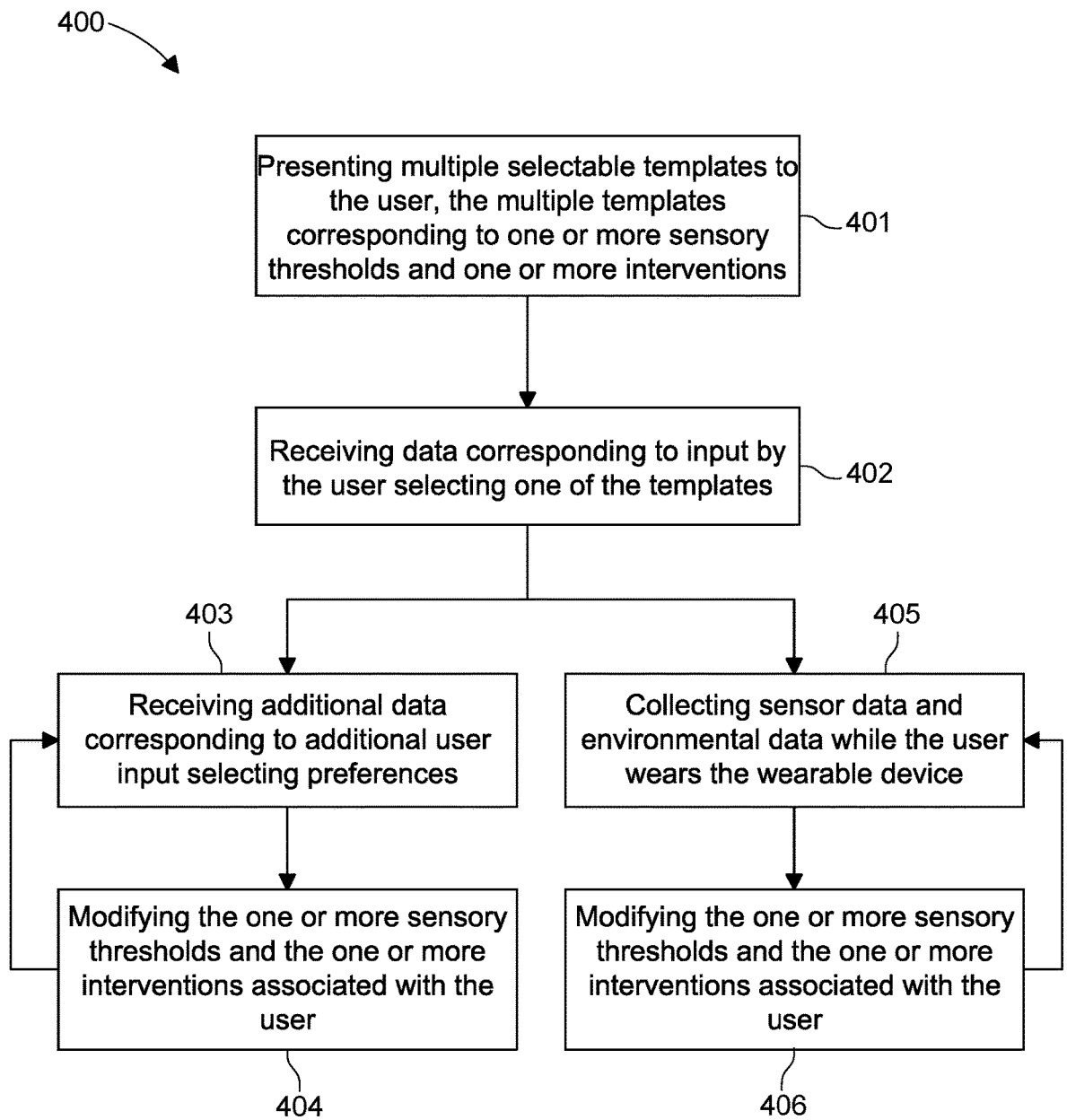
FIG. 20 shows an operational flow diagram depicting an example method for initializing and iteratively updating one or more sensory thresholds and one or more interventions associated with a specific user, in accordance with some implementations of the disclosure.

FIG. 20 shows an operational flow diagram depicting an example method 400 for initializing and iteratively updating one or more sensory thresholds and one or more interventions associated with a specific user. In some implementations, method 400 can be implemented by one or more processors (e.g., one or more processors of wearable device 10 and/or mobile device 20) of a wearable device system executing instructions stored in one or more computer readable media (e.g., one or more computer readable media of wearable device 10 and/or mobile device 20). Operation 401 includes presenting multiple selectable templates to the user, the multiple templates corresponding to one or more sensory thresholds and one or more interventions. The multiple selectable templates can be presented via a GUI (e.g., using wearable device 10 and/or mobile device 20). Operation 402 includes receiving data corresponding to input by the user selecting one of the templates. After user selection of one of the templates, the one or more sensory thresholds and one or more interventions associated with the template can be associated with the user. For example, the one or more sensory thresholds and one or more interventions can be stored in a datastore 30 including an identification and/or user profile corresponding to the user. As described above, operations 401-402 can be performed during and/or after an initialization process.

Operation 403 includes receiving data corresponding to user input selecting preferences. The preferences can comprise audio preferences, visual preferences, physiological/psychophysiological preferences, alert preferences, guidance preferences, and/or intervention preferences. Operation 404 includes in response to receiving additional data corresponding to additional user input selecting preferences, modifying the one or more sensory thresholds and the one or more interventions associated with the user. For example, the datastore thresholds and interventions can be updated. As depicted, operations 403-404 can iterate over time as the user desires to further define the thresholds/interventions and/or as the user develops new preferences.

Operation 405 includes collecting sensor data and environmental data while the user wears the wearable device. Operation 406 includes in response to collecting the sensor data and/or environmental data while the user wears the wearable device, modifying the one or more sensory thresholds and the one or more interventions associated with the user. As depicted, operations 405-406 can iterate over time as the user utilizes the wearable device system to provide sensory relief. The frequency with which the one or more sensory thresholds and the one or more interventions are updated in response to newly-collected data can be configurable, system-defined, and/or user-defined. For example, updates can depend on the amount of data that is collected and/or the amount of time that has passed. In some implementations, operations 405-406 can be skipped. For example, the user can disable updating the thresholds and/or interventions based on actual use of the wearable device.

In some implementations, the wearable device can be configured to communicate with and/or control IoT devices that present stimuli. For example, based on configured thresholds for a user, the wearable device can control the operation of smart devices such as networked hubs, networked lighting devices, networked outlets, alarm systems, networked thermostats, networked sound systems, networked display systems, networked appliances, and other networked devices associated with the user. For instance, the audio output (e.g., loudness and balance) of a networked sound system and/or display output (e.g., brightness, contrast, and color balance) of networked display system can be altered to meet individual sound or visual thresholds. To synchronize communication and operation between the wearable devices and IoT devices, the devices can be linked to an account of the user, which can be configured via an application running on a smartphone (e.g., native home control application) or other device (e.g., mobile device 20). In some instances, behavior or one or more scenes for an IoT device can be preconfigured based on the thresholds associated with the user. The behavior or scenes can be activated when the wearable device detects that it is in the presence (e.g., same room) of the IoT device.

Figure 21:
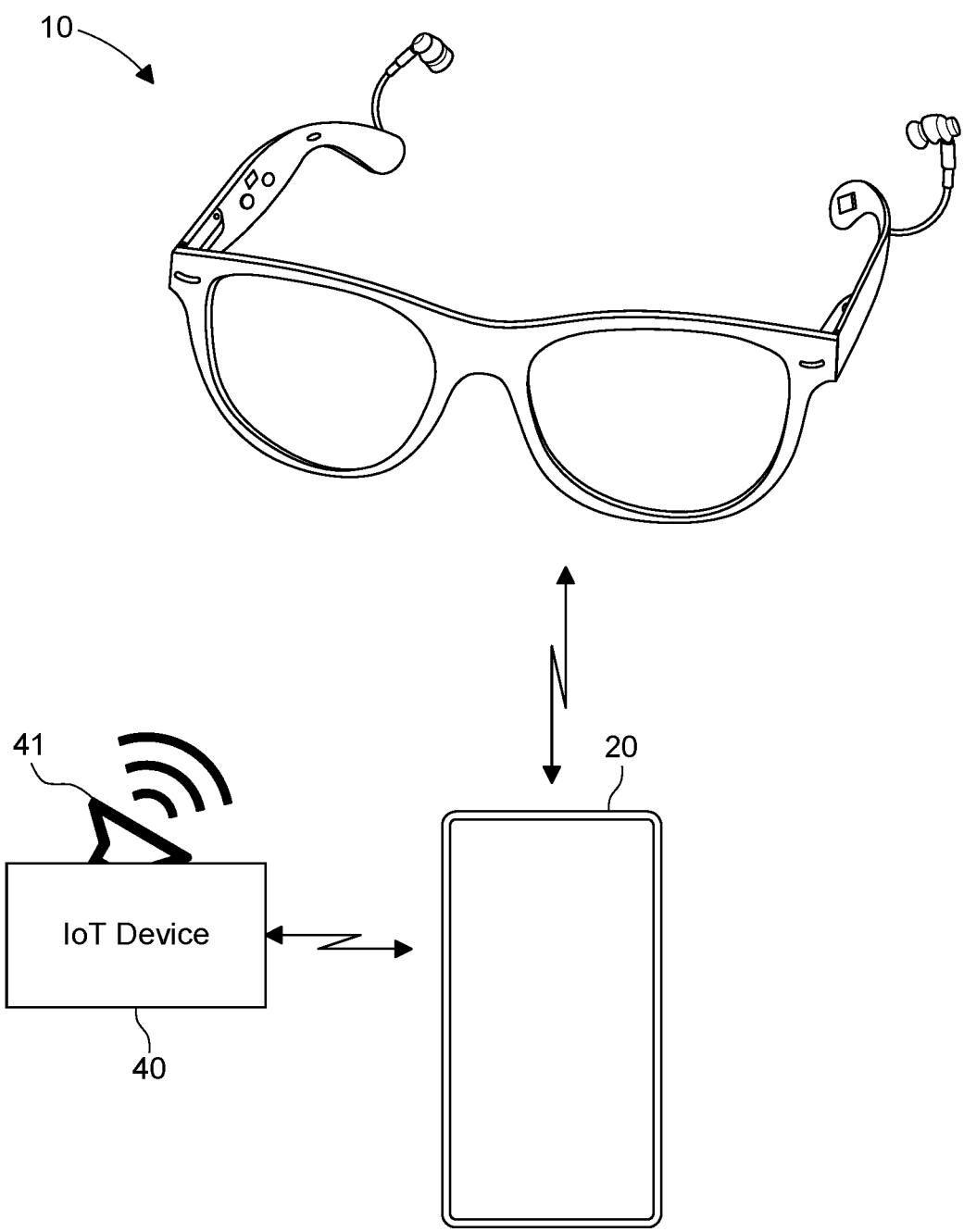
FIG. 21 depicts a wearable device system including a wearable device in communication with a mobile device that controls an IoT device with a speaker, in accordance with some implementations of the disclosure.
Figure 22:
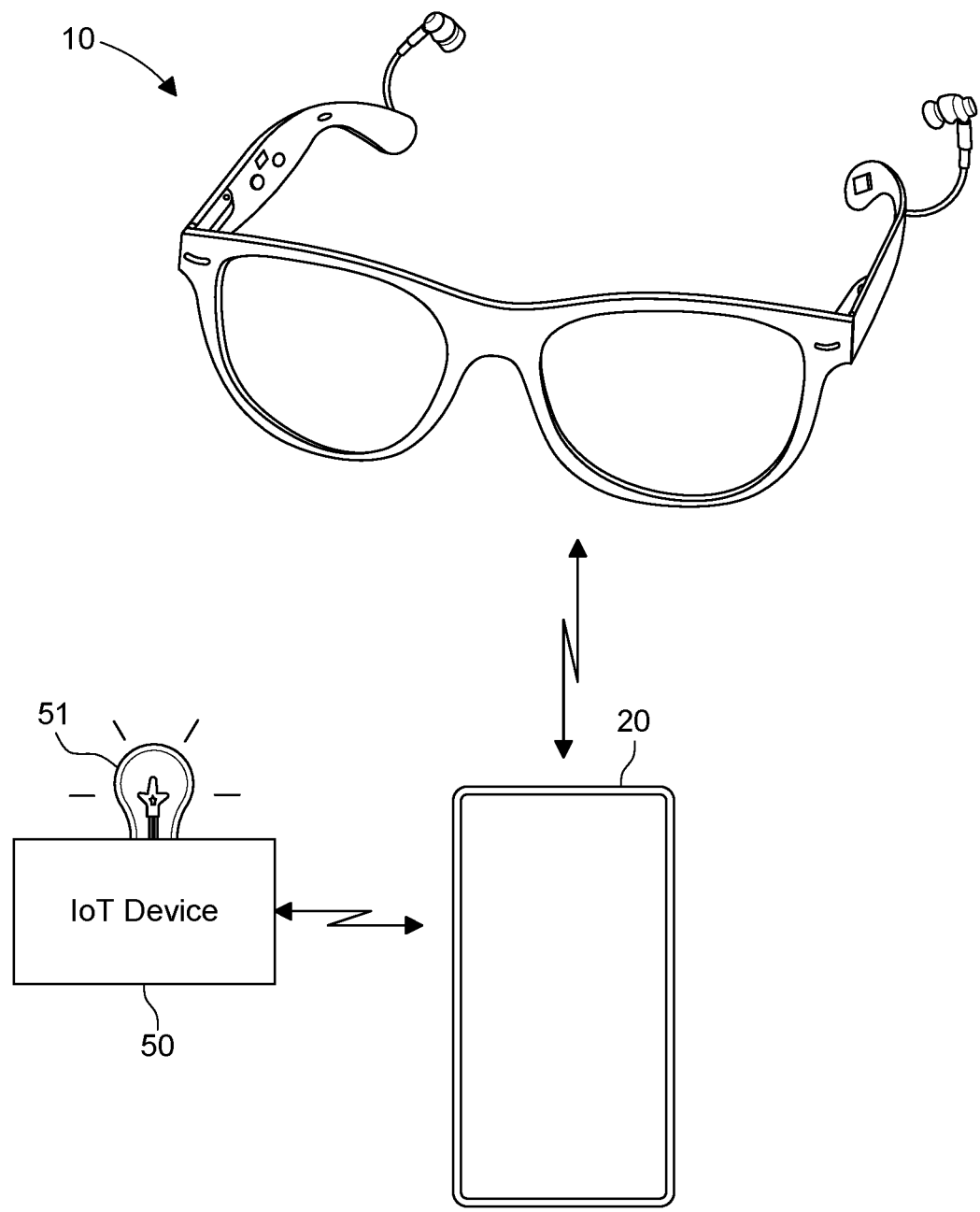
FIG. 22 depicts a wearable device system including a wearable device in communication with a mobile device that controls an IoT device with a light emitting device, in accordance with some implementations of the disclosure.

By way of illustration, FIG. 21 depicts a wearable device system including a wearable device 10 in communication with a mobile device 20 that controls an IoT device 40 with a speaker 41. As another example, FIG. 22 depicts a wearable device system including a wearable device 10 in communication with a mobile device 20 that controls an IoT device 50 with a light emitting device 51. During operation, wearable device 10 can use one or more sensors to collect a sensory input stimulus. This sensory input stimulus can be transmitted to a mobile device 20 that compares the sensory input stimulus with one or more sensory thresholds specific to the user (e.g., thresholds 31) to determine an intervention to be provided to the user, to provide the user relief from distractibility, inattention, anxiety, fatigue, and/or sensory issues.

In the example of FIG. 21, the sensory input stimulus can be generated at least in part due to sound emitted by the speaker 41 of the IoT device 40. For example, the user can generate a physiological/psychophysiological response to music and/or other sounds being played at a certain frequency and/or range of frequencies by speaker 41. In that scenario, the intervention can include the mobile device 20 controlling IoT device 40 to filter, in the frequency domain, an audio signal such that sound output by speaker 41 plays in a frequency that does not induce the same physiological/psychophysiological response in the user.

In the example of FIG. 22, the sensory input stimulus can be generated at least in part due to light emitted by the light emitting device 51 of the IoT device 50. For example, the user can experience discomfort when the output light is too bright or too cool (e.g., >4000K) in color temperature. This discomfort can be measured using the sensory input stimulus collected by the one or more sensors of the wearable device 10. In that scenario, the intervention can include the mobile device 20 controlling IoT device 50 to filter an optical signal of light device 51 to lower a brightness and/or color temperature of light output by the lighting device 51.

Although the foregoing examples depict the mobile device 20 as communicating with and controlling IoT devices 40, 50, it should be appreciated that these functions can instead be performed by the wearable device 10.

The wearable device can include various user interface components, including but not limited to mobile phones, laptops, tablets, desktop computers, and the like, and any user interface known in the field can be used. In some implementations, the wearable device can be synchronized with a smartphone. For example, the wearable device can be configured to accept calls, adjust call volume, present notification sounds or vibrations, present ringtones, etc. The wearable device can be granted access to user contacts, text messages or other instant messages, etc. In some instances, the intensity of sounds or vibrations, or the pattern of sounds or vibrations, presented via mobile integration can depend on configured thresholds of the user. The initial configuration and personalization of the wearable device can be conducted via an application installed on a smartphone or other device.

The wearable device can include one or more network interfaces (e.g., WiFi, Bluetooth, cellular, etc.) for communicating with other networked devices and/or connecting to the Internet. For example, a WiFi interface can enable the wearable device to select and communicatively couple to a local network, which can permit communication with IoT devices. Bluetooth can enable pairing between the wearable device and a smartphone or other device.

The wearable device can include or communicatively couple to one or more datastores (e.g., memories or other storage device) that are accessed during its operation. Storage can be local, over a network, and/or over the cloud.

Storage can maintain a record of user preferences, user performance, trained models, and other data or instructions required to operate the device.

In an exemplary embodiment, a wearable device is operated as described herein. The wearable device can remain in passive mode, i.e., non-operating mode, before it is worn by a user. This can optimize battery life.

Once in active mode, i.e., when the wearable device is in an operating mode, the wearable device detects and responds to one or more sensory cues selected from a myriad of sensory cues received and detected by one or more sensors located on the wearable device. Such sensory cues can include environmental and physiological/psychophysiological signals, and the like. The wearable device also provides additional and appropriate resolution in response to the sensory cues via alerts, filters, and guidance to the user whenever personalized thresholds for the use are exceeded. Thresholds and interventions can be iteratively set, adjusted, muted, and otherwise cancelled at any time and throughout the use of the wearable device by the user by returning to the computer/application.

Various types of sensory cues can be received and detected by the wearable device, including visual, auditory, and physiological/psychophysiological cues, but are not limited thereto. In an exemplary embodiment, visual distractions can be detected via eye tracking and pupillometry monitored by in infrared sensor that can be surface mounted on an inner side of the wearable device, for example, at an intersection of frame rim/right hinge temple and aimed at an eye of the user, for e.g., the right eye or the left eye or both. In an exemplary embodiment, auditory distractions and audiometric thresholds can be monitored by subminiature and wired electret microphones that can be surface mounted on an outer side of the end pieces, near the intersection of the frame front and temples. In an exemplary embodiment, physiological/psychophysiological distractions, interoceptive thresholds and user head sway can be monitored by a galvanic skin sensor that is surface-mounted on an inner side of the left earpiece and in direct contact with the skin just above the user's neckline and/or an inertial movement unit that is internally mounted on an inner side of the wearable device, and can be located behind an ear piece. The various detection components described herein are merely exemplary, and any suitable components can be used.

Various types of resolutions (interventions or digital mediations) can be provided to the user in response to the sensory cues received by the wearable device. The resolutions may include visual, auditory and physiological/psychophysiological resolutions, but are not limited thereto. In an exemplary embodiment, the visual resolutions can be delivered through a haptic driver that can be internally mounted on an inner side of an ear piece and behind an inertial movement unit intersection of frame rim/right hinge temple. Visual resolutions can be provided via unique vibrations associated with optical distractions when a pupillary or inertial/head sway threshold is detected. In another exemplary embodiment, the visual alerts can be delivered by a stereophonic bone conduction that can be surface mounted on an inner side of wearable device, for example, at both temples midway between the hinges and temple tips and coming into direct contact with the user's left and right skull in front of each ear and provides either a beep tone and/or pre-recorded spoken guidance in the event a pupillary or inertial/head sway threshold is detected. In another exemplary embodiment, auditory resolutions can be delivered to the user through a single, haptic driver by providing uniquely coded vibrational alerts in the event a sonic threshold is detected and/or through a bone conduction transducer that provides both beep tone, pre-recorded spoken guidance and/or real-time filtering using digital signal processing (DSP) for those distracting, environmental audiometric events (e.g., compression, equalization, noise reduction, spatial panning, limiting, phase adjustment, and gating) when a sonic threshold(s) is/are detected and can be processed according to user's personalization settings. For example, in an exemplary embodiment, real-time digital audio streams recorded by microphones connected to the wearable device provide the microprocessor with audio data that undergo system manipulation to achieve a predetermined goal. As described, the DSP produces feedback in the form of altered audio signals (the filtered intervention) that ameliorates volume (amplitude, compression, noise reduction), tonal (equalization), directional (spatial, etc.). As another example, guidance may include one or more tonal alerts retrieved from a datastore.

In an exemplary embodiment, the device can be configured to boost certain audible frequencies depending on the user's age or hearing. For example, the device can boost low, mid, and/or high frequencies depending on the user's age and/or hearing profile. In some cases, the device can execute instructions to provide a hearing test to generate the hearing profile. A control can be provided to enable or disable sound boosting.

In an exemplary embodiment, physiological/psychophysiological resolutions can be delivered to the user through a haptic driver mentioned above and by providing uniquely coded vibrational alerts in the event a physiological/psychophysiological, anxiety, fatigue or other interoceptive thresholds are detected and/or through a bone conduction transducer, which provides both beep tone, and/or pre-recorded spoken guidance for similar threshold alert and guidance. The various resolution components described herein are merely exemplary, and any suitable components can be used.

In an exemplary embodiment, the wearable device may also include an internally mounted central processing unit, that may further include subminiature printed circuit boards combined with a self-contained connected and rechargeable power source, wireless transceiver and analog/digital multiplexers reside within both earpieces and provide evenly weighted distribution to wearer.

As described herein, the comparing means compares the sensory input stimulus recorded by the one or more sensors with the database of one or more user-specific sensory thresholds to obtain a sensory resolution for a user. The comparing means performs the aforementioned functions as follows.

The user-specific thresholds can be obtained by having the user complete a decision-tree styled survey (similar in scope to the survey described in the Sustained Attention to Response Test (SART) protocol described herein), and then a microprocessor measures the user-specific thresholds against ecological and physiological/psychophysiological data streams to deliver appropriate intervention assistance. In an exemplary embodiment, the user-specific thresholds can dynamically change using a machine learning capability.

An exemplary embodiment of how input stimulus is compared to stored data to generate user-specific interventions is illustrated via a block diagram in FIG. 16, but this application is not limited thereto. In the exemplary embodiment illustrated in FIG. 16, six components make up the wearable device's input section and include: an optical module 301; an inertial measurement unit (IMU) 304; an audio sensor 305; a galvanic module 306; a temperature sensor 309; and a biopotential analogue front end (AFE) 310. In combination, these components deliver both ecological (environmental) and physiological/psychophysiological data to a sensor hub 311 (multiplexer), and the data is processed (typically through wireless, bi-directional communication, though it can be directly connected) with the system's microprocessor (e.g., ARM Cortex) for rapid analysis and comparison to existing thresholds, characteristics, and user-preferences. The microprocessor 312 (e.g., ARM microprocessor) then delivers the appropriate commands for interventional activities to be processed by those related system components as described herein. The six components are further described as follows.

The optical module 301 includes: (i) an inward facing pair of infrared sensors 302 that monitor pupillary response, portending to a user's focus and attentional lability; and (ii) a single outward facing sensor to determine ecological/environmental cues of a visual nature. A tuned optical AFE 303 provides the appropriate pupillary data stream for processing and simultaneously provides an environmental data stream for image recognition allowing the microprocessor 312 to determine visual environmental cues for which the user is responding. In both cases, image recognition (whether pupillary response, saccades, computer screen, books, automobile roadways, office/academic surroundings, etc.) rely on a computer vision technique that allows the microprocessor 312 to interpret and categorize what is seen in the visual data stream. This type of image classification (or labelling) is a core task and foundational component in comparing real-time visual input to a library/catalogue of pre-labelled images that are interpreted and then serve as the basis for an intervention, provided that the user's thresholds are exceeded (or unsurpassed).

The IMU 304 measures and reports a body's specific force (in this case, the user's head/face). It also provides angular rate and orientation using a combination of accelerometers, gyroscopes, and magnetometers to deliver a data stream relating to the user's head sway and attentional focus, when compared and contrasted to the optical AFE 303 and processed similarly against pre-labelled and classified data. In some implementations, the IMU can include a 3-axis gyroscope/accelerometer.

Similar in scope to the optical module 301, the audio sensor(s) 305 provide environmental data streams of a sonic nature which can be compared to known aural signatures that have been labelled and available for computer micro processing. The aural signatures that reach frequency, amplitude, spatial, time-delay/phase and similar user-selected thresholds could then be delivered for interventional processing.

Both the galvanic module 306 and temperature sensor 309 provide physiological/psychophysiological and ambient/physiological data streams that measures the wearer's electrodermal activity (EDA), galvanic skin response (GSR), body and ambient temperature. These are utilized in combination with the biopotential AFE 310 resulting in real-time and continuous monitoring of the wearer's electrical skin properties, heart rate, respiratory rate, and blood pressure detection. Like the previous sensors, all are timestamped/synchronized for microprocessor processing, analysis, labelling/comparison and interventional activation.

The biopotential AFE 310 provides electrocardiogram (ECG) waveforms, heart rate and respiration, which in turn, feeds forward to the microprocessor 312 to assist with a user's physiological/psychophysiological state, processing, and attentional focus/anxiety/fatigue intervention(s).

Figure 17:
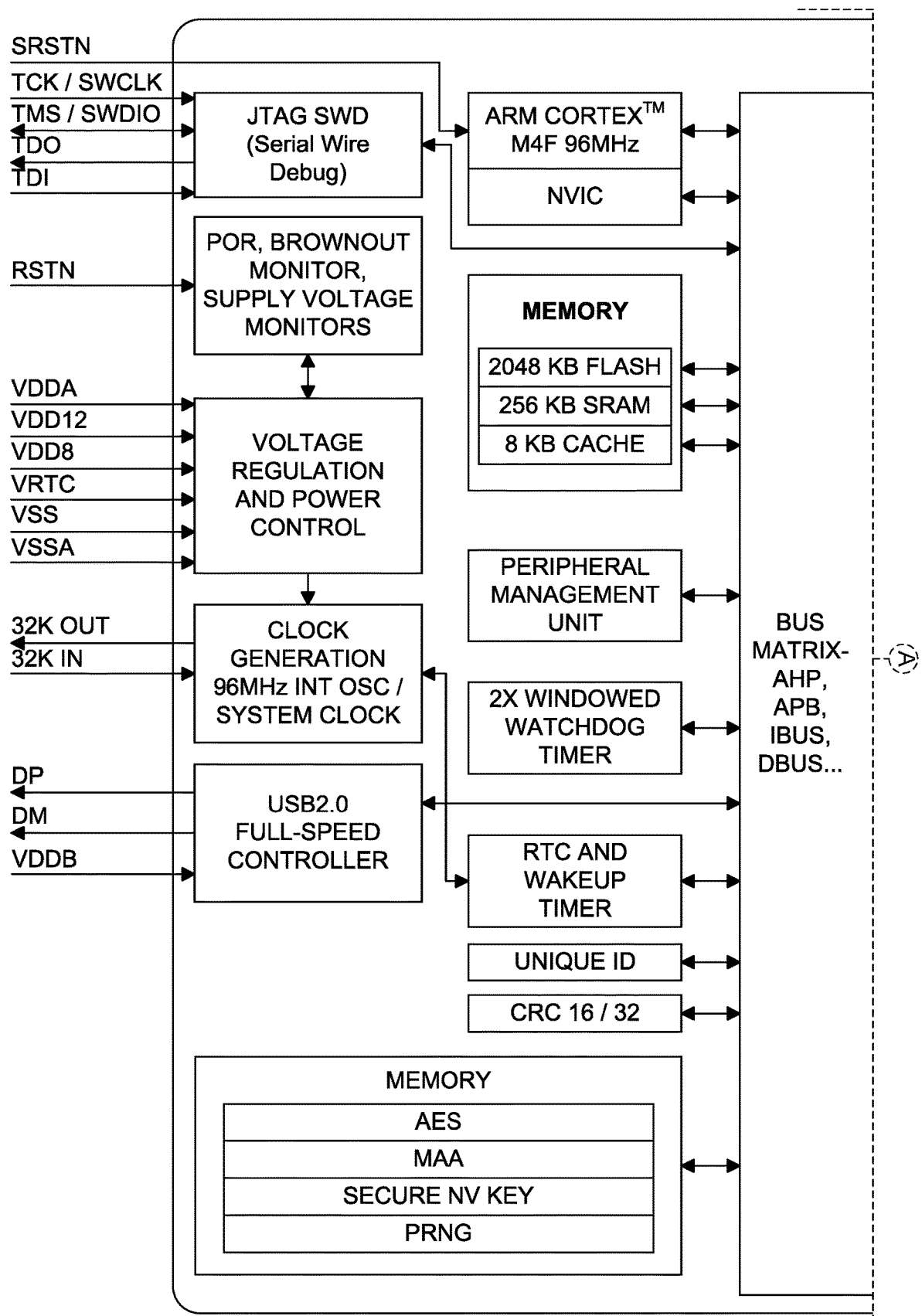
FIG. 17 is a block diagram of additional microprocessor details (ARM processor) of a wearable device, in accordance with some implementations of the disclosure.
Figure 17:
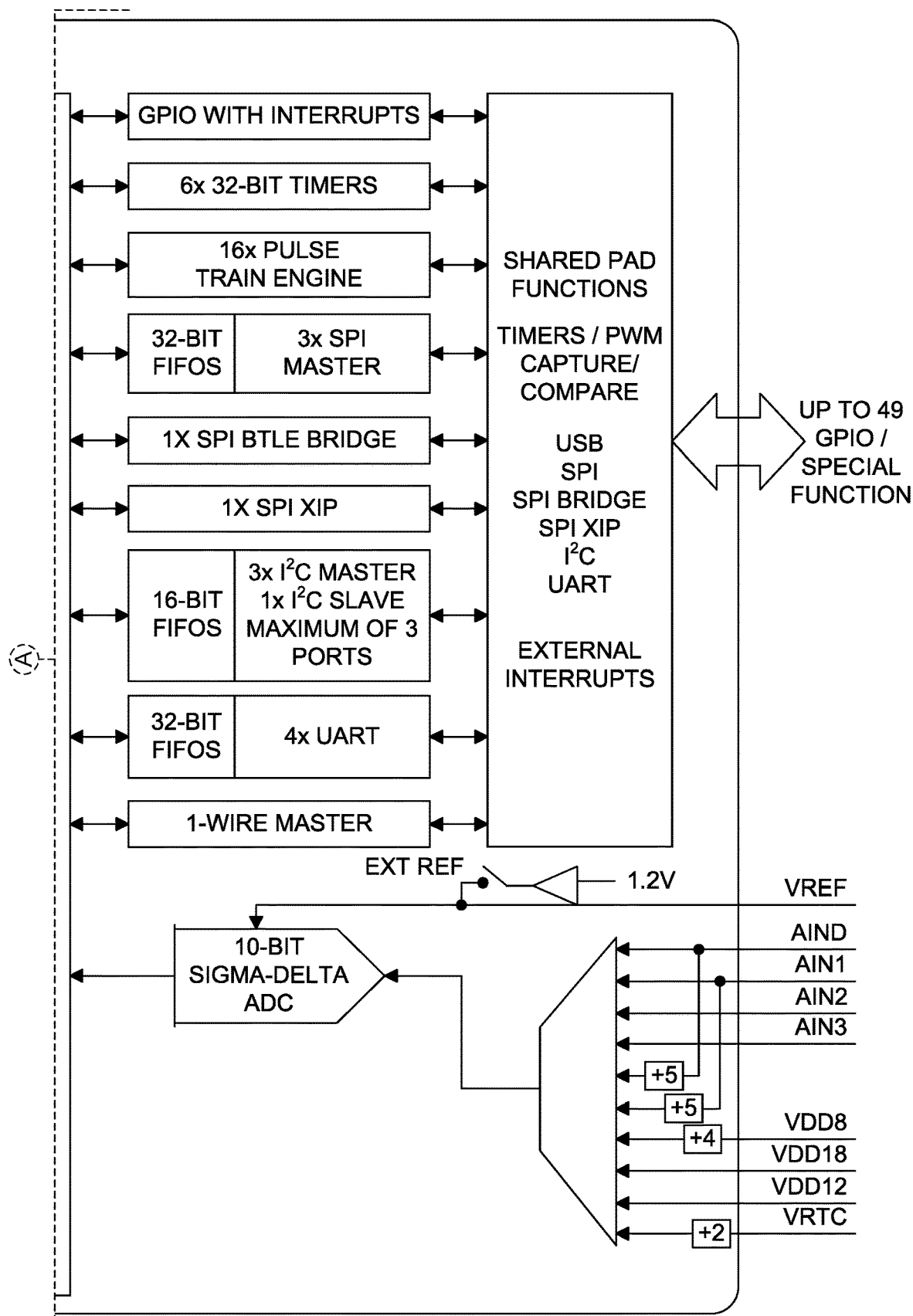

An additional block diagram providing additional microprocessor details (ARM processor) is illustrated in FIG. 17.

A catalogue of user-specific cues and resolutions can be stored in a database in communication with the software stored in and executed from the wearable device and the control program/app, and available for machine learning purposes providing the application and hardware with ever-increasing understanding of user environments and physiology cues, alerts, filters, and guidance. An artificial intelligence (AI) algorithm continuously processes user personalization, input cues and uniquely crafted resolutions to further narrow and accurately predict and respond to physiological/psychophysiological input and responses. This machine learning and AI algorithms increase user training and promote greater autonomy, comfort, alertness, focus and mental health. The catalogue is available for user and professional analyses, data streams and progress reports are available for clinical study, medical practitioner/telemedicine, evaluation, and further review.

In some implementations, the wearable device preferences can be modified by the user to optimize device battery life. For example, the device can be configured to operate in a power saving mode that conserves battery life by making the sensor(s) less sensitive, limits power for less used operations, or otherwise operates in a manner to maximize battery life. Alternatively, the user can have the option of selecting an enhanced processing mode that emphasizes processing (e.g., makes the sensor(s) more sensitive) but uses more battery per unit of time.

In some implementations, the wearable device can be associated with an application that provides diagnostic data relating to the user, system, or for a caretaker/healthcare professional. For example, user diagnostic data can include user preferences, user responsivity, and generated issues and warnings. System diagnostic data can include environment and device responsivity, and issues and warnings. Caretaker/healthcare professional diagnostic data can include user efficacy performance (e.g., sonic, visual, or interoceptive), and any areas of concern such as wearer guidance or device guidance.

As alluded to above, real-time filtering of audio signals can be implemented in response to collecting sensory data from one or more sensors of the wearable device. As contrasted with adjusting time or overall amplitude of the signal experienced by the listener, this filtering can take place in the frequency domain and affect at least a center frequency (Hz), a cut or boost (dB), and/or a width (Q). For example, all low frequency hum associated with a real-time detection of machinery and/or light ballasts in an environment can be eliminated and/or otherwise reduced, minimized and/or mitigated. This can be implemented by adjusting, in real-time, the offending and nearby frequencies, either with a band-pass, or low cut, high pass filter, with specific adjustments fine-tuned to the user's personalized profile. In some implementations audio filtering can also apply to additional domains, including time, amplitude, and spatial positioning (e.g., to filter distracting sounds that modulate from a given direction).

While some implementations have been primarily described in the context of modifying and/or filtering distracting sounds (i.e., audio interventions), the technology described herein can implement a similar set of interventions related to visual stimuli, either separately or in combination with other types of stimuli. For example, interventions such as alerts, guidance, and/or combinations without filtering mediations can be implemented. As further described below, visual interventions can be based upon pupillary response, accelerometers, IMU, GSR detection, and/or video of the wearer's environment. In some implementations, identified visual interventions can work in concert with audio modifications.

Figure 23:
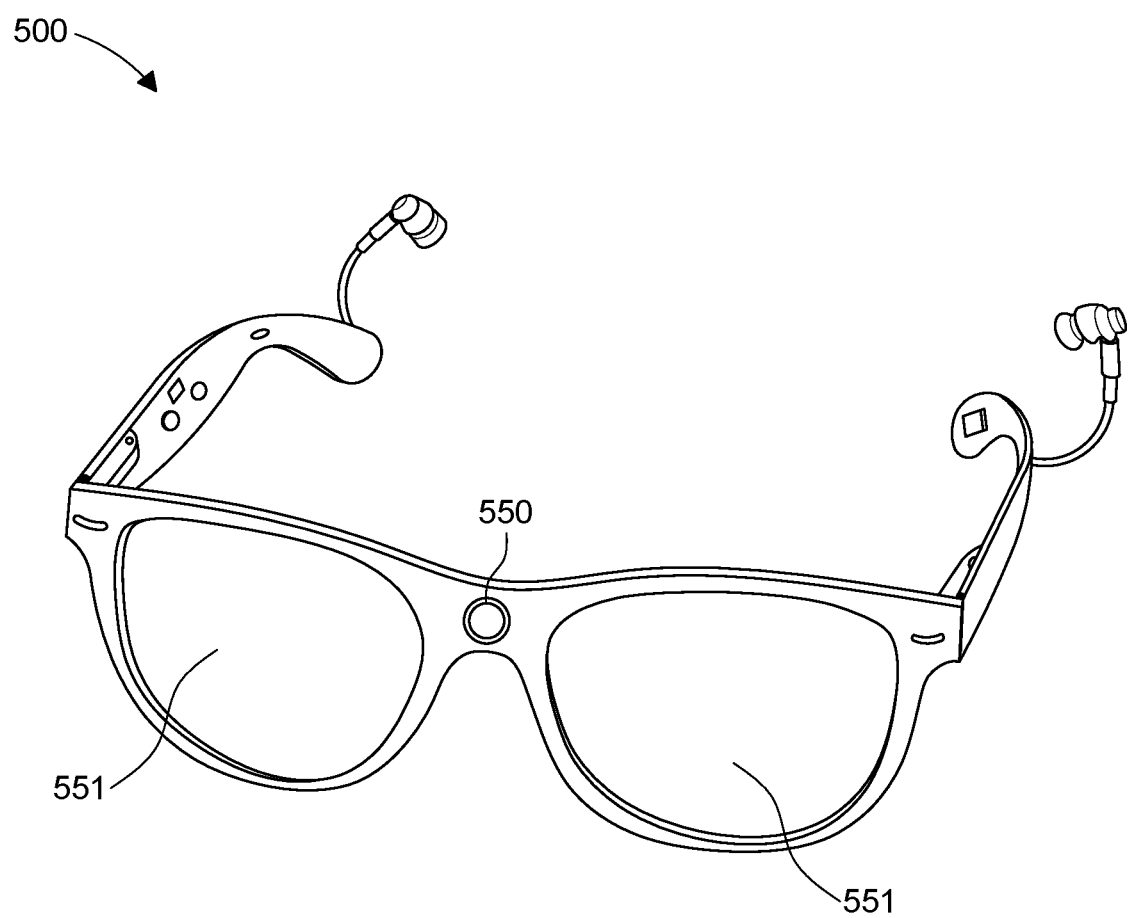
FIG. 23 depicts an example wearable device that can be utilized to provide visual interventions, in accordance with some implementations of the disclosure.

FIG. 23 depicts an example wearable device 500 that can be utilized to provide visual interventions, in accordance with some implementations of the disclosure. As depicted, wearable device 500 can include the sensors and/or transducers of wearable device 10. To support certain visual interventions, wearable device 500 also includes a camera 550 and display 551. As such, wearable device 500 is implemented as a wearable HMD. Although a glasses form factor is shown, the HMD can be implemented in a variety of other form factors such as, for example, a headset, goggles, a visor, combinations thereof and the like. Although depicted as a binocular HMD, in some implementations the wearable device can be implemented as a monocular HMD.

Display 551 can be implemented as an optical see-through display such as a transparent LED and/or OLED screen that uses a waveguide to display virtual objects overlaid over the real-world environment. Alternatively, display 551 can be implemented as a video see-through display supplementing video of the user's real world environment with overlaid virtual objects. For example, it can overlay virtual objects on video captured by camera 550 that is aligned with the field of view of the HMD.

The integrated camera 550 can capture video of the environment from the point of view of the wearer/user of wearable device 500. As such, as further discussed below, the live video/image feed of the camera can be used as one input to detect visual objects that the user is potentially visually sensitive to, and trigger a visual intervention.

In some implementations, real-time overlay interventions can be implemented whereby visual objects and/or optical interruptions are muted, squelched, minimized, mitigated and/or otherwise removed from a wearer's field of vision. In some implementations, the system's transducer components (e.g., microphones and/or outward facing optics) can be used in concert with on-board biological sensors and/or projection techniques that train/detect, analyze/match/predict, and/or modify optical cues and/or visible items that correlate to a wearer's visual sensitivity, attention, fatigue and/or anxiety thresholds. In some implementations, disrupting visual, optical, and/or related scenery can be filtered in real-time such that a wearer does not notice that which is distracting.

In particular embodiments, one or two types of real-time optical enhancement (REOPEN) algorithms can be implemented to detect, predict, and/or modify visual inputs that decrease distraction/mental health issues and increase attention, calmness, and/or focus. The algorithms can provide real-time (i) live-editing of visual scenes, imagery and/or object and advanced notification for distracting optics that match a user's visual profile; and/or, (ii) live-modification of visual distractions without advanced notification. Interventions that can be delivered in real time using a REOPEN algorithm are illustrated by FIGS. 24A-24C, further discussed below.

In one embodiment, a Realtime Optical Enhancement and Visual Apriori Intervention Algorithm (REOPEN-VAIL) can be implemented to train/detect, analyze/match/predict, and/or modify visual items that a user deems distracting (e.g., based upon a previously-described and/or created personalized preferences profile) and compares these to prior and/or current physiological/psychophysiological responses to the environment. Upon detecting a threshold crossing and/or match between interoceptive reactivity (egocentric) and visual cue (exocentric video) detection, REOPEN-VAIL can provide iterative analysis, training, enhancement, contextual modification, and/or advanced warning of optical distractions prior to the wearer's ability to sense these visual and/or related physiological/psychophysiological cues.

In one embodiment, a Visual A Posteriori Intervention Algorithm (VASILI) can be implemented to use multimodal learning methods to train/detect, analyze/match and/or modify visual items that previously a user deems distracting (e.g., based upon previously described or created preferences, prior and/or current physiological/psychophysiological responses, etc.). In the case of VASILI, as contrasted with REOPEN-VAIL, the optics provide contextual modifications without advanced warning of distractibility in the form of interventions that are delivered following the system's identification of either ecological and/or the wearer's physiological/psychophysiological cue(s), in real-time after the user has been exposed to the visual distraction, and as part of an iterative process that can serve as a basis for future training, sensing, and/or apriori algorithms.

Various interventions can potentially be delivered in real time using a REOPEN algorithm. For example, as depicted by FIG. 24A, in response to detection of a certain visual object (e.g., a distracting visual object and/or visual anomaly), haptic alerts, tone alerts, guidance alerts, combinations thereof and the like can be delivered to notify the wearer. The guidance alerts can provide user-selectable verbal instructions of anticipated visual distraction and/or coaching to intervene with continued focus, calmness, and/or attention. The aforementioned guidance alerts can be implemented as visual and/or text based guidance that is viewable to the wearer, via a displayed (e.g., using display 551) user selectable system visible to one and/or both eyes and/or sightlines to intervene with continued focus, calmness, attention, combinations thereof and the like. (e.g., FIG. 24B).

In some implementations, visual distractions (e.g., certain objects, faces, etc.) can be rendered such that they appear as opaque and/or obscure. This blurring effect can blur the identified, distracting, and/or otherwise offending image as a user-selectable and/or predefined intervention affecting what the wearer sees. (e.g., FIG. 24B).

In some implementations, a visual scene can be rendered with a modified background, eliminating the visual distraction, and/or identified image. The system can interpolate nearby images to the distracting object and/or replicate the background by overlaying a "stitched" series of images that naturally conceal and/or suppress the sensory effects of the offending optics, all of which are user-selectable. (e.g., FIG. 24A).

In some implementations, a predetermined, user-selectable emoticon and/or place-holder image can be rendered that camouflages the distracting optic and/or visual disruption. (e.g., FIG. 24B).

In some implementations, a visual distraction can be rendered with a modified color palette and/or related pigmentation can be modified to user-preference to reduce the effects of distraction, sensitivity, focus, anxiety, and/or fatigue, and/or combinations thereof and the like (e.g., FIG. 24C).

In some implementations, a visual distraction can be rendered with edited brightness and/or sharpening of images that are user-selectable as either muted and/or modified visuals (e.g., FIG. 24C).

In some implementations, a visual distraction can be rendered with an edited size such that images are augmented and/or modified such they become more prominent, larger, and/or highly visible (e.g., FIG. 24C).

The principles of the present invention includes certain exemplary features and embodiments, and effects thereof, will now be described by reference to the following non-limiting examples.

Figure 25:
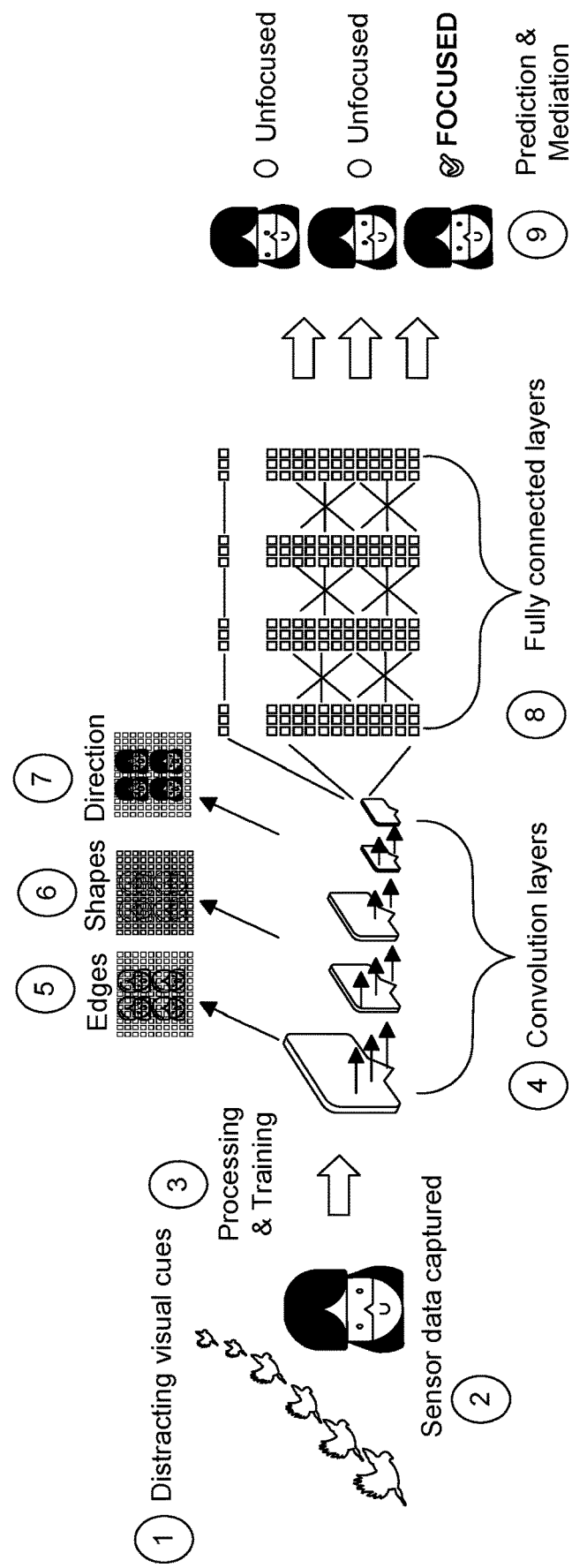
FIG. 25 depicts one particular example of a workflow that uses a real-time optical enhancement algorithm to provide interventions, in real-time, in a scenario where there is a distracting visual source, in accordance with some implementations of the disclosure.

FIG. 25 depicts one particular example of a workflow that uses a REOPEN algorithm to provide interventions, in real-time, in a scenario where there is a singular distracting visual source (e.g., birds flying across the sky and causing the individual to become unfocused from work). In this example, the algorithm is implemented using a convolutional neural network (CNN). As depicted, distracting stimuli can be visualized by the individual wearing a wearable device (e.g., wearable device 500) that captures cues and then processes and trains on that data (e.g., environmental and/or psychophysiology). Convolution layers of the CNN are formed and/or iteratively examined, for example, visual data that triggers the distraction—or physiology such as pupillary movement, including edges, shapes, and/or directional movement. Connected layers digitize the prior convolutional layers. This can be repeated for multimodal data types such that when layers correlate to pre-defined "eyes on target", a learned state of focused activity can be recorded. Conversely, when pupillary movement is uncoordinated with a target and/or activity, a separate learned event can be memorialized and/or tagged as unfocused activity, resulting in delivery of a digital mediation until a "focused" condition is observed.

For example, in the case of a REOPEN-VAIL algorithm, an apriori intervention could be one that has already been trained on the flow depicted in FIG. 25, and then sensed by the system pursuant to a similar external cue and/or an early reflection of pupillary unfocused prediction. This could generate an alert prior to the actual long-term individual state in an attempt to mediate prior to distractibility. In the event of a failure in the REOPEN-VAIL (e.g., the individual continues to remain out of focus for a period of time, e.g., greater than about 5 seconds or otherwise dictated by the personalized paradigm), the posteriori flow could repeat, this time offering mediations consisting of alerts, guidance, and potentially filtering to mute, eliminate, mitigate, minimize and/or otherwise modify the offending distraction.

PPI Study

A PPI study was conducted to identify dependent/thematic variables and dependent/demographic factors related to the utilization of the wearable device. The PPI participants included verbally able, autistic and neurotypical adolescents and adults aged 15-84. All participants had intelligence in the normal or above average range and the majority were living independent lives, i.e., study participants did not fall into the general learning disabilities range. Participants provided health/medical conditions and disability information relevant to their opinions about distractibility, focus and anxiety at both school and work. Before the study, participants provided informed consent along with a verifiable ASC diagnosis, where applicable. All participants were invited to take part in a Focus Group, User Survey Group or both.

The Focus Group included 15 participants, ages 17-43, and participants studied distractibility and attentional focus. The main task of the Focus Group was to comment on sensory issues and provide input into the design of a user survey to ensure relevance to autism and adherence to an autism-friendly format.

The User Survey Group included 187 participants, ages 18-49, and provided first-person perspectives on distractibility and focus while gathering views and opinions of which aspects of technological aid/support would be most welcomed and have the biggest impact on sensory, attentional, and quality of life issues.

Embedded within the PPI study was a Lived Experience Attention Anxiety Sensory Survey (LEA$^2$Se) developed for participant expression and used as a preparatory point to discuss focus, distractibility, anxiety, sensory and attentional difficulties, and needs. The LEA$^2$Se participants were encouraged to specify interests, attitudes, and opinions about receiving technology supports. This study was dispensed online.

Pre-Trial Battery Examination (PTBE)

196 autistic participants were recruited via opportunity sampling. After exclusion, 188 participants were left (109 males, 79 females), of which 12.2% were 18-20 years old, 21.2% were 21-29 years, 60.8% were 30-39 years and 5.8% were 40-49 years old. For the purpose of the PTBE, variables that tap into different aspects of an autistic individual's experience were designed. After identifying the variables of interest, questions which addressed these variables were allocated a numerical variable. Some questions were not allocated to any variable, and therefore were not analyzed in this study. Table 1 shows the resultant variables, the number of questions that fell under each variable, and an example of the type of questions used to investigate that variable. Each participant received a score for each of these variables, which was calculated by averaging their responses to the questions that fell under that variable. The variables are mutually exclusive (i.e., no question was included in the computation of more than one variable). To assess validity of the variables, inter-item correlations for each variable were investigated, all of which had a Cronbach's alpha greater than 0.80, which demonstrates high internal validity.

TABLE 1

| Variable | No. of Items | Cronbach's Alpha | Sample Question |
|---|---|---|---|
| Sensitivity Impact (SI) | 9 | .871 | "I have considered abandoning or interrupting my job/employment or academic studies because of sensitivity to my environment" |
| Anxiety Proneness (AP) | 25 | .947 | "Certain sounds, sights or stimuli make me feel nervous, anxious or on edge" |
| Distractibility Quotient (DQ) | 9 | .839 | "I often begin new tasks and leave them uncompleted" |
| Technology Tolerance (TT) | 11 | .885 | "I think I would enjoy owning a wearable device if it helped reduce anxiety, lessen distraction or increase focus at work, school, seminars, meeting or other locations" |
| Visual Difficulty Quotient (VDQ) | 4 | .919 | "I have difficulty in bright colourful or dimly lit rooms" |
| Sound Difficulty Quotient (SDQ) | 6 | .821 | "I find sounds that startle me or that are unexpected as . . . " (distracting-not distracting) |
| Physiological Difficulty Quotient (PDQ) | 3 | .925 | "My sensitivity sometimes causes my heart rate to speed up or slowdown" |

Figure 2:
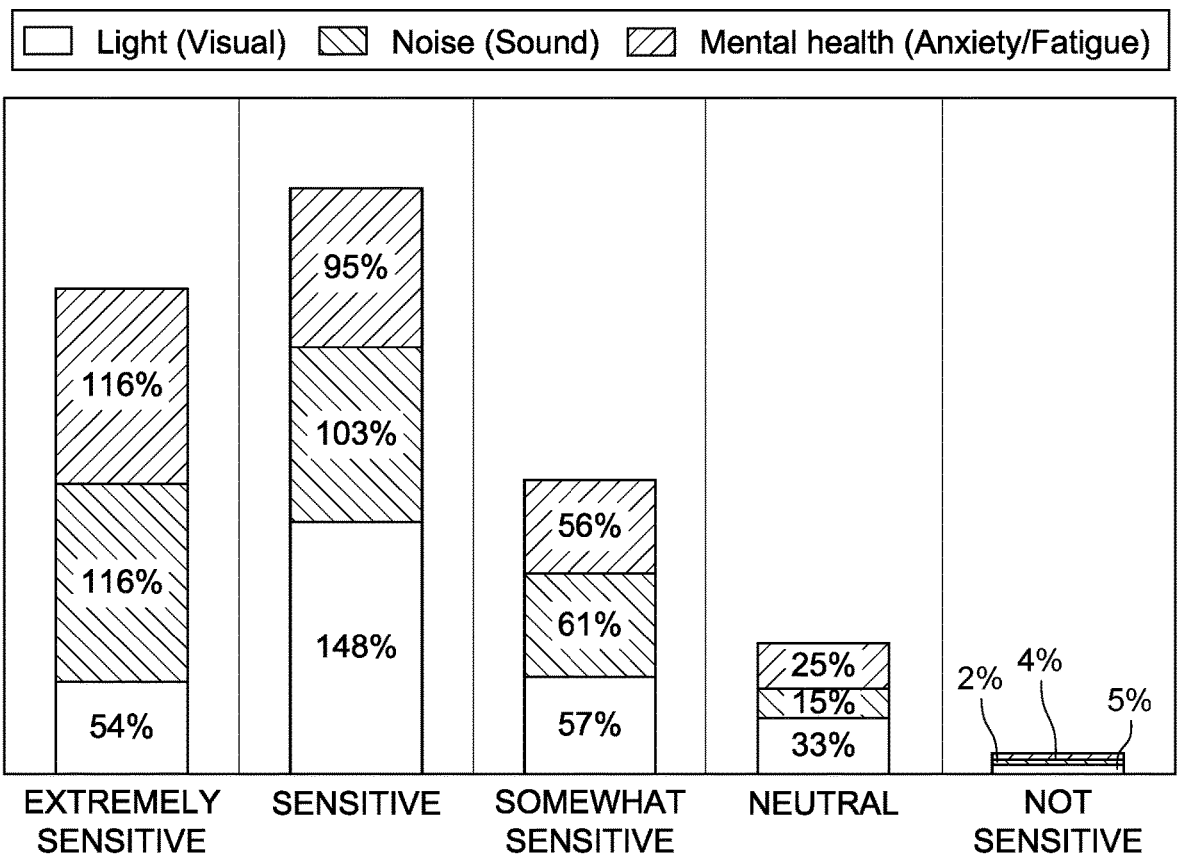
FIG. 2 is a graphical representation of sensitivities across three modalities—visual, aural and anxiety—as observed in Pre-Trial Battery Examination (PTBE), as described herein.
Figure 3:
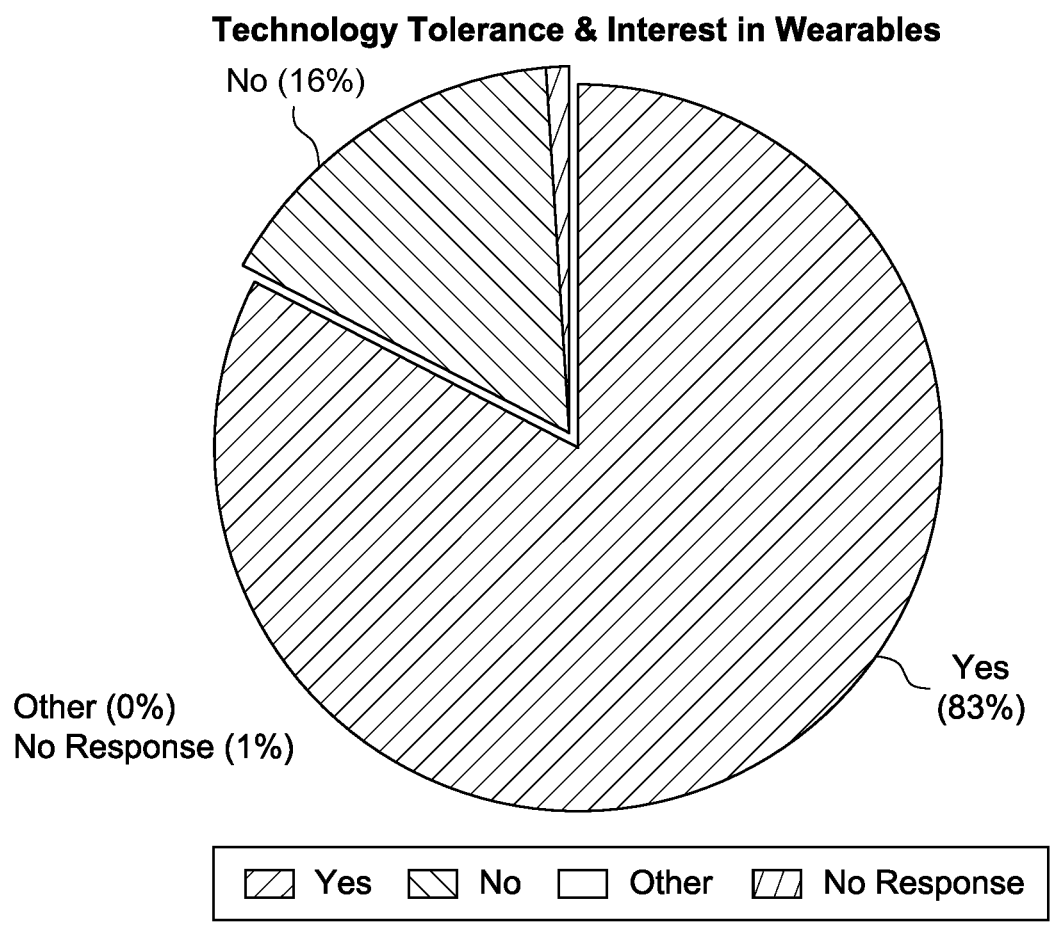
FIG. 3 is a graphical representation of interest in a wearable device among autism spectrum condition (ASC) participants in PTBE.

Various pilot outcomes using benign data are depicted in FIGS. 2 and 3. These graphics report sensitivity across three modalities (visual, aural and anxiety) along with wearable interest among ASC participants for visually distracting stimuli. Kruskal-Wallis H testing on the study population indicated:

a statistically significant difference in sensitivity impact, anxiety proneness, distractibility quotient, technology tolerance, visual difficulties and physiological/psychophysiological difficulties, but no statistically significant difference in sound difficulties, based on age;

a statistically significant difference in sensitivity impact and sound difficulties, but no statistically significant difference in anxiety proneness, distractibility quotient, technology tolerance, visual difficulties, physiological/psychophysiological difficulties, based on gender;

a statistically significant difference in sensitivity impact, anxiety proneness, distractibility quotient, technology tolerance, sound difficulties, visual difficulties and physiological/psychophysiological difficulties, based on education level; and a statistically significant difference in sensitivity impact, anxiety proneness, distractibility quotient, technology tolerance, sound difficulties, visual difficulties, but no statistically significant difference in physiological/psychophysiological difficulties, based on different employment levels.

Sustained Attention to Response Test (SART)

A SART study was conducted subsequent to the PPI study and PTBE. The study included online testing designed to test sensory issues affecting participants diagnosed or identifying with ASC. Specifically, this study examined a subset of components within a wearable prototype to answer two questions: (i) is it possible to classify and predict autistic reactivity/responsiveness to auditory (ecological) disturbances and physiological/psychophysiological distractors when autistic individuals are assisted through alerts, filters and guidance; and (ii) can the exploration of Multimodal Learning Analytics (MMLA) combined with supervised artificial intelligence/machine learning contribute toward understanding autism's heterogeneity with high accuracy thereby increasing attentional focus whilst decreasing distractibility and anxiety.

This study is grounded in Attention Schema, Zone of Proximal Development, Multimodal Discourse Analysis and Multimodal Learning Analytics theories, and makes use of both evaluator-participatory and user-participatory methodologies including iterative development and evaluation, early-user integration, phenomena of interest and persistent collaboration methodologies.

Figure 4:
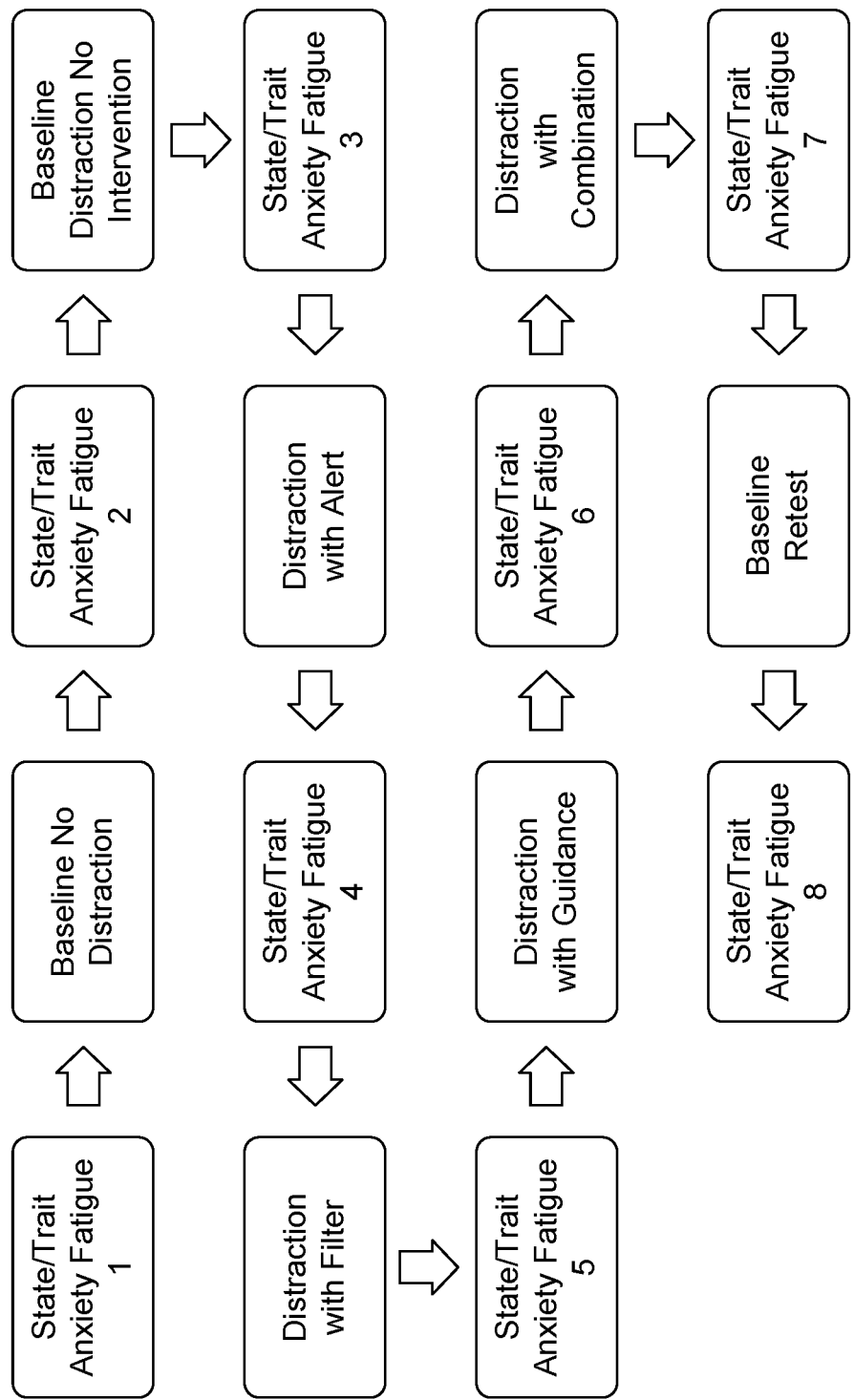
FIG. 4 is a flowchart of a standard study protocol of Sustained Attention to Response Task (SART) testing.
Figure 5:
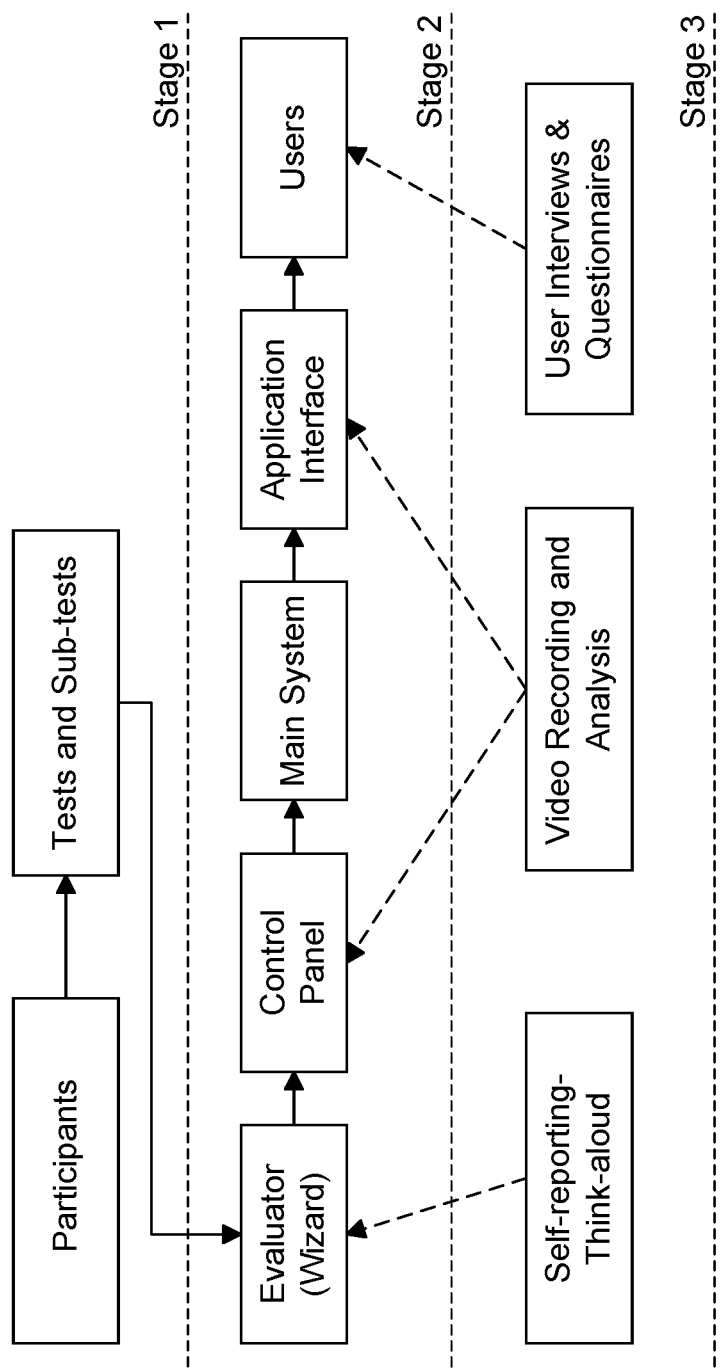
FIG. 5 is a flowchart of a standard Wizard of Oz (Wizard of Oz) study protocol.

In an exemplary study protocol, baseline testing and related scores are derived both procedurally on pre- and post-subtests to create putative, cognitive conflicts during subtests that may result in a hypothesized and measurable uptick in both distractibility and anxiety. Simultaneously, this upsurge will likely pool with diminished focus and conical attentional performance. Finally, and during the latter subtests, a "confederate" (human wizard) will present a collection of hand-crafted alerts, filters and guidance. These will emulate the operation of the wearable intervention by offsetting and counterbalancing distracting aural stimuli. To reduce fatigue effect, these interventions will either exist in counterbalanced, randomized and possibly multiple sessions. Alternatively, a combination of alerts, filters and guidance will be provisioned to lessen overall length of the experiments, as shown in Table 2 below and illustrated in FIG. 4.

The delivery of isolated and permuted support may produce broad measures of test responses. Mixed method (qualitative and quantitative evaluations) combined with participants' overt behaviors obtained through audio and video recordings may provision coding and analysis with sample accuracy synchronization to the systems software. Depending upon sample size and time constraints, this design considers post-hoc video analyses (e.g., participant walk-through) in either a structured or liberal form. These examinations may help facilitate recall, precision and provide further understanding of anxiety and other episodic testing moments.

TABLE 2

| Test | Description |
| --- | --- |
| Baseline SART | Standard sustained attention test without sonic disturbances. |
| Subtests including interventions | Subtest I.: Standard sustained attention test (SART) with sonic disturbance. Subtest II.: SART with combined filters and sonic disturbances. Subtest III.: SART with combined alerts and sonic disturbances. Subtest IV.: SART with combined guidance and sonic disturbances. Subtest V.: SART with combined filters, alerts, guidance and sonic disturbances. |
| Follow-on baseline SART | Standard sustained attention test without sonic disturbances. |

This study tests a sub-system mock-up using multimodal, artificial intelligence-driven (MM/AI) sensors designed to provide personalized alerts, filters, and guidance to help lessen distractibility and anxiety whilst increasing focus and attention by enhancing cognitive load related to unexpected ecological and physiological/psychophysiological stimuli. The study uses a series of online experiments in which the wearable's operation is simulated by a confederate, human operator. This study proposes within-subjects, two-condition SART employing multimodal sensors during which a user's performance is measured (Robertson, I. H., Manly, T., Andrade, J., Baddeley, B. T., & Yiend, J. (1997). 'Oops!': Performance correlates of everyday attentional failures in traumatic brain injured and normal subjects. Neuropsychologia, 35(6), 747-758). Importantly, tasks were performed, and data was collected, with and without the effects of distracting sonic stimuli (the singular modality) accompanied by various combinations of advanced alerts, audio filtering and return-to-task guidance. This phase of the study included forty (40) participants, including 19 autistic participants and 21 non-autistic participants.

The classic SART paradigm, which is regarded as an exemplar of both high reliability and validity, requires participants to withhold pressing a computer key during the on-screen appearance of a target image. This study modifies SART by flipping the keystroke sequence; that is, rather than holding a key "down" throughout the majority of the test, the assigned key was depressed only when a target appeared. This provided greater reliability and reproducibility when testing at distance and online (Anwyl-Irvine, A. L., Massonié J., Flitton, A., Kirkham, N. Z., Evershed, J. K. (2019). Gorilla in our midst: an online behavioural experiment builder. Behavior Research Methods). Performance on the SART correlates significantly with performance on tests of sustained attention. Research indicates that SART does not, however, correlate well to other types of attentional measures, "supporting the view that [SART] is indeed a measure of sustained attention" (Robertson et al., 1997, 747, 756). This study employs SART specifically because studies like Robertson's corroborate that this methodology is fundamentally impervious to effects of age, estimated intelligence scoring or other intellectual measures.

Additionally, and within this study, SART tasks are performed, and data is collected, with and without the effects of distracting sonic stimuli. This modality serves as both the singular and irrelevant foil, when accompanied by various subtest combinations of advanced alerts, audio filtering and return-to-task guidance models. These combinations serve as the intervention(s). The study subtests exploit visual search of targets against competing and irrelevant foils (e.g., alpha-numeric). Supplementing these textual targets with additional contesting modalities (e.g., sonic foils and interventions) makes this SART study novel compared to previously-conducted studies. SART requires participants to "actively inhibit competing distractors and selective activation of the target representation. Memory factors are minimal in these tasks, as the targets are simple and are prominently displayed to subjects in the course of testing" (Robertson, I. H., Ward, T., Ridgeway, V., & Nimmo-Smith, I. (1996). The structure of normal human attention: The Test of Everyday Attention. Journal of the International Neuropsychological Society, 2(6), 525, 526). Though reaction time and other temporal measures are considered in developing participant scores, this study rules out the possibility that subtests only measure sampling speed of processing as qualitative mental health measures are also integrated.

The first PPI study and PTBE facilitated a deeper understanding of the lived experiences of autistic individuals' and their focus, distractibility and anxiety concerns with a particular focus on later-life, educational and workplace experiences. The PPI study and PTBE also provided information regarding a potential decrease in both anxiety and sensitivity as autistic people age, and that these trends differ within specific modalities. Stability is achieved across various ages for a sonic variable but varies for both visual and physiological/psychophysiological variables. Further, anxiety and sensitivity may not relate across gender. And while there are downward aging trends in both technology tolerance and distractibility, there is variation in ages 30-39 perhaps due to the massive size of this particular sample.

The study design is rooted in a SART/WoZ design and includes online experiments whereby system operations were simulated by a human operator armed with prior, hand-crafted interventions and scripts that support participants' testing (Bernsen, N. O., Dybkjær, H., & Dybkjær, L. (1994). Wizard of oz prototyping: How and when. Proc. CCI Working Papers Cognit. Sci./HCI, Roskilde, Denmark). The Wizard of Oz (WoZ) study design provides economical and rapid implementation and evaluation, and has gained academic acceptance and popularity for decades. (Bernsen et al., 1994); (Robertson et al., 1997); (Fiedler, A., Gabsdil, M., & Horacek, H. (2004, August). A tool for supporting progressive refinement of wizard-of-oz experiments in natural language. In International conference on intelligent tutoring systems (pp. 325-335)); (Maulsby, D., Greenberg, S., & Mander, R. (1993, May). Prototyping an intelligent agent through Wizard of Oz. In Proceedings of the INTERACT'93 and CHI'93 conference on Human factors in computing systems (pp. 277-284)). These supports may lessen distractibility/anxiety whilst increasing attention by enhancing cognitive load related to unexpected stimuli. WoZ proposes a within-subjects, two-condition SART employing multi-modal sensors during which a user's errors of commission, errors of omission, reaction time, state-anxiety, and fatigue levels are computed. (Burchi, E., & Hollander, E. (2019). Anxiety in Autism Spectrum Disorder); (Ruttenberg, D. (2020). The SensorAble Project: A multi-sensory, assistive technology that filters distractions and increases focus for individuals diagnosed with Autism Spectrum Condition. MPhil/PhD Upgrade Report. University College London).

Memory factors are minimized in SART testing, as visual tasks are modest and tried out by participants prior to testing. Though intervallic measures are included in scoring participant performance, there are other critical metrics resulting from both qualitative and quantitative scoring. As mentioned in Robertson (1996), these do not create cognitive burdens of similar dynamics and characteristics; therefore, they do not constitute a myopic or simplified sampling speed of processing measure. Further, this study separates visual sustained tasks from auditory distractions, which in turn avoids cross-modality and interference concerns.

The study utilized t-test/correlation point biserial models (Faul, F., Erdfelder, E., Lang, A.-G., & Buchner, A. (2007). G*Power 3: A flexible statistical power analysis program for the social, behavioral, and biomedical sciences. Behavior Research Methods, 39, 175-191). Computations were based upon a given a, power and effect size. Generally, T-tests are calculations that inform the significance of the differences between groups. In this case, it answers whether or not the data between autistic and non-autistic scores (measured in means) could have happened by chance. Alpha (a) is a threshold value used to judge whether a test statistic is statistically significant, and was selected by the inventor (typically 0.05). A statistically significant test result (p=probability and p≤0.05) indicates that the test hypothesis is false or should be rejected, and a p-value greater than 0.05 means that no effect was observed. The statistical power of a significance test (t-test) depends on: (i) the sample size (N), such that when N increases, the power increases; (ii) the significance level (a), such that when a increases, the power increases; and (iii) the effect size, such that when the effect size increases, the power increases.

Half the sample included neurotypical participants and half identified as or possessed an ASC diagnoses. All participants utilized pre/post WoZ manipulations. Baseline testing and related scores were derived both procedurally on pre- and post-subtests. Putative, cognitive conflicts during subtests that may result in a hypothesized and measurable uptick in both distractibility and anxiety were created. Simultaneously, this upsurge likely pooled with diminished focus and conical attentional performance.

Finally, and during the latter subtests, a "confederate" (human wizard) presented a collection of hand-crafted alerts, filters and guidance. These emulated the operation of the wearable intervention by offsetting and counterbalancing distracting aural stimuli. To reduce fatigue effect, these interventions existed in counterbalanced, randomized and multiple sessions. Alternatively, a combination of alerts, filters and guidance were provisioned to lessen overall length of the experiments, as illustrated in FIG. 3.

The delivery of isolated and permuted support produced broad measures of test responses. Mixed method (qualitative and quantitative evaluations) combined with participants' overt behaviors obtained through audio and video recordings provisioned coding and analysis with sample accuracy synchronization to the systems software. Depending upon sample size and time constraints, this design considers post-hoc video analyses (e.g., participant walk-through) in either a structured or liberal form. These examinations may help facilitate recall, precision and provide further understanding of anxiety and other episodic testing moments.

Reliability was tested by administering the procedure to a sub-group of autistic and non-autistic subjects on one occasion over a period of 7 separate trials. The I. H. Robertson protocol was used owing to its heritage and wide acceptance in the scientific community (Robertson et al., 1997).

In the SART procedure, 100 single letters (e.g., A through Z) were presented visually for up to a 5-minute period. Each letter was presented for 250-msec, followed by a 900-msec mask. Subjects responded with a key press for each letter, except 10 occasions when the letter "X" appeared, where they had to withhold (inhibit) a response. Subjects used their preferred hand. The target letter was distributed throughout the 100 trials in a non-fixed, randomized fashion. The period between successive letter onset was 1150-msec. Subjects were asked to give importance to accuracy first followed by speed in doing the task.

The letters were equally presented in identical fonts (Arial) and size (36 point) corresponding to a height of 12.700008 mm. The mask following each digit consisted of a white square with no border or fill coloring. The total area of the mask was dependent upon the user's screen size (e.g., the entire screen would be considered the maskable area). By way of comparison, a 10-inch diagonal screen would produce a 25 cm diagonal mask for a laptop and a 40 cm diagonal mask for a tablet. Similarly, a 15-inch diagonal and 20-inch diagonal screen would produce a 38.10 cm mask and 50.80 cm mask for both laptop and tablet, respectively.

Each session was preceded by a practice period consisting of 15 presentations of letters, two of which were targets. Further, a self-assessed state-trait anxiety and state-trait fatigue inventory (STAFI) was conducted prior to and following each of the seven SART/WoZ trials (Spielberger, C. D. (1972). Conceptual and methodological issues in research on anxiety. Anxiety: Current Trends in Theory and Research on Anxiety). The fatigue portion in the more commonly used anxiety only inventory was combined to measure trait and state anxiety and fatigue. STAFI have been historically used in clinical settings to diagnose anxiety and to distinguish it from depressive syndromes. The STAFI is appropriate for those who have at least a sixth grade reading level (American Psychological Association. (2011). The State-Trait Anxiety Inventory (STAI). American Psychological Association).

Participants selected from five state anxiety items including illustrations and text that depicted how they were feeling at the moment of query, including: "1—Extremely anxious", "2—Slightly anxious", "3—Neither anxious nor calm", "4—Slightly calm" or "5—Extremely calm"; "I am worried"; "I feel calm"; I feel secure." Lower scores indicated greater anxiety.

Similarly, five fatigue items included illustrations and text that depicted feelings at the moment of query, including: "1—Extremely tired", "2—Slightly tired", "3—Neither awake nor tired", "4—Slightly awake", or "5—Extremely awake". Lower scores indicate greater fatigue.

Performance on the SART clearly requires the ability to inhibit or withhold a response. This is made more difficult when distractors are introduced into the testing paradigm. Specifically, hand-crafted sonics of varying amplitude, frequency, time/length, distortion, localization, and phase were introduced to mimic those sounds that might occur in office, workplace, education, and scholastic settings.

A total of twenty-eight (28) sound sources were played over a duration of five-minutes and included office industrial, fire alarms, telephone ringing, busy signals and dial tones, classroom lectures, photocopier and telefacsimile operations, footsteps, sneezes, coughs, pencil scribbling, and the like.

Prior to testing, this study accomplished similar testing through pre-programmed sensing and related interventions. The scripting of sonic stimuli, along with fabricated participant alerts, filters and guidance were operationalized to give the sensation and response of customized interventional support. These smart-system components were pre-defined, and the sensor cause and effect become evaluative to stabilize system operation, encourage autonomous testing and synchronized data recording. As in Forbes-Riley, K. and Litman, D. 2011, Designing and evaluating a wizarded uncertainty-adaptive spoken dialogue tutoring system, Computer Speech & Language 25, 105-126, this study leverages WoZ in place of multiple system components; the combination of which presents a fully intelligent and integrated system. The human wizard is predominantly a conductor/evaluator whose functions and monitoring of programmatic materials are unidentified to the participant. Users make selections through a "dumb" control panel, provisioning their customized alerts, filters and guidance. Importantly, the mechanism advances autonomy by providing specific functionalities for participant evaluation, whilst ostensibly eliminating evaluator influence. In selecting these components, the following questions are reviewed: What requirements should the evaluator meet before conducting a study? How does the evaluator follow the plan, and what measurements will reflect test and sub-test flow? How should control panel component be designed, and how would this affect its operation? How does the evaluator's personal behavior affect system operation?

All studies were administered and hosted in the Gorilla Integrated Development Environment (IDE) and available through most common web browsers and appliances (Anwyl-Irving et al., 2019). All audio, video and related ecological/interoceptive data were presented and collected in real time via the IDE and evaluator.

Figure 18:
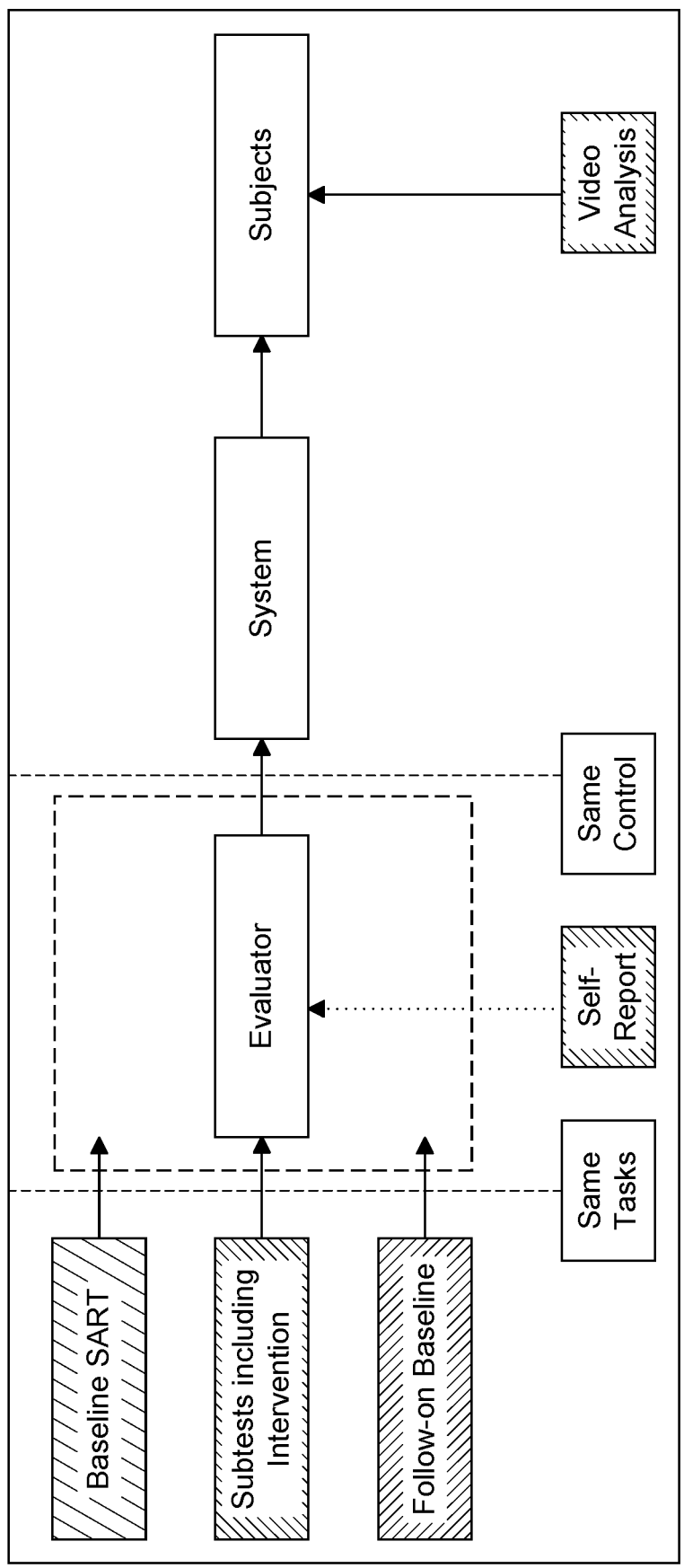
FIG. 18 is a flowchart of the various components of the study variables, in accordance with some implementations of the disclosure.

Study Variables:

The overarching study was divided into four components including: (i) the PPI study and PTBE described earlier; (ii) the evaluator (including tasks, self-reports and controls); (iii) the system prototype (a non-wearable sub-system); and (iv) the participants (who were recorded). Study variables are listed in Table 3A, and illustrated in FIG. 18:

TABLE 3A

| Variable | Type |
| --- | --- |
| Filter | Independent |
| Alert | |
| Guidance | |
| System | |
| Participant | |
| Evaluator | |
| Interventional combinations: assistance | Dependent |
| Improvement: focus | |
| Improvement: attention | |
| Improvement: technology tolerance | |
| Reduction: anxiety | |
| Reduction: distractibility | |
| Reduction: discomfort | |

Figure 6:
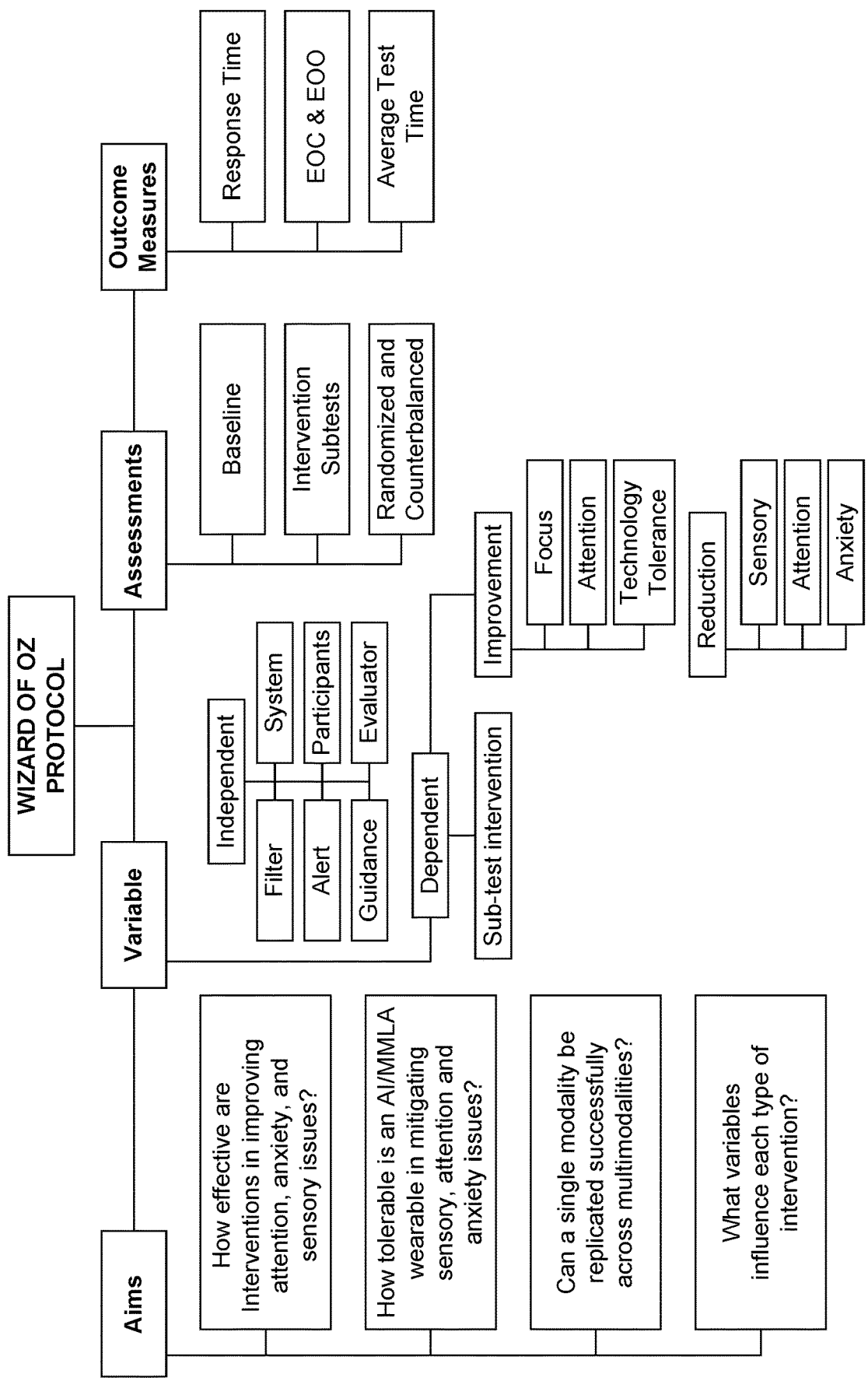
FIG. 6 is a flowchart of the SART/WoZ study protocol, in accordance with some implementations of the disclosure.

SART/Wizard of Oz Protocol Design:

FIG. 6 is a flowchart illustrating the SART/WoZ Protocol used in this study, and includes four higher-order classes that include study aims, variables, assessments, and outcome measures. Study questions, independent and dependent variables, potential assessments/activities and expected results are also depicted. Based upon this SART/WoZ Protocol design, the corresponding class descriptions are listed in Table 3B3:

TABLE 3B

| Class | Descriptors |
|---|---|
| Aims | How effective are alerts, filters & guidance in improving intention, reducing both distraction and anxiety in ASC individuals? |
| | How tolerable is an Ai/MMLA wearable (even as a WOz) in mitigating sensory issues? |
| | Can a single modality system be replicated successfully across multimodalities? |
| | What variables influence each type of intervention? |
| Variables | See Table 3A above |
| Assessments | Sustained Attention to Response Task (SART) at baseline no distraction or intervention followed by state anxiety Likert assessment. |
| | Sustained Attention to Response Task (SART) at with audio foils and-either: |
| | (i) varying interventions followed by state anxiety Likert assessment -or- |
| | (ii) combined interventions followed by state anxiety Likert assessment. |
| | Sustained Attention to Response Task (SART) return to baseline followed by state anxiety Likert assessment. |
| Outcome measures | Response time |
| | Average test time |
| | Percentage correct responses |
| | Anxiety/mental health quotient |

Testing Procedures:

Each participant took part in a single experimental session after first completing consent and demographic forms. The session commenced with a short (1-2 minute) tutorial to ensure that the participant was comfortable with the proper operation of the testing software, and to introduce the participant to the importance of staying within range of the web camera and pointing devices for proper monitoring of the environment and their physiology. After the tutorial, participants were advised that the evaluator was available throughout the session to help monitor the system and to answer any questions between tests. Participants were not advised of the evaluator's contribution to the testing (WoZ), that any alerting, filtering or guidance programming was pre-defined prior to the experiment, or that their control of the system preferences was of a placebo nature.

The WoZ testing (from baseline through multiple interventions and then a return to baseline) included three phases. Phase I commenced with Baseline I cognitive testing; that is, there were neither distracting cues nor interventions. Phase II introduced accompanying filters, alerts and guidance applied in concert with randomized sonic distractions and testing. Phase III reintroduced a return to baseline to ensure that participants' recovery and responses were not memorized and that randomization effects were properly sustained.

Alerts, Filters and Guidance Structure:

The alerts and guidance of this study protocol utilizes Amazon Polly™, a neural text-to-speech (TTS) cloud service designed to increase engagement and accessibility across multiple platforms (Neels, B. (2008). Polly. Retrieved Dec. 17, 2020, from https://aws.amazon.com/polly/). Polly's outputs, as listed in Table 4, are cached within the testing system and portends personification of a safe, uncontroversial, newscaster speaking in a style that is tailored to specific use cases.

TABLE 4

| Stimulus Event/Cue | Amazon Polly™ Script |
|---|---|
| Alert: distracting interoceptive | Hi. I sensed a physiological event that I wanted to alert you to. |
| Alert: distracting noise | Hi. I've sensed a noise that may distract you, and I wanted to alert you in advance. |
| Alert: distracting visual | Hi. I've sensed a visual event that may distract you, and I wanted to alert you in advance. |
| Filter: distracting noise | I am filtering the noise to help you re-focus. |
| Guidance: encouragement | That's it. I am sensing that you're doing quite well at the moment and that you're feeling more in control, relaxed and ready to resume your task. |
| Guidance: encouragement 2 | Good job. |
| Guidance: encouragement 3 | Well done. |
| Guidance: encouragement 4 | Congratulations. Keep up the great effort. |
| Guidance: encouragement 5 | I am proud of you. |
| Guidance: filtering reminder | By filtering noise, reminding you to take a deep breath and relax your body, you can more easily return to your current task. |
| Guidance: general re-focus | Hi. I wanted to provide you with some friendly guidance to help you re-focus now. |
| Guidance: general relaxation | I want to suggest you take a deep breath and relax your body position to help you re-focus. |
| Guidance: motivational reminder | If you're feeling tired or not motivated to focus on your work, perhaps a few deep breaths, combined with a quick stretch or standing up might be useful. |
| Guidance: re-focus reminder | I am providing this reminder to help you re-focus. |
| Guidance: self-error | Oops, I made a mistake. Sorry . . . I'm still learning what you might find distracting. The more I work for you, the more accurate I'll become. Thanks for understanding. |

A single modality of varying sonic distractions was scheduled for testing during this study. While both sonic and visual cues can easily be programmed, for fidelity and deeper understanding, the experiments were conducted with audio cues only. The stimuli events and cues are listed in Table 5, along with their accompanying filter name and description. The success and efficacy of a prototype wearable device, according to an exemplary embodiment, can be assessed on the basis of participant data collected (both quantitative and qualitative) during testing administration of these stimulus event and the participant's performance.

TABLE 5

| Stimulus Event /Cue | Filter type | Description |
|---|---|---|
| Sonic: Spatial ambiguity | Sonic imager | Psycho-acoustic spatial imaging adjustment to enhance, alter or eliminate stereo separation. |

TABLE 5-continued

| Stimulus Event /Cue | Filter type | Description |
|---|---|---|
| Sonic: Amplitude distortion | Linear multiphase compressor | Adjusts adaptive thresholds, makeup gain, and finite response filters across features five user-definable bands with linear phase crossovers for phase distortion-free, multiband compression. |
| Sonic: Amplitude over-modulation | | |
| Sonic: Amplitude under-modulation | | |
| Sonic: frequency band anomaly (low) | Linear phase equalizer | Up to five bands of low band and broadband frequency reduction with nine phase types |
| Sonic: frequency band anomaly (low- | | |
| Sonic: frequency band anomaly (hi- | | |
| Sonic: frequency band anomaly (hi) | | |
| Sonic: time anomaly (RT60 < 50 | C1 Compressor | Expansion, gaining, and equalization sidechaining to eliminate sonic tail through split-band dynamics, look ahead transient processing and phase correction. |
| Sonic: time anomaly (delay < 30 | | |
| Sonic: time anomaly (delay > 30 | | |
| Sonic: time anomaly (delay >50-100 milliseconds) | | |
| Sonic: phase distortion 1 < x < 30 milliseconds | In phase aligner | Real time, dual waveform processing for alignment, sidechain to external file, delay control to time compensation, phase shift curve adjustments and correlation recovery. |

Protocol Testing Measures:

Participants were instructed to remain in close proximity to their computer's web camera and in direct contact with at least one of their pointing devices (e.g., mouse, trackpad, keyboard) at all times during the experiment. Participants were also informed that: measures of engagement, focus, comfort, productivity, and autonomy would be tested; environmental and physiological/psychophysiological monitoring (e.g., ecology and interoceptive) would occur during testing; and participant head sway, pupillary responsivity, GSR, environmental sound and vision would be collected.

Interventions:

As the study proceeded, participants received combinations of support by way of alerts prior to distraction and/or filtered audio cues (e.g., distractions that are muted, spatially centered, etc.). Optionally, participants also received post-stimuli guidance to help them return to tasks/activities/tests.

Data Collection Method:

This study utilized three data capturing methods direct computer input/scoring, video analysis and self-reporting. The first is integrated in the Gorilla application, the second aims to record and make possible observations of subjects' system interactions, and the third may reflect the participant's and evaluator's operation experiences (Goldman, N., Lin, I.-F., Weinstein, M. and Lin, Y.-H. 2003. Evaluating the quality of self-reports of hypertension and diabetes. Journal of Clinical Epidemiology 56, 148-154).

Participants:

The PPI study of verbally abled, autistic (ASC) participants consented to: (i) focus groups exploring distractibility/attention; and (ii) a Lived Experience Attention Anxiety Sensory Survey (LEA$^2$Se) indicating first-person perspectives on sensory, attention and mental health measures. LEA$^2$Se was developed, customized and further modified by fifteen (15) participants who gave autistic voice related to sensory, attentional, and anxiety questions and issues. The LEA$^2$Se was presented to both autistic and non-autistic participants consented to an Online Questionnaire (autistic: N=187, female=75; non-binary=5; non-autistic: N=174, female=85; non-binary=3) consisting of 103-items for autistic and 48-items for non-autistic participants. The questionnaire LEA$^2$Se was then utilized as the basis for the WoZ Proof-of-Concept/Trial (POC/T, N=5, 2=ASC, 3=NT, 4/1=F/M) and final trials/experiments. The POC/T confirmed adequate systems operation, and translation from user interfaces to data collection devices and downstream to analysis applications.

Following the POC/T implementation and prior to the SART/WoZ trials, the PTBE was administered (N=131; 71=ASC, 60=NT; 59=M, 72=F). Each participant was given four discrete tests including the matrix reasoning item bank (MaRs-IB): a novel, open-access abstract reasoning items for adolescents and adults; the Autism-Spectrum Quotient (AQ): a 50-item self-report questionnaire for measuring the degree to which an adult with normal intelligence has the traits associated with the autistic spectrum; and the Adult ADHD Self-Report Scale (ASRS A and ASRS B) Symptom Checklist: a self-reported questionnaire used to assist in the diagnosis of adult Attention Deficit Hyperactivity Disorder (ADHD) and specifically daily issues relating to cognitive, academic, occupational, social and economic situations.

Based on the PTBE results, a well-matched cohort of SART/WoZ participants were selected for demographics and test battery results. This yielded a nearly 50/50 balance in neurodifferences between experiment and control groups (N=40; 19=ASC/21=NT; 15=M/24=F/1=non-Binary) so that seven randomized, control trials of pre/post sensory manipulation could take place.

Data analysis examined the use of variables derived from the PPI study and PTBE described earlier to understand the lived experience of autistic individuals relating to distractibility, attention, and anxiety. These variables and supporting data were used to predict how participants of differing ages and gender might perform on tasks accompanied by distracting visual, audio, and physiological/psychophysiological cues. These variables include: Sensitivity Impact; Anxiety Proneness; Distractibility Quotient; Visual Difficulty Quotient; Sound Difficulty Quotient; physiological/psychophysiological (Interoceptive) Difficulty Quotient; and Correlation. Of these, 6 variables, 3 of which are contextually related to different modalities, were tested in this study. The descriptive statistics and correlations for these variables are listed in Table 6:

TABLE 6

| Variable | Median | IQR | AP | DQ | SDQ | VDQ | PDQ |
|---|---|---|---|---|---|---|---|
| Sensitivity Impact (SI) | 2.50 | 1.13 | .872 | .713 | −0.50 | −.750 | −.622 |
| Anxiety Proneness (AP) | 2.44 | 0.74 | | .748 | −0.86 | −.753 | −.619 |
| Distractibility Quotient | 2.56 | 1.33 | | | −.241 | −.822 | −.786 |
| Visual Difficulty Quotient | 5.50 | 3.50 | | | | .255 | .217 |

TABLE 6-continued

| Variable | Median | IQR | AP | DQ | SDQ | VDQ | PDQ |
|---|---|---|---|---|---|---|---|
| Sound Difficulty Quotient | 4.50 | 2.00 | | | | | .866 |
| Physiological Difficulty | 5.67 | 5.00 | | | | | |

Stepwise Regression:

Dummy variables were created for both age and gender (i.e., the only demographic factors that were not correlated), and were combined with sensitivity, anxiety and distractibility variables (SI, AP and DQ) embedded within a stepwise regression analysis to predict scores in sound, visual and physiological/psychophysiological/interoceptive modalities. The model(s) with the highest R2/significance are reported in Table 7:

TABLE 7

Sound

Predictors: Distractibility Quotient, Gender, Sensitivity Impact
Model Significance: $F(3, 185) = 12.98$, $p < .001$
DQ: $t = -2.82$  $p < .001$  $\beta = -.476$
Gender: $t = 3.94$  $p < .001$  $\beta = .272$
SI: $t = 2.32$  $p < .021$  $\beta = .233$
$R = .419$
$R^2 = 17.5\%$ Visual Predictors: Distractibility Quotient, Sensitivity Impact
Model Significance: $F(2, 185) = 241.46$, $p < .001$
DQ: $t = -9.40$  $p < .001$  $\beta = -.528$
SI: $t = -6.89$  $p < .001$  $\beta = -.387$
$R = .85$
$R^2 = 72.4\%$ Physiological Predictors: Distractibility Quotient
Model Significance: $F(1, 185) = 329.43$, $p < .001$
DQ: $t = -18.15$  $p < .001$  $\beta = -.800$
$R = .80$
$R^2 = 64\%$ Standard Regression One categorical variable regressed (i.e., either age or gender, depending on which was significant in the previously conducted ANOVAs) with a continuous variable (either Sensitivity Impact [SI], Distractibility Quotient [DQ] or Anxiety Proneness [AP], depending on which had the highest correlation) onto the three modalities (e.g., sound, visual and physiological/psychophysiological), all of which serve as dependent variables in this study. Standard regression values are shown in Table 8:

TABLE 8

Sound

More correlated to DQ than SI
Gender + DQ = $R^2$ of 15.1%
Age is not correlated (ANOVA wasn't significant)
Anxiety proneness has higher correlation, but not significant with gender Visual Age + SI + DQ = $R^2$ of 73.5% (but DQ and SI are correlated)
Age + SI = $R^2$ of 64.1%
Gender not significant in ANOVA TABLE 8-continued Physiological Age + DQ – $R^2$ = 65.7%
Gender not significant PTBE Results/Data Analysis:

For the initial run of SART/WoZ participants (N=37, mean age 25.70, S.D.=7.442), their mean PTBE scores ranked as follows: MaRs-IB=62.20% and 18.64; AQ=24.51 and 12.66; ASRS-1=3.19 and 1.66; and ASRS-2=5.51 and 3.30). Independent samples tests for all PTBE results yielded MaRs-IB of (F=0.166, t=−0.295, df=35 and Sig. 2-tailed=0.769); AQ of (F=0.046, t=4.494, df=35 and Sig. 2-tailed=0.000), ASRS-1 of (F=0.281, t=2.757, df=35 and Sig. 2-tailed=0.009); and ASRS-2 of (F=0.596, t=2.749, df=35 and Sig. 2-tailed=0.009). Demographic independent sample tests were insignificant across age, gender, handedness, education, employment, income, status, children, home, and location.

For PTBE participants (N=131; autistic=71, non-autistic=60, and those who were tapped for the SART/WoZ) an ANOVA comparing autistic versus non-autistic participants utilizing Levene's test showed that the variance was significant in all scores such that: MaRs-IB scores were (F(1, 129)=4.143, p=0.044), AQ scores were (F(1, 129)=81.090, p<0.001), ASRS-1 scores were (F(1, 129)=4.832, p=0.030), and ASRS-2 scores were (F(1, 129)=8.075, p=0.005).

Figure 7:
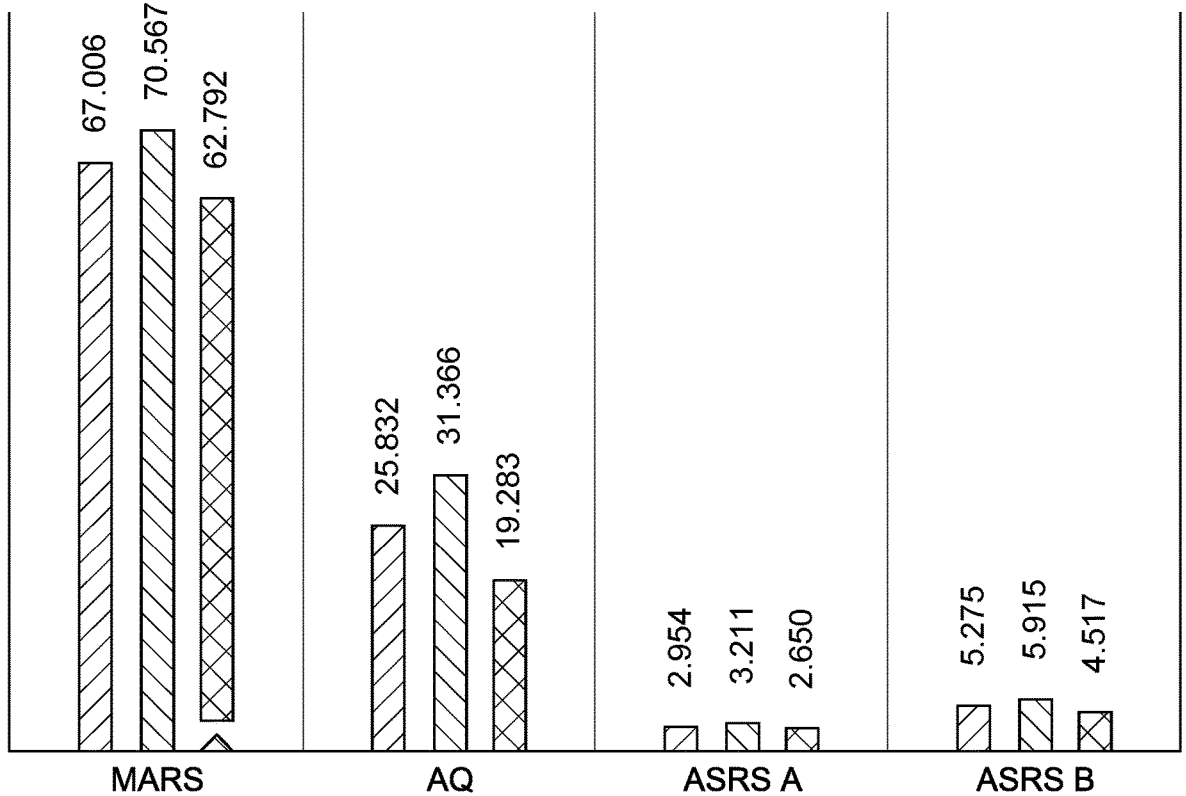
FIG. 7 is a graphical representation of recruitment scores of study participants for the wearable device studies.

Similarly, and for the identical sample, an ANOVA comparing participants' genders utilizing Levene's test showed that the variance was insignificant in MaRs-IB scores were (F(1, 129)=0.143, p=0.705), AQ scores were (F(1, 129) =0.008, p<0.930), ASRS-1 scores were (F(1, 129)=0.973, p=0.326), and ASRS-2 scores were (F(1, 129)=0.018, p=0.893). Cohort and group score averages are listed in Table 9, and shown in FIG. 7:

TABLE 9

| MaRs-1B | Cohort N = 131 | ASC N = 71 | NT N = 60 |
|---|---|---|---|
| Average | 67.006% | 70.567% | 62.792% |
| Maximum | 100.000% | 100.00% | 92.308% |
| Minimum | 18.667% | 18.667% | 20.000% |
| AQ (50) | N = 131 | N = 71 | N = 60 |
| Average | 25.832 | 31.366 | 19.283 |
| Maximum | 45.000 | 45.000 | 41.000 |
| Minimum | 3.000 | 9.000 | 3.000 |
| ASRS (Everyday Distractibility/Attention) | N = 131 | N = 71 | N = 60 |
| Score A Ave | 2.954 | 3.211 | 2.650 |
| Score B Ave | 5.275 | 5.915 | 4.517 |
| Score A Max | 6.000 | 6.000 | 6.000 |
| Score A Min | 0.000 | 0.000 | 0.000 |
| Score B Max | 12.000 | 12.000 | 11.000 |
| Score B Min | 0.000 | 0.000 | 0.000 |

SART/WoZ Results/Data Analysis:
Errors of Commission (EOC) Performance

Figure 8A:
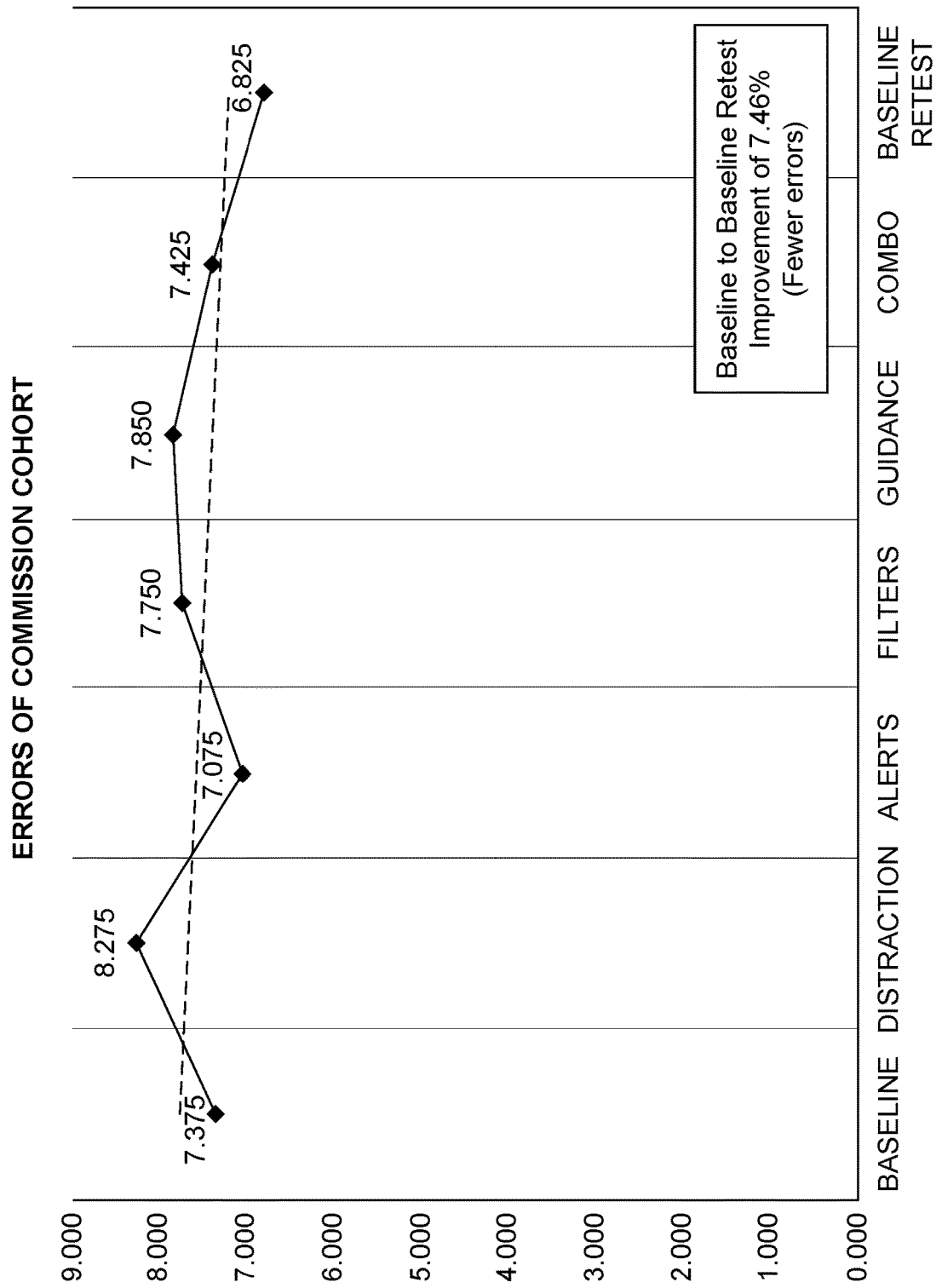
FIGS. 8A to 8C are graphical representations of the Errors of Commission (EOC) of the full cohort of participants in the SART/WoZ study described herein.
Figure 8B:
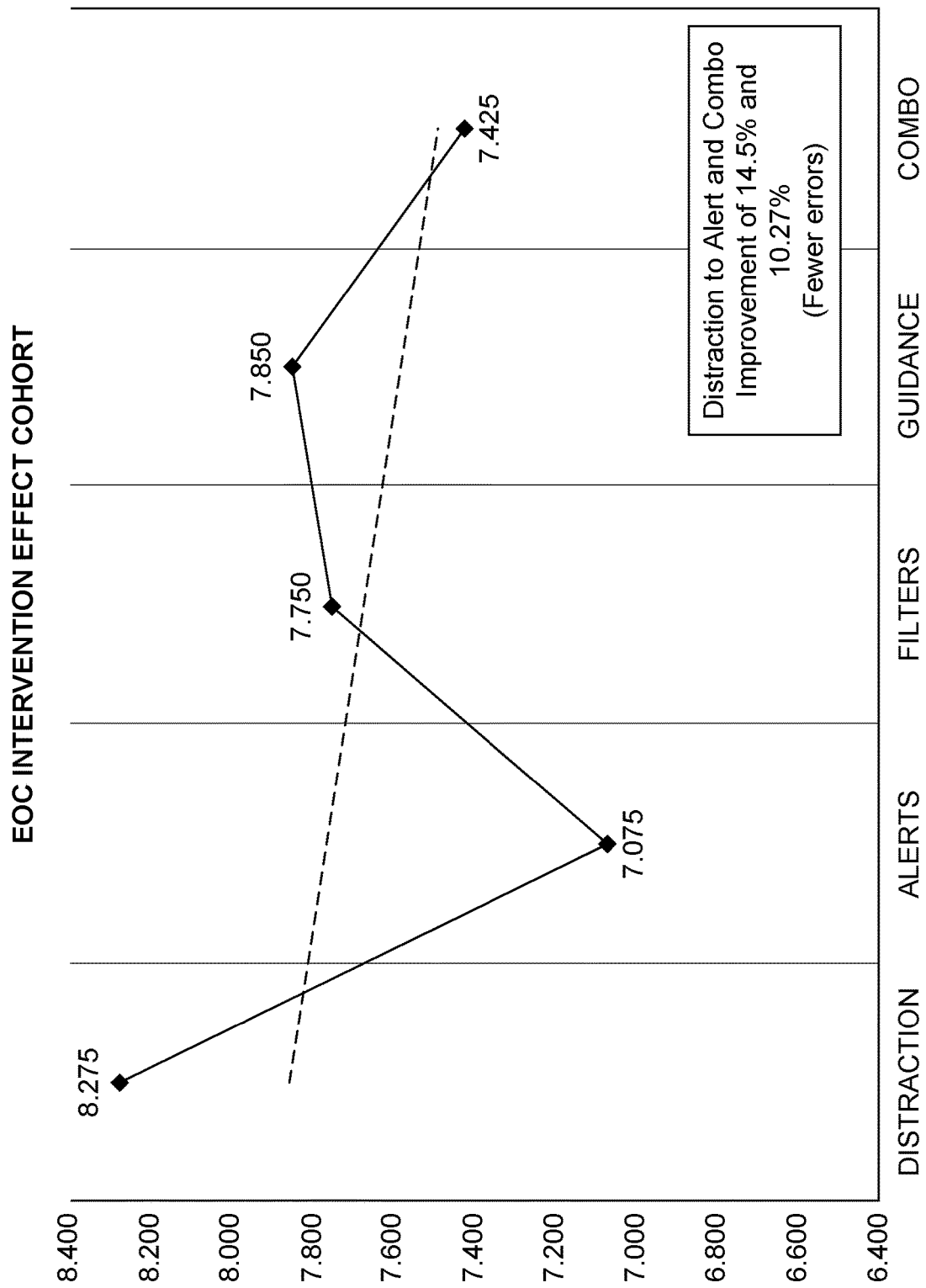
Figure 8C:
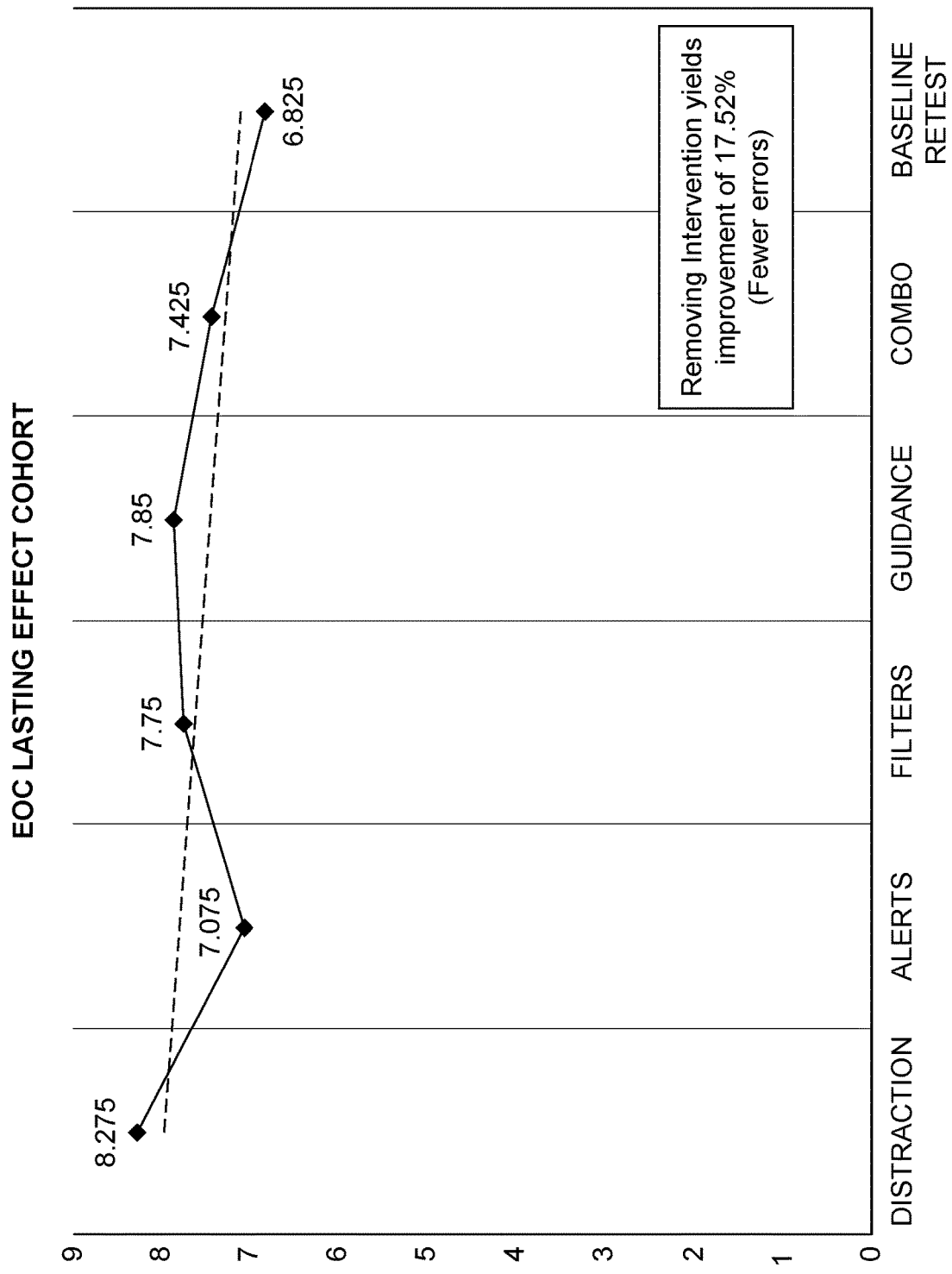

For the entirety of the SART study, and from baseline-to-baseline retest, the performance of the cohort (N=40) consisting of autistic/ASC (N=19) and neurotypical/non-autistic/NT participants (N=21) exhibited an improvement in performance. That is, there was an average reduction in Sustained Attention to Response Task (SART) errors equaling 7.46% for all inhibition measures across the entire cohort (FIG. 8A). The same cohort averaged an improvement of 14.50% (again, in error reduction) for a different interval; that is, from the onset of distraction cues to alert intervention. Finally, similar improvements occurred from distraction cues to a differing intervention (this time 10.27%) for combinatorial assistance (e.g., alerts, filters, and guidance; FIG. 8B). Regardless of the intervention, improvements were markedly prevalent for the entire cohort. Remarkably, and even after interventional cessation, a long-lasting improvement of 17.52% reduction in errors persisted among the cohort once the four technological assists were suspended (FIG. 8C). This resulted in a specific and average improvement of 1.45 fewer errors per participant, regardless of their diagnoses (group membership). In each measure, the improvement trend line was well correlated (baseline to baseline, intervention only, and intervention removal).

Errors of Commission Response Times (EOC-RT)

In general, response times increased for the entire cohort when participants experienced exposure to interventional assistance. Regardless of counterbalancing trials and their internal randomization, the cohort's improved accuracy occurred because of increased/slowing RT (e.g., 21.74% increase from baseline to alert intervention). Note that a slowing in RT is actually a desired effect from the intervention, as is explained in detail below. It is worth mentioning that unlike EOC, there was insignificant last effect of RT (resulting in 10.69% faster responses once interventions ceased).

Figure 9A:
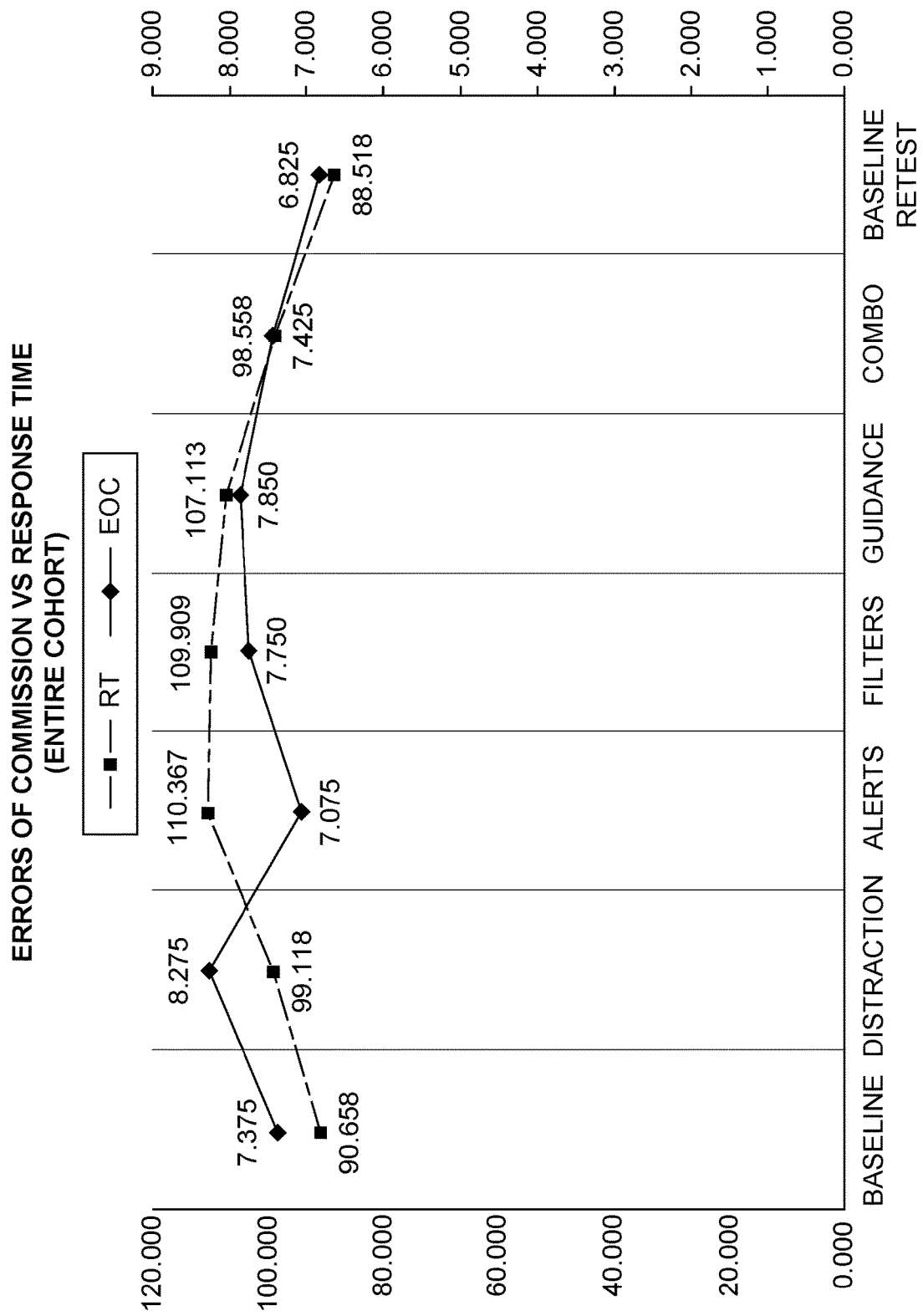
FIGS. 9A to 9C are graphical representations of EOC as it relates to Response Time (RT) of the full cohort of participants in the SART/WoZ study described herein.
Figure 9B:
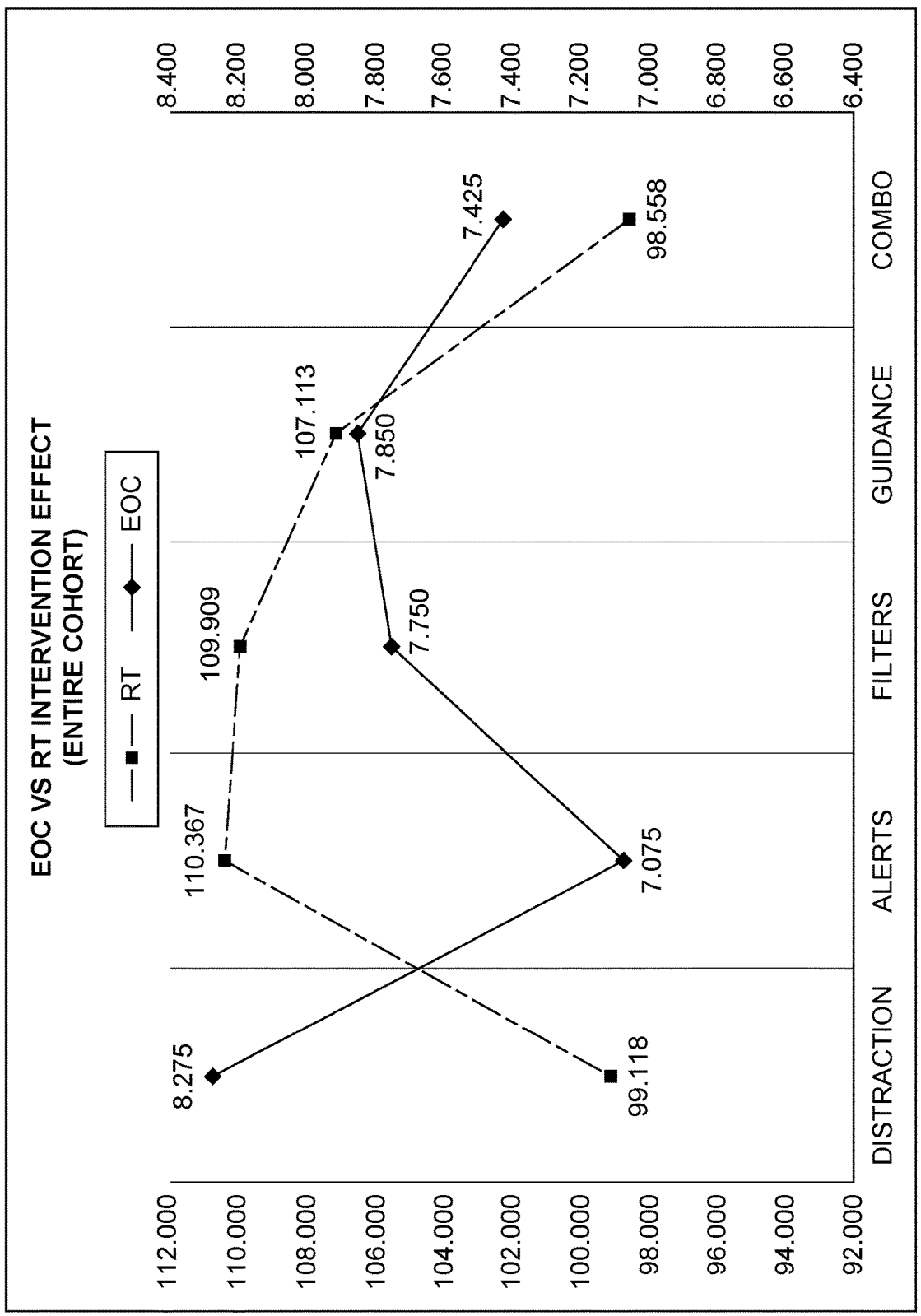
Figure 9C:
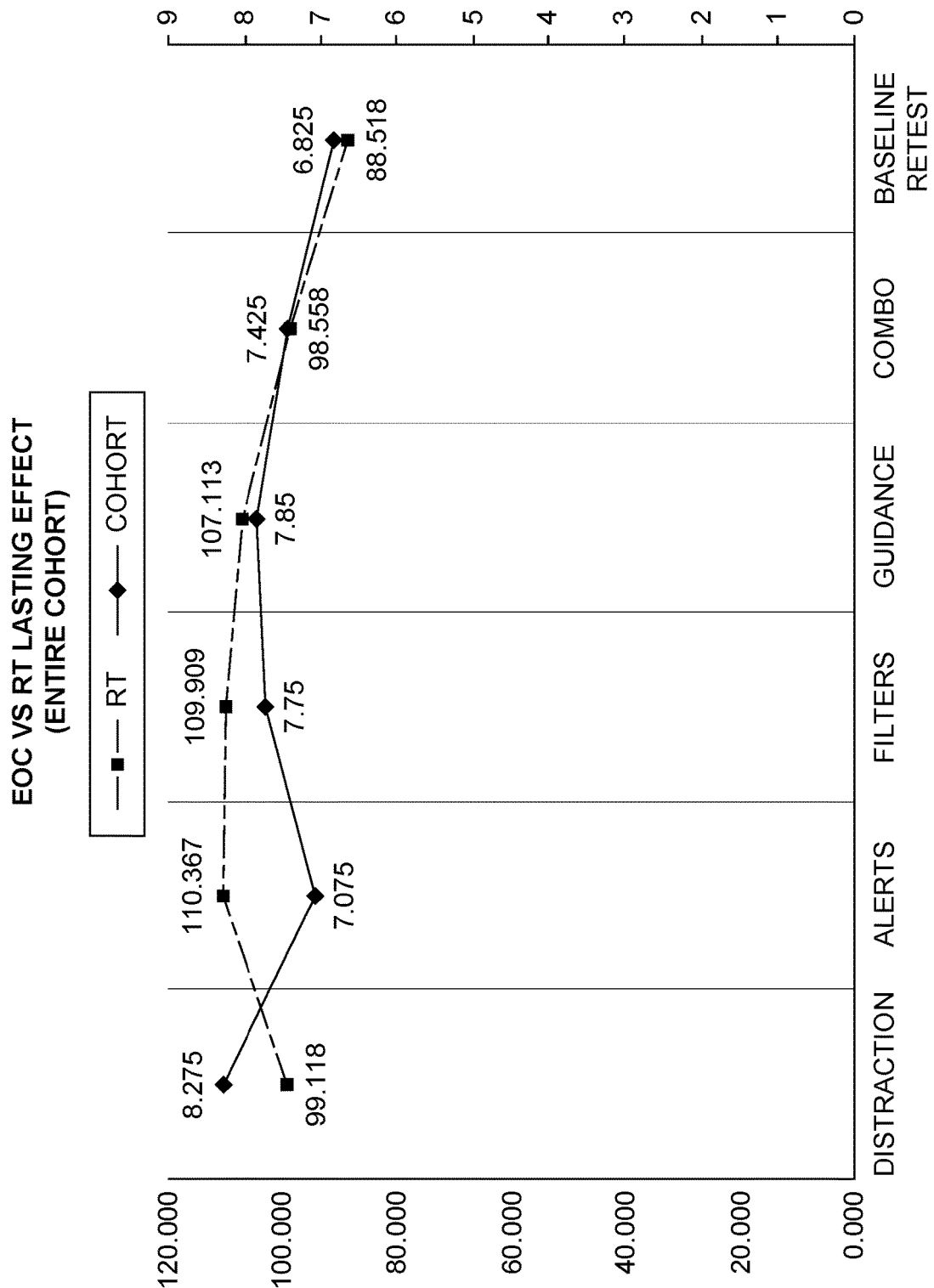

In comparison, autistic response times were shorter (faster) than neurotypical controls. This can be due to various factors differentiating neurodiverse responsivity-including, but not limited to, greater neural processing, differences in genetic makeup affecting sensory reactivity, and superior activity in the visual cortex (Schallmo, M.-P., & Murray, S. (2016). People with Autism May See Motion Faster. 19). For errors of commission, autistic participants experienced a RT increase of 19.39% (i.e., a desired slowing from onset of distraction to guidance intervention) while neurotypical counterparts produced an undesirable decreased in RT (speeding up) of nearly one percent (−0.74%) for the same period. Reaction timing's effect on accuracy saw an improvement of for 8.67% ASC participants and a 1.27% increase for neurotypical (NT) participants. These results are shown in FIGS. 9A to 9C, which are graphical representations of EOC as it relates to Response Time (RT) of the full cohort of participants in the SART/WoZ study described herein. FIG. 9A shows the EOC vs RT from starting baseline to final baseline, FIG. 9B shows the EOC vs RT intervention effect, and FIG. 9C shows the lasting effect of EOC vs RT.

Note that a slowing of reaction time portends to greater mindfulness, which can be defined as a participant's awareness of their internal feelings and a subsequent ability to maintain awareness without evaluation or judgement (e.g., defined as an outcome). Therapeutically speaking, the wearable device described herein cultivates mindfulness vis a vis bespoke intervention (assistive technology). This helps to shift and shape a participant's wandering mind and their awareness. Essentially, the participants in this study become more aware, productive, and comfortable through alerts, filters, and guidance when exposed to sensory interruptions during a Sustained Attention to Response Task (SART). Over time, participants become more attentive, less sensitive, less anxious, and less fatigued.

Realizing that slowing RT is not an unfavorable outcome, but rather a desirable one, the data suggests that NT participants who previously experience decreasing RTs (speeding up that produce smaller performance gains) can be further improved by utilizing alerts rather than guidance. This results in NTs experiencing a desirable increase in RT (slowing down). Specifically, and for the period of onset of distraction to alert, both ASC and NT slow their RTs. As a result, EOC improved among both autistic and non-autistic participants by 26.01% and 17.59%, respectively. For the same period, ASC and NT participants improved their RTs by 2.94% and 1.9%, respectively.

While neurotypical gains in accuracy appear small (i.e., from 1.27% to 1.9%), this represents a 50% (49.60%) improvement. Thus, slowing response times, resulting from custom interventional assists, create better performance outcomes. Autistic performance also improved by 200% (e.g., 8.67% to 26.01% accuracy). These results are shown in Tables 10A and 10B:

TABLE 10A

Slower (ASC) vs. Faster (NT)
Response Times ffect on Accuracy

| EOC (with guidance intervention) | Response Times Increase | Accuracy Increase |
| --- | --- | --- |
| ASC | 19.39% | 8.67% |
| NT | (−0.74%) | 1.27% |

TABLE 10B

Slower (ASC and NT)
Response Times Effect on Accuracy

| EOC (with alert intervention) | Response Times Increase | Accuracy Increase |
| --- | --- | --- |
| ASC | 2.94% | 26.01% |
| NT | 17.59% | 1.9% |

The divergence between speeding and slowing RTs (and its effect on experimental and control groups) is not accidental. Evidence of reverse RT effect on accuracy; that is, faster RT produces greater accuracy, is supported after repeated interventional assists are removed and then measured. The long-lasting effect of fewer errors (e.g., 17.92% and 17.09% reductions for ASC and NT, respectively) occurred even when response times lessened (e.g., 21.48% and 2.688% faster RTs for ASC and NT, respectively). These are small, but meaningful reductions amounting to average gains of 19.095 ms for autistic and 2.913 ms for non-autistic participants. Still, lasting intensification in performance occurred, despite diminishing response times.

The trend or tendencies of response times provide interesting considerations. Specifically, and for the entirety of the seven trials, autistic and non-autistic RTs diverge. Autistic RTs increased from 88.89 ms to 69.80 ms for baseline to baseline-retest (a speeding up of 29.78 ms over the period). In comparison, neurotypical RTs decreased from 82.59 ms to 105.46 ms, or a slowing down of 22.86 ms. This renders a 52.64 ms gap between the experimental and control group that is modulated once interventions are applied.

Figure 10A:
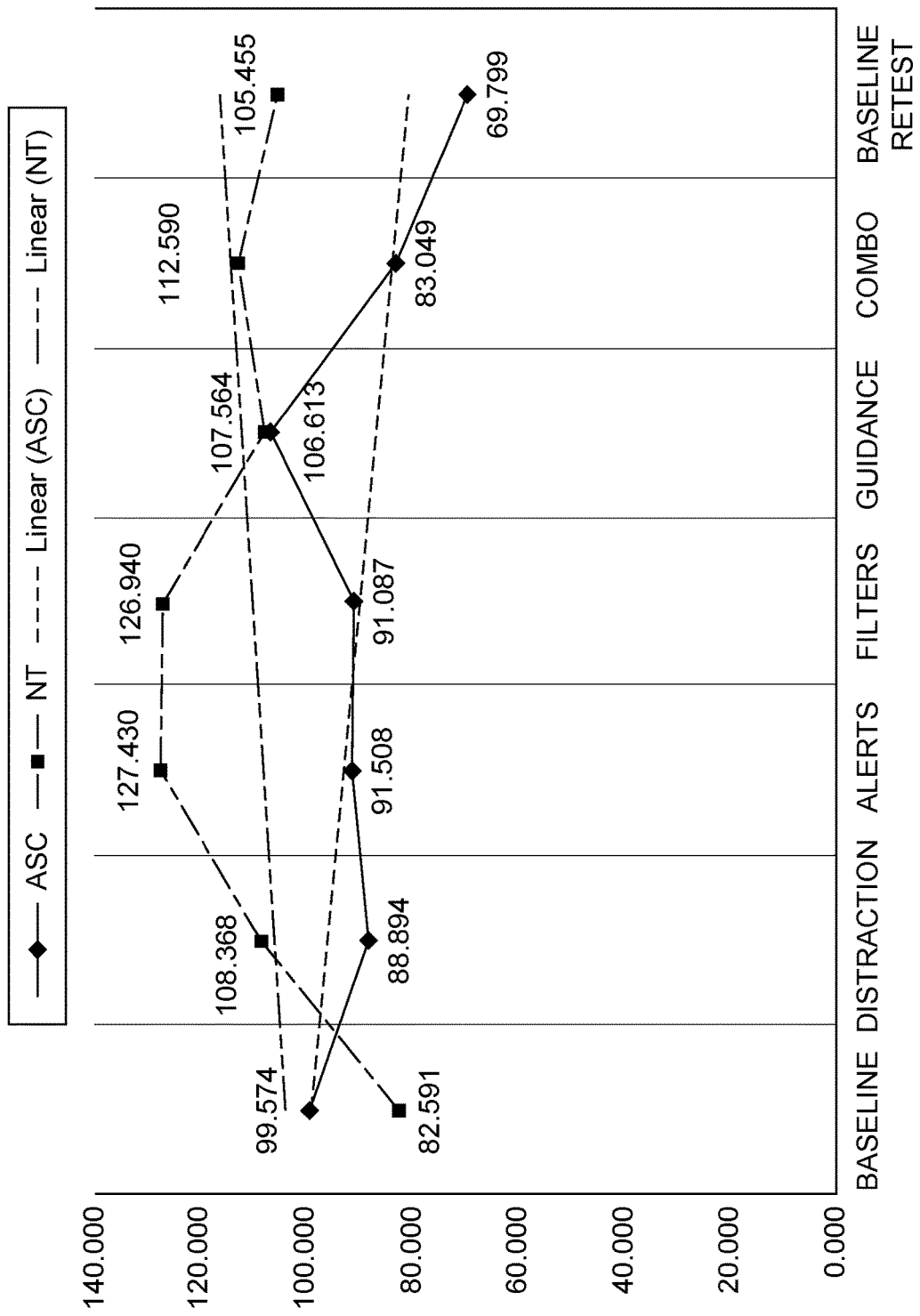
FIGS. 10A to 10C are graphical representations of EOC grouped by study participants.
Figure 10B:
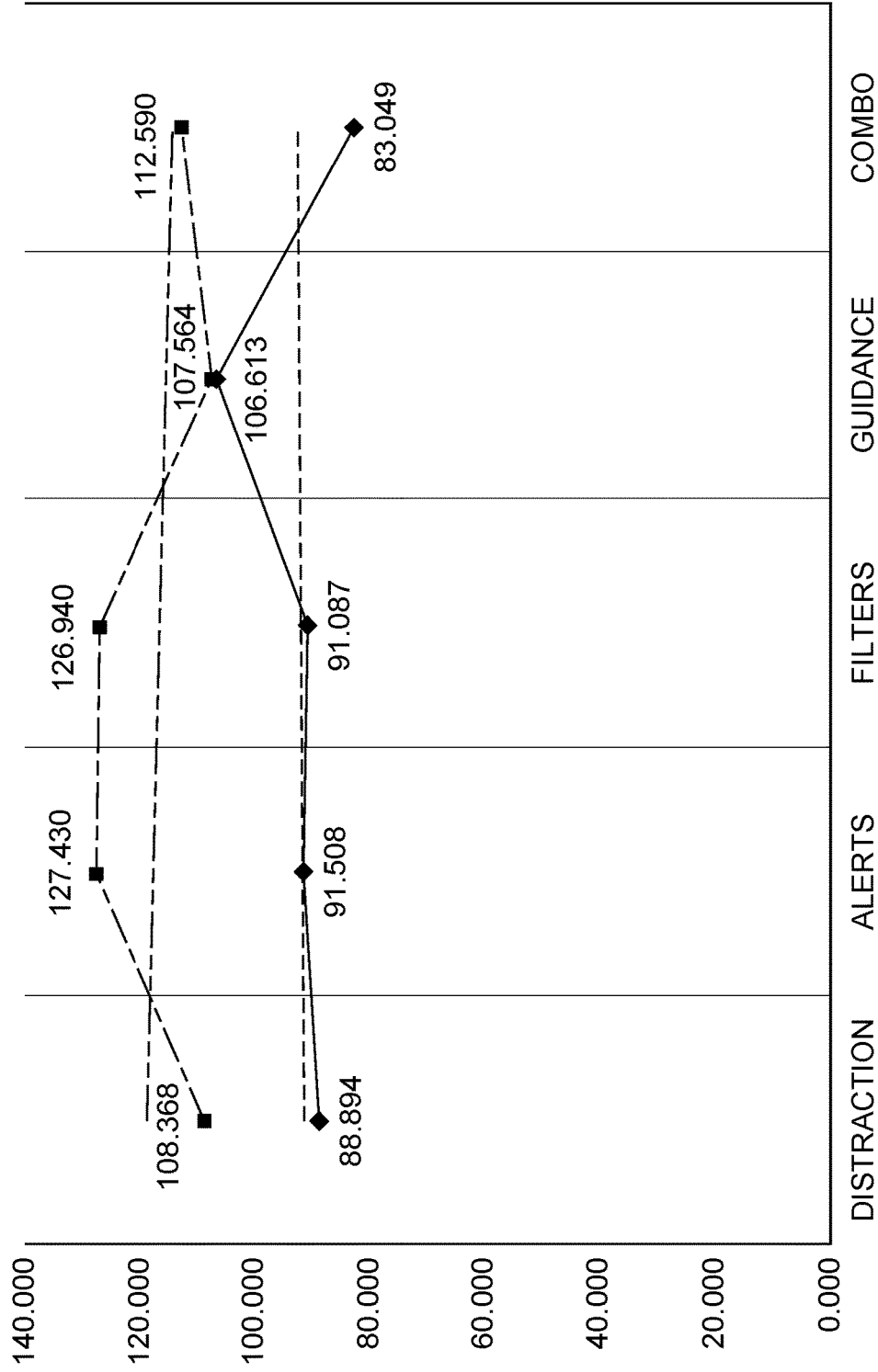
Figure 10C:
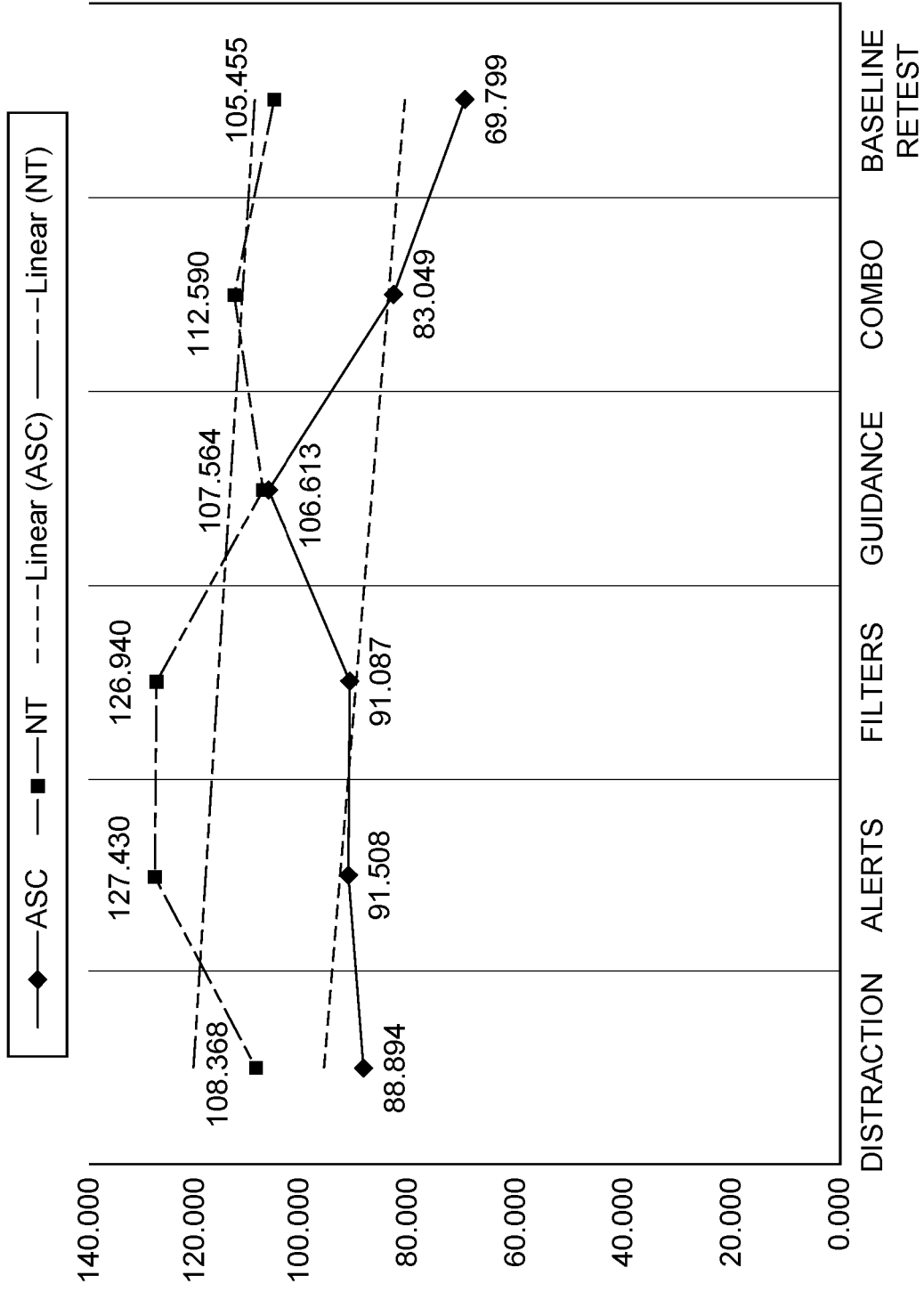

Explicitly, RTs increase (slow down) 17.72 ms for both ASC (i.e., from distraction onset to guidance intervention) and for NT (i.e., by 19.06 ms for distraction onset to alert interventions). These represent the maximum increases in RT for both groups and are non-contrasting (i.e., again, both slow down). Equally significant is RTs lasting effect; that is, neither autistic nor non-autistic participants benefit from a slowing RT once the intervention is removed. Both ASC and NT groups speed up their responses by 19.10 ms and 2.91 ms, respectively (even though there is positive lasting performance by way of fewer errors). These results are shown in FIGS. 10A to 10C.

Figure 11A:
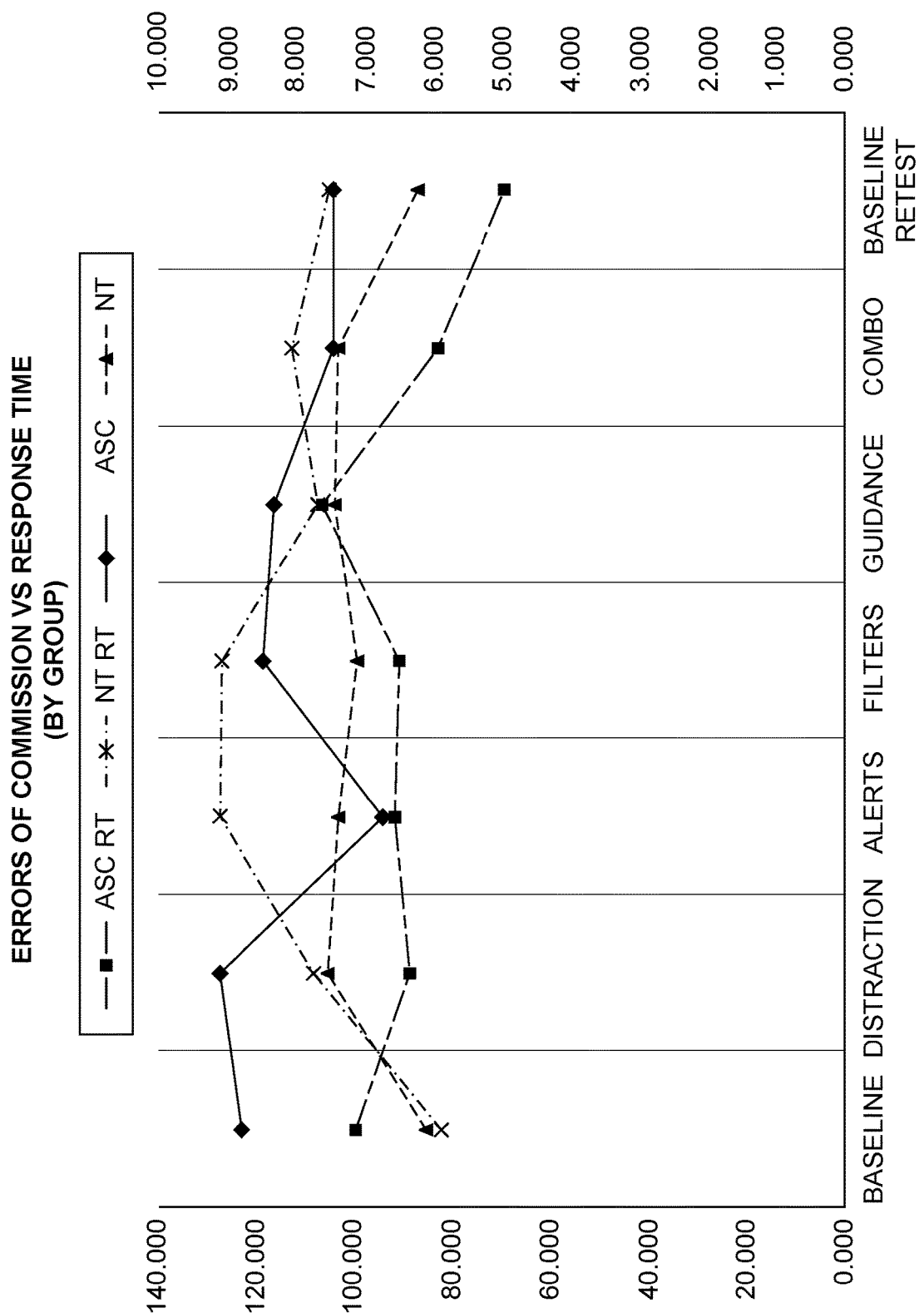
FIGS. 11A to 11C are graphical representations of EOC vs RT grouped by study participants.
Figure 11B:
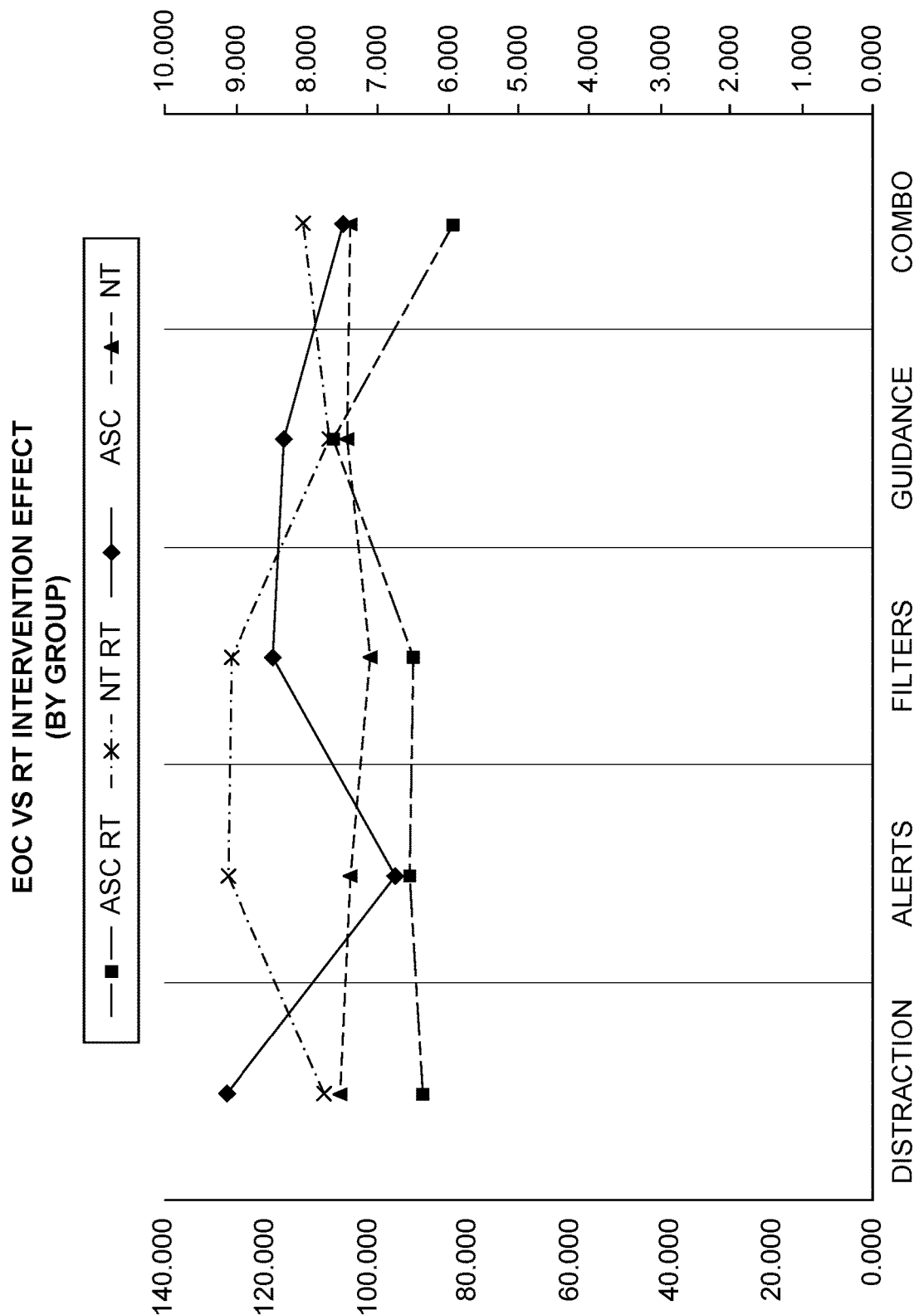
Figure 11C:
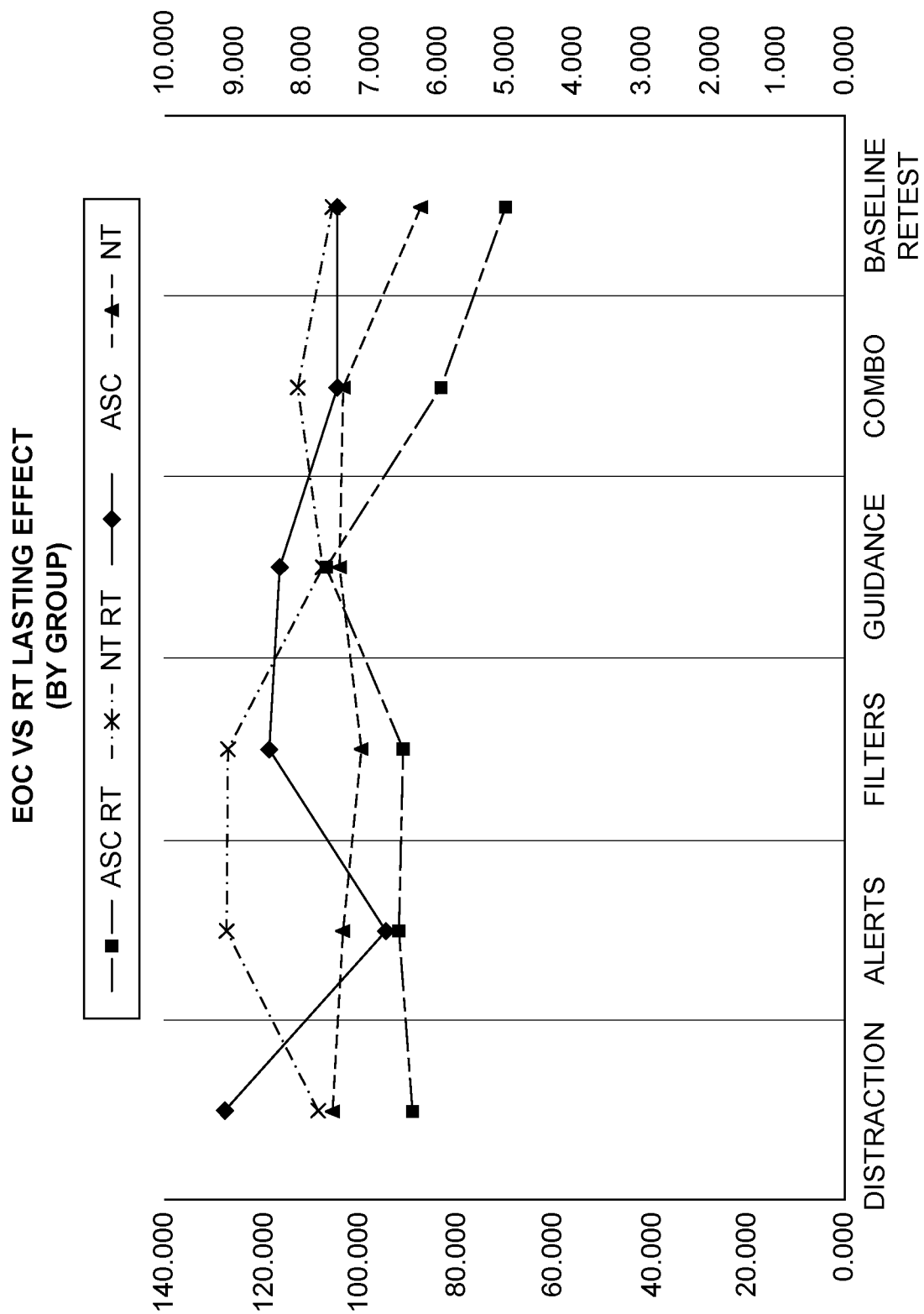

Additionally, as shown in FIGS. 11A to 11C, autistic response times are typically faster than neurotypical participants for the same tasks and interventions. Similarly, while reduced errors (improved performance) occurs across both groups, autistic participants exhibit greater variability in improvement, while neurotypical participants produce fewer errors overall. The only exception we see is for combined interventions (e.g., alerts, filters, and guidance) where both NT and ASC are equivalent a lessoning to 7.4 errors each.

In summary, as a cohort and within subjects/groups, performance increase (e.g., fewer errors) stems from interventional support applied and measured from the onset of a sensory distraction to assistive technology. A 14.5% improvement for the entire cohort results with alert intervention. Modulating the intervention (i.e., applying filters and guidance to the alerts) results in variable improvement as well. The cohort improved 10.27% in performance from a combination of these interventions. Autistic participants revealed greater performance (26.01% fewer errors) with alert intervention, while non-autistic enjoyed a 5.7% improvement through filter interventions. Lasting effects on performance improvement among the entire cohort (17.52%) and individual groups (ASC 17.92% and NT 17.09%) continued well after interventions were suspended.

Reaction times increase when participants receive assistive technologies. By slowing down, participants enable and experience greater mindfulness which yields increased performance. From baseline to alert interventions, the cohort averaged a 21.74% slowing in RT and from the onset of distraction to alerts, the slowing was 11.35%. When removing interventions of any kind and from baseline to baseline-retesting, RT sped up (decreased) by 10.69%. From an experimental to control group comparison, autistic and non-autistic participants diverge with RTs decreasing for ASC participants and increasing for NT subjects. Nonetheless, both groups benefit under interventional measures with increased performance, while neither group benefits from any lasting effect on RTs once assistive technologies are removed.

Figure 12A:
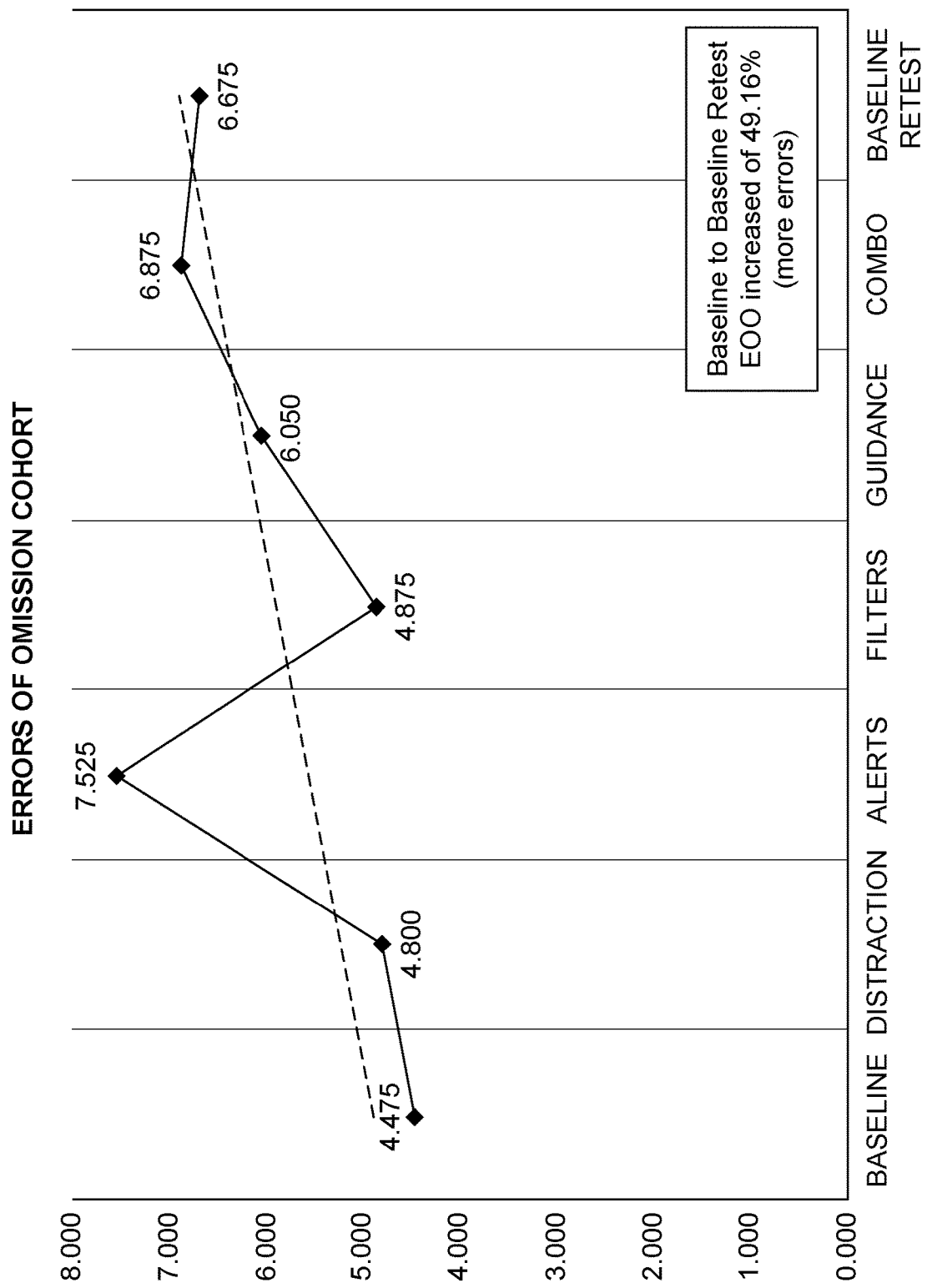
FIGS. 12A to 12C are graphical representations of the Errors of Omission (EOO) of the full cohort of participants in the SART/WoZ study described herein.

Errors of Omission (EOO) Performance:

For the entirety of the SART study, and in addition to studying cohort performance (N=40, ASC=19, NT=21) on Errors of Commission (e.g., not inhibiting a response when instructed to do so), Errors of Omission were also analyzed. EOO refer to not responding properly for any stimulus when inhibition is not warranted or instructed. For the same testing period and from baseline-to-baseline retest, EOO increased 49.16%. This means that there was an average increase in Sustained Attention to Response Task (SART) measuring, on average, 2.2 errors per participant (FIG. 12A).

Figure 12B:
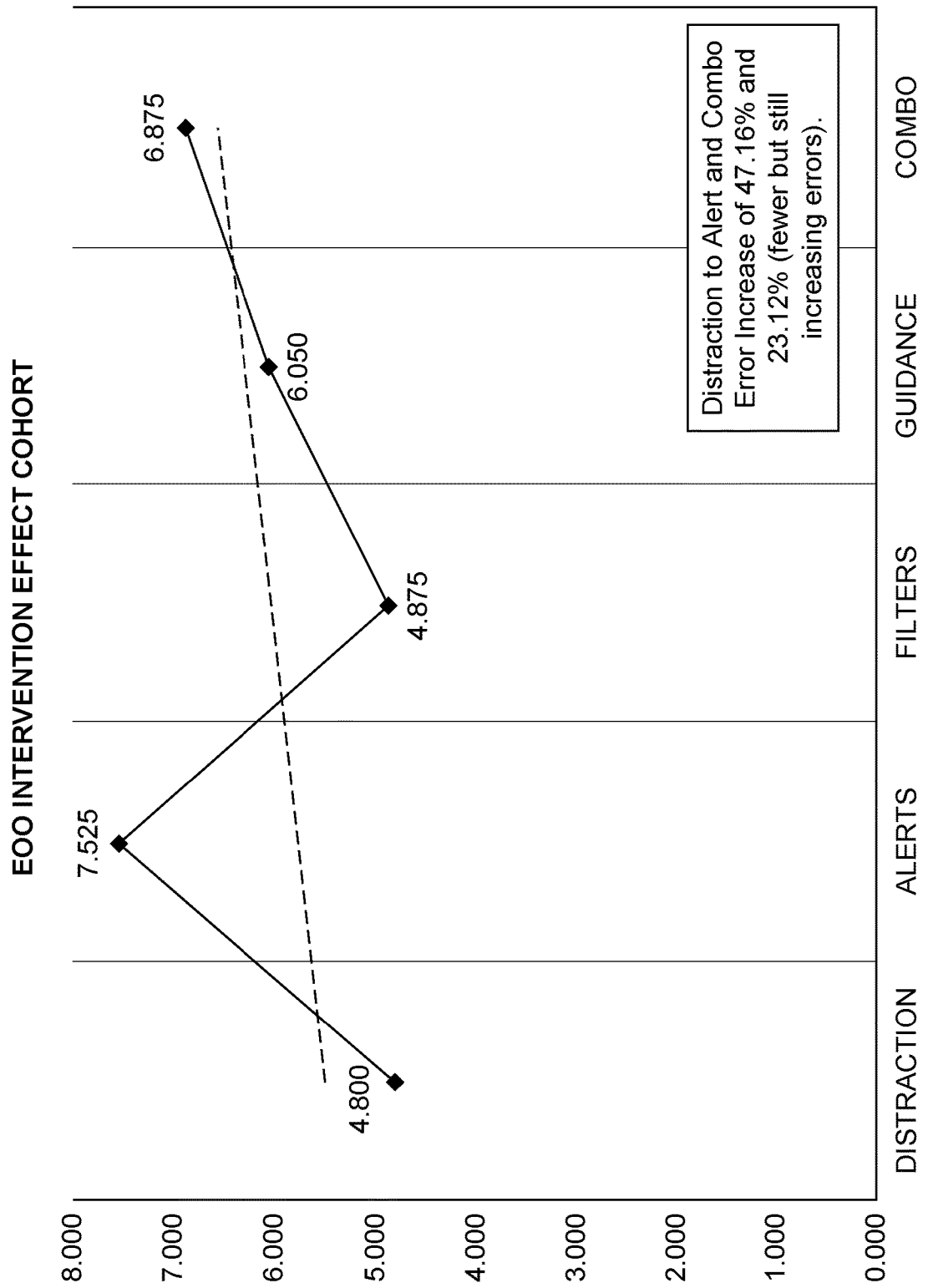
Figure 12C:
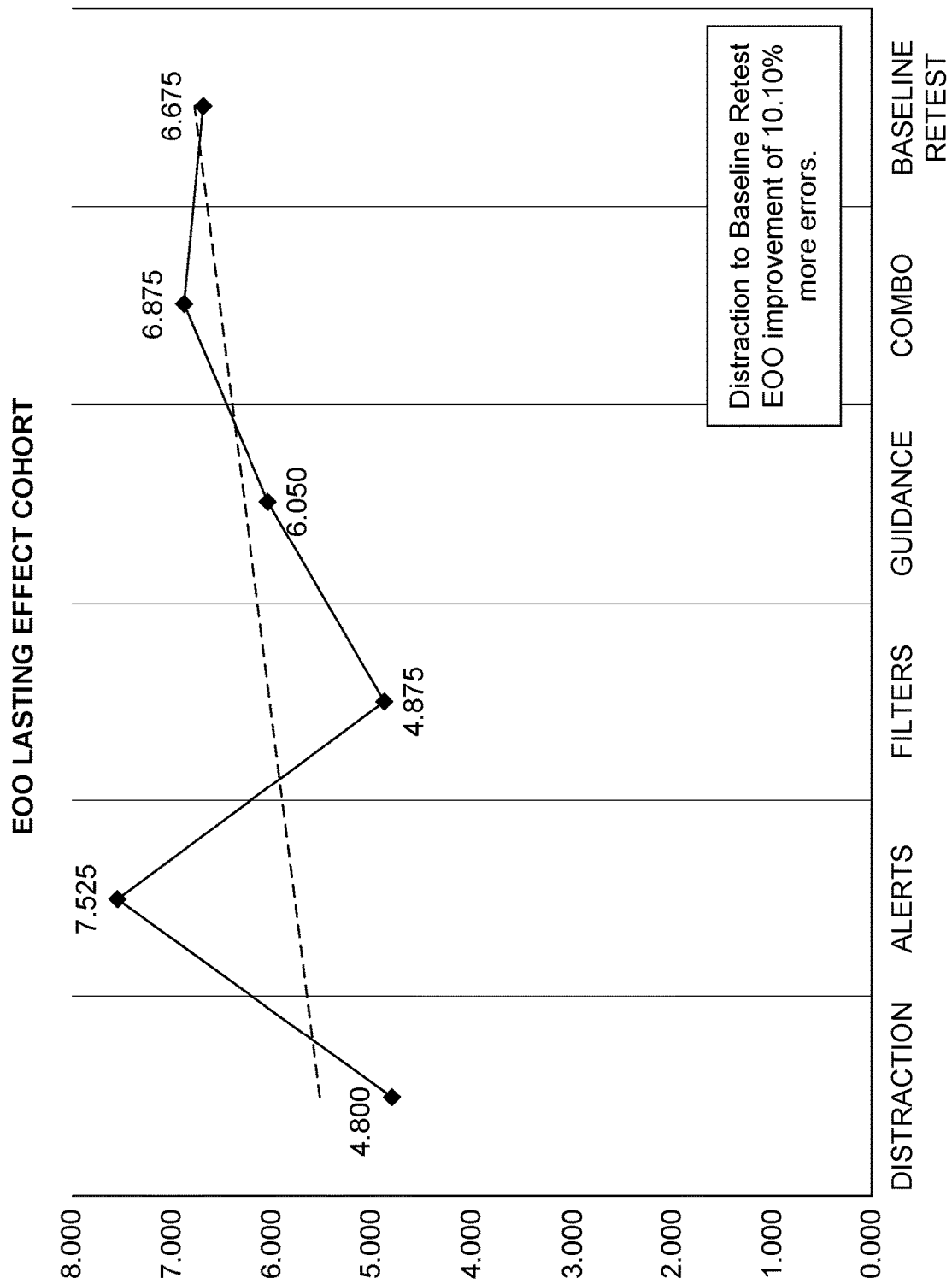

While not a desirable result, the cohort averaged an improvement when interventions were present. Specifically, and from the onset of distraction cues to alert interventions there were 47.60% fewer EOO. Similar improvements occurred from distraction cues to combinatorial interventions (though this time a smaller improvement of 23.12%), as seen in FIG. 12B.

Remarkably, a long-lasting improvement of 10.10% reduction in EOO persisted among the cohort once the four technological assists were suspended (FIG. 11C). This was calculated by measuring the error percentage increase from baseline to baseline-retest and then subtracting the error improvement measured from distraction through baseline-retest. For each participant, this corresponded to an average of 1.86 fewer errors for each, regardless of their diagnoses/group membership. In each measure, the improvement trend line was well correlated (baseline to baseline, intervention only, and lasting effect).

Errors of Omission Response Times (EOO-RT)

Figure 13A:
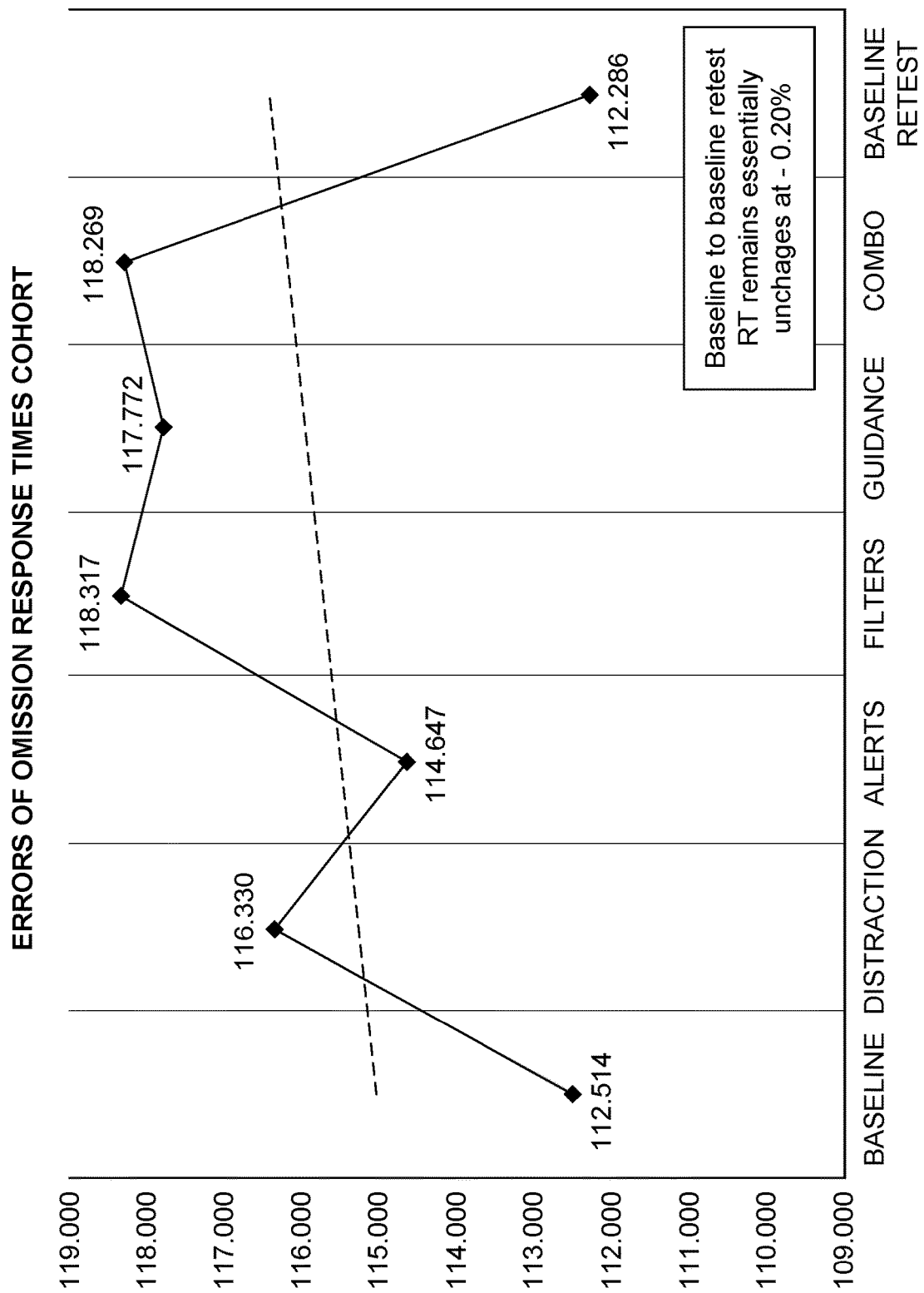
FIGS. 13A to 13C are graphical representations of EOO as it relates to RT of the full cohort of participants in the SART/WoZ study described herein.
Figure 13B:
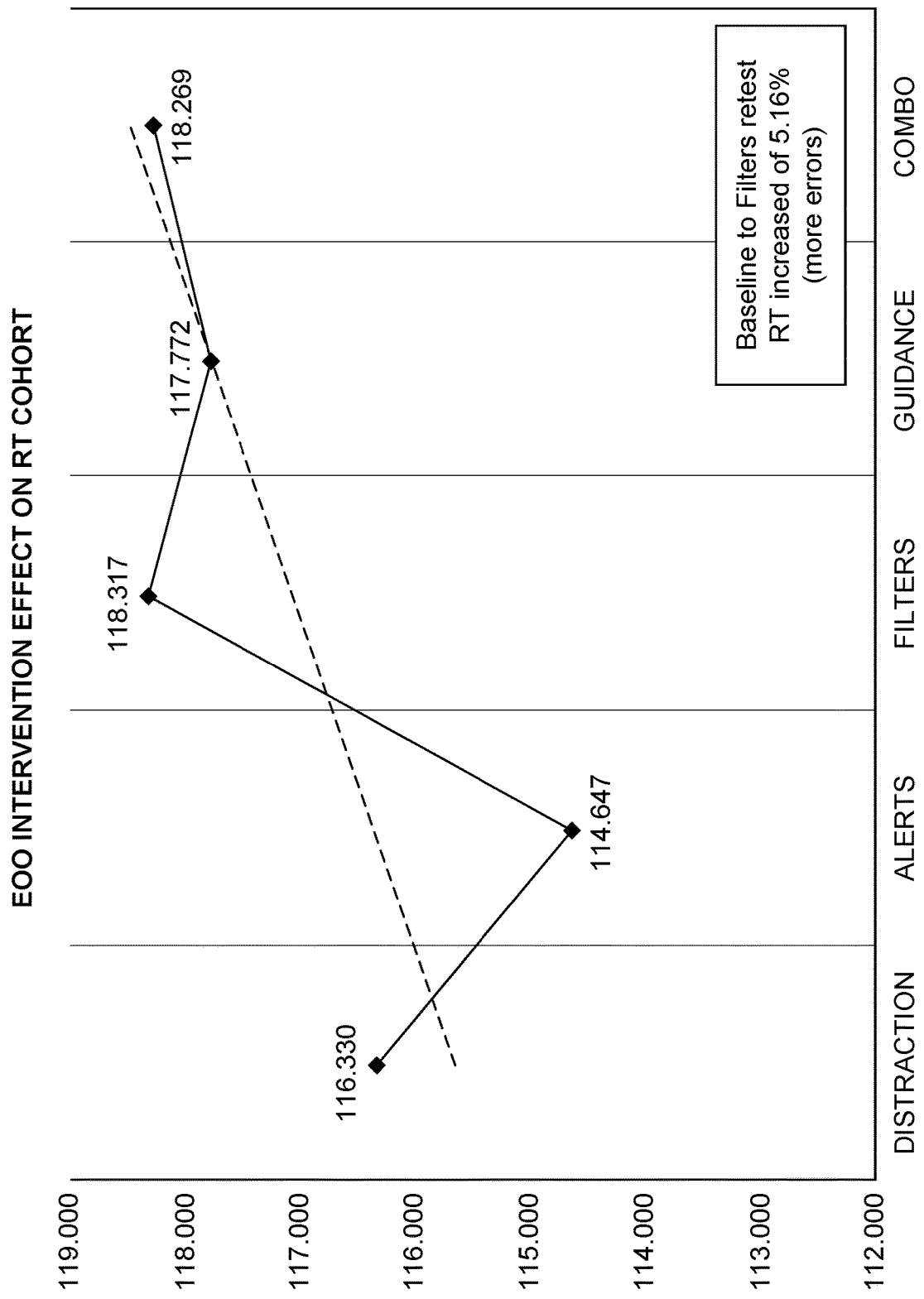
Figure 13C:
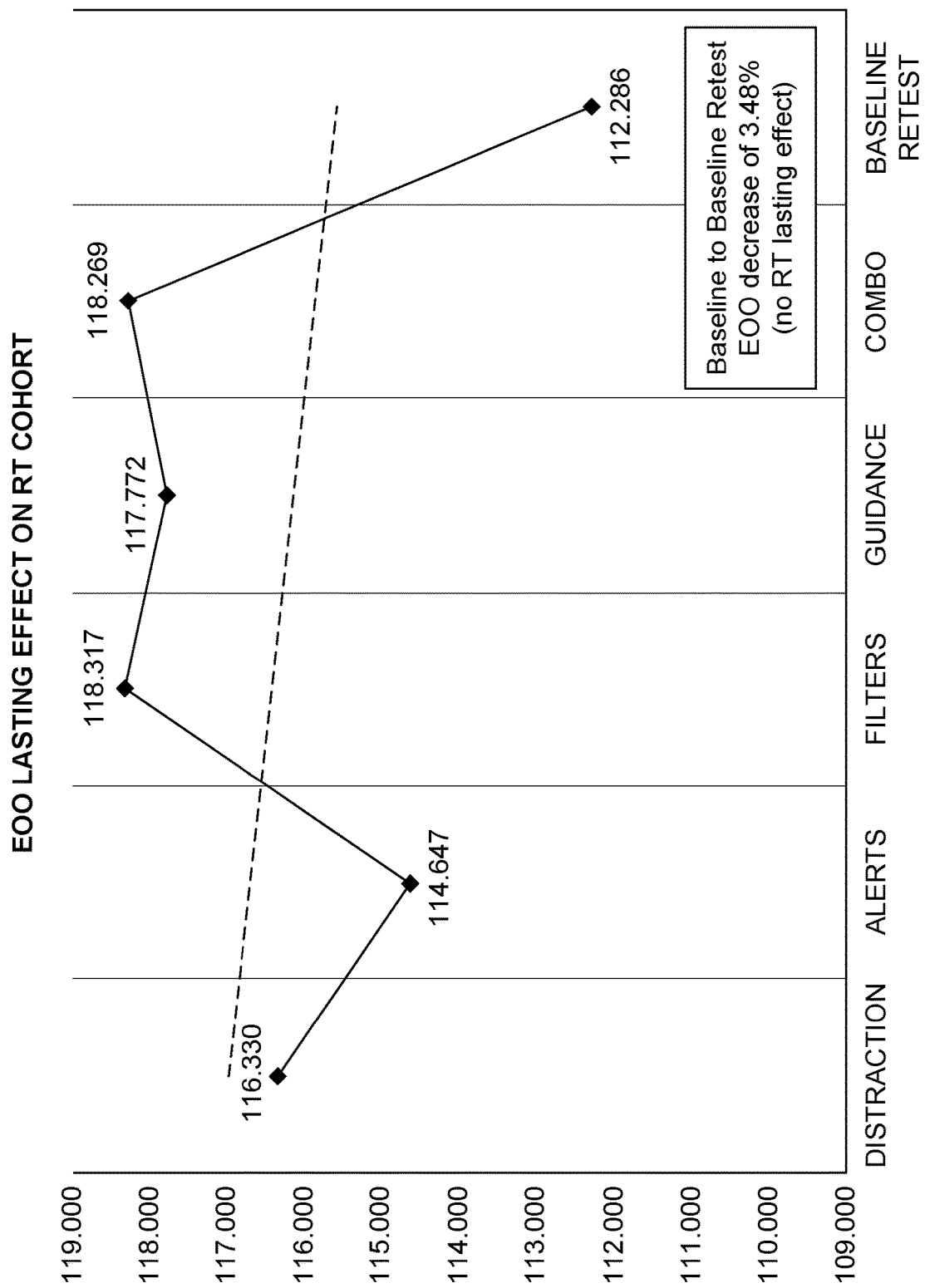

In general, response times for the entire cohort increased when participants experienced exposure to interventional assistance, but not from baseline to baseline-retest (which remained relatively flat at −0.20%; FIGS. 13A to 13C). Regardless of counterbalancing trials and their internal randomization, the cohort's initial reduced and eventually improved EOO accuracy occurred because of increased/slowing RT (e.g., 5.16% increase from Baseline to Filter intervention). Again, this slowing in RT is a desired effect from the intervention, as is explained earlier in the EOC section. It is worth mentioning that unlike Errors of Commission, there was insignificant lasting effect of RT (resulting in 30.48% faster responses once interventions ceased).

EOO response times resembled EOC for autistic participants; in that, both were faster than neurotypical controls, due in part to previously mentioned neuronal processing and responsivity. Thus, autistic participants experienced an RT increase of 9.28% (i.e., a desired slowing from onset of distraction to filters intervention), while neurotypical counterparts produced an undesirable decrease in RT (speeding up) of nearly one percent (4.44%) for the identical intervention.

Figure 14A:
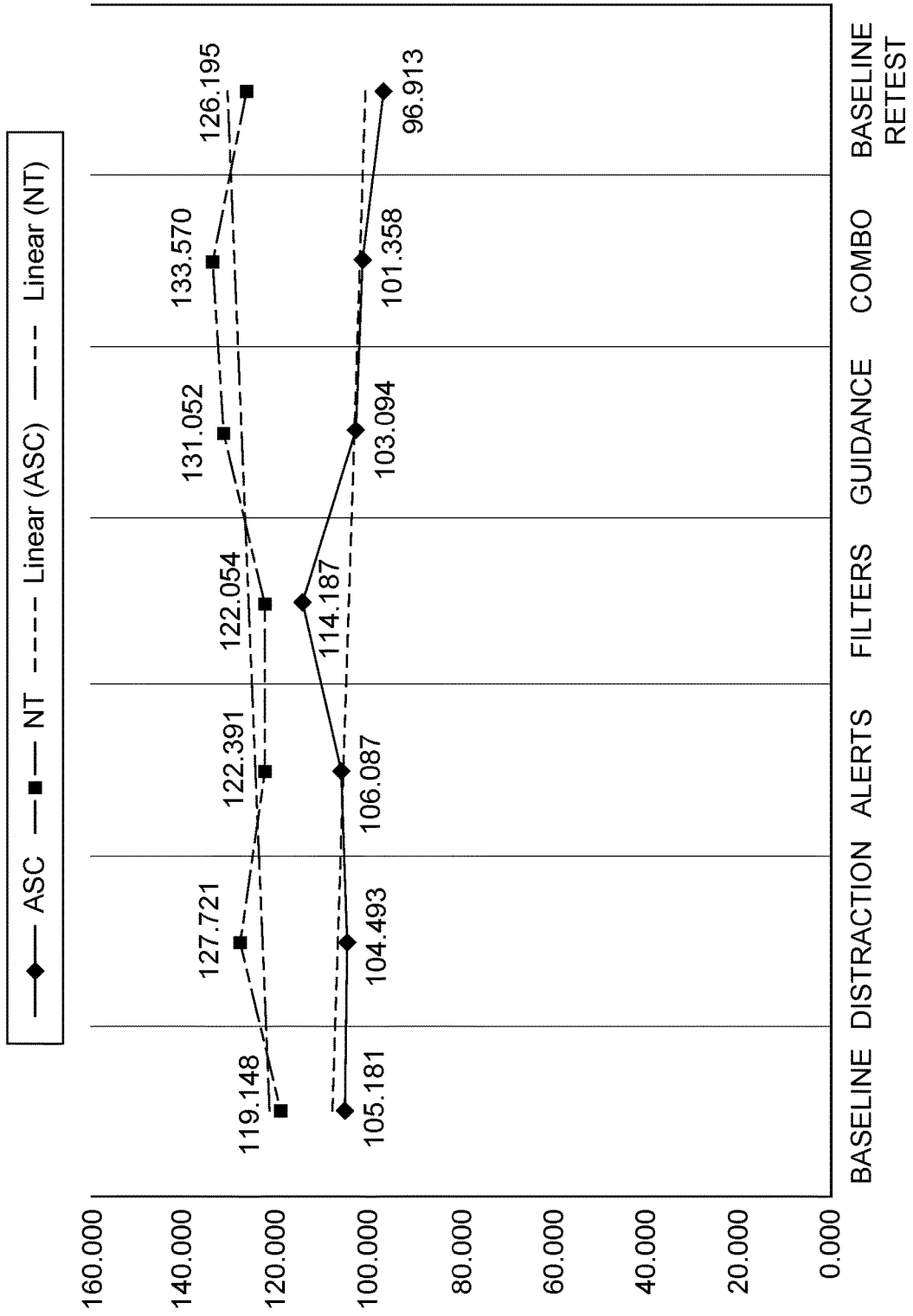
FIGS. 14A to 14C are graphical representations of EOO grouped by study participants.
Figure 14B:
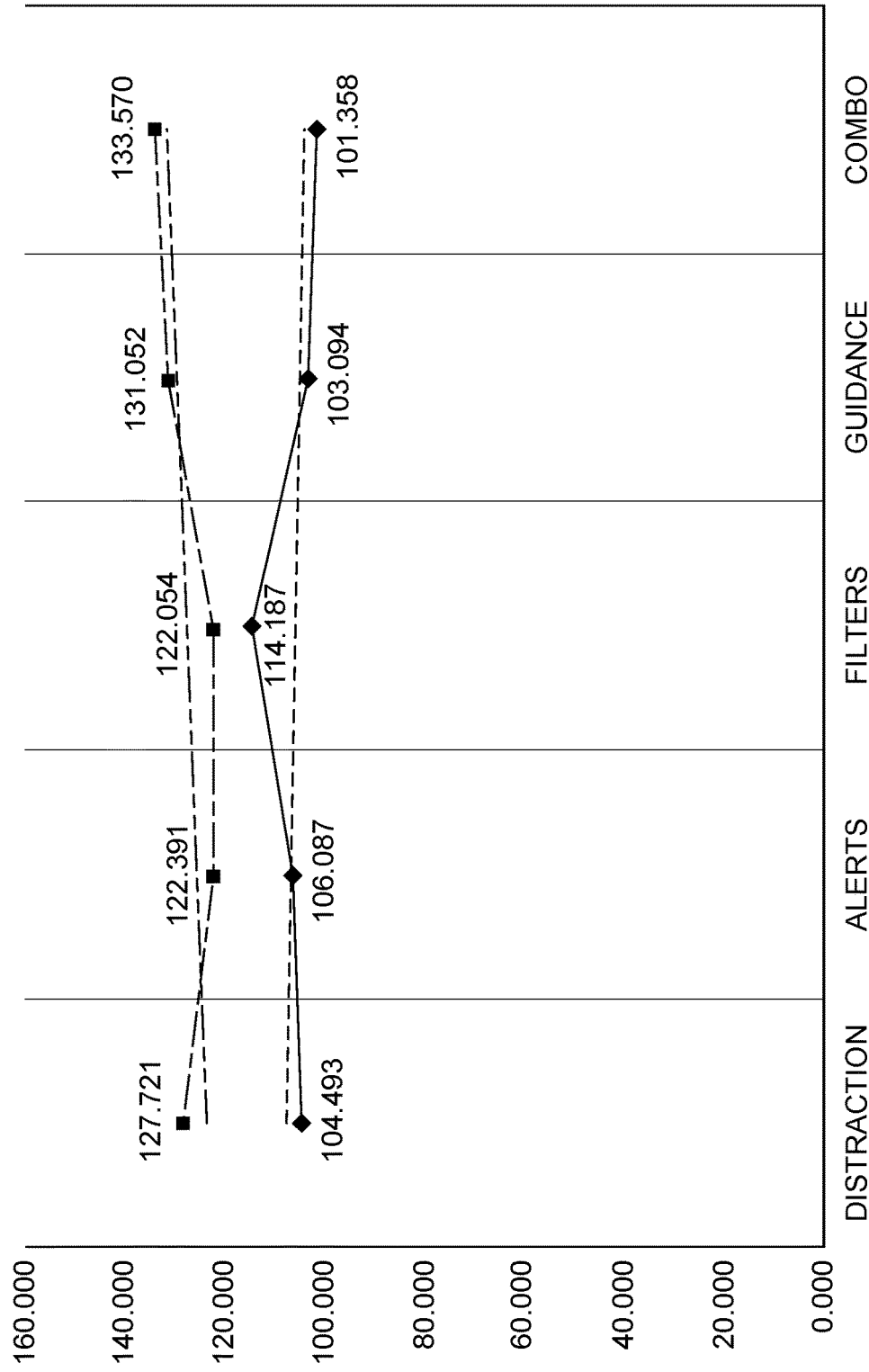
Figure 14C:
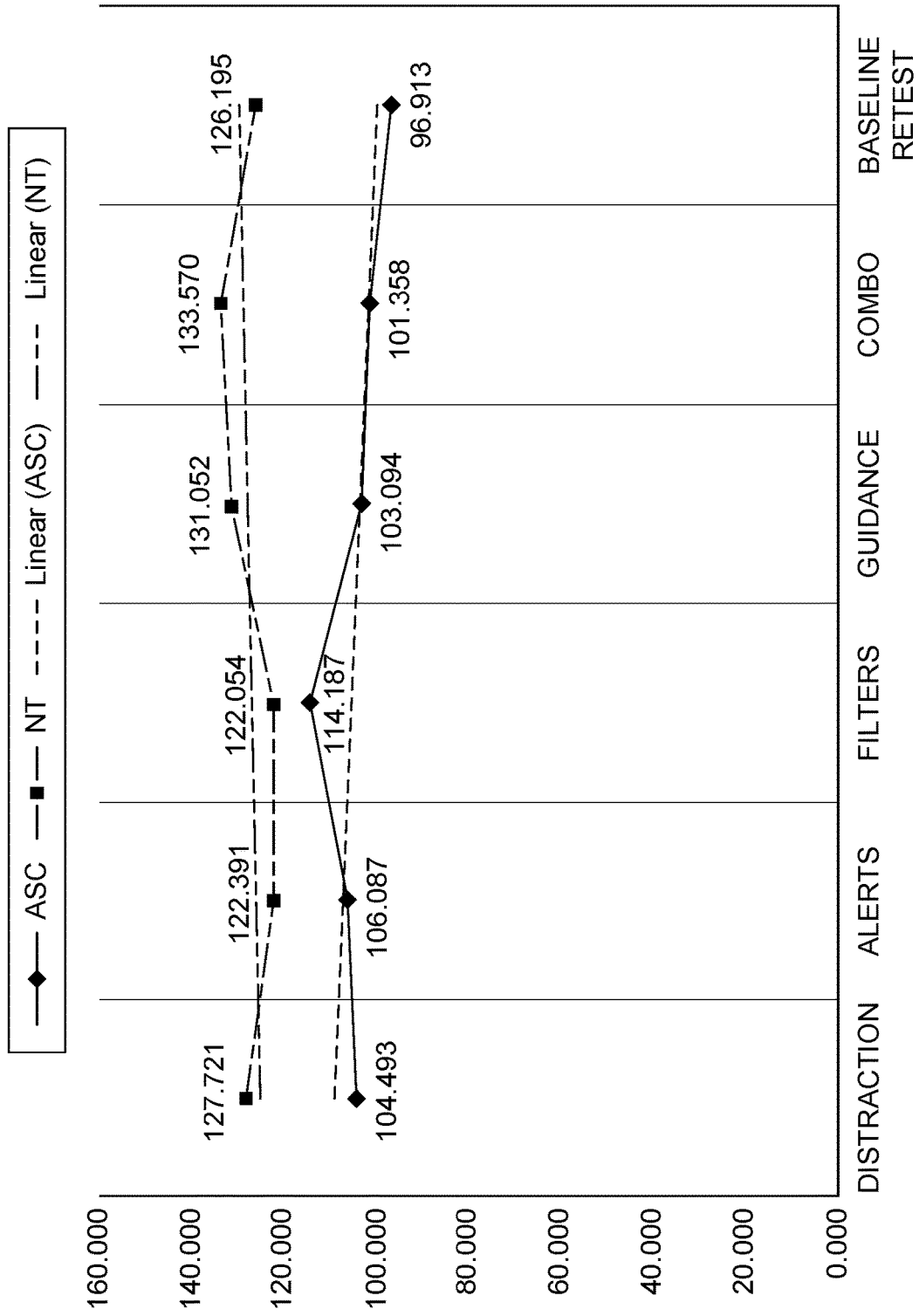

In comparison to EOC RT, neurotypical results are slightly faster (poorer), for e.g., EOC vs. EOO yielded 126.94 ms to 122.05 ms. Considerably more favorable results occurred for ASC participants (e.g., EOC vs. EOO yielded 91.02 ms to 114.19 ms). Contrastingly, RTs' lasting effect on performance observed as a reduction (speeding up) for ASC (7.25%) and a relative flattening, albeit a slight reduction (1.2%) for NT participants. These results are shown in FIGS. 14A to 14C.

RTs also effect Errors of Omission, when comparing autistic and non-autistic groups. There is a lessening of EOO (though these still produce inaccuracies) among neurodiverse participants (−15.12%). Similarly, an increase in accuracy (less EOOs) are exhibited among neurotypical participants. Unsurprisingly, faster RT (4.44% in the case of NT participants from distraction to filter) did, in fact, create more errors (15.09%). As would also be expected, slower RTs among autistic participants (9.28%) resulted in fewer EOOs (15.12%). Curiously, both groups responded oppositely to similar intervention (by way of RTs), and by equal and opposite magnitudes in accuracy with NTs (not ASC participants) experiencing greater errors.

This seem implausible; but, when regarding the entirety of data (i.e., baseline to baseline-retest) for study participants, the RT and EOO curves are indeed inversely proportional. Longer RT produces, as expected, fewer EOO. Less correlated, however, are neurotypical RT. Higher (desirable) NT RTs produce fewer errors (also desired) under filter intervention. However, greater RTs with guidance produce more EOOs (undesirable). Thus, and depending upon the group, longer RT have a diminishing return on accuracy. Where Errors of Commission better correlate with response time variance, Errors of Omission do not correlate well to RT.

Even though there is an improvement among autistic participants bearing greater accuracy, this occurs through an unusual lessening of EGG response times. Greater accuracy (29.07%) and improvement from distraction onset to guidance intervention occurs with less RT slowing. Additional deceleration (9.28%) from distraction to filtering produces more inaccuracies (15.12%). Non-autistic participants accuracy performs as expected; that is, an increase from −4.4% to −1.39% (e.g., a slowing of RT) produces an 8.5% increase in accuracy (15.09% to 23.59%). These results are shown in Tables 11A and 11B:

TABLE 11A

Slower (ASC) vs. Faster (NT)
Response Times Effect on Accuracy

| EOO (with Filter intervention for both ASC and NT) | Response Times Increase | Accuracy Increase |
|---|---|---|
| ASC | 9.28% | (−15.12)% |
| NT | (−4.44%) | 15.09% |

TABLE 11B

Slower (ASC and NT)
Response Times Effect on Accuracy

| EOO (with Guidance intervention) | Response Times Increase | Accuracy Increase |
|---|---|---|
| ASC | 1.24% | 29.07% |
| NT | (−1.39)% | 23.59% |

As presented, the correlation between speeding and slowing RTs (and its effect on the accuracy of experimental and control groups) is not accidental for EOC. Contrastingly, there is a divergence in EOO scores. Evidence of reverse RT effect on accuracy does occur; that is, faster RT don't always produce greater inaccuracy.

Figure 15A:
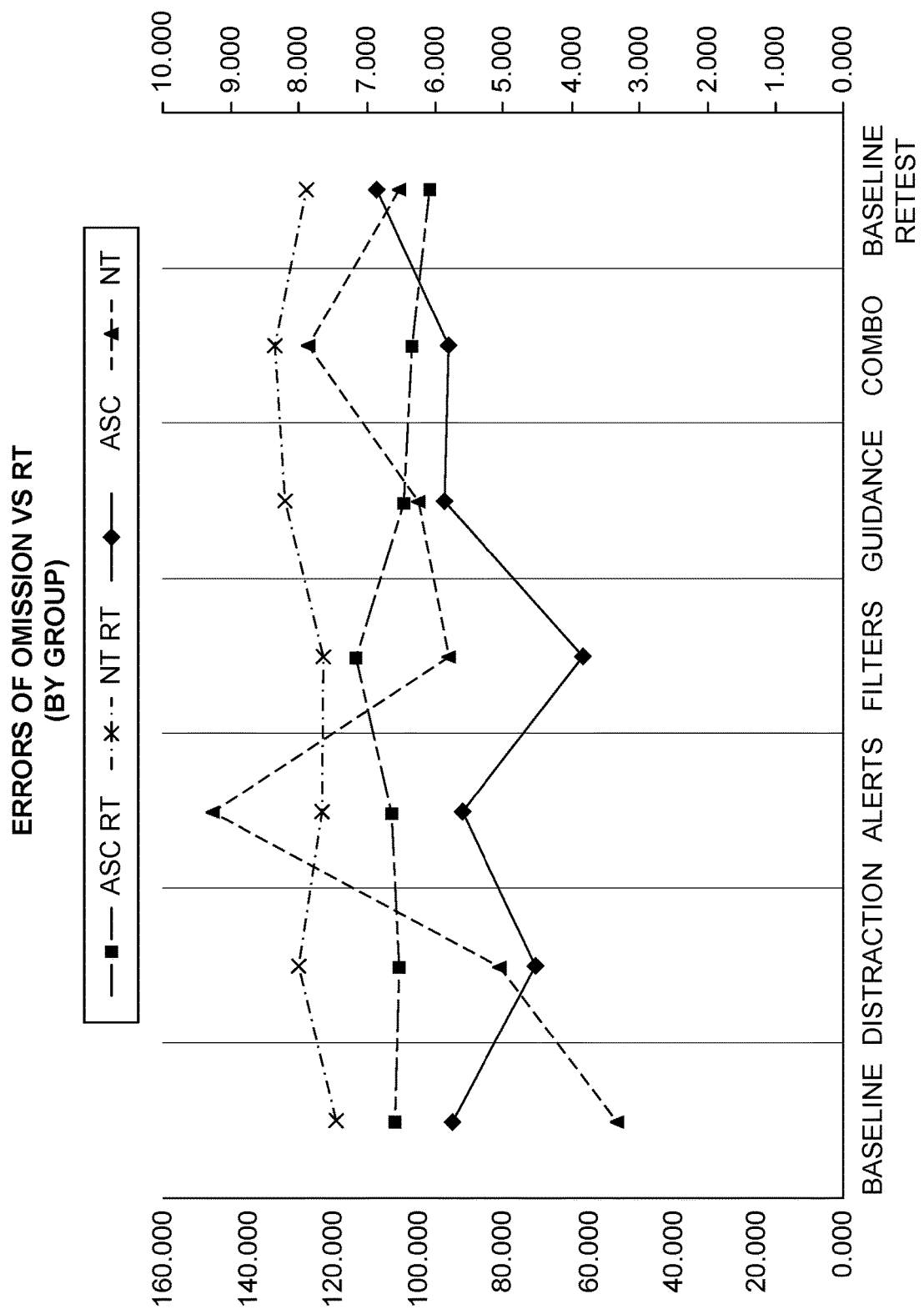
FIGS. 15A to 15C are graphical representations of EOO vs RT grouped by study participants.
Figure 15B:
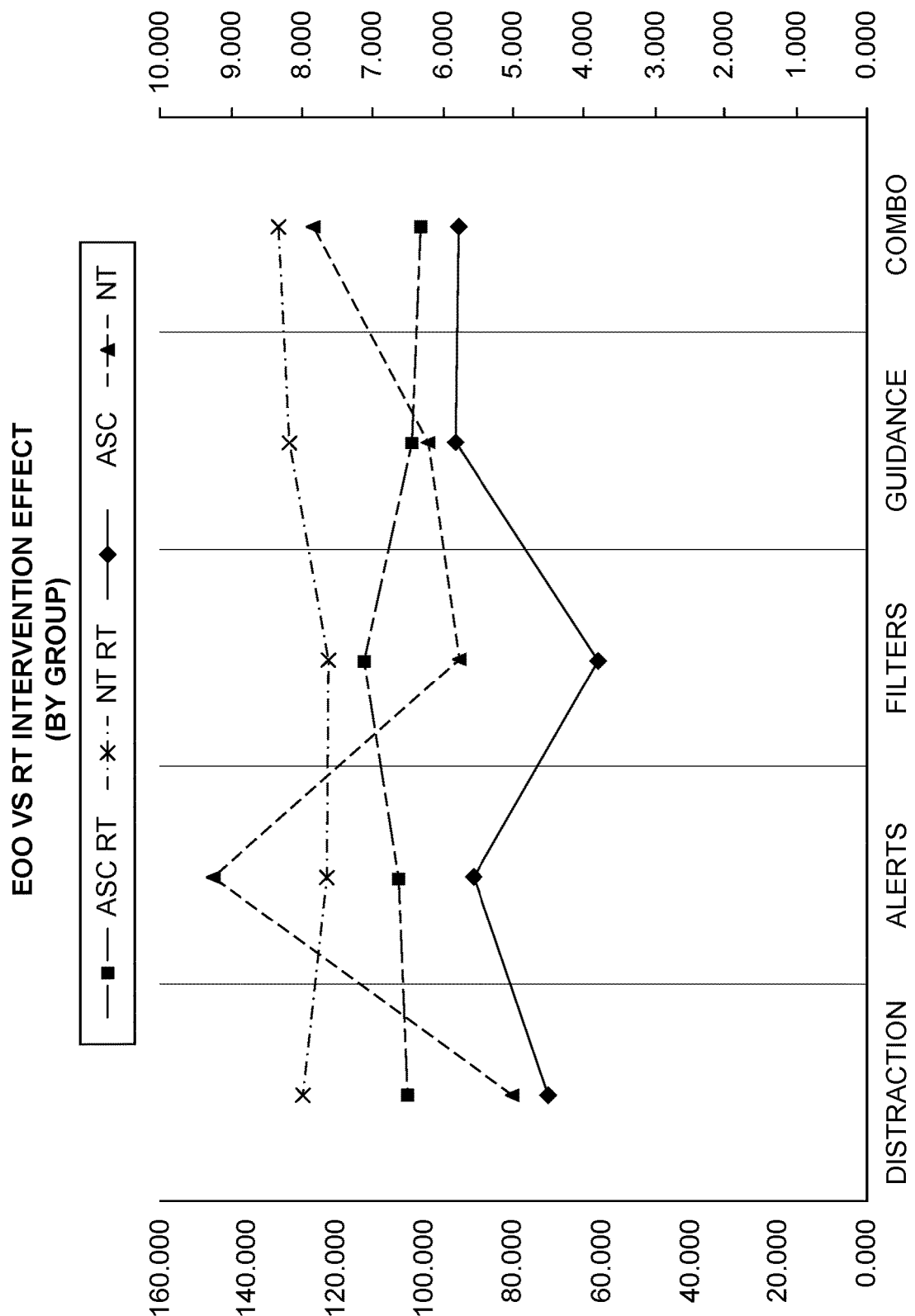
Figure 15C:
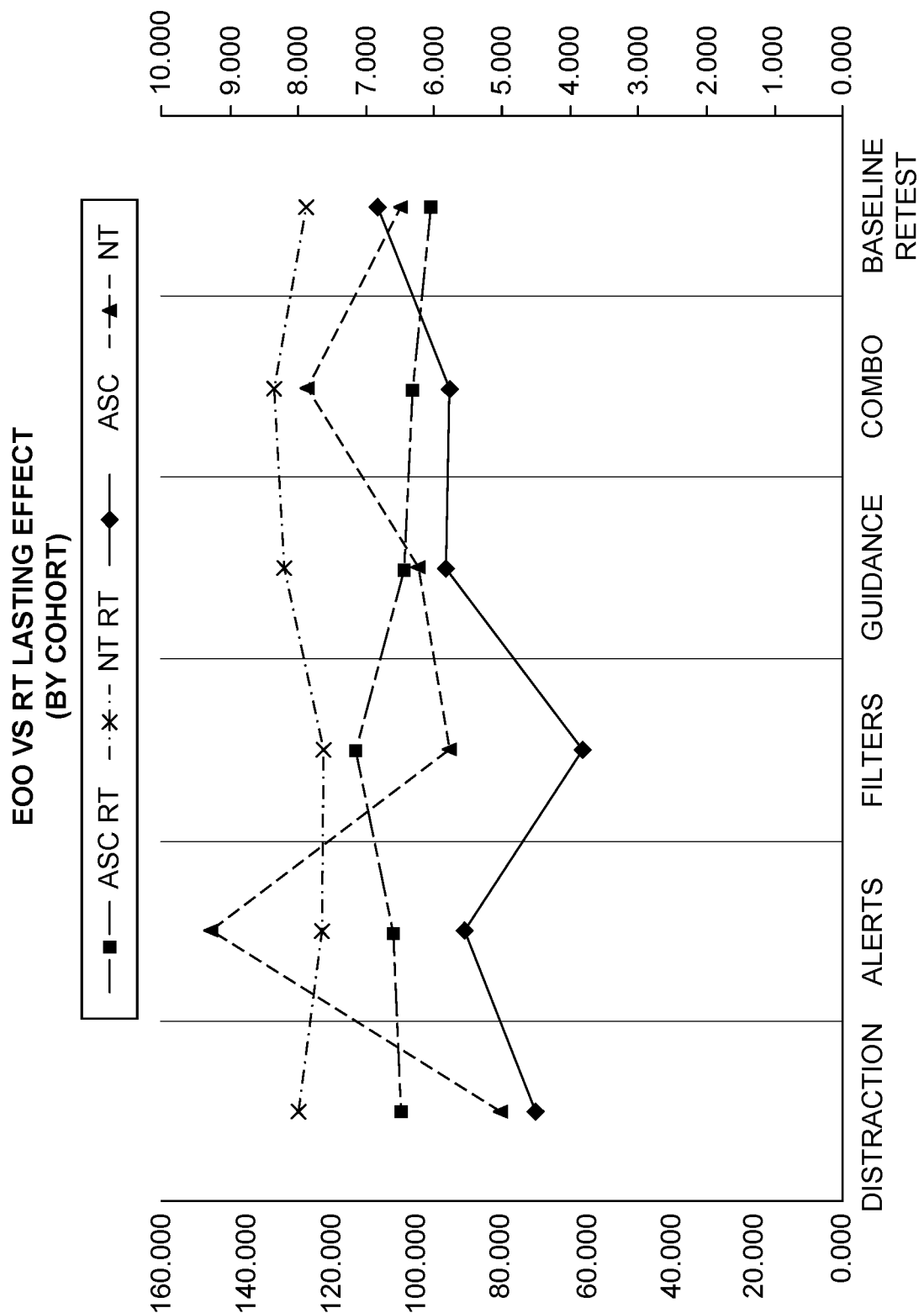

In the previous table, autistic response times that increased 9.28% resulted in a negative accuracy increase (e.g., inaccuracy). However, a speeding up (or reduction of response times to 1.24%) produced greater accuracy (29.07%). This unexpected autistic divergence is not exhibited in neurotypical EOO. The increase in speed (−4.44%) produces a lower accuracy of 15.09% errors, while a slowing to 1.39% (an increase in speed) produces expected and higher accuracy (23.59%). These results are shown in FIGS. 15A to 15C.

The long-lasting effect of fewer errors is absent (e.g., both ASC and NT see increased EOC by 51.16% and 29.25%, respectively) while RT accelerated 7.58 ms for autistic and 1.53 ms for non-autistic participants. While increased errors are expected when RT is faster, this is in direct contrast to EOC lasting effect. Put simply, just as RT errors of omission does correlate well to EOC, the lasting effect exhibited on EOO performance/accuracy does not hold true for EOO.

Like EOC RT, EOO responses for autistic participants response remain both narrow and consistently faster than their more variable and neurotypical counterparts. And while reduced errors of omission (improved performance) occurs across autistic participants, there is less variability in this improvement, while neurotypical participants don't necessarily produce fewer errors. This is in stark contrast to EOC data. These results are shown in FIGS. 15A to 15C.

In summary, unlike the identical cohort and within subjects/groups that experienced a performance increase (e.g., fewer errors of commission), errors of omission were not equally reduced from the onset of a sensory distraction to assistive technology. While a 15.16% reduction in EOO occurred for autistic participants (from distraction onset to filter intervention), no reduction occurred for any interventional application among neurotypical participants.

The combined effect on the entire cohort also proved unremarkable from an EOO improvement standpoint. Again, only the autistic (experimental) group experienced benefits. It's worth mentioning that modulating the intervention to other forms (e.g., alters, guidance and combinations) had no appreciable improvement for neurodiverse participants. Only filter intervention proved assistive. Lasting effects of performance improvement eschewed the entire cohort as there were 10.10% more errors of omission. The same remained consistent for experimental and control groups once interventions were suspended (e.g., 51.16% and 29.25% increase in EOO for ASC and NT, respectively).

Reaction times increased for the entire cohort when assistive technologies were invoked. By slowing down, participants enable and experience greater mindfulness which yields increased performance. From baseline to filter interventions, ASC participants averaged a 9.28% slowing in RT and from the onset of distraction to alerts, the slowing was 1.535%. Neurotypical participants undesirably sped up 4.44% under the same filter interventions but managed to slow down for both guidance (2.61%) and combination interventions (4.58%).

When removing entire cohort interventions of any kind and from baseline to baseline-retesting, RT sped up (decreased) by 3.48%. Thus, there was no significant lasting effect on EOO RT.

Similarly, and for both experimental to control groups, autistic and non-autistic participants experienced decreasing RTs and no significant lasting effect on EOO. ASC RTs sped up 7.25% whilst NT RTs sped up 1.20%.

As alluded to above, the PPI study examined issues and connections among three variables: sensory (sensitivity), mental health (anxiety and fatigue), and distractibility (attention). The PPI study was used to develop a sensitivity mental health distractibility model, depicted by FIG. 26, designating how anxiety and fatigue can mediate sensory sensitivity and distractibility, within both autistic and non-autistic diagnostic groups. The model of FIG. 26 links sensory cues (e.g., labeled #1 that includes an individual's hyper, hypo- and sensory-seeking characteristics) to mental health mediators (e.g., labeled #2 that describes an individual's anxiety and/or fatigue) to distractibility (e.g., labeled #3 that explains an individual's capacity to focus/maintain attention). From an ordering standpoint, the model extends sensory cues through mental health characteristics that can further modulate an individual's attentional reactivity, versus a straight line leading from cue to distractibility alone. While sensitivity has been previously hypothesized to disrupt top-down and bottom-up attention, the model of FIG.

26 embodies a new and lateral relationship more fully depicting an autistic individual's sensitivity and attention processing.

Figure 27:
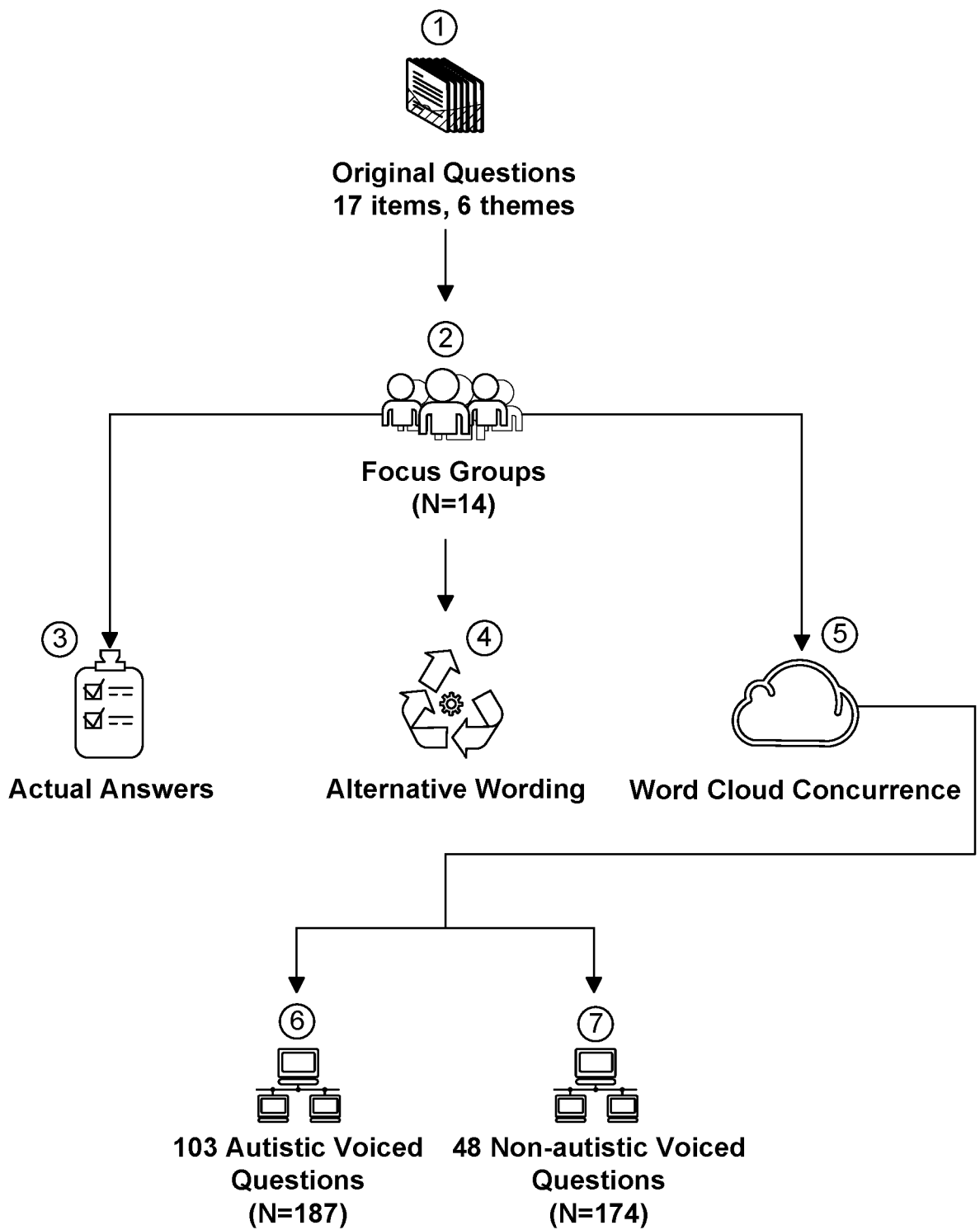
FIG. 27 is a flowchart depicting a design/method of the PPI study described herein.

FIG. 27 is a flowchart depicting the design/method of the PPI study discussed above. The PPI study was implemented in two parts. The first phase consisted of five autistic-only (14 adults, 18-54-year-old) online focus groups to better understand daily experiences relating to sensory sensitivity (FIG. 27, Item #2). The focus groups examined how sensory sensitivity impacted both attention and mental health across three themes: (i) lived experience in adult contexts of higher education institutions, employment, and social venues; (ii) technology tolerance, and digital mediations that can help autistic individuals in adverse sensory environments; and (iii) language that was relevant, easy to understand, and autism-friendly for the Phase 2 questionnaire with a larger group of participants.

As depicted by FIG. 27, Item #6 and #7, the second phase involved an online questionnaire of both autistic (N=187) and non-autistic participants (N=174). Both groups answered questions about their own sensory-sensitivity (visual, auditory, and physiological), focus (distractibility), and mental health (anxiety and fatigue), and—in the case of the autistic-only group—questions about their interest, personal desire, and tolerance of assistive technologies. The questionnaire design provided for diversity in lived experiences by allowing opportunities for open-ended responses, in addition to multiple choice questions.

Table 12 shows the demographics of the participants in the first phase of the PPI study.

TABLE 12

| Feature | Autistic (N = 14) |
|---|---|
| Sex | |
| Female | 7 |
| Male | 6 |
| Non-binary | 1 |
| Age | |
| 18-20 | 7 |
| 21-29 | 2 |
| 31-39 | 5 |
| Location | |
| UK | 8 |
| US | 6 |

Participants were recruited through opportunity sampling using both university databases in the UK and US, combined with worldwide social media. All individuals identified themselves as autistic and/or indicated they possessed a form diagnosis. Participants ages 17-38 years (N=14, female=7; non-binary=1) participated in one of five scheduled focus groups, each with a minimum of two and a maximum of four people. Each hour-long online, focus group utilized on screen presentations to guide discussions, which helped delve into participants' lived experience about sensory sensitivity, technology, attention, and mental health. A collection of more than 100 questions was summarized and combined into seventeen items and arranged across six overarching topics (FIG. 27, Item #1) depicted by Table 13.

TABLE 13

| Themes and questions |
|---|
| What distracts you more: auditory or visual cues?<br>If you think about sensitivity and its impact on you, how has this affected your performance on the job, and your autonomy, or your quality of life?<br>Theme 1: Sensitivity/Impact |
| Q.1. What type of sensitivity, distraction, anxiety or focusing issues have you experienced lately or throughout your life?<br>Q.2. How have these affected your performance, autonomy, quality of life, etc.?<br>Theme 2: Anxiety/Fatigue |
| Q.3. Are you likely to become anxious/fatigued if you experience sensitive stimuli like sounds, visuals, etc.?<br>Q.4. How does this affect your ability to focus, complete tasks, enjoy hobbies, affect you physically, etc?<br>Theme 3: Over-sensitivity |
| Q.5. Would you describe yourself as over-sensitive, under-sensitive or sensory seeking when it comes to sounds, visuals, etc.?<br>Q.6. How are you at dealing with interruptions, staying focussed, or working in distracting environments?<br>Q.7. What opinions do you have about distraction, anxiety, fatigue, and attention?<br>Theme 4: Technology and Devices |
| Q.8. How often do you use Smart Devices like iWatch, FitBit and Smart Clothing?<br>Q.9. What are your thoughts about Smart Devices like Body Cameras, Bone Conduction Headphones and Mobile Phones?<br>Q.10. Do you ever use smart glasses or other wearables?<br>Q.11. Do you enjoy technology?<br>Theme 5: Technology Tolerance |
| Q.12. Would you enjoy learning how wearable devices may help in challenging places with focus, distraction, and anxiety?<br>Q.13. How might a device help if it alerted you to customized stimuli that affects just you?<br>Q.14. Would you be more likely to use a wearable provided that only you controlled when/if you were assisted? |

TABLE 13-continued

Theme 6: Experience

Q.15. How would you describe your sensitivity to distracting sounds and distracting visuals?
Q.16. Do you enjoy distracting places and seek them out?
Q.17. Would you describe yourself as sensitive or unaffected by distracting stimuli?

These questions corresponded to screen presentations and were read aloud by the researcher to prompt participant responses. As participants replied, participants were reminded to express their thoughts and feelings about how technologies can be used to accommodate them in their daily living and assist with activities (FIG. 27, Item #3). For example, when asking Q.6.: about how one "deals with interruptions, staying focused, or working in distracting environments?", the researcher might follow a participant's response by probing more deeply by inquiring: "what type of assistive device might help you resist or contend with the interruptions you just described at your job; or how would the technology help you succeed?".

Participants were encouraged to describe any concerns they had about the wording of questions (e.g., ambiguity, terminology that was difficult to understand, and the relevancy of topics under consideration) and to freely provide alternatively wording using autistic-friendly language (FIG. 27, Item #4). For example, a participant identified Q.3. as unclear because it was too broad; they suggested rephrasing it to a Yes/No question: "Soft sounds make me nervous and tired". Upon concluding the final meeting, all focus group audio/video recordings were transcribed and imported into a qualitative data analysis (QDA) computer software for further analysis. These transcripts were coded—first by arranging responses into the six previous topics, then by participant valence, and finally by any suggested, alternative wordings. The QDA software was programmed to output a list of response words that were mentioned ten or more times, shown by Table 14 below.

TABLE 14

(Commonly used participant expressions in response to focus group questions (occurring at least 10 or more times).

| Chapter 1 Topics (expressions not bolded) | Mixed | Negative | Neutral | Positive | Total |
|---|---|---|---|---|---|
| Sensitivity/Impact | | | | | |
| Other Venues | 3 | 10 | 1 | 9 | 23 |
| School | 5 | 13 | 1 | 4 | 23 |
| Social | 19 | 34 | 2 | 20 | 75 |
| Work | 1 | 18 | 4 | 11 | 34 |
| Anxiety/Fatigue | | | | | |
| Anxiety | 9 | 36 | 2 | 9 | 56 |
| Insomnia | 2 | 7 | 1 | 2 | 12 |
| Over-sensitivity | | | | | |
| Distraction | 2 | 12 | 0 | 0 | 14 |
| Focus | 4 | 11 | 1 | 2 | 18 |
| Interruptions | 1 | 20 | 1 | 0 | 22 |
| Job performance | 0 | 10 | 1 | 1 | 12 |
| Networking and Socialization | 1 | 15 | 0 | 1 | 17 |
| Sensitivity and aging | 2 | 8 | 0 | 2 | 12 |
| Technology and Devices | | | | | |
| Light hyposensitivity | 0 | 4 | 0 | 6 | 10 |
| Light sensitivity | 1 | 15 | 1 | 4 | 21 |
| Sensory seeking | 10 | 11 | 3 | 13 | 37 |
| Sound sensitivity | 9 | 42 | 2 | 8 | 61 |
| Technology Tolerance | | | | | |
| Non-tolerance | 2 | 10 | 0 | 2 | 14 |
| Tolerance | 4 | 8 | 1 | 17 | 30 |
| Experience | | | | | |
| Alert | 2 | 5 | 1 | 26 | 34 |
| Filter | 0 | 2 | 0 | 10 | 12 |
| Guidance | 0 | 4 | 0 | 20 | 24 |
| Device interest | 1 | 2 | 1 | 18 | 22 |

The twenty-two response words were arranged along with their counts into the six, original topics, which permitted examining the existence, prominence, and word relation to sensory, attention, technology, and mental health issues.

As depicted by Table 14, prominent words were split into one of four valence categories, which illustrated how participants expressed concern of these issues within the thematic context and of the questions asked of them. For example, a participant may have described their 'positive' interest in using a technology to help overcome anxiety, or they expressed neither 'positive' nor 'negative' feelings (i.e., 'neutral') about light sensitivity, etc. Higher valence counts (totaling 10 or more) were judged to be more important than lower counts. These counts were used to develop phase 2 PPI questions, further discussed below.

Suggested modifications to wording of questions was studied, and the QDA computer software was used to output a list of alternative words depicted by Table 15.

TABLE 15

(Autistic-friendly, alternative words used to create Phase 2 questionnaire).

| Alternative Word | Count | Weighted % |
|---|---|---|
| people | 102 | 2.34% |
| things | 101 | 2.32% |
| distractions | 87 | 2.00% |
| help | 65 | 1.49% |
| lights | 65 | 1.49% |
| anxiety | 58 | 1.33% |
| noises | 57 | 1.31% |
| focus | 48 | 1.10% |
| places | 47 | 1.08% |
| sensitive | 46 | 1.06% |
| technology | 43 | 0.99% |
| time | 43 | 0.99% |
| feel | 40 | 0.92% |
| anxious | 39 | 0.90% |
| loud | 39 | 0.90% |
| bother | 35 | 0.80% |
| music | 33 | 0.76% |
| hear | 28 | 0.64% |
| sensory | 28 | 0.64% |
| environments | 27 | 0.62% |
| device | 27 | 0.62% |
| interruptions | 27 | 0.62% |
| sleeping | 25 | 0.57% |
| happen | 24 | 0.55% |
| talk | 24 | 0.55% |
| glasses | 22 | 0.51% |
| understand | 22 | 0.51% |
| heard | 22 | 0.51% |
| control | 21 | 0.48% |
| look | 21 | 0.48% |
| affect | 19 | 0.44% |
| alert | 18 | 0.41% |
| seeking | 18 | 0.41% |
| cause | 17 | 0.39% |
| difficult | 17 | 0.39% |
| room | 17 | 0.39% |
| visual | 17 | 0.39% |
| social | 17 | 0.39% |
| situation | 16 | 0.37% |
| bright | 16 | 0.37% |
| annoying | 15 | 0.34% |
| watches | 15 | 0.34% |
| body | 15 | 0.34% |
| different | 15 | 0.34% |
| wearable | 15 | 0.34% |
| filter | 14 | 0.32% |

Figure 28:
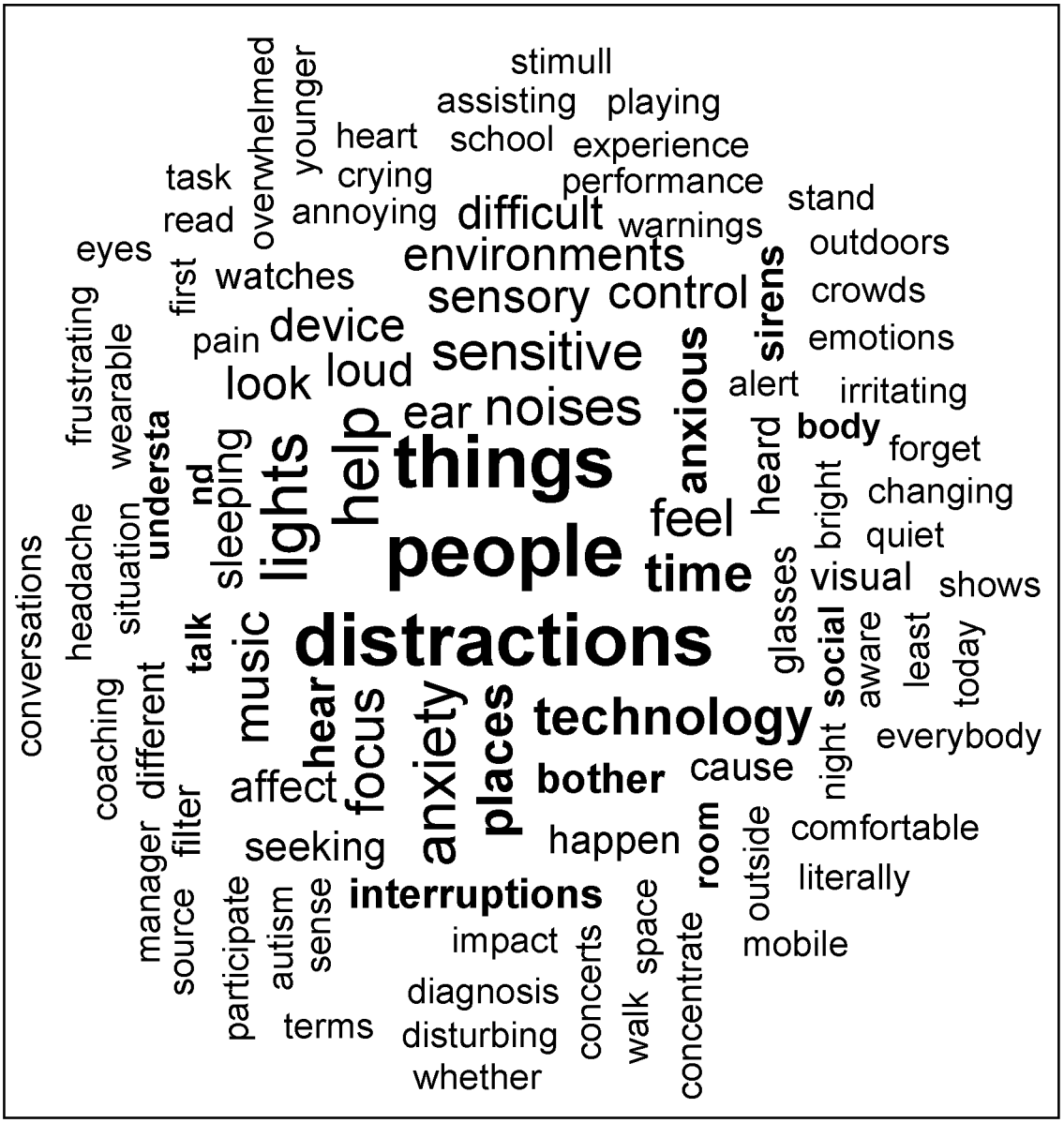
FIG. 28 depicts a word cloud derived from alternative, autistic-voiced expressions during the PPI study described herein.

Forty-six items ranked by word count and weighting (i.e., individual word count divided by the total count of all alternatives) were sorted. Table 15 was used to reword 79 of the original 103 questions by replacing troublesome words with alternatives suggested by participants. Question modifications were also based upon a visualization report (FIG. 27, Item #5; and FIG. 28).

At the conclusion of the final focus group, a word cloud depicting autistic-voiced expressions was created using data from Table 15. The word cloud is depicted by FIG. 28. The participants were sent the word cloud to gauge their satisfaction with alternative words and received unanimous approval (both written email reply and/or follow-on internet chat). This concurrence was used to help select which questions would be re-voiced to reflect autistic alternative wording. For example, participants mentioned that:

Centrally located, larger, and darker colored word cloud terms would be appropriate to compose phase 2 questions using alternative like "things", "people", and "distractions".

Items just outside the cloud's midpoint would be suitable when questioning sensory cues and reactivity, including "needing help", "feeling anxious", and "being bothered".

Words near the cloud's edge were appropriate to compose questions about technology, including "wearable", "coaching", and "assisting". These were supportive when questioning outcomes about "comfort[able]", "participat[ion]", and "performance".

Table 16 shows the demographics, including gender, age, and education level, of the participants in the second phase of the PPI study.

TABLE 16

|  | Autistic (N = 187) | Non-autistic (N = 174) |
|---|---|---|
| Gender |  |  |
| Male | 107 | 86 |
| Female | 75 | 85 |
| Non-binary | 3 | 3 |
| Age |  |  |
| 18-20 | 24 | 22 |
| 21-29 | 42 | 37 |
| 31-39 | 111 | 108 |
| 41-49 | 10 | 7 |
| Education level |  |  |
| University without degree | 33 | 53 |
| University with degree | 132 | 87 |
| Graduate school | 22 | 34 |

Participants were recruited similarly to focus group individuals using university websites and social media. Non-autistic individuals were recruited and well-matched to ensure compatibility with their neurodiverse counterparts. Both group's eligibility criteria included ages between 18-49 and English-language proficiency. Non-autistic participants were specifically required not to self-identify or possess an autism diagnosis. After eliminations, a total sample of N=361 individuals were analyzed (i.e., 187 autistic and 174 non-autistic participants).

The online questionnaire was designed to expand the initial focus group inquiry beyond word usage and their alternations to data collection that described sensory patterns, technology experiences, and desire for accommodations—all described using genuine, clear, and relatable language by a larger sample of respondents who might share experiences identified by the smaller group of original participants.

A majority of phase two questions were derived from various sources including the UCL Student Mental Health Survey (SENSE; McCloud et al., 2019), the Stanislaus State Concentration Questionnaire (CQ, 2019), the CogniFit Online Cognitive Assessment Battery for Concentration (CAB-AT, 2018), the Cognifit Cognitive Assessment for ADHD Research (CAB-ADHD, 2018), and those from semi-structured interviews developed by Ashburner and colleagues (2013). These questions were supplemented and/or fine-tuned by the researchers.

Using alternative words, 79 of the original 103 questions that were deployed online to autistic only participants (FIG. 27, Item #6) were modified. A second questionnaire was deployed using the same wording but for non-autistic participants (FIG. 27, Item #7). 55 of the original 103 questions that focused on technology usage and tolerance were excluded from the non-autistic version, including, for example: "How often do you use a smart watch?"; "I think I would enjoy owning a wearable device that knows my preferences about what I find distracting"; and "I would be interested in learning how a wearable device might help me in environmentally noisy situations", as it was thought that such questions would be less helpful when comparing sensitivity, attention, anxiety, and fatigue characteristics between diagnostic groups. Their removal yielded a 48-item non-autistic questionnaire.

Online demographic responses were imported using QDA software, and examined as follows:

Demographic questions. Education was used as proxy to gauge intelligence levels, to match groups on ability, in deference to autistic heterogeneity (Mottron, 2004), and to avoid collecting intelligence quotient (IQ) data.

Sensory sensitivity variables. Inquiry spanned modalities using three input variables: visual, auditory, and physiological. Unless otherwise specified, a 5-point Likert scale was utilized with responses ranging from strongly disagree (1 point) to strongly agree (5 points). Mean scores were computed and ranged from 1-5 with higher scores indicating greater sensitivity. Sample queries included "At work or at school, I have experienced sensitivity, distractibility or anxiety because of visual reasons (for example: lighting, movements, colours, etc.)" and "I am sensitive to vibrating wearables (for example, a mobile phone, FitBit, iWatch or another notifying device)".

Visual Sensitivity Variable (VSV). Nine questions—derived from Stanislaus State's Concentration Questionnaire (CQ, 2019) and a Cognitive Assessment Battery for Concentration (CAB-AT; Cognifit 2018)—defined motion, light, and other cues having an adverse bearing on one's activities. Sample queries included "I am easily distracted or sensitive to certain environmental sights visions" and "I avoid visually stimulating environments".

Auditory Sensitivity Variable (ASV). Seven questions—derived from the Stanislaus State Concentration Questionnaire (CQ, 2019), the Cognitive Assessment Battery for ADHD Research (CAB-ADHD; Cognifit, 2018), and semi-structured interviews (Ashburner et al., 2013)—described loud, startling, and other cues unfavorably affecting individuals. Examples questions included "I am easily distracted or sensitive to certain environmental sounds (for example, noises, loudness, pitches, conversations)" and "I would describe sounds like humming of lights or refrigerators, fans, heaters or clocks ticking as distracting". Four questions were reverse scored reflecting higher scores that indicating greater sensitivity.

Physiological Sensitivity Variable (PSV). Six questions—derived from the Stanislaus State Concentration Questionnaire (CQ, 2019), and the Cognitive Assessment Battery for ADHD Research (CAB-ADHD; Cognifit, 2018)—related to exocentric effects and egocentric sensations of attention and anxiety. Sample queries include "I do not like being touched" and "I am easily distracted or sensitive to certain physiological feelings of thoughts (for example anxiousness, racing thoughts, ringing in my ears)".

Anxiety Variable (AV). 16 questions—derived from UCL's Student Mental Health Survey (SENSE; McCloud et al., 2019), interviews (Ashburner et al., 2013), a Cognitive Assessment Battery for Concentration (CAB-AT; Cognifit 2018)—described how sounds, sights, and sensations affect anxiety. Questions included "Certain sounds, sights, or stimuli make me feel nervous, anxious, or on edge" and "Nothing really distracts me or makes me anxious". Three questions were reverse scored reflecting higher scores that indicated greater anxiety.

Distractibility Variable (DV). 10 questions—derived from UCL's Student Mental Health Survey (SENSE; McCloud et al., 2019), from the Stanislaus State Concentration Questionnaire (CQ, 2019), and the Cognitive Assessment Battery for ADHD Research (CAB-ADHD; Cognifit, 2018), and interviews (Ashburner et al., 2013)—described participant's susceptibility to distraction in daily life. Queries included "I often begin new tasks and leave them uncompleted", and "If interrupted, I can switch back to what I was doing very quickly". Two questions were reverse scored reflecting higher scores indicating susceptibility to distraction.

Autism Spectrum Quotient (AQ-10). 10 questions—derived from the Autism Spectrum Quotient (Allison et al., 2012)—examined only non-autistic individuals who may have undiagnosed and/or milder levels of autistic symptomatology (Baron-Cohen et al., 2001). These measures were used to ensure in-group participant matching and determine if subclinical traits existed in non-diagnosed individuals. The AQ-10 is a subset of the larger 50-item survey and uses a four-point Likert Scale ranging from Definitely Agree to Definitely Disagree across 10 questions. A single point maximum is scored for each answer and totals scores of six or greater indicate concentrations of autistic traits.

Demographic exploration was carried out through descriptive statistics, chi-square, and Mann Whitney-U tests. Matching diagnostic groups and significant differences between individuals were obtained by conducting independent sample t-tests. Serial one-way ANOVA tests revealed significance in anxiety and distractibility differences as they related to demographic features. Tukey post hoc tests confirmed where significances were identified between diagnostic groups. Pearson's correlations established robustness among variables, and linear regressions identified predictive anxiety and distractibility characteristics.

Figure 26:
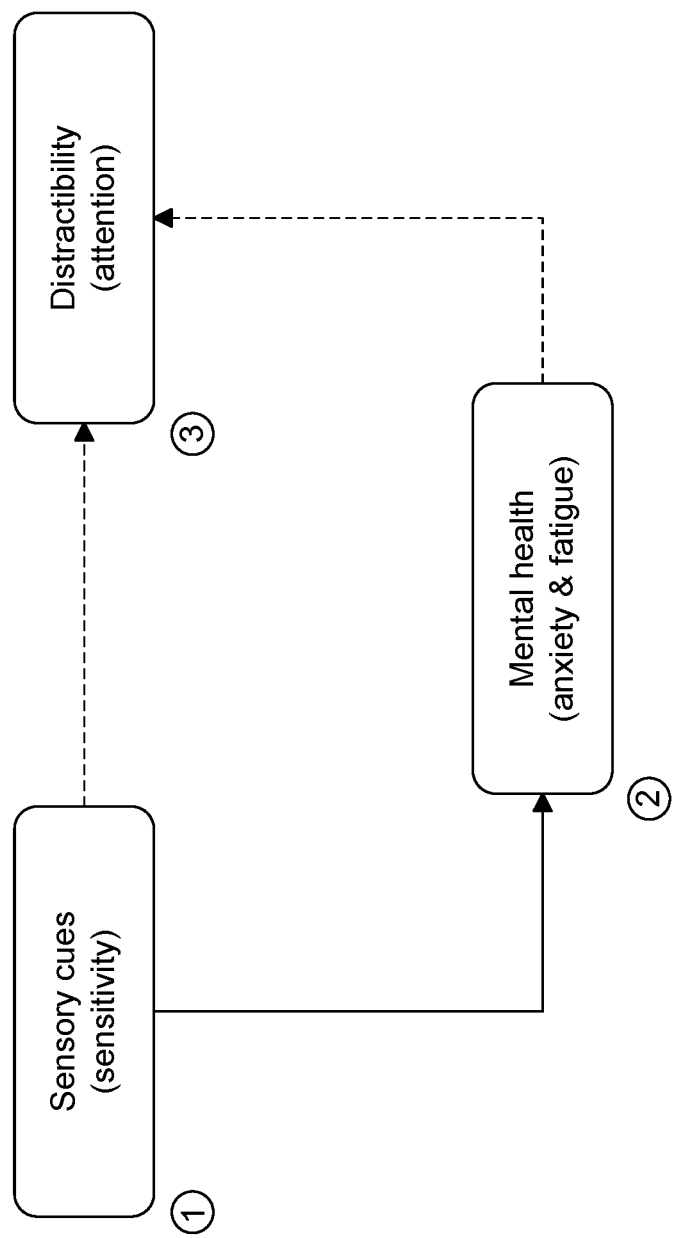
FIG. 26 depicts a sensitivity mental health distractibility model, in accordance with some implementations of the disclosure.

Diagnostic mediation analyses tested the hypothesis connecting anxiety as an intermediary between sensory and distractibility (See FIG. 26). A statistical package was used to carry out analysis evaluating measurement errors, adjusting with bootstrapping techniques (e.g., random sampling with replacement bias-corrected and accelerated 95% confidence intervals; 1000 resamples).

A chi-square test of independence was performed to examine the relationship between gender across diagnostic groups. The relation between these variables was not significant at p<0.05 ($\chi2$=2.946, p=0.229). Mann-Whitney U tests were conducted to determine whether there was a difference in age (U=16213, p=0.948) and education (U=15461.5, p=0.356) across diagnostic groups; neither result was significant at p<0.05.

The mean distribution of anxiety and distractibility scores for diagnostic groups across demographic variable are depicted in FIG. 29, which shows graphs of mean anxiety and distractibility/attention scores. A series of one-way between subjects ANOVA tests were conducted to compare differences in anxiety and distractibility scores across various demographic features. The autistic group revealed a significant effect of age on both anxiety, $F(3,183)$=6.733, and distractibility scores $F(3,183)$=10.856, both at the p<0.001*level.

Post hoc comparisons using the Tukey HSD test indicated that for anxiety, 30-39-year-olds scored significantly higher than 18-21-year-olds (mean difference=0.377, p=0.008), and 40-49-year-olds scored significantly higher than 18-21-year-olds (mean difference=0.830, p<0.001), 22-29-year-olds (mean difference=0.525, p=0.022), and 30-39-year-olds (mean difference=0.453, p=0.042). For distractibility, Post hoc comparisons using the Tukey HSD test indicated that 30-39-year-olds scored significantly higher than both 18-21-year-olds (mean difference=0.468, p<0.001) and 22-29-year-olds (mean difference=0.261, p=0.005), and that 40-49-year-olds scored significantly higher than both 18-21-year-olds (mean difference=0.614, p=0.001) and 22-29-year-olds (mean difference=0.407, p=0.040).

There were no significant differences for non-autistic participants, including those for anxiety scores, $F(3,170)$=1.462, p=0.227, or distractibility scores, $F(3,170)$=2.430, p=0.067, across any age group. However, there was a significant difference for non-autistic participants who exhibited anxiety scores and sex, $F(2,171)$=4.289, p=0.015. Post hoc comparisons using the Tukey HSD test indicated that females scored significantly higher than males (mean difference=2.911, p=0.024); however, there was no significant differences for non-autistic participants' sex on distractibility scores, $F(2,171)$=0.514, p=0.599.

There was a significant difference in anxiety scores for autistic participants between sexes, $F(2,184)$=16.944, p<0.001, with Tukey post hoc tests revealing that non-binary participants scored significantly higher than male (mean difference=1.301, p<0.001) and female participants (mean difference=1.156, p<0.001). For autistic individuals, there were significant differences in distractibility between sexes, $F(2,184)$=6.551, p=0.002. Post hoc distractibility comparisons using the Tukey HSD test indicated that non-binary, autistic participants scored significantly higher than male autistic participants (mean difference=0.702, p=0.002) and female autistic participants (mean difference=0.588. p=0.015).

There was a significant effect from education on autistic individuals for anxiety scores, $F(2,184)$=3.915, p=0.022; however, there was no significance for non-autistic participants, $F(2,171)$=0.148, p=0.863. Post hoc comparisons using the Tukey HSD test indicated that autistic participants who attended graduate school scored significantly higher on anxiety than individuals with an under-graduate degree (mean difference=3.418, p=0.016). There was no significant effect of education on distractibility for autistic participants, $F(2,184)$=2.108, p=0.124; however, there was a significant effect from education on distractibility for non-autistic participants, $F(2,171)$=4.360, p=0.014. Post hoc comparisons using the Tukey HSD test revealed non-autistic individuals without a university degree scored significantly higher in distractibility than those with a degree (mean difference=0.364, p=0.016).

Table 17 shows sensory sensitivity variables and mental health scores and statistics for diagnostic groups, including means scores and between group differences.

TABLE 17

| Sensory and Mental Health Variables | Autistic (N = 187) | Non-autistic (N = 174) | t(df), p |
|---|---|---|---|
| Visual, M (SD, range) | 3.218 (.763, 1.06-4.78) | 2.501 (.918, 0.33-4.39) | t(359) = −8.090, p < .001* |
| Auditory, M (SD, range) | 3.008 (.635, 1.79-5.00) | 3.136 (.912, 0.43-5.00) | t(359) = .0585, p < .559 |
| Physiological, M (SD, range) | 4.213 (.653, 1.83-5.00) | 3.686 (.882, 1.00-5.00) | t(359) = −6.681, p < .001* |
| Anxiety, M (SD, range) | 3.417 (.539, 2.00-4.94) | 3.283 (.731, 1.19-4.75) | t(359) = −1.993, p < .047* |
| Distractibility, M (SD, range) | 3.523 (.464, 2.20-4.80) | 3.427 (.763, 1.30-4.90) | t(359) = −1.443, p < .157 |

*p is significant at .05

The 187 autistic participants demonstrated significantly greater levels of visual, $t(359)$=−8.090, p<0.001, and physiological sensitivity, $t(359)$=−6.681, p<0.001, compared to the 174 non-autistic individuals. Autistic members exhibited significantly greater levels of anxiety, $t(359)$=−1.993, p=0.047; however, in this study there was no significant effect for either auditory sensitivity, $t(359)$=0.585, p=0.559, or distractibility scores, $t(359)$=1.443, p=0.157.

Tables 18 and 19 show sensitivity and outcome variable correlations for non-autistic and autistic participants.

TABLE 18

| (Pearson's correlations for non-autistic participants) | | | | |
|---|---|---|---|---|
| | Visual | Auditory | Physiological | Anxiety | Distractibility |
| Visual | | .605* p < .01 | .544* p < .01 | .678* p < .01 | .522* p < .01 |
| Auditory | | | .511* p < .01 | .602* p < .01 | .435* p < .01 |
| Physiological | | | | .704* p < .01 | .549* p < .01 |

TABLE 18-continued (Pearson's correlations for non-autistic participants)

| | Visual | Auditory | Physiological | Anxiety | Distractibility |
|---|---|---|---|---|---|
| Anxiety | | | | | .587* |
| | | | | | p < .01 |
| Distractibility | | | | | |

*p is significant at .05

TABLE 19

(Pearson's correlations for autistic participants)

| | Visual | Auditory | Physiological | Anxiety | Distractibility |
|---|---|---|---|---|---|
| Visual | | .172 | .526* | .703* | .509* |
| | | p = .18 | p < .01 | p < .01 | p < .01 |
| Auditory | | | .255* | .474* | .416* |
| | | | p < .01 | p < .01 | p < .01 |
| Physiological | | | | .633* | .664* |
| | | | | p < .01 | p < .01 |
| Anxiety | | | | | .798* |
| | | | | | p < .01 |
| Distractibility | | | | | |

*p is significant at .05

As depicted by Tables 18-19, a Pearson correlation coefficient (Bonferroni adjusted) was computed to assess the linear relationship between non-autistic and autistic adults. There was a positive correlation for non-autistic participants indicating significance between each of the sensitivity and the outcome variables (mental health), and all the sensory variables. There was a similar significantly positive correlation for autistic participants between each sensitivity variable and the outcome variables (mental health); however, the relationship between visual and auditory scores failed to reach significance (r=0.172, p=0.180), while the association between auditory and physiology was nominally correlated (r=0.255, p<0.01). Both diagnostic groups exhibited correlations with the outcome variables (i.e., anxiety and fatigue).

Unique predictor variables were modeled on anxiety and attention scores (Tables 20-21). Both autistic and non-autistic visual, auditory, and physiological variables were examined as predictors, and demographic variables were added as covariates. For both diagnoses, education and age were not significant predictors and were excluded from further analysis. Non-binary individuals were excluded due to small sample sizes. Sexes were dummy coded (i.e., 0—Male; 1—Female), and positive beta scores indicated significance between non-autistic females and outcome variables. All sensitivity variables and sexes uniquely predicted non-autistic anxiety; the model accounted for 64.7% of the variance in anxiety scores (F=81.46, p<0.001). Similarly, and for autistic individuals, all sensory variables uniquely predicted anxiety and the model accounted for 76.4% of the variance in anxiety scores (F=112.54, p<0.001). Note that sex did not contribute towards anxiety scores for the autistic group.

TABLE 20

(Model predicting anxiety for non-autistic participants)

| | β | t | P |
|---|---|---|---|
| Visual | .241 | 4.96 | <.001* |
| Auditory | .141 | 2.97 | .003* |

TABLE 20-continued (Model predicting anxiety for non-autistic participants)

| | β | t | P |
|---|---|---|---|
| Physiological | .377 | 7.90 | <.001* |
| Sex | .221 | 3.27 | .001* |

($R^2$ = .647, F = 786.031, p = .0001)

TABLE 21

(Model predicting anxiety for autistic participants)

| | β | t | P |
|---|---|---|---|
| Visual | .377 | 13.15 | <.001* |
| Auditory | .192 | 6.06 | <.001* |
| Physiological | .383 | 7.02 | <.001* |
| Sex | .020 | 5.12 | .606 |

($R^2$ = .764, F = 142.916, p < .0001)

All input variables were entered as predictors of distractibility for both diagnostic groups, in addition to demographic variables. For non-autistic individuals, age and sex did not significantly predict distractibility and was excluded from evaluation. Visual cues, physiological cues, and education significantly predicted attention. Interestingly sound sensitivity did not (p=0.239) (See Table 22). The model explained 40.2% of the non-autistic variance in distractibility scores (F=28.407, p<0.001); and by augmenting the model with anxiety scores, this amount increased by 2%—with and all variables (excluding sound) remaining significant predictors (See Table 23).

TABLE 22

(Model predicting distractibility for non-autistic participants)

| | β | t | P |
|---|---|---|---|
| Visual | .241 | 3.22 | .002* |
| Auditory | .077 | 1.18 | .239 |
| Physiological | .312 | 4.89 | <.001* |
| Education | -.174 | -2.68 | .008* |

($R^2$ = .402, F = 28.407, p < .001)

TABLE 23

(Model predicting distractibility for non-autistic participants (anxiety added))

| | β | t | P |
|---|---|---|---|
| Visual | .138 | 1.96 | .052 |
| Auditory | .036 | .555 | .580 |
| Physiological | .211 | 2.93 | .004* |
| Education | -.174 | -2.73 | .007* |
| Anxiety | .284 | 2.79 | .006* |

($R^2$ = .429, F = 25.2, p < .001)

Visual, sound, and physiological sensitivity were significant predictors of distractibility for autistic diagnoses; however, demographic variables were not significant (See Table 24). The non-autistic model explained 59.2% of the variance in distractibility scores (F=88.52, p<0.001), which increased 9% when including anxiety scores (F=98.645, p<0.001). Note, however, the visual and auditory scores were not significant distractibility once anxiety was included (See Table 25).

TABLE 24

(Model predicting distractibility autistic participants)

|  | β | t | P |
|---|---|---|---|
| Visual | .211 | 6.23 | <.001* |
| Auditory | .183 | 5.09 | <.001* |
| Physiological | .297 | 7.38 | <.001* |

($R^2$ = .592, F = 88.52, p < .001)

TABLE 25

(Model predicting distractibility autistic participants (anxiety added))

|  | β | t | P |
|---|---|---|---|
| Visual | .049 | 1.31 | .193 |
| Auditory | .059 | 1.64 | .103 |
| Physiological | .185 | 4.79 | <.001* |
| Anxiety | .464 | 7.29 | <.001* |

($R^2$ = .684, F = 98.645, p < .001)

Figure 31:
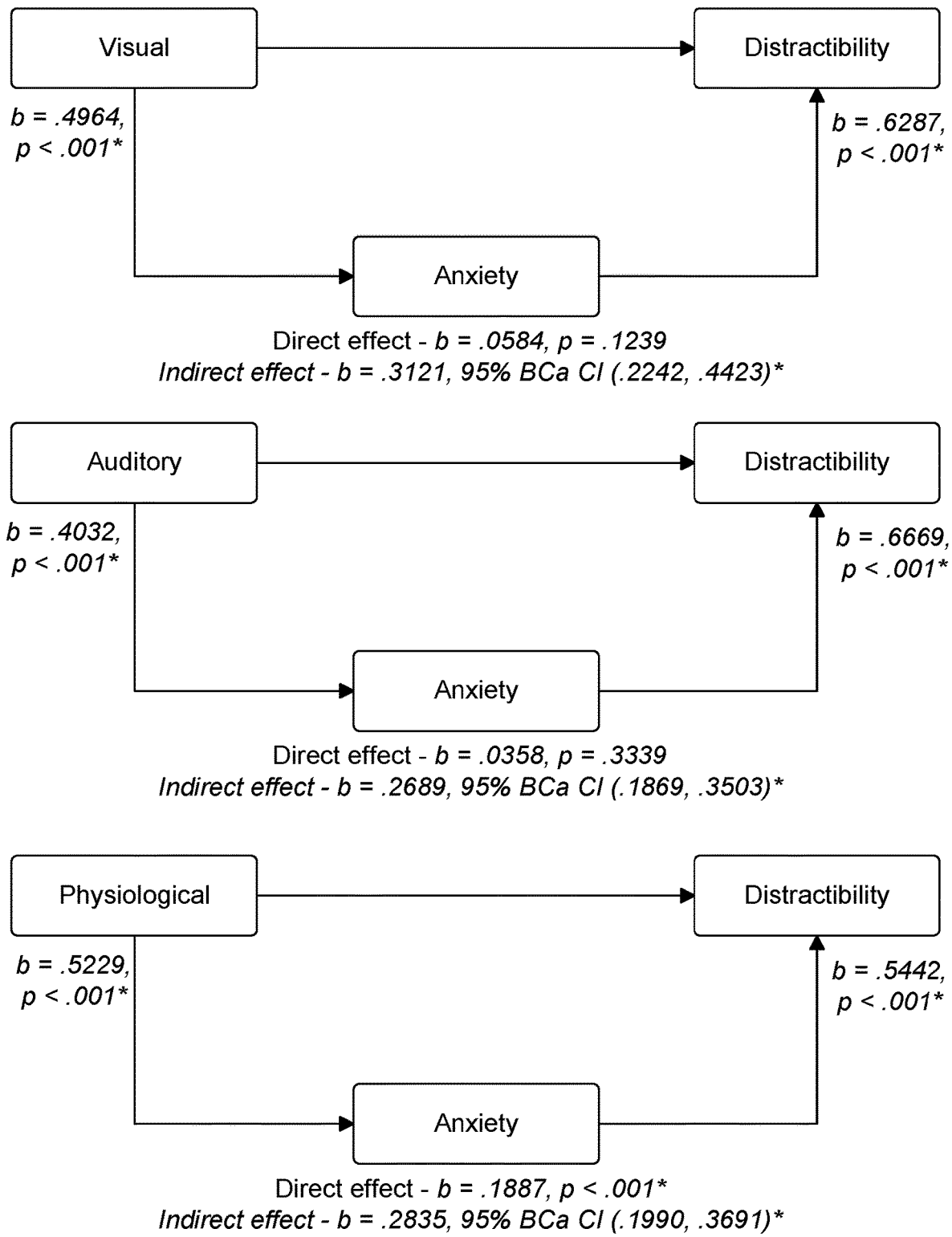
FIG. 31 depicts autistic mediation models, in accordance with some implementations of the disclosure.

To test the hypothesis that there is an indirect effect of anxiety that mediates the relationship between sensory sensitivity (cues) and attention (distractibility), a hierarchical multiple regression analysis was conducted (See FIG. 30, showing non-autistic mediation models, and FIG. 31, autistic mediation models). There was a correction for bias and acceleration of bootstrapped confidence intervals (1000 resamples) that do not overlap with zero, all of which indicated significant relations.

For non-autistic participants, the relationship between visual sensitivity and distractibility was significantly and directly mediated by anxiety scale scores (b=0.247, 95% BCa CI (0.136, 0.352)). We also confirmed anxiety was a significant and direct mediator between physiological sensitivity and distractibility (b=0.2361, 95% BCa CI (0.1261, 0.3680)). Education was added as a covariate in both cases. As sound sensitivity was not predictive in the regression models, auditory sensitivity was not tested for in the mediation model.

For autistic individuals, there was a significant indirect effect of anxiety for visual (b=0.3121, 95% BCa CI (0.2242, 0.4423)) and auditory sensitivity (b=0.2689, 95% BCa CI (0.1869, 0.3503)); however, the direct effect for neither was significant; hence, anxiety neither fully mediates the relationship between both visual and auditory sensitivity and distractibility for autistic individuals. However, anxiety significantly mediated the indirect relationship between physiological sensitivity and distractibility (b=0.2835, 95% BCa CI (0.1990, 0.3691)), and the direct effect was significant—indicating partial mediation.

The relationship between non-autistic individuals' AQ score and study variables in the PPI study was examined to ensure matching both in-group participants and to exclude individuals who exhibit subclinical traits that would influence outgroup comparisons (See Table 16).

TABLE 26

(Pearson's correlations between AQ score and study variables)

|  | Visual | Auditory | Physiological | Anxiety | Distractibility |
|---|---|---|---|---|---|
| AQ | .295* | .200 | .240* | .286* | .471* |
|  | p < .01 | p = .08 | p < .01 | p < .01 | p < .01 |

*p is significant at .05

The PPI study found that a significant positive correlation exists between non-autistic AQ scores and all study variables excluding sound. This suggests that individuals who score higher on the autism spectrum (those with less non-autistic traits) are more likely to experience visual and physiological sensitivity accompanied by higher levels of anxiety and distractibility, consistent with between-group results.

The regression models were supplemented with non-autistic AQ to examine predictive outcomes of anxiety and distractibility; however, there was no significant effect (p=0.198). However, the amount of model variance did increase 8% with the addition of AQ scores as a predictor of distractibility and was a significant predictor of distractibility score (p<0.001) when included within the regression model (See Table 27).

TABLE 27

(Model predicting distractibility for non-autistic participants)

|  | β | t | P |
|---|---|---|---|
| Visual | .107 | 1.708 | .089 |
| Physiological | .202 | 3.04 | .003* |
| Education | −.162 | −2.79 | .006* |
| Anxiety | .255 | 2.781 | .198 |
| AQ | .140 | 5.261 | <.001* |

($R^2$ = .508,
F = 34.76,
p < .001)

As taken from the state anxiety and state fatigue survey, means and standard deviations for participants' level of self-rated anxiety and fatigue after the Distraction SART and the Intervention SARTs, discussed above, are presented in Table 28. Given the data was not normally distributed, a Wilcoxon Signed-Rank test was conducted to explore whether the digital mediator was tolerated by participants based on their self-reported anxiety and fatigue.

TABLE 28

(Mean (SD) anxiety & fatigue levels between each SART)

|  | ASD: M (SD) | NT: M (SD) |
|---|---|---|
| Distraction Anxiety | 3.06 (1.39) | 3.43 (1.03) |
| Intervention Anxiety: Alert | 2.83 (1.15) | 3.33 (0.86) |
| Intervention Anxiety: Filter | 2.61 (1.09) | 2.81 (0.75) |
| Intervention Anxiety: Guidance | 2.78 (1.26) | 3.14 (0.65) |
| Intervention Anxiety: Combination | 2.56 (1.15) | 2.81 (0.87) |
| Intervention Anxiety: Best | 2.33 (1.02) | 2.62 (0.80) |
| Distraction Fatigue | 2.67 (1.19) | 2.95 (1.05) |
| Intervention Fatigue: Alert | 2.61 (1.33) | 2.95 (1.05) |
| Intervention Fatigue: Filter | 2.44 (1.25) | 2.81 (1.08) |
| Intervention Fatigue: Guidance | 2.94 (1.35) | 3.00 (0.89) |
| Intervention Fatigue: Combination | 2.47 (1.18) | 2.62 (0.86) |
| Intervention Fatigue: Best | 2.28 (1.13) | 2.52 (0.87) |

N = 39. Minimum possible values were 1 and maximum possible values were 5. Distraction Fatigue, Intervention Fatigue Alert and Intervention Fatigue Combination were each missing 1 data point.

For the non-autistic group, self-rated anxiety was significantly lower following the Filter Intervention SART (Mdn=3.0) relative to the Distraction SART (Mdn=4.0; T=10.0, Z=−2.36, p=0.02). Similarly, self-reported anxiety and fatigue were significantly lower following the Combination Intervention SART (Anxiety: Mdn=3.0; Fatigue: 2.0) in comparison to the Distraction SART (Anxiety: T=610.50, Z=−2.35, p=0.02; Fatigue: Mdn=3.0; T=10.00, Z=−1.94, p=0.05). Lower anxiety scores related to a participant feeling calmer, while lower fatigue scores related to a participant feeling more alert.

By contrast, there were no significant differences in anxiety or fatigue between the Distraction and each Intervention SART for the autistic participants. Given that autism is a highly heterogeneous disorder, and the aim of this intervention is to tailor the mediations to the varying preferences of the individual, the analysis was subsequently conducted on participants' score from their best-performing intervention (and not averaged mediations). Indeed, when using the best intervention, autistic participants' self-reported anxiety was lower in the Best Intervention SART (Mdn=2.0) than the Distraction SART (Mdn=3.50; T=5.00, Z=−2.24, p=0.02). Similarly, autistic participants' self-reported fatigue was lower in the Best Intervention SART (Mdn=2.00) compared to the Distraction SART (Mdn=2.50; T=0.00, Z=−2.33, p=0.02).

When applying the same logic to the non-autistic group in which best-performing intervention scores were analysed, similar results were found. Self-reported anxiety was lower in the Best Intervention SART (Mdn=3.00) relative to the Distraction SART (T=13.00, Z=−2.78, p=0.01). Self-reported fatigue was also lower in the Best Intervention SART (Mdn=2.00) compared to the Distraction SART (T=12.00, Z=−2.32, p=0.02).

A Mann-Whitney test indicated that both diagnostic groups found the best intervention similarly helpful as they did not significantly differ in terms of the difference in their self-reported anxiety or fatigue between the Distraction SART and the Best Intervention SART ($U_{anxiety}$=174, p=0.66; $U_{fatigue}$=182, p=0.83) respectively.

To explore whether interventions improved performance on the SART despite the presence of distraction, a repeated measures ANOVA was conducted (having checked for independence, sphericity, and normal distribution) to compare performance between the conditions (baseline, distraction, intervention) and diagnostic group. The variables were not normally distributed (except for EoC, but the sample size was sufficiently large such that the repeated measures ANOVA should be robust against this assumption violation. Further, as in the previous analyses, scores from participants' best-performing intervention were used. Means and standard deviations of variables are presented in Table 29.

TABLE 29

(Mean (SD) performance between the conditions)

| | M (SE) |
|---|---|
| RT EoO Baseline | 111.79 (8.34) |
| RT EoO Distraction | 115.75 (10.05) |
| RT EoO Intervention | 142.50 (12.28) |
| RT EoC Baseline | 76.90 (9.00) |

TABLE 29-continued (Mean (SD) performance between the conditions)

| | M (SE) |
|---|---|
| RT EoC Distraction | 85.57 (13.33) |
| RT EoC Intervention | 154.98 (17.10) |
| EoO Baseline | 5.17 (1.32) |
| EoO Distraction | 5.33 (1.29) |
| EoO Intervention | 2.77 (1.50) |
| EoC Baseline | 6.27 (0.51) |
| EoC Distraction | 7.29 (0.57) |
| EoC Intervention | 4.97 (0.44) |

N = 39.
RT measured in milliseconds (ms).

RT EoO differed significantly across the three conditions, F(1.37, 50.81)=11.74, p<0.01. A post-hoc pairwise comparison using Bonferroni correction showed that RT EoO was slower in the Intervention (M=142.50, SE=12.28) relative to the Baseline (M=111.79, SE=8.34, p<0.01) and Distraction (M=115.75, SE=10.05, p<0.01). However, there was no main effect of group F(1,37)=1.40, p=0.25, and no interaction between condition and diagnostic group, F(2,74)=0.56, p=0.51.

Similarly, RT EoC significantly differed across the three conditions, F(1.52, 56.36)=16.92, p<0.01. A post-hoc pairwise comparison using Bonferroni correction showed that RT EoC significantly increased between the Baseline (M=76.90, SE=9.00) and Intervention (M=154.98, SE=17.10) as well as between the Distraction (M=85.57, SE=13.33) and Intervention (p<0.01). However, there was no main effect of group F(1, 37)=3.00, p=0.09 or an interaction between condition and diagnostic group, F(2, 74)=1.12, p=0.32.

Having met both assumptions of normality and sphericity, a repeated measures ANOVA determined that EoC differed significantly across the three conditions, F(2,74)=12.5, p<0.01. A post hoc pairwise comparison using Bonferroni correction showed fewer EoC in the Intervention (M=4.97, SE=0.44) relative to both the Baseline (M=6.27, SE=0.51, p=0.02) and Distraction (M=7.29, SE=0.57, p<0.01). However, there was no main effect of group F(1, 37)=0.00, p=0.95, or an interaction between condition and diagnostic group, F(2,74)=0.39, p=0.68.

Finally and surprisingly, EoO did not significantly differ across the three conditions, F(1.38, 50.95)=2.54, p=0.11, nor was there a main effect of group F(1, 37)=0.19, p=0.67, nor an interaction between condition or diagnostic group, F(2, 74)=1.89, p=0.17.

To determine whether the performance and self-reported mental health data correlated with one another, a Spearman's rank correlation (given the data was non-normal) was conducted. Table 30, below, depicts the results.

TABLE 30

(Spearman's Rank Correlation: Ecological & Physiological Measures)

| | | 1 | 2 | 3 | 4 | 5 | 6 |
|---|---|---|---|---|---|---|---|
| Autistic | 1. Best Anxiety Intervention Score | | | | | | |
| | 2. Best Fatigue Intervention Score | 0.71** | | | | | |
| | 3. Best EoC RT | −0.05 | −0.02 | | | | |
| | 4. Best EoO RT | −0.36 | −0.25 | 0.35 | | | |
| | 5. Best EoC | −0.18 | 0.06 | −0.30 | −0.10 | | |
| | 6. Best EoO | 0.177 | −0.15 | −0.35 | −0.51* | 0.075 | |

TABLE 30-continued (Spearman's Rank Correlation: Ecological & Physiological Measures)

|  |  | 1 | 2 | 3 | 4 | 5 | 6 |
|---|---|---|---|---|---|---|---|
| Non-autistic | 1. Best Anxiety Intervention Score |  |  |  |  |  |  |
|  | 2. Best Fatigue Intervention Score | 0.38 |  |  |  |  |  |
|  | 3. Best EoC RT | 0.04 | 0.27 |  |  |  |  |
|  | 4. Best EoO RT | 0.15 | 0.15 | **0.79\*\*** |  |  |  |
|  | 5. Best EoC | −0.34 | **−0.56\*\*** | −0.45\* | −0.46\* |  |  |
|  | 6. Best EoO | −0.02 | 0.12 | 0.35 | 0.09 | −0.13 |  |

N = 39;
\*p < 0.05 (two-tailed);
\*\*p < 0.001 (two-tailed).
Bold indicates correlation is significant at alpha level corrected by Bonferroni method. The diagnostic groups were analyzed independently to prevent correlations of the whole sample concealing any diverging underlying trends. Indeed, different correlations were revealed between the two groups.

For the autistic group, best fatigue intervention (the intervention that produced the lowest fatigue rating) scores were correlated with best anxiety intervention (the intervention that produced the lowest anxiety rating) scores ($r_s$=0.71, p<0.01, N=18), such that lower anxiety was associated with lower fatigue in the Intervention SART. Similarly, best EoO was negatively correlated with best EoC ($r_s$=−0.51, p=0.03, N=18), such that more errors of omission were associated with fewer errors of commission. No performance variables appeared to correlate with any self-reported mental health variables in the autistic group.

In contrast, the correlations in the non-autistic group revealed a different pattern. Best EoC was correlated with both RT EoO ($r_s$=-0.46, p=0.04, N=21) and RT EoC ($r_s$=−0.45, p=0.04, N=21), such that more errors of commission were associated with reduced reaction time for errors of omission and understandably, reduced reaction time of errors of commission. Best RT EoO was also highly associated with best RT EoC ($r_s$=0.79, p<0.01, N=21). Interestingly, best EoC was also correlated with best Fatigue Intervention Scores ($r_s$=−0.56, p<0.01, N=21), suggesting when participants felt less fatigued, they made fewer errors of commission.

A multiple linear regression with enter method was used to predict EOC performance in the Intervention SART from participants' anxiety and fatigue levels, education level, diagnostic group, and best intervention type. A preliminary analysis suggested that the assumption of normal distribution was met (Shapiro-Wilk test; p=0.17). Further the assumption of multicollineaity was met given none of the predictor variables correlated with each other by more than 0.7. However, none of the predictor variables correlated with the dependent variables by more than 0.3. A Cook's Distance test revealed that there was one influential data point which was then excluded from the analysis to ensure the Cook's distance remained below 1 and the Standard Residual remained between −3 and 3. The model did not explain a statistically significant amount of variance in EOC performance, $F(5, 32)$=0.83, p=0.54, $R^2$=0.12, $R^2_{adjusted}$=−0.02. Each variable is presented in Table 31.

TABLE 31

(Multiple Regression Predicting EOC performance in the Intervention SART from Anxiety, Fatigue, Education, Diagnostic Group and Best Intervention Type)

|  | B | SE B | β |
|---|---|---|---|
| Anxiety | 0.43 | 0.59 | 0.15 |
| Fatigue | 0.66 | 0.56 | 0.25 |

TABLE 31-continued (Multiple Regression Predicting EOC performance in the Intervention SART from Anxiety, Fatigue, Education, Diagnostic Group and Best Intervention Type)

|  | B | SE B | β |
|---|---|---|---|
| Education | 0.48 | 0.98 | 0.09 |
| Diagnostic group | 0.08 | 0.95 | 0.2 |
| Intervention type | 0.03 | 0.07 | 0.07 |

N = 38;
\*p < 0.05 (two-tailed);
\*\*p < 0.01 (two-tailed).

A multinominal logistic regression was performed to model the relationship between diagnostic group, age, education, and gender with the best performance intervention. As shown in Table 32, this regression was repeated such that the reference category was varied between the intervention types (alert, filter, guidance, combination).

TABLE 32

(Multinominal Logistics Regression Predicting Best Performance Intervention from Diagnostic Group, Age, Education & Gender)

|  | $\chi^2$ (Alert) | $\chi^2$ (Filter) | $\chi^2$ (Guidance) | $\chi^2$ (Comb) | df |
|---|---|---|---|---|---|
| Diagnostic group | 16.95\* | 16.95\* | 16.95\* | 16.95\* | 7 |
| Age | 12.68 | 12.68 | 12.68 | 12.68 | 7 |
| Education | 18.31\*\* | 18.31\*\* | 18.31\*\* | 18.31\*\* | 7 |
| Gender | 7.63 | 7.63 | 7.63 | 7.63 | 7 |

N = 39;
\*p < 0.05 (two-tailed);
\*\*p < 0.01 (two-tailed).
Parentheses denote the reference category The regressions produced the same results. The addition of the predictors to the model significantly improved the fit between the model and the data, $\chi^2$ (28, N=39)=43.40, Nagelkerke $R^2$=0.70, p=0.03. Significant unique contributions were made by Diagnostic Group ($\chi^2$=16.95, p=0.02) and Education ($\chi^2$=18.31, p=0.01). Goodness of fit was explored through the Pearson chi-square statistic which indicated a good fit since this was a non-significant result, $\chi^2$=141.61, p=1.00.

Post-hoc Chi-square of Independence tests were subsequently run to identify the characteristics of diagnostic group and education that were associated with best intervention type. It appeared that there was not a significant relationship between diagnostic group (autistic vs. non-autistic) and best intervention type, $\chi^2$ (7, N=39)=3.87, p=0.80), nor was there a significant relationship between education (university vs non-university) and best intervention type, $\chi^2$ (7, N=38)=11.43, p=0.12).

A binary logistic regression was conducted to ascertain the effects of diagnostic group, age, gender, or education on the likelihood that participants performed best using alerts. A preliminary analysis suggested that the assumption of multicollinearity was met (tolerance=Diagnostic Group: 0.88; Age: 0.67; Gender: 0.93; Education: 0.62). An inspection of standardized residual values revealed that there were two outliers (Std. residual—2.24; 2.56), which were kept in the dataset. The model was not statistically significant, $\chi^2$(5, N=39)=4.82, p=0.44 suggesting that it could not distinguish between those who performed best with alerts and those who did not. The model explained between 11.6% (Cox & Snell R square) and 16.4% (Nagelkerke R square) of the variance in the dependent variable and correctly classified 69.2% of cases. As shown in Table 33, none of the predictors significantly contributed to the model.

TABLE 33

(Logisitic Regression Predicting Best Intervention Type Alert from Diagnostic Group, Age, or Education)

| | B | SE | Wald | df | p | OR |
|---|---|---|---|---|---|---|
| Diagnostic Group | 0.03 | 0.80 | 0.00 | 1 | 0.97 | 1.03 |
| Age | −0.02 | 0.06 | 0.08 | 1 | 0.78 | 0.98 |
| Education | 1.73 | 0.98 | 3.15 | 1 | 0.08 | 5.66 |

N = 39;
*p < 0.05 (two-tailed);
**p < 0.01 (two-tailed).

A binary logistic regression was conducted to ascertain the effects of diagnostic group, age, gender, or education on the likelihood that participants performed best using filters. A preliminary analysis suggested that the assumption of multicollinearity was met (tolerance=Diagnostic Group: 0.88; Age: 0.67; Gender: 0.93; Education: 0.62). An inspection of standardised residual values revealed that there were no outliers. The model was not statistically significant, $\chi^2$ (5, N=39)=5.93, p=0.31 suggesting that it could not distinguish between those who performed best with filters and those who did not. The model explained between 14.1% (Cox & Snell R square) and 19.6% (Nagelkerke R square) of the variance in the dependent variable and correctly classified 66.7% of cases. As shown in Table 34, none of the predictors significantly contributed to the model.

TABLE 34

(Logisitic Regression Predicting Best Intervention Type Filter from Diagnostic Group, Age, or Education)

| | B | SE | Wald | df | p | OR |
|---|---|---|---|---|---|---|
| Diagnostic Group | 1.30 | 0.79 | 2.68 | 1 | 0.10 | 3.66 |
| Age | −0.09 | 0.08 | 1.33 | 1 | 0.25 | 0.92 |
| Education | 0.57 | 0.92 | 0.39 | 1 | 0.53 | 1.78 |

N = 39;
*p < 0.05 (two-tailed);
**p < 0.01 (two-tailed).

A binary logistic regression was conducted to ascertain the effects of diagnostic group, age, gender, or education on the likelihood that participants performed best using guidance. A preliminary analysis suggested that the assumption of multicollinearity was met (tolerance=Diagnostic Group: 0.88; Age: 0.67; Gender: 0.93; Education: 0.62). An inspection of standardised residual values revealed that there were no outliers. The model was not statistically significant, $\chi^2$ (5, N=39)=2.64, p=0.76 suggesting that it could not distinguish between those who performed best with guidance and those who did not. The model explained between 6.5% (Cox & Snell R square) and 9.4% (Nagelkerke R square) of the variance in the dependent variable and correctly classified 76.9% of cases. As shown in Table 35, none of the predictors significantly contributed to the model.

TABLE 35

(Logisitic Regression Predicting Best Intervention Type Guidance from Diagnostic Group, Age, or Education)

| | B | SE | Wald | df | p | OR |
|---|---|---|---|---|---|---|
| Diagnostic Group | 0.27 | 0.79 | 0.11 | 1 | 0.74 | 1.30 |
| Age | 0.05 | 0.06 | 0.71 | 1 | 0.40 | 1.05 |
| Education | −0.18 | 0.90 | 0.04 | 1 | 0.84 | 0.84 |

N = 39;
*p < 0.05 (two-tailed);
**p < 0.01 (two-tailed).

A binary logistic regression was conducted to ascertain the effects of diagnostic group, age, gender, or education on the likelihood that participants performed best using a combination of the interventions. A preliminary analysis suggested that the assumption of multicollinearity was met (tolerance=Diagnostic Group: 0.88; Age: 0.67; Gender: 0.93; Education: 0.62). An inspection of standardised residual values revealed that there were no outliers. The model was not statistically significant, $\chi^2$(5, N=39)=0.39, p=1.00 suggesting that it could not distinguish between those who performed best with combinations and those who did not. The model explained between 1.0% (Cox & Snell R square) and 1.4% (Nagelkerke R square) of the variance in the dependent variable and correctly classified 66.7% of cases. As shown in Table 36, none of the predictors significantly contributed to the model.

TABLE 36

(Logisitic Regression Predicting Best Intervention Type Combination from Diagnostic Group, Age, or Education)

| | B | SE | Wald | df | p | OR |
|---|---|---|---|---|---|---|
| Diagnostic Group | 0.18 | 0.73 | 0.06 | 1 | 0.81 | 1.19 |
| Age | −0.02 | 0.06 | 0.15 | 1 | 0.70 | 0.98 |
| Education | 0.14 | 0.85 | 0.03 | 1 | 0.94 | 0.90 |

N = 39;
*p < 0.05 (two-tailed);
**p < 0.01 (two-tailed).

A series of one-way ANOVA tests were conducted to determine whether there were significant differences in fatigue and distractibility scores based on the various demographic categories. Having met the assumption of homogeneity of variance for the non-autistic group, there was no significant effect of age on fatigue, F(3, 158)=0.43, p=0.73, or distractibility, F(3, 158)=2.23, p=0.09. In contrast, for the autistic group, the assumption of homogeneity of variance was violated. Therefore, the Welch test was used to conduct the analysis. This showed that there was a significant effect of age on fatigue for the autistic group, t(30.78)=12.53, p<0.01 as well as on distractibility, t(32.99)=7.83, p<0.01. Post-hoc comparisons using the Games-Howell test revealed that for fatigue, the 30-39-year-olds scored significantly lower than 18-21-year-olds (mean difference=1.01, p<0.01), and significantly lower than the 22-29-year-olds (mean difference=0.49, p=0.01). Further, the 41-49-year-olds scored significantly lower than the 18-21-year-olds (mean difference=1.26, p<0.01) and significantly lower than the 22-29-year-olds (mean difference=0.74, p=0.04). For distractibility, the post-hoc Games-Howell test revealed that 41-49-year-olds scored significantly higher on distractibility compared with the 18-22-year-olds (mean difference=0.61, p<0.01) and the 22-29-year-olds (mean difference=0.41, p=0.02). Further, the 31-39-year-olds scored significantly higher than the 18-22-year-olds (mean difference=0.47, p=0.01) as well as the 22-29-year-olds (mean difference=0.26, p=0.02).

Given the assumption of homogeneity of variance based on the median was met for both diagnostic groups, a one-way ANOVA revealed that there were no significant differences between the genders on their fatigue scores (Autistic: F(2, 184)=2.83, p=0.06; Non-autistic: F (2, 159)=0.85, p=0.43). Similarly, in the non-autistic group, the genders did not significantly differ on their distractibility scores, F(2, 159)=0.46, p=0.64. However, in the autistic group, the genders did significantly differ on their distractibility scores F(2, 184)=6.55, p<0.01. A post-hoc Tukey test revealed that autistic participants who attended graduate school scores significantly more on distractibility than those who did not have a degree (mean difference=−0.70, p<0.01) and those who had a degree (mean difference=−0.59, p=0.02).

Finally, for the non-autistic group, there were no significant differences between the educational groups on their fatigue scores F(2, 159)=0.56, p=0.57. However, the educational groups did significantly differ on their distractibility scores in the non-autistic group, F(2, 159)=4.47, p=0.01. A post-hoc Tukey test revealed that those without a degree scored significantly higher on distractibility than those who attended graduate school (mean difference=0.40, p=0.01). For the autistic group, the educational groups significantly differed in their fatigue scores F(2, 184)=5.03, p=0.01. A post-hoc Tukey test revealed that those participants who had attended graduate school scored significantly lower on fatigue than those without a degree (mean difference=0.64, p=0.01). In terms of distractibility, the autistic educational groups did not significantly differ on the Welch test, t(41.93)= 1.85, p=0.17.

A one-way ANOVA revealed that there were no significant differences between the genders on their fatigue scores (Autistic: F(2, 184)=2.83, p=0.06; Non-autistic: F (2, 159)= 0.85, p=0.43). Similarly, in the non-y significantly differed in their fatigue scores F(2, 184)=5.03, p=0.01. A post-hoc Tukey test revealed that those participants who had attended graduate school scored significantly lower on fatigue than those without a degree (mean difference=0.64, p=0.01). In terms of distractibility, the autistic educational groups did not significantly differ on the Welch test, t(41.93)=1.85, p=0.17.

Table 37 shows the mean scores of the three sensory sensitivity variables, as well as the mean anxiety, fatigue, and attention scores across the two diagnostic groups. Independent samples t-tests were conducted to compare the scores on each of the variables across the diagnostic groups. Autistic adults reported significantly greater levels of visual sensitivity, t(313.31)=−7.83, p<0.01, and physiological sensitivities, t(292.46)=−6.09, p<0.01, compared with the non-autistic group. Autistic individuals also reported lower levels of fatigue (meaning they tend to be more alert) in comparison to the non-autistic population, t(347)=5.13, p<0.01. There were no significant differences between the groups on their mean scores on the other variables.

TABLE 37

(Mean Sensitivity Scores and between group differences)

| | ASD: M (SD) | NT: M (SD) | t(df) |
|---|---|---|---|
| Visual | 3.22 (0.76) | 2.50 (0.92) | −7.83 (313.31)** |
| Auditory | 3.01 (0.63) | 3.14 (0.93) | 0.64 (278.27) |
| Physiological | 4.21 (0.65) | 3.70 (0.88) | −6.09 (292.46)** |
| Anxiety | 3.42 (0.54) | 3.30 (0.74) | −1.71 (289.77) |
| Fatigue | 2.24 (0.75) | 2.67 (0.79) | 5.13 (347)** |
| Distractibility | 3.52 (0.46) | 3.42 (0.78) | −1.40 (253.63) |

N = 349;
*p < 0.05 (two-tailed);
**p < 0.01 (two-tailed).

Table 38 shows Bonferroni adjusted Spearman rank correlations between the variables for both the non-autistic and autistic groups. Application of the Kolmogorov-Smirnov test revealed that most variables, except for visual and anxiety in the non-autistic group, were non-normal. For the non-autistic group, significant associations were found between each of the sensory sensitivity variables and the outcome variables (anxiety, fatigue, and distractibility), as well as between all the sensory sensitivity variables. A similar pattern of association was found for the autistic group, except for the relationship between visual and auditory which was not significant (r=0.11, p=0.13).

TABLE 38

(Spearman's Rank Correlation)

| | | 1 | 2 | 3 | 4 | 5 | 6 |
|---|---|---|---|---|---|---|---|
| Autistic | 1. Visual | | | | | | |
| | 2. Auditory | 0.11 | | | | | |
| | 3. Physiological | 0.35* | 0.19* | | | | |
| | 4. Anxiety | 0.73* | 0.40* | 0.41* | | | |
| | 5. Fatigue | −0.69* | −0.27* | −0.45* | −0.81* | | |
| | 6. Distractibility | 0.52* | 0.36* | 0.49* | 0.70* | −0.71* | |
| Non-autistic | 1. Visual | | | | | | |
| | 2. Auditory | 0.58* | | | | | |
| | 3. Physiological | 0.52* | 0.46* | | | | |
| | 4. Anxiety | 0.66* | 0.56* | 0.64* | | | |
| | 5. Fatigue | −0.56* | −0.50* | −0.52* | −0.76* | | |
| | 6. Distractibility | 0.49* | 0.40* | 0.50* | 0.55* | −0.43* | |

N = 349;
*p < 0.05 (two-tailed);
**p < 0.01 (two-tailed).
Bold indicates correlation is significant at alpha level corrected by Bonferroni method. The diagnostic groups were analysed independently to prevent correlations of the whole sample concealing any diverging underlying trends. Indeed, different correlations were revealed between the two groups.

Given the significant associations between the variables in Table 38, a series of linear regressions were conducted to analyse the unique contribution of each variable when predicting fatigue and distractibility, having first checked for multicollinearity. Visual, sound, and physiological sensitivity variables as well as demographic variables (age, gender, education) were added as predictors of fatigue scores. For the non-autistic group, Table 39 shows that while the demographic variables did not predict fatigue, all the sensory variables uniquely predicted fatigue, with the model accounting for 47% of the variance in fatigue (F(6, 155)= 23.07, p<0.01). For the autistic group, Table 40 shows that all the sensory variables as well as age uniquely predicted fatigue, although education and gender did not (F(6, 180)= 64.39, p<0.01). The model accounted for 68% of the variance in fatigue.

TABLE 39

(Non-autistic: Regression predicting fatigue)

|  | B | SE B | β |
|---|---|---|---|
| Visual | −0.26 | 0.07 | −0.30** |
| Auditory | −0.15 | 0.07 | −0.18* |
| Physiological | −0.31 | 0.07 | −0.34** |
| Age | 0.02 | 0.07 | 0.02 |
| Gender | 0.04 | 0.09 | 0.02 |
| Education | −0.07 | 0.07 | −0.06 |

N = 162;
*p < 0.05 (two-tailed);
**p < 0.01 (two-tailed).
$R^2 = 0.47$
F = 23.07,
p < 0.01

TABLE 40

(Autistic: Regression predicting fatigue)

|  | B | SE B | β |
|---|---|---|---|
| Visual | −0.44 | 0.05 | −0.45** |
| Auditory | −0.13 | 0.05 | −0.11** |
| Physiological | −0.37 | 0.06 | −0.32** |
| Age | −0.17 | 0.05 | −0.17** |
| Gender | −0.09 | 0.06 | −0.07 |
| Education | −0.06 | 0.06 | −0.04 |

N = 187;
*p < 0.05 (two-tailed);
**p < 0.01 (two-tailed).
$R^2 = 0.68$
F = 64.39,
p < 0.01

Table 41 shows a regression predicting distractibility from the sensory variables as well as the demographic variables for the non-autistic group. The model predicted 41.9% of the variance in distractibility, F(6, 155)=18.65, p<0.01. Both visual and physiological sensory variables were significant unique predictors of fatigue. In contrast, as depicted by Table 42, the model predicting distractibility for the autistic group showed a different pattern, F(6, 180)=47.35, p<0.01 and predicted 61.2% of the variance in distractibility. All variables bar education were significant unique predictors of distractibility.

TABLE 41

(Non-autistic: Regression predicting distractibility)

|  | B | SE B | β |
|---|---|---|---|
| Visual | 0.23 | 0.07 | 0.27** |
| Auditory | 0.08 | 0.07 | 0.10 |
| Physiological | 0.31 | 0.07 | 0.35** |
| Age | −0.13 | 0.08 | −0.11 |
| Gender | −0.06 | 0.09 | −0.04 |
| Education | −0.14 | 0.07 | −0.12 |

N = 162;
*p < 0.05 (two-tailed);
**p < 0.01 (two-tailed).
$R^2 = 0.42$,
F = 18.65,
p < 0.01

TABLE 42

(Autistic: Regression predicting distractibility)

|  | B | SE B | β |
|---|---|---|---|
| Visual | 0.19 | 0.04 | 0.32** |
| Auditory | 0.19 | 0.04 | 0.26** |
| Physiological | 0.27 | 0.04 | 0.37** |
| Age | 0.07 | 0.03 | 0.12* |
| Gender | 0.09 | 0.04 | 0.11* |
| Education | −0.03 | 0.04 | −0.04 |

N = 187;
*p < 0.05 (two-tailed);
**p < 0.01 (two-tailed).
$R^2 = 0.61$,
F = 47.35,
p < 0.01

The next regression predicted distractibility again but included fatigue. For the non-autistic group, the model predicted 43.2% of the variance in distractibility, F(7, 154)= 16.72, p<0.01. Visual, physiological and education were significant unique predictors of distractibility. However, the other variables, including fatigue were not significant predictors of distractibility. In contrast, for the autistic group, the regression predicting distractibility including fatigue showed that, not only did the model predict 70.5% of the variance in distractibility (F(7, 179)=61.19, p<0.01), but that fatigue, auditory and physiological sensory variables were unique predictors of distractibility. Table 43 shows the results for the non-autistic group. Table 44 shows the results for the autistic group.

TABLE 43

(Non-autistic: Regression predicting distractibility (adding fatigue))

|  | B | SE B | β |
|---|---|---|---|
| Visual | 0.19 | 0.07 | 0.22** |
| Auditory | 0.06 | 0.07 | 0.07 |
| Physiological | 0.27 | 0.07 | 0.30** |
| Age | −0.13 | 0.08 | −0.11 |
| Gender | −0.06 | 0.09 | −0.04 |
| Education | −0.15 | 0.07 | −0.13* |
| Fatigue | −0.15 | 0.08 | −0.15 |

N = 162;
*p < 0.05 (two-tailed);
**p < 0.01 (two-tailed).
$R^2 = 0.43$,
F = 16.72,
p < 0.01

TABLE 44

(Autistic: Regression predicting distractibility (adding fatigue))

|  | B | SE B | β |
|---|---|---|---|
| Visual | 0.04 | 0.04 | 0.07 |
| Auditory | 0.15 | 0.03 | 0.20** |
| Physiological | 0.14 | 0.04 | 0.20** |
| Age | 0.01 | 0.03 | 0.02 |
| Gender | 0.06 | 0.04 | 0.07 |
| Education | −0.05 | 0.04 | −0.06 |
| Fatigue | −0.34 | 0.05 | −0.54** |

N = 187;
*p < 0.05 (two-tailed);
**p < 0.01 (two-tailed).
$R^2 = 0.71$,
F = 61.19,
p < 0.01

Figure 32:
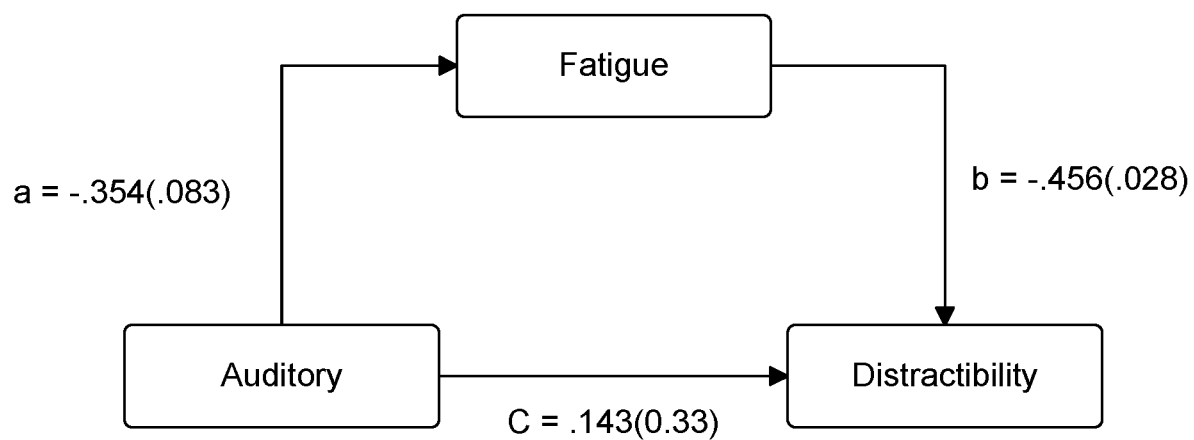
FIG. 32 depicts an autistic mediation model predicting distractibility from auditory via fatigue, in accordance with some implementations of the disclosure.
Figure 33:
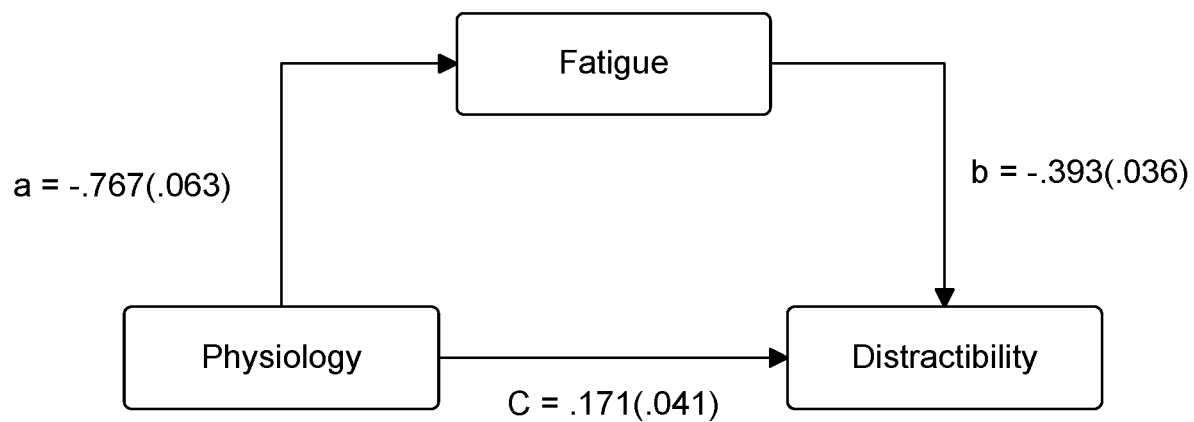
FIG. 33 depicts an autistic mediation model predicting distractibility from physiology via fatigue, in accordance with some implementations of the disclosure.

Mediation analysis was performed to explore the indirect effect of fatigue on the relationship between distractibility and auditory as well as physiological sensitivity variables (given they were both unique predictors of distractibility). The analysis was only run for the autistic group given that fatigue did not appear to be a significant predictor of distractibility for the non-autistic group. First, the direct effect of auditory and then separately, physiology on fatigue was then calculated through a bivariate regression. There was a significant result for both (auditory: B=−0.35, SE B=0.08, p<0.01; physiology: B=−0.77, SE B=0.06, p<0.01). A multiple regression including both fatigue and auditory (fatigue: B=−0.46, SE B=0.03, p<0.01; auditory: B=0.14, SE B=0.03, p<0.01), as well as a separate regression including both fatigue and physiology (fatigue: B=−0.39, SE B=0.04, p<0.01; physiology: B=0.17, SE B=0.04, p<0.01) were run to predict distractibility. The Sobel test was then conducted to test the indirect effect for statistical significance for each model. For the model including auditory, as shown in FIG. 32, the indirect effect is z=4.13, p<0.01, concluding that a partial mediation occurred between auditory sensory on distractibility via fatigue. For the model including physiology, as shown in FIG. 33, the indirect effect is z=8.12, p<0.01, suggesting that a partial mediation occurred between physiology sensory on distractibility via fatigue.

Given that physiological sensory sensitivity, fatigue and AQ scores were non-normally distributed, a Spearman's Rank correlation was conducted to determine the relationship between AQ score and the study variables (Table 45).

TABLE 45

(Spearman's Rank Correlation: AQ Score and Study Variables)

|  | Visual | Auditory | Physiological | Anxiety | Fatigue | Distractibility |
|---|---|---|---|---|---|---|
| AQ | 0.09 | 0.13 | 0.03 | 0.06 | 0.16 | 0.38** |

N = 140;
*p < 0.05 (two-tailed);
**p < 0.01 (two-tailed).
Bold indicates correlation is significant at alpha level corrected by Bonferroni method.

AQ scores were only collected from 140 non-autistic individuals in the study, therefore only these participants were included in the analysis. Distractibility was the only variable significantly associated with AQ scores (r=0.38, p<0.01), suggesting that those non-autistic individuals with higher autistic symptomology were more likely to score higher on distractibility.

AQ score was then included in the regression models predicting distractibility in non-autistic participants. The results are shown in Table 46. The model accounted for 53% of the variance in distractibility, F(8, 131)=18.07, p<0.01. Visual, physiological and education remained significant predictors of distractibility. AQ score too appeared to be a significant predictor of distractibility. Interestingly though, in comparison to the model without AQ (Table 43), fatigue now appeared to be a significant predictor of distractibility when AQ was included in the model. Such a change implies there may be a confounding effect of AQ.

TABLE 46

(Non-autistic: Regression predicting distractibility (adding AQ))

|  | B | SE B | β |
|---|---|---|---|
| Visual | 0.21 | 0.08 | 0.24** |
| Auditory | −0.02 | 0.07 | −0.02 |
| Physiological | 0.22 | 0.07 | 0.25** |
| Age | −0.08 | 0.07 | −0.07 |
| Gender | −0.01 | 0.09 | 0.01 |
| Education | −0.15 | 0.07 | −0.14* |
| Fatigue | −0.24 | 0.08 | −0.25** |
| AQ Score | 0.14 | 0.03 | 0.33** |

N = 162;
*p < 0.05 (two-tailed);
**p < 0.01 (two-tailed).
$R^2 = 0.53$,
F = 18.07,
p < 0.01

FIGS. 34A-34B show summary results of the PPI study described herein, which provided a basis for conducting and refining the SART/WOz clinical study described herein. As depicted by FIG. 34A, different associations between individual demographics (e.g., age sex, and education) and anxiety, fatigue, and/or focus were found in the autistic group versus the neurotypical group. Additionally, it was found that the autistic group tended to be more sensitive to visual and physiological stimuli, and less fatigued. As depicted by FIG. 34B, it was found that in some cases anxiety and fatigue mediated sensory sensitivity in a different manner for the autistic group versus the non-autistic group. For example, whereas for autistic individuals it was found that fatigue significantly mediated the indirect and direct relationship between auditory sensitivity and distractibility, no such relationship was found for non-autistic individuals. Some of the findings of the regression analysis in the PPI study included:

For Distractibility Only Prediction and for non-autistic participants, both visual, physiological, and education were predictors. For autistic participants, all variables were predictors, except for education.

For Fatigue Only Predictions and for non-autistic participants, all sensory variables were predictors (no demographics predicted). For autistic participants, all variables were predictors, except for gender and education.

For Anxiety Only Predictions and for non-autistic participants, all sensory variables were predictors and gender. For autistic participants, all variables were predictors, but no demographics.

For Fatigue and Anxiety Predictions and for non-autistic participants, anxiety and gender were predictors. For autistic participants, all visual, physiological, anxiety, and age were predictors.

For Distractibility and Fatigue Prediction for non-autistic participants, visual, physiological and education were predictors (demographics did not). For autistic participants, auditory, physiological, and fatigue were predictors.

For Distractibility and Anxiety Prediction for non-autistic participants, physiological, education, and anxiety were predictors. For autistic participants, physiological and anxiety were predictors.

For Distractibility, Fatigue and Anxiety Prediction for non-autistic participants, visual, physiological, and anxiety were predictors. For autistic participants, auditory, physiological, anxiety, and fatigue were predictors.

For Distractibility Only Prediction with AQ-10 tests and for non-autistic participants only, physiological, education, anxiety, and AQ were predictors. Autistic participants were excluded as they did not take the AQ-10.

FIGS. 35A-35B show summary results of the SART/WOz clinical study described herein. As described above, the study involved multiple trials that tested different mediations/interventions and different sensory cues. As depicted by FIG. 35A, all mediations/interventions (e.g., alert, filter, guidance, or combination hereof) were found to improve anxiety in both autistic and non-autistic individuals. By contrast, only some mediations (e.g., filters, or combination) were found to improve fatigue whereas others (e.g., guidance) were found to potentially be detrimental. In either case, mediations that were customized to particular individuals for each group were found to be the most effective. Although it was initially expected that only individuals in the autistic diagnoses group (i.e., the experiment group) would be the beneficiaries of digital mediations, surprisingly performance improvements were also present in the control group of non-autistic participants. As such, the benefits of increased performance by fewer errors, improved timing, and/or relief from anxiety and fatigue was found in both groups.

As depicted by FIG. 35B, overall performance for all users, as measured by a reduction in EoC, a reduction in EoO, a better reaction time (slower) for EoC, and response time (slower) for EoO, improved with a personalized mediation. In this case, the percentage change is measured in the change in errors or increase in reaction time/response time. As depicted "baseline to distraction" shows the change from baseline (no distracting cues present) to a distraction added. Performance was improved for all users when mediations were personalized, regardless of whether the mediation was added to baseline or after a distraction. As discussed above, it is anticipated that one of the mechanisms of achieving performance improvement is that by virtue of a personalized mediation causing a user to slow down (e.g., as measured by an increase in reaction time) and experience greater mindfulness, the participant stays focused for longer. This was particularly found to be the case in autistic participants. In practice, and depending on a given task the user is performing, this increase in response/reaction time can be on the order of tens of ms (e.g., 50 ms).

Figure 36A:
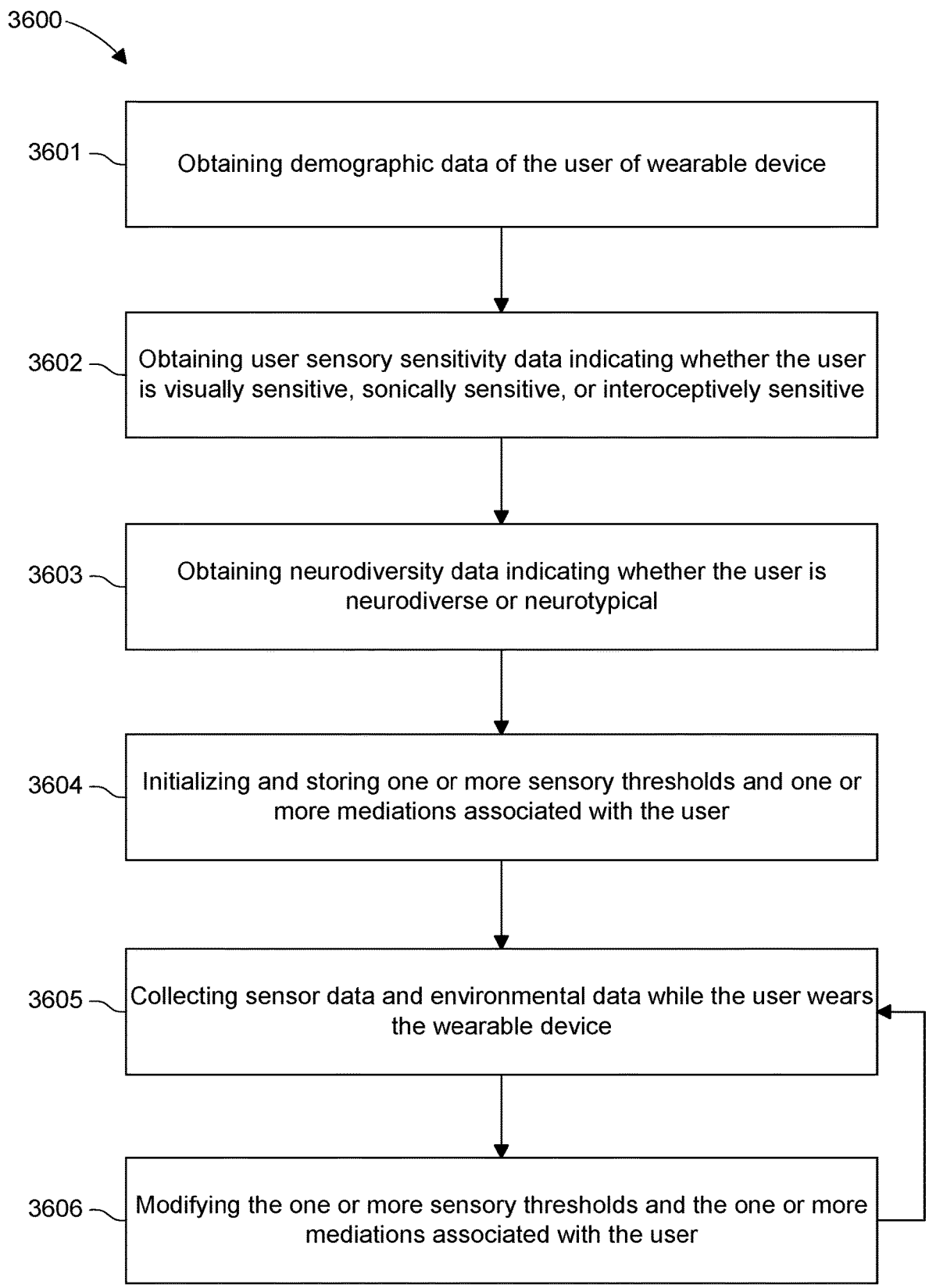
FIG. 36A is an operational flow diagram illustrating an example method for initializing and iteratively updating one or more sensory thresholds and one or more mediations associated with a specific user, in accordance with some implementations of the disclosure.

As the foregoing PPI study and SART/WOz clinical study illustrate, the optimal mediations for a given user can be predicted given data specific to the user and correlations between user performance and user characteristics such as demographics, sensory sensitivities, and status as autistic or non-autistic. As such, the multi-assistive wearable technology described herein can better initialize and/or optimize the one or more sensory thresholds and mediations associated with a user. For example, FIG. 36A is an operational flow diagram illustrating an example method 3600 for initializing and iteratively updating one or more sensory thresholds and one or more mediations associated with a specific user. In some implementations, method 3600 can be implemented by one or more processors (e.g., one or more processors of wearable device 10 and/or mobile device 20) of a wearable device system executing instructions stored in one or more computer readable media (e.g., one or more computer readable media of wearable device 10 and/or mobile device 20).

Operation 3601 includes obtaining demographic data of the user of the wearable device. This can include receiving user input at a user interface indicating an age, education level, gender, or other demographic data of the user.

Operation 3602 includes obtaining user sensory sensitivity data indicating whether the user is visually sensitive, sonically sensitive, or interoceptively sensitive. This can include receiving user input at the user interface indicating whether the user of the wearable device is visually sensitive, sonically sensitive, or interoceptively sensitive. In some cases, the user input can includes input at a GUI including one or more responses by the user to one or more prompts that are indicative of whether the user is visually sensitive, sonically sensitive, and/or interoceptively sensitive. These responses can indicate user preferences to certain sensory inputs such as stimuli that the user prefers, stimuli that make the user uncomfortable, the user's perceived and/or measured sensitivity to different stimuli, and the like. In some implementations, the response can include responses to questions as described with reference to the studies discussed above.

Operation 3603 includes obtaining neurodiversity data indicating whether the user is neurodiverse or neurotypical. For example, the neurodiversity data can indicate whether the user is autistic or non-autistic. In some implementations, the system can store a first identifier that indicates whether the user is neurodiverse or neurotypical. In some implementations, the neurodiversity data can be obtained by user input at a user interface indicating whether the user has been diagnosed as neurotypical. In other implementations, further discussed below, the wearable device system can be configured to perform a method for providing a diagnostic prediction of whether the user is neurodiverse or neurotypical.

Operation 3604 includes initializing and storing the one or more sensory thresholds and one or more mediations associated with the user. The thresholds and mediations associated with the user can be based on the user sensory sensitivity data, the demographic data, and/or the neurodiversity data. In some cases, the demographic data can be ignored.

Operation 3605 includes collecting sensor data and environmental data while the user wears the wearable device.

Operation 3606 includes in response to collecting the sensor data and/or environmental data while the user wears the wearable device, modifying the one or more sensory thresholds and the one or more mediations associated with the user. As depicted, operations 3605-3606 can iterate over time as the user utilizes the wearable device system to provide sensory relief. The frequency with which the one or more sensory thresholds and the one or more mediations are updated in response to newly-collected data can be configurable, system-defined, and/or user-defined. For example, updates can depend on the amount of data that is collected and/or the amount of time that has passed. In some implementations, operations 3605-3606 can be skipped. For example, the user can disable updating the thresholds and/or mediations based on actual use of the wearable device.

Figure 36B:
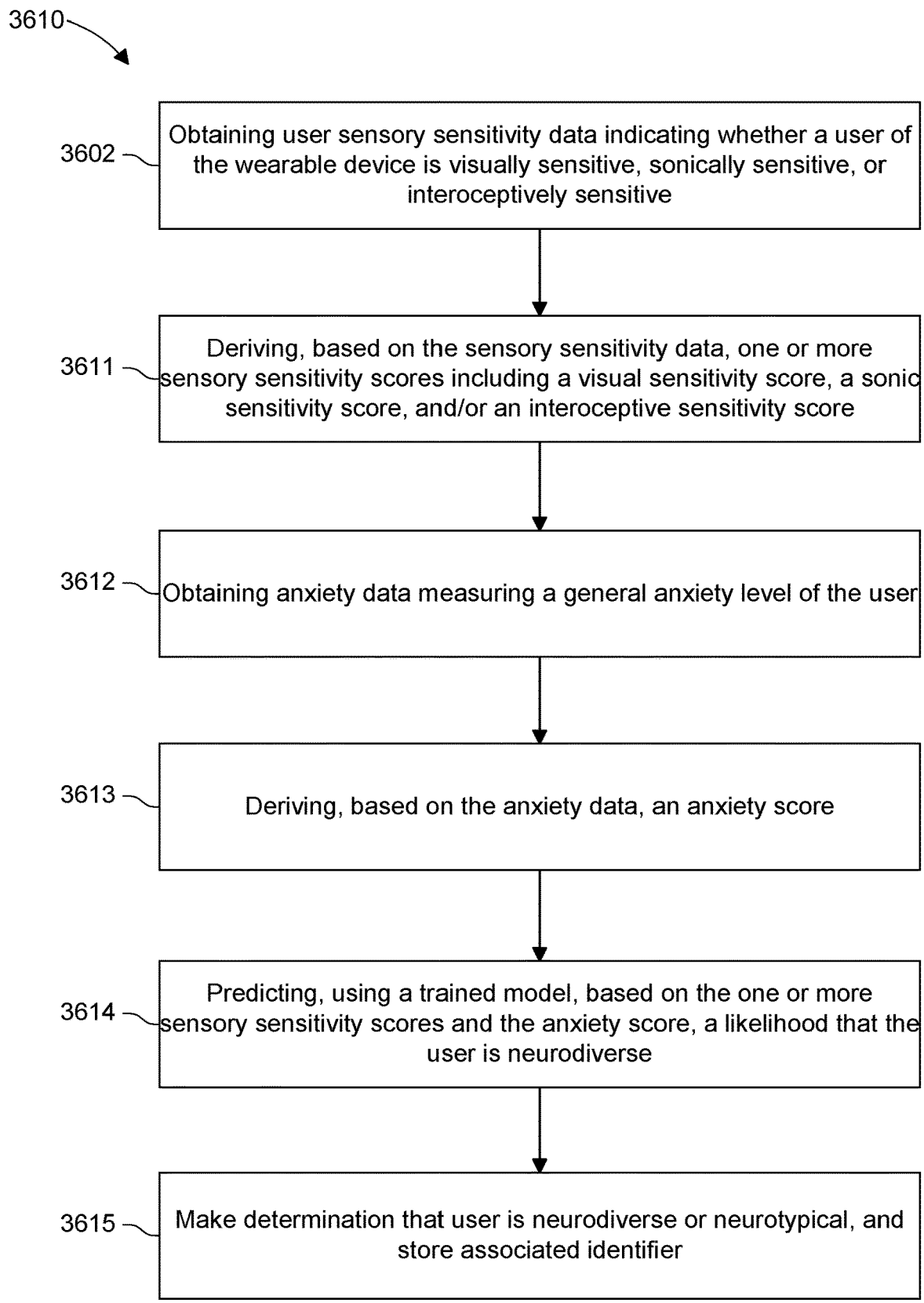
FIG. 36B is an operational flow diagram illustrating an example method for predicting whether a user is neurodiverse (e.g., autistic) or neurotypical, in accordance with some implementations of the disclosure.
Figure 36C:
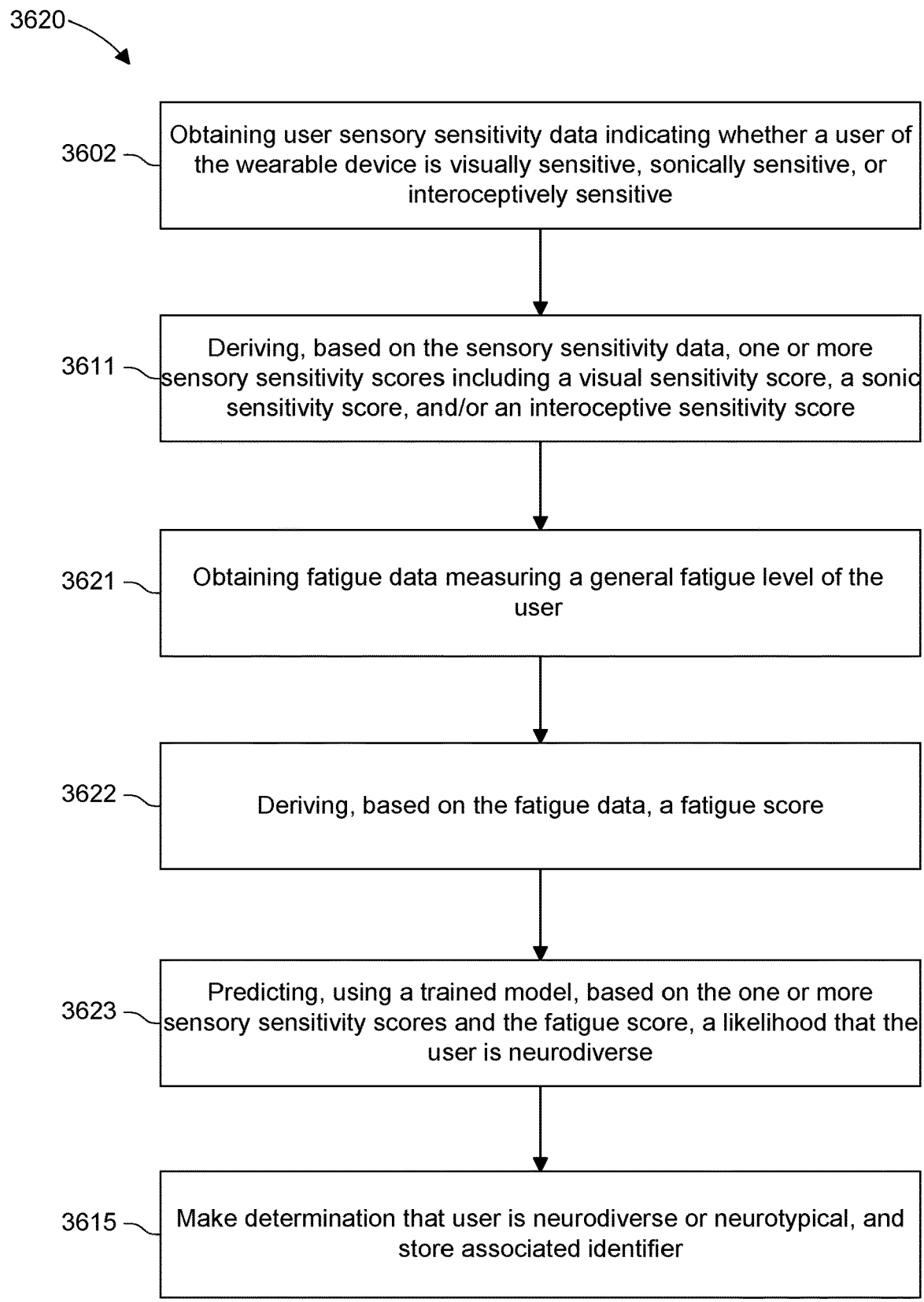
FIG. 36C is an operational flow diagram illustrating an example method for predicting whether a user is neurodiverse (e.g., autistic) or neurotypical, in accordance with some implementations of the disclosure.

As the foregoing PPI study and SART/WOz clinical study also illustrate, anxiety and fatigue can mediate sensory sensitivity in a different manner for autistic versus non-autistic users. In some implementations, the features found to be correlated with autistic versus non-autistic users can provide a basis for training a model that given, specific features corresponding to a user (e.g., sensory sensitivity features, anxiety features, fatigue features, demographic features, etc.) outputs a prediction (e.g., as a likelihood/probability) that a user is autistic or not autistic. For example, FIG. 36B and FIG. 36C are operational flow diagrams illustrating example methods 3610, 3620 for predicting whether a user is neurodiverse (e.g., autistic) or neurotypical. In some implementations, method 3610 or method 3620 can be implemented by one or more processors (e.g., one or more processors of wearable device 10 and/or mobile device 20) of a wearable device system executing instructions stored in one or more computer readable media (e.g., one or more computer readable media of wearable device 10 and/or mobile device 20).

In method 3610, operation 3602 can be performed as discussed above. Operation 3611 includes deriving, based on the sensory sensitivity data, one or more sensory sensitivity scores including a visual sensitivity score, a sonic sensitivity score, and/or an interoceptive sensitivity score. For example, based on the user's response to the prompts, one or more scores (e.g., normalized on a scale such as 0-100) can be derived. Operation 3612 includes obtaining anxiety data measuring a general anxiety level of the user. For example, this can include receiving at a GUI one or more responses by the user to one or more prompts indicating an anxiety level of the user in different contexts. Operation 3613 includes deriving, based on the anxiety data, an anxiety score. For example, based on the user's response to the prompts, a score (e.g., normalized on a scale such as 0-100) can be derived. Operation 3614 includes predicting, using a trained model, based on the one or more sensory sensitivity scores and the anxiety score, a likelihood that the user is neurodiverse. The model can be configured/trained to predict a probability of autism based at least on features includes an anxiety level/score and one or more sensory sensitivity levels/scores of a given user. Each of the features can be weighted differently. It should be noted that the model can also be trained to consider other features (e.g., demographic data) when making the prediction. Operation 3615 includes making a determination that user is neurodiverse or neurotypical, and storing an associated identifier. For example, if the prediction output by the model meets a threshold (e.g., >80% probability), a prediction that a user is autistic can be made. In some implementations, the system can validate the prediction by measuring the user's performance in response to certain tasks when mediations are present and not present. This performance can be measured using the wearable device and/or mobile device by administering SARTs as discussed above. The level of improvement in the user's performance, given a particular mediation, can further validate whether the predicted diagnosis is correct or incorrect.

In method 3620, operations 3602, 3611, and 3615 can be performed as described above. Operation 3621 includes obtaining fatigue data measuring a general fatigue level of the user 3621. For example, this can include receiving at a GUI one or more responses by the user to one or more prompts indicating a fatigue level of the user in different contexts. Operation 3622 includes deriving, based on the fatigue data, a fatigue score. For example, based on the user's response to the prompts, a score (e.g., normalized on a scale such as 0-100) can be derived. Operation 3623 includes predicting, using a trained model, based on the one or more sensory sensitivity scores and the fatigue score, a likelihood that the user is neurodiverse 3623. The model can be configured/trained to predict a probability of autism based at least on features includes a fatigue level/score and one or more sensory sensitivity levels/scores of a given user. Each of the features can be weighted differently. It should be noted that the model can also be trained to consider other features (e.g., demographic data) when making the prediction. In some implementations, both anxiety and fatigue features can be considered in the trained model.

In some implementations, the multi-sensory, assistive wearable technology described herein can be implemented using a network topology that ensures user data privacy and facilitates ethical relationships among device layers, systems, and stakeholders such as the user/wearer, the user's family, the user's therapist, and/or the user's general practitioner. To this end, edge and fog computing can be implemented using devices localized at the system's perimeter to facilitate and secure any cloud connectivity using devices localized at the system's perimeter. These devices can be independent and connect to both sensors and applications while serving as data transceivers between components, software, and—only when required—the cloud. This can provide desirable and reliable constraints for data computation, particularly as sensitive data can be substantial, often disorganized, and subject to exploitation. Owing to the cloud's limitations for exposure, fog computing can provide additional layers of efficiency and security.

Figure 37:
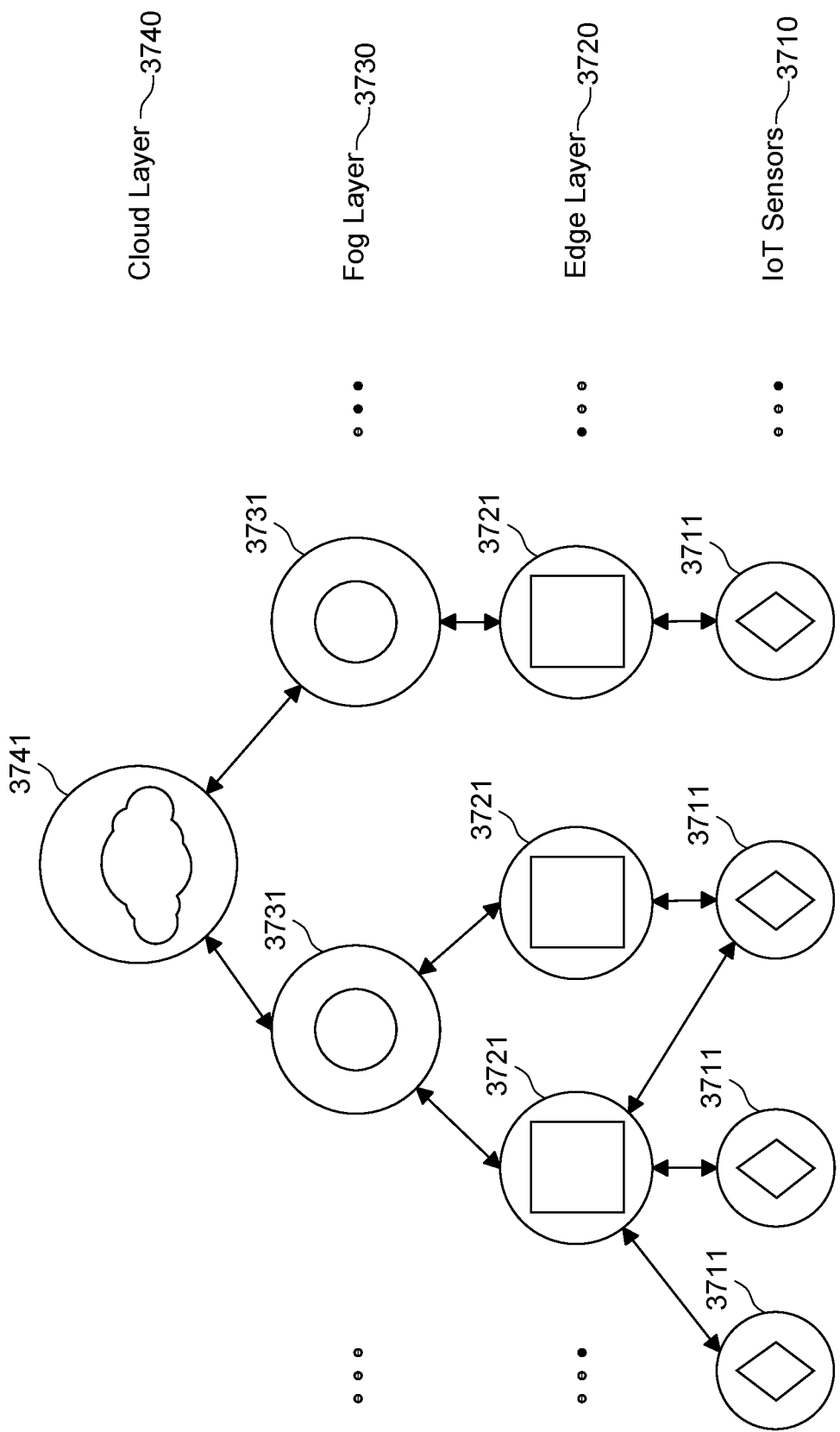
FIG. 37 illustrates an example system architecture/topology for implementing fog data processing, in accordance with some implementations of the disclosure.

By way of example, FIG. 37 illustrates an example system architecture/topology for implementing fog data processing in accordance with some implementations of the disclosure. The system architecture includes IoT sensors 3710, edge layer 3720 including edge nodes 3721, fog layer 3730 including fog nodes 3731, and cloud layer 3740 including one or more cloud computing devices 3741. Although FIG. 37 will be primarily described in context of a system architecture as applied to a single user/wearer, it should be appreciated that this system architecture can be extended to multiple independent users.

IoT sensors 3710 can be sensors implemented as part of a wearable device (e.g., wearable device 10 or wearable device 500. For example, the sensors can include a pupillometry sensor 204, a galvanic skin sensor 205, an inertial movement unit 206, a temperature sensor 309, an audio sensor 309, an image sensor (e.g., as part of camera 550), etc. The IoT sensors 3710 can also include sensors that are in the same environment as the wearer but implemented in a different device. For example, the sensors can include sensors implemented in a mobile device 20 (e.g., GPS or motion sensors), ambient temperature sensors, image sensors of external IoT devices, audio sensors of external IoT devices, etc.

Edge nodes 3721 and fog nodes 3731 can be implemented in hardware including, but not limited to, client-side wearable devices (e.g., wearable device 10 or 500), a mobile device 20, and/or locally (i.e., pre-cloud) operated servers or database devices that can be provided by the provider of the wearable device system.

As depicted, the fog layer 3730 resides between the edge layer 3720 and cloud layer 3740. In some implementations, the edge nodes can reside between the cloud nodes and fog nodes. In some implementations, some edge nodes reside between cloud nodes and fog nodes, and some fog nodes reside between edge nodes and cloud nodes. As fog node(s) 3731 receive data from edge node(s) 3721 they can filter the data by deterministically passing only appropriate data to the cloud computing devices 3741 for processing, storage, networking, etc. For example, edge and fog computations can be implemented where an ecological parameter (e.g., temperature) or physiological parameter (e.g., heart rate) is regularly sensed and collected as data (e.g., every second of operation) to align user fatigue and anxiety with other ecological/physiological measures. Without the presence of fog layer 3730, every sensor measurement could potentially be transmitted to a cloud application to accommodate the user/wearer and downstream monitoring for therapists, general practitioners, and/or family members. A rules-based fog layer 3730 could prevent this excessive data transfer from congesting the network and/or compromising the user's privacy/security. For example, a fog node 3731 can be configured to pass only critical data as it occurs (e.g., excessive temperature spikes), or only data collected by certain sensors (e.g., no image or sound data is made available to the cloud).

The fog node(s) 3731 or edge nodes 3721 can also encrypt any data prior to making it available to a cloud computing device 3741 such that information can remain pseudonymized, thereby protecting the user's privacy. During operation, all encryption, decryption, and purging of data can take place locally at the user level and not using cloud software or hardware.

The edge nodes 3721 can be responsible for maintaining a middleware position that manages data flow, encryption/decryption, and ultimately expunging data once it is no longer needed. In some implementations, the same device can function as both a fog node and an edge node.

By virtue of localizing data management and processing in the "fog", various benefits can be realized by the stakeholders (e.g., user) and/or the wearable device system. First, data processing near the end-user can improve data access, allowing storage to be buffered away from expensive, inefficient, and insecure/unethical activities. For example, this can prevent data collection for marketing or sale. "Fogging", by focusing data processing at the wearable device or within a local network of the wearable device can also bypass low-speed connectivity, i.e., expensive and slower cloud transmission rates are not required for a grounded application. Additionally, by localizing data management/processing/storage, data protection and privacy rules can be controlled and managed by the user, allowing configuration of what can and cannot be collected, transmitted, and/or stored. For example, localization can occur within a LAN and/or ad-hoc network of the wearable device (e.g., 10) and/or mobile device (e.g., 20) coupled to the wearable device.

In some implementations, a cloud layer 3740 can include a data lake (DL) repository that stores machine learning (MIL) data that is not personalized, including images, audio, and/or video. Some or most of this data can be public domain. During operation, the fog layer 3730 can compare private and distracting conditions (e.g., as determined from data collection by the wearable device) to the data stored in the cloud layer 3740. In this configuration, the edge layer 3720 can coordinate data flows to the cloud layer 3740, only allowing the most limited flow to the cloud, while the fog layer 3740 can be used to detect distractions by the user based at least in part by the repository of data stored on the cloud layer 3740. As such, the system can operate without the cloud layer personally identifying a user.

In some implementations, all personalized user data, including thresholds, sensory resolutions, mediations, demographic data, diagnostic data, etc. can be stored at the local level. Deep learning and machine learning data (e.g., auditory, visual, etc.) distractibility data can be encrypted and stored globally, while real-time comparative reactivity to ecological and physiological data can be momentarily stored locally.

Figure 38B:
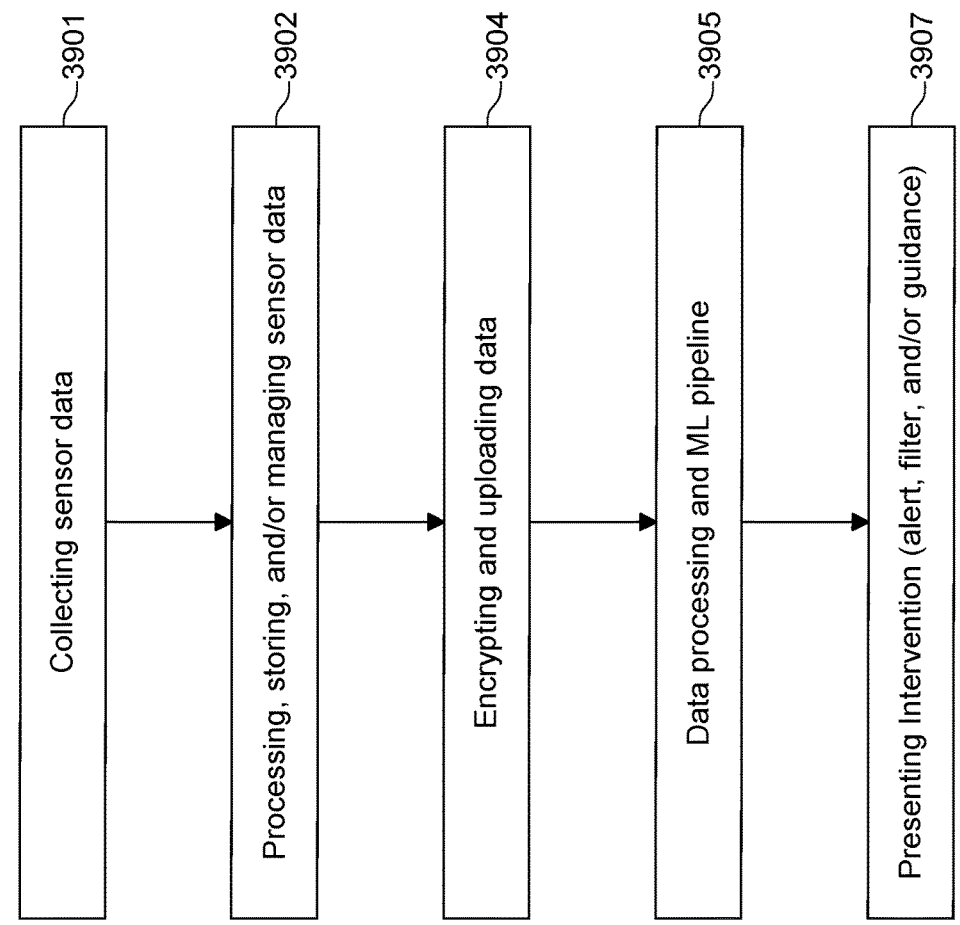
FIG. 38B is a flow diagram illustrating operations that are performed by the system of FIG. 38A, in accordance with some implementations of the disclosure.
Figure 38A:
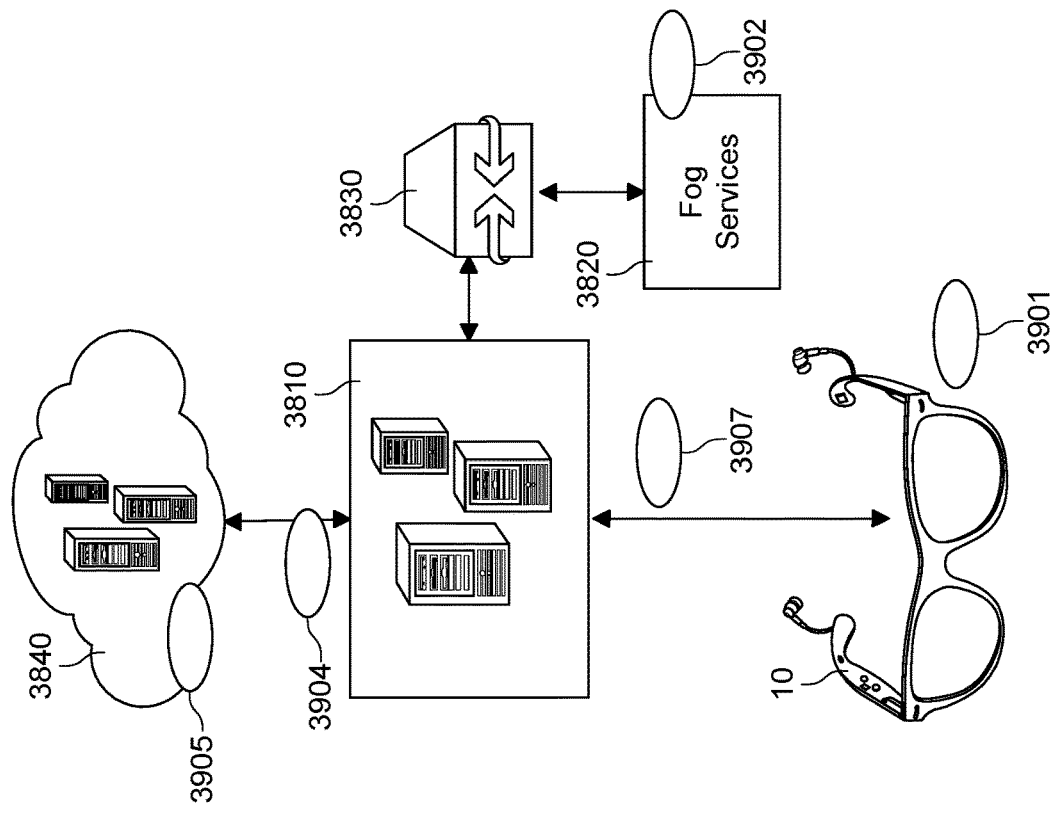
FIG. 38A depicts a particular example of a wearable system architecture, including data flows, that leverages fog and edge computing, in accordance with some implementations of the disclosure.

FIG. 38A depicts a particular example of a wearable system architecture, including data flows, that leverages fog and edge computing, in accordance with some implementations of the disclosure. FIG. 38B is a flow diagram illustrating operations that are performed by the system of FIG. 38A, in accordance with some implementations.

The system of FIG. 38A includes a wearable device 10, one or more edge services 3810, fog services 3820, gateway 3830 that can mediate communication between edge server 3810 and fog services 3820, and one or more cloud computing devices 3840. In some implementations, the functionalities of edge server 3810 can be implemented in wearable device 10 or a mobile device 20 communicatively coupled to wearable device 10.

Operation 3901 includes wearable device 10 collecting sensor data. For example, one or more sensors of the wearable device 10 can be used to record a sensory input stimulus to the user. This can include sensing ecological and physiological/psychophysiological data as described above. In some implementations, other devices besides wearable device 10, but in the same environment as wearable device 10 (e.g., a mobile device 20), and collect sensor data.

Operation 3902 includes one or more fog nodes of fog services 3820 processing, storing, and/or managing the sensor data that was collected. In some implementations the one or more fog nodes include a datastore that stores and/or manages the sensor data. In some implementations, the one or more fog nodes include a datastore that stores one or more sensory thresholds specific to a user of the wearable device 10 (e.g., one or more sensory thresholds selected from auditory, visual, or physiological sensory thresholds). In some implementations, the one or more fog nodes compare the sensory input stimulus with the one or more sensory thresholds specific to the user to determine that an intervention could be required.

Operation 3904 includes the edge server(s) 3810 encrypting and uploading data to the one or more cloud computing devices 3840. For example, if the fog services 3820 determined, after reviewing a subset of sensor data, that a threshold has been met, this subset of sensor data that trigged the determination can be encrypted by edge server 3810 and uploaded to the cloud.

Operation 3905 includes applying a data processing and machine learning pipeline/process. The pipeline can be performed using at least one or more cloud computing devices. Operation 3907 includes presenting an intervention/mediation to the user. As an example, a user can be visually distracted, which triggers changes in pupillary measurements. The updated pupillary measurements can result in a threshold being met that causes a mediation/intervention (e.g., alert to the user to refocus) to be presented to the user. The mediation can be triggered as follows. At the time of the pupillary measurement, an outward facing camera (e.g., as incorporated in a wearable device) captures an image of an object causing the distraction (e.g., the camera captures an image in the direction of the pupillary gaze). If the image matches or is sufficiently similar to (e.g., as determined by calculating a similarity score based on image features) a publicly stored image on the cloud of the same/similar object that was previously tagged as a personalized trigger for the user as a distracting cue, the mediation can be triggered. The machine learning pipeline can be used to match the captured image to the cloud's data store, and the image can be confirmed up and downstream as a distracting image. To make the comparison can be processed based on different parameters, including color, shape, edge detection, etc.

Figure 47:
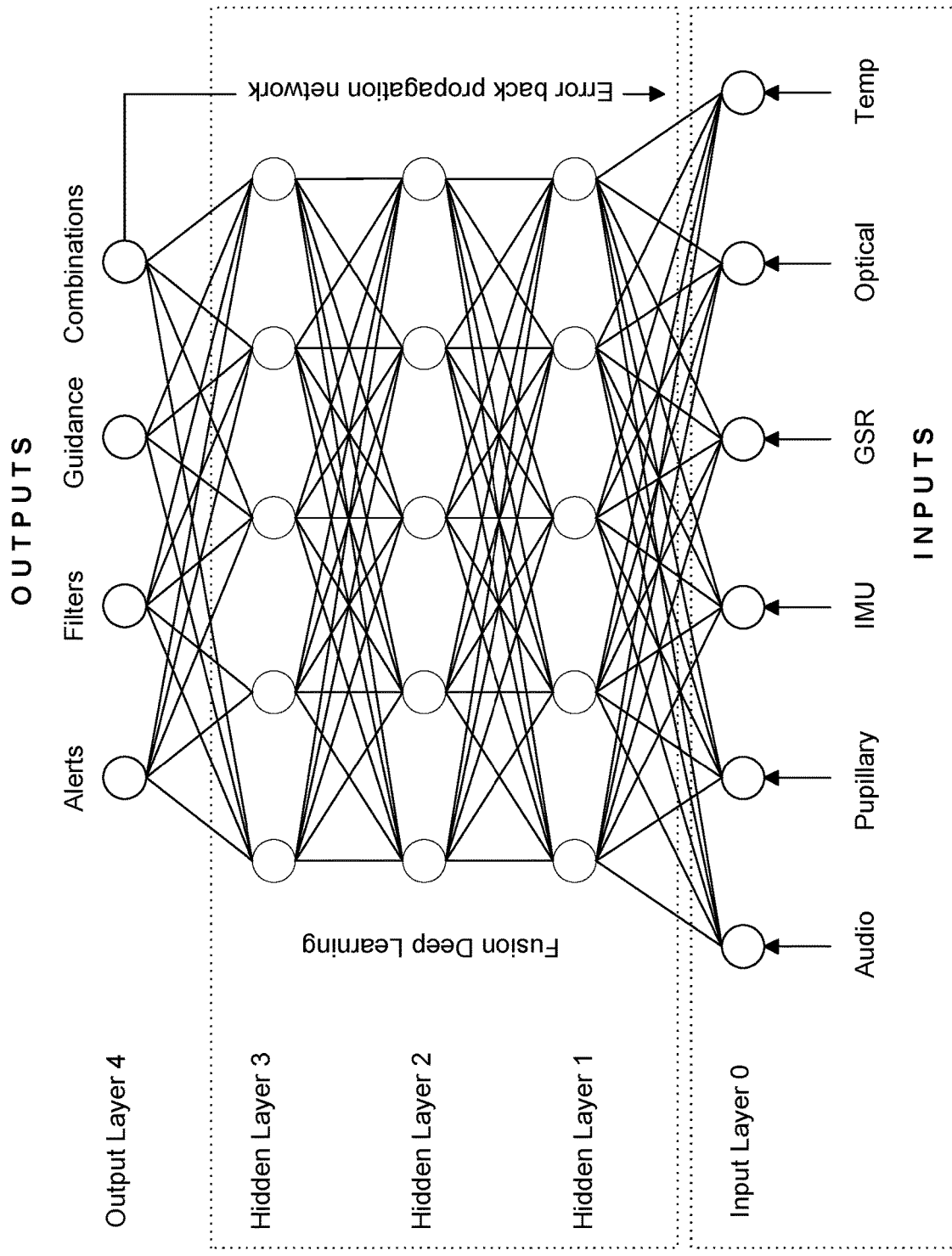
FIG. 47 illustrates one example of a fusion-based, deep learning model, in accordance with some implementations of the disclosure.

In some implementations, an FBDL model can be used to generate customized mediations given data from one or more sensors as inputs. Deep learning is a machine learning category that uses neural network algorithms that memorialize data for analysis and prediction. Neural networks use hidden layers to obtain features by connecting one another for replicable outcomes (output layers). FBDL confines connections between input and hidden layers so that every veiled unit attaches to a sub-section of its corresponding input. Hence, lower dimensioned characteristics can be derived by arbitrarily sampling big data. FIG. 47 illustrates one example of a FBDL model, in accordance with some implementations of the disclosure. As depicted, inputs can be one or more different types of sensor data, including audio data, pupillary data, IMU data, GSR data, optical data (e.g., image data), temperature data, etc. Through multiple layers the FBDL can be trained to recognize, based on the input data, a particular/personalized mediation type depending on recognition, where the mediation can be an alert, filter, guidance, or combination thereof.

Open Learner Model

Various implementations of the technology described herein can leverage an OLM to graphically represent (e.g., using a GUI) the current progress of users of multi-sensory, assistive wearable technology (e.g., neurodiverse individuals) such that the users or other interested party (e.g., therapist) can visualize, track, and/or reflect on their progress. OLM components can be incorporated into the systems and methods described herein to improve individual's hyper-, hypo-, and sensory-seeking challenges, which may affect task accuracy (i.e., performance), and mental health (i.e., calmness and alertness), particularly when distracted by eco or psychophysiological cues. Mediations that are fully transparent can provision results better than those that limit user's data access, straightforward system control, confidence, and trust in technologies.

While the majority of OLM data collected and used in some conventional technologies is fully exposed (e.g., disclosed) to a large number of individuals, with minimal safeguards for security and privacy, the technology described herein incorporates OLM in a system designed to promote security, privacy, and efficient use of computational resources, including bandwidth and storage. For example, the systems and methods described herein can utilize OLM in tandem with fog and edge networking as discussed above. Additionally, the GUI associated with the OLM model can be used to set access controls.

FIGS. 39-45 depict an OLM framework in accordance with some implementations of the disclosure. The depicted OLM framework includes three tables (FIGS. 40, 42, and 44) and four flowcharts (FIGS. 39, 41, 43, and 45). The OLM framework depicts custom labeled characteristics pertinent to securing data by the individual user/wearer and their support (e.g., therapist, family, etc.) During operation, a wearer may select/actuate controls on a GUI to determine how little or how much data can be sensed, collected, processed, and/or shared on a feature-by-feature basis. As depicted, characteristics or features can be divided into what elements are important and to be sensed, mediated, and/or stored, how this is accomplished, and access privileges for reviewing and administering these functions.

Figure 39:
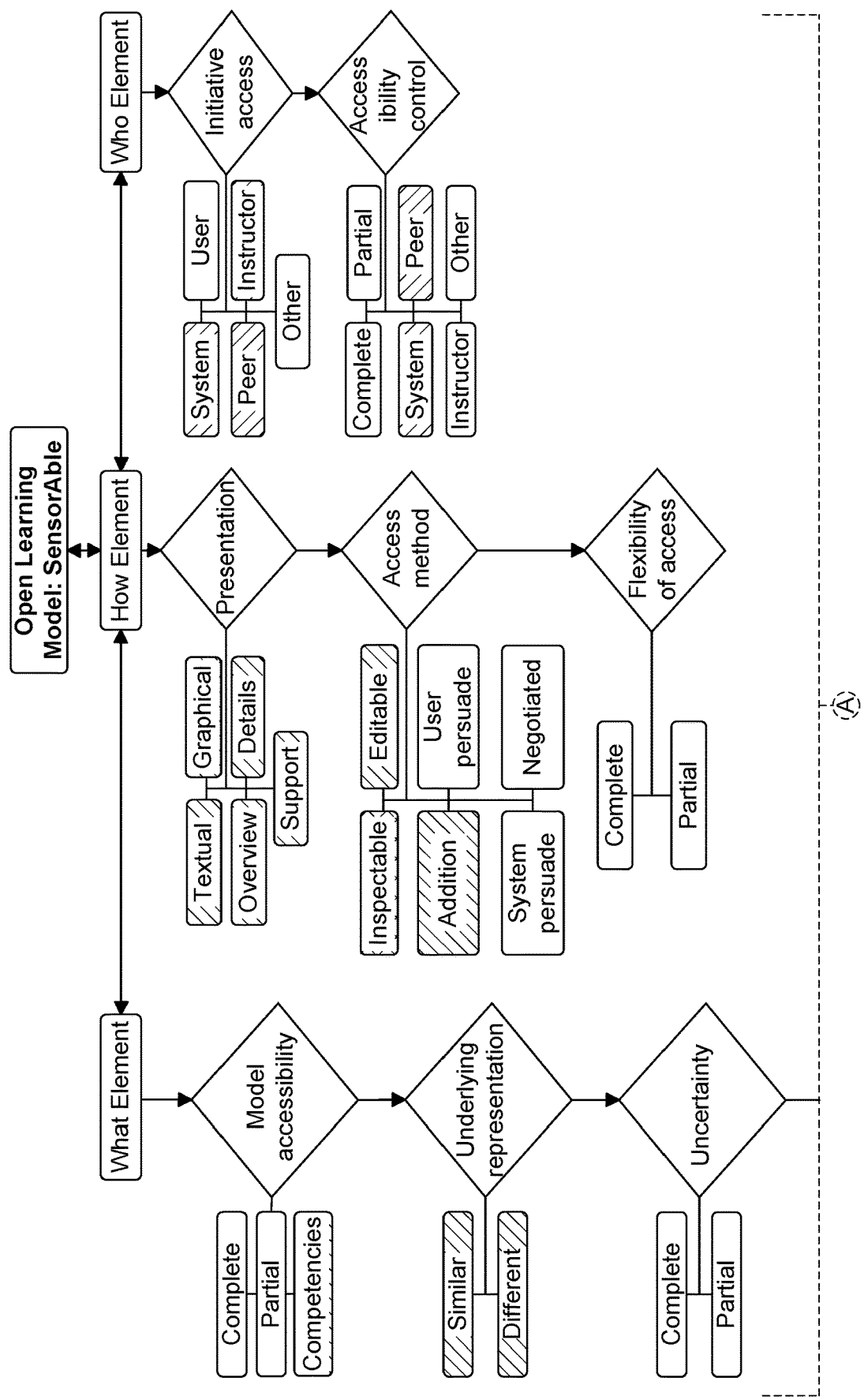
FIG. 39 is a high-level flowchart of an Open Learner Model (OLM) framework, in accordance with some implementations of the disclosure.
Figure 39:
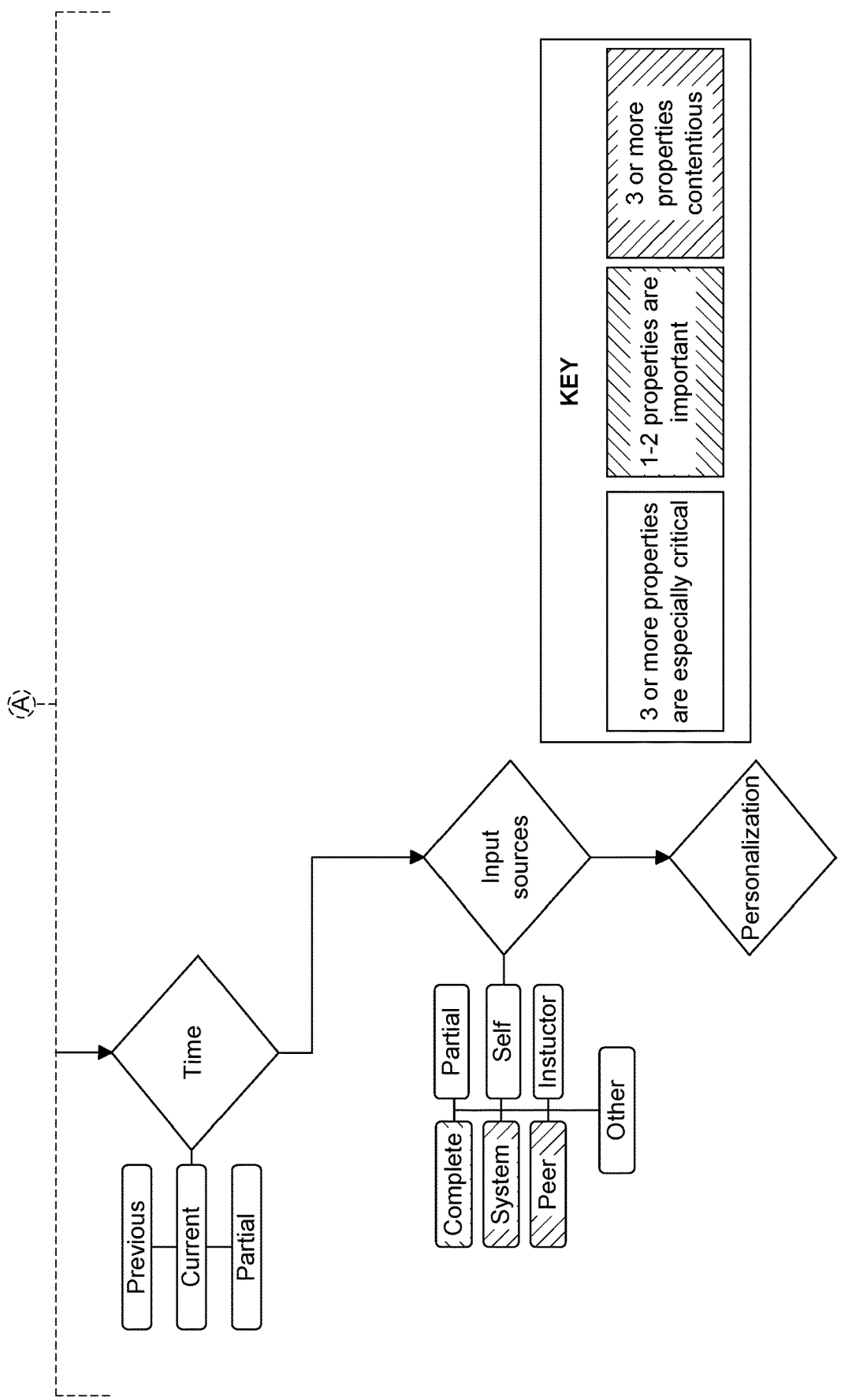
Figure 41:
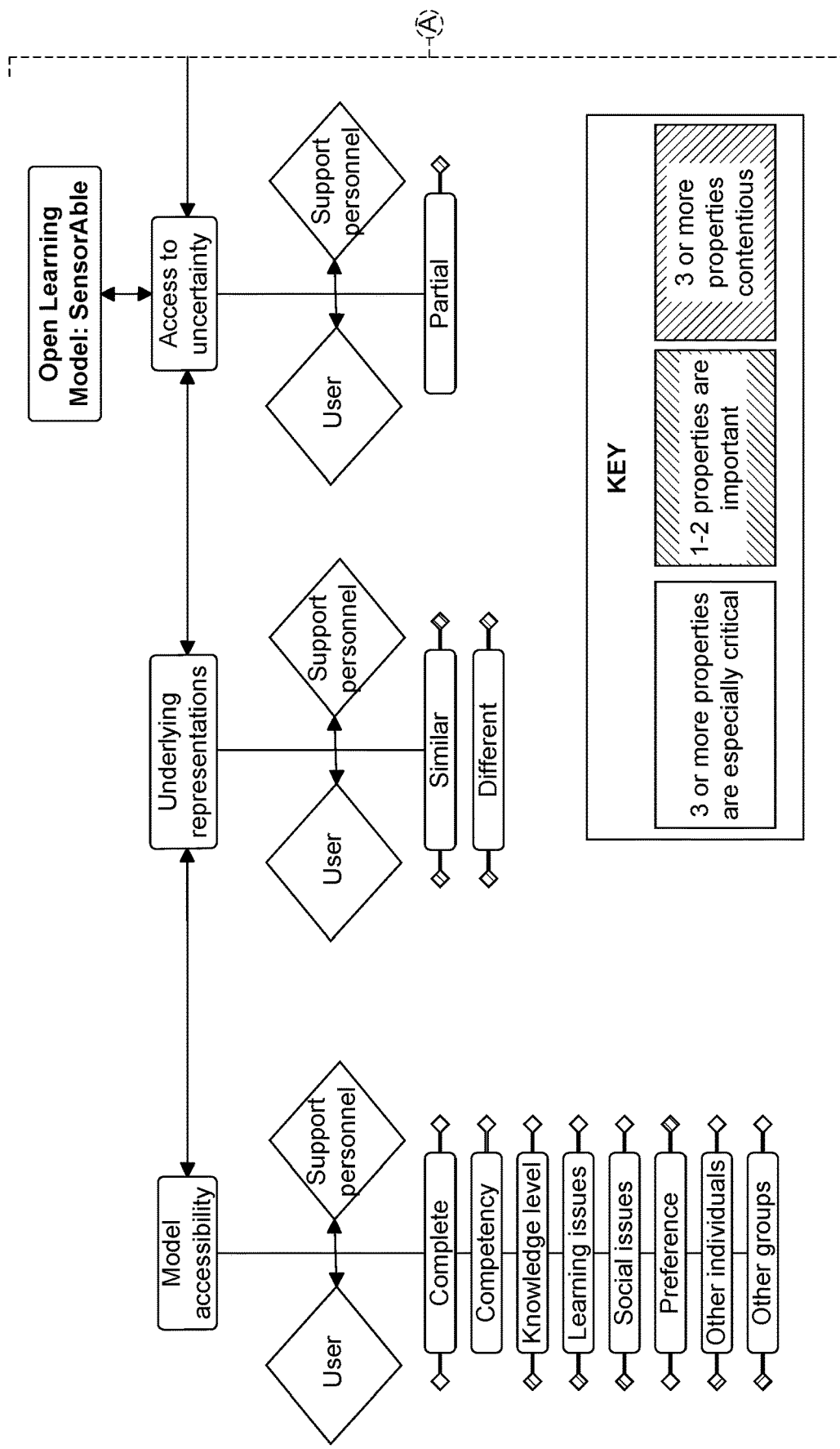
FIG. 41 depicts a flowchart of the OLM described herein, the flowchart depicting what is available.
Figure 41:
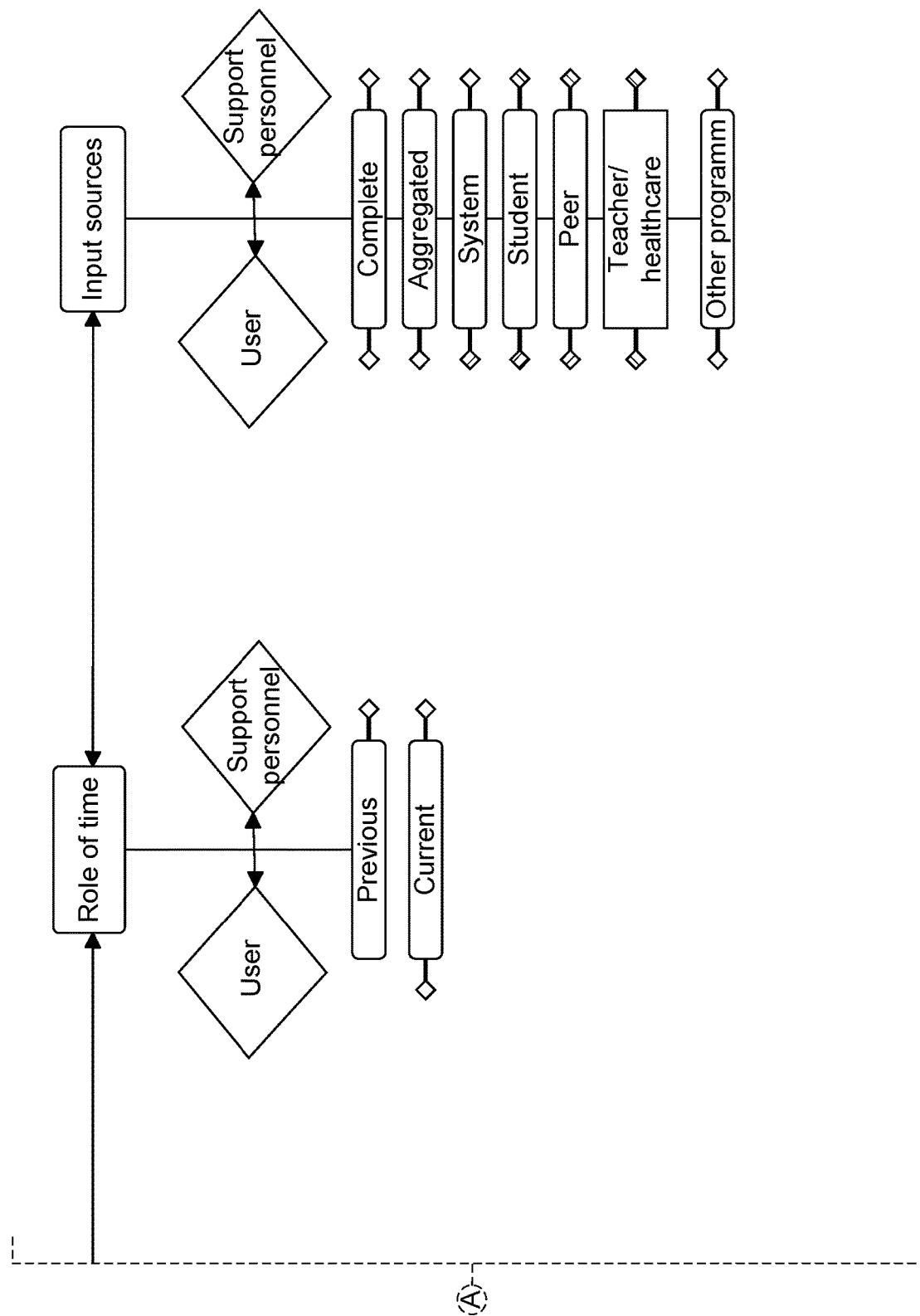

FIG. 39 is a high-level flowchart of the OLM framework. This example OLM framework defines eleven elements (i.e., model accessibility, presentation, access method, accessibility control, etc.) within three categories, their corresponding properties (i.e., complete, partial, current, future, etc.), and their description (i.e., a textual explanation of each purpose element) used in defining the specific OLM (See tables of FIGS. 40, 42, 44, left to right). These properties signify levels of accessibility purpose elements across eleven aspect columns (i.e., from left to right including right to access, control through trust, assessment, etc.). Each aspect uses ranking levels to differentiate elements from one another (i.e., those deemed critical or especially critical are marked X and XX, respectively; those deemed debatable are marked=; and those not relevant are left blank).

One of the OLM maps describes "what is available" (FIGS. 40-41) by addressing the extent of model accessibility, underlying representations, access to uncertainty, role of time, access to source issues, and access to model personalization. By way of example, the model's extent of accessibility (Item #1) is predominantly open "Completely" across the board with critical availability to nearly all stakeholders.

Figure 43:
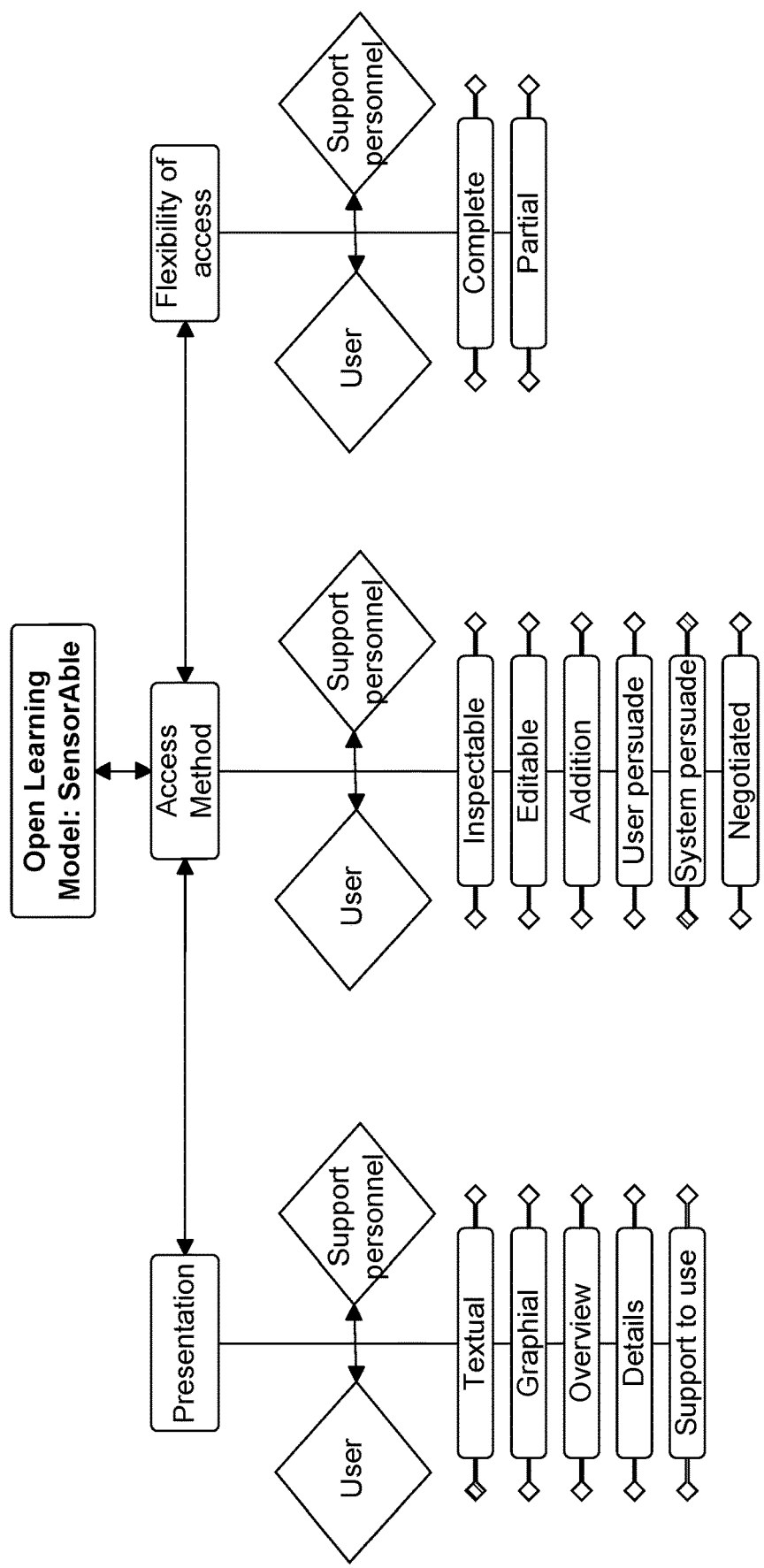
FIG. 43 depicts a flowchart of the OLM described herein, the flowchart depicting how the model is presented to stakeholders.
Figure 45:
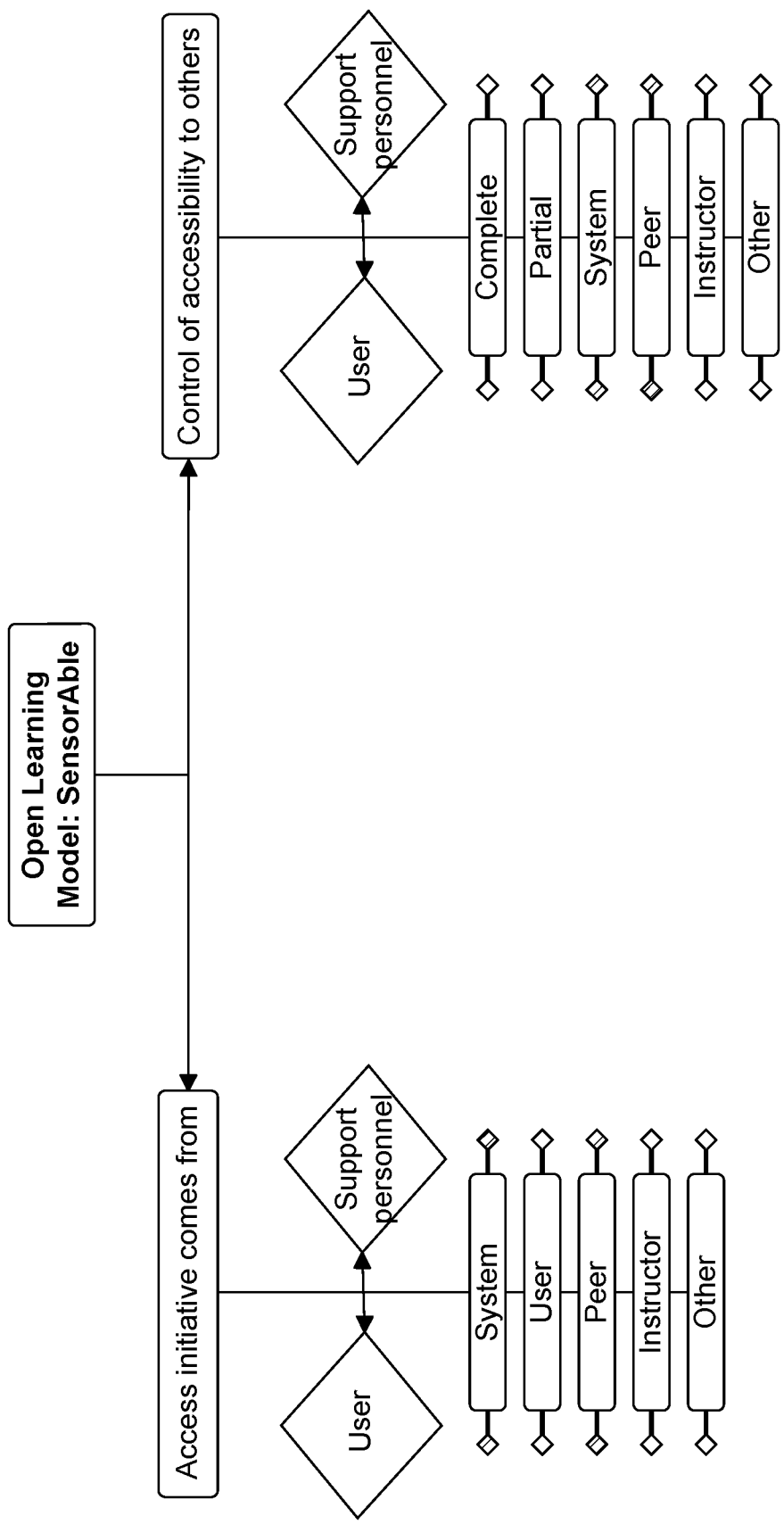
FIG. 45 depicts a flowchart of the OLM described herein, the flowchart depicting who controls access over others.

One of the OLM maps describes "how the model is presented" to stakeholders, including friends and acquaintances (FIGS. 42-43). Included are presentation details (i.e., word cloud, skill meters, radar plots, etc.), access methods (i.e., inspectable, editable, user versus system persuasion, etc.), and access flexibility. Compared to the "what is available" table, this table include elements tagged with critical and especially critical rankings.

One of the OLM maps describes "who controls access" (FIGS. 44-45) discloses two purpose elements that map focal points (i.e., whom accessibility is derived from) and dominant access (i.e., who controls access over others).

Figure 46:
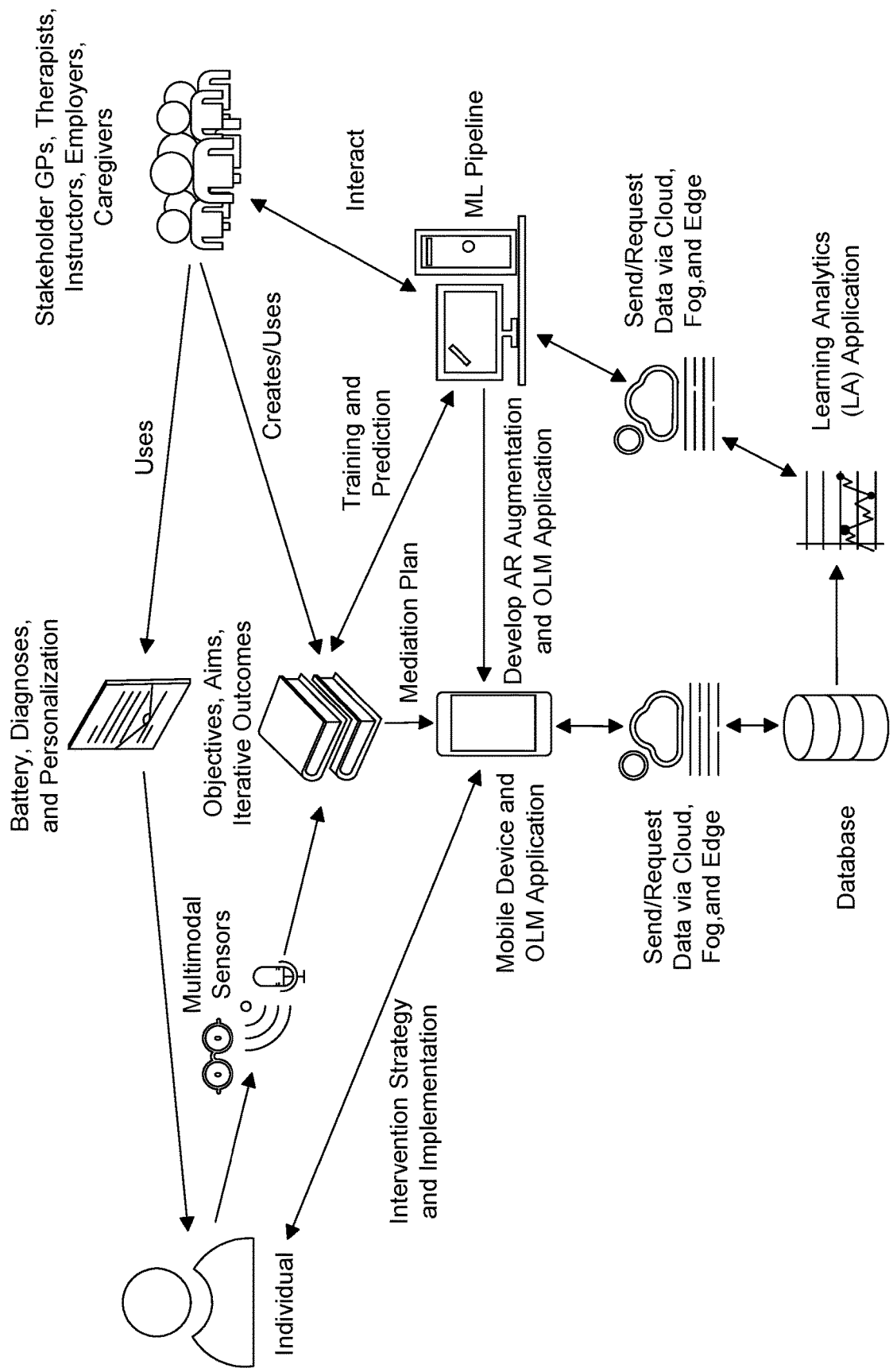
FIG. 46 depicts a system that implements an augmented reality-based multimodal learning analytic framework, in accordance with some implementations of the disclosure.

Some implementations of the multi-sensory assistive wearable technology described herein can leverage an AR-supported framework of development, analysis, and assessment criteria. In this case, the AR support can refer to the use of AR to sonically or visually replace certain auditory or visual information presented to the user, such as, for example, blurring, squelching, or erasing an offending image, or performing digital signal processing of an audio signal to make it less distracting. The framework can provide a mechanism for implementing improved OLM, quantified self (QS) frameworks, and/or multimodal learning analytic (MMLA) frameworks. To this end, FIG. 46 depicts a system that implements an AR-based MMLA framework, in accordance with some implementations of the disclosure. As depicted, the system is configured to implement at least three functions for the user and/or other stakeholders of the multi-sensory assistive wearable technology described herein: battery, diagnoses, and personalization; objectives, aims, and iterative outcomes; and mediative strategy and digital accommodations via technology (e.g., using multi-modal sensors and implementing intervention strategies). Depending on configured access controls, stakeholders including users can maintain accessibility throughout the framework As depicted by FIG. 46, general practitioners, therapists, instructors, employers, caregivers, and/or educators can help guide the aforementioned three functions. Sensory sensitivity, attention, mental health objectives, aims, and iterative outcomes can be augmented using AR augmentation and/or OLM applications. The individual can be a neurodiverse or potentially neurodiverse individual who can be at-risk in social settings, an employee at work, and/or student in a higher education institution venue. Battery and diagnostics (i.e., MaRs-IB, ASRS, AQ-50, etc.) including individual sensitivity and mediation profiles (ISIP) can be developed for each user. As described herein, an ISIP can refer to a data profile provisioned by one or more mobile application(s) and used daily by a user to customize their reactivity and provide behavior modification (e.g., using the Distraction Intervention Desire Questionnaire). An ISIP can help personalize user-specific sensory thresholds and/or sensory resolutions, described herein, that can affect alert, filter, and guidance interventions provided for a given user.

In some implementations, ISIPs can utilize state-based anxiety and fatigue monitoring (SAFE) and randomized, regular feedback (FADE) to ensure ethical compliance, efficacy, and user satisfaction. Data can be stored on wearable devices (e.g., wearable devices 10) mobile devices (e.g. mobile device 20), and/or other devices within a LAN or ad-hoc network of the wearable device/mobile device, and available for OLM application parsing or stakeholder review. Owing to the data's sensitive, contextual and personalized nature, the majority of information can localized, and processed-wherever possible-only using edge and fog transmission as described above with reference to FIGS. 37 and 38A-38B. Cloud processing, transmission, and storage can be minimized or avoided entirely to preserve privacy/security and ensure ethical robustness. Further security can be enabled through encryption/decryption policies that provide additional safeguarding layers whenever stakeholders review or process sensitive data.

Figure 48:
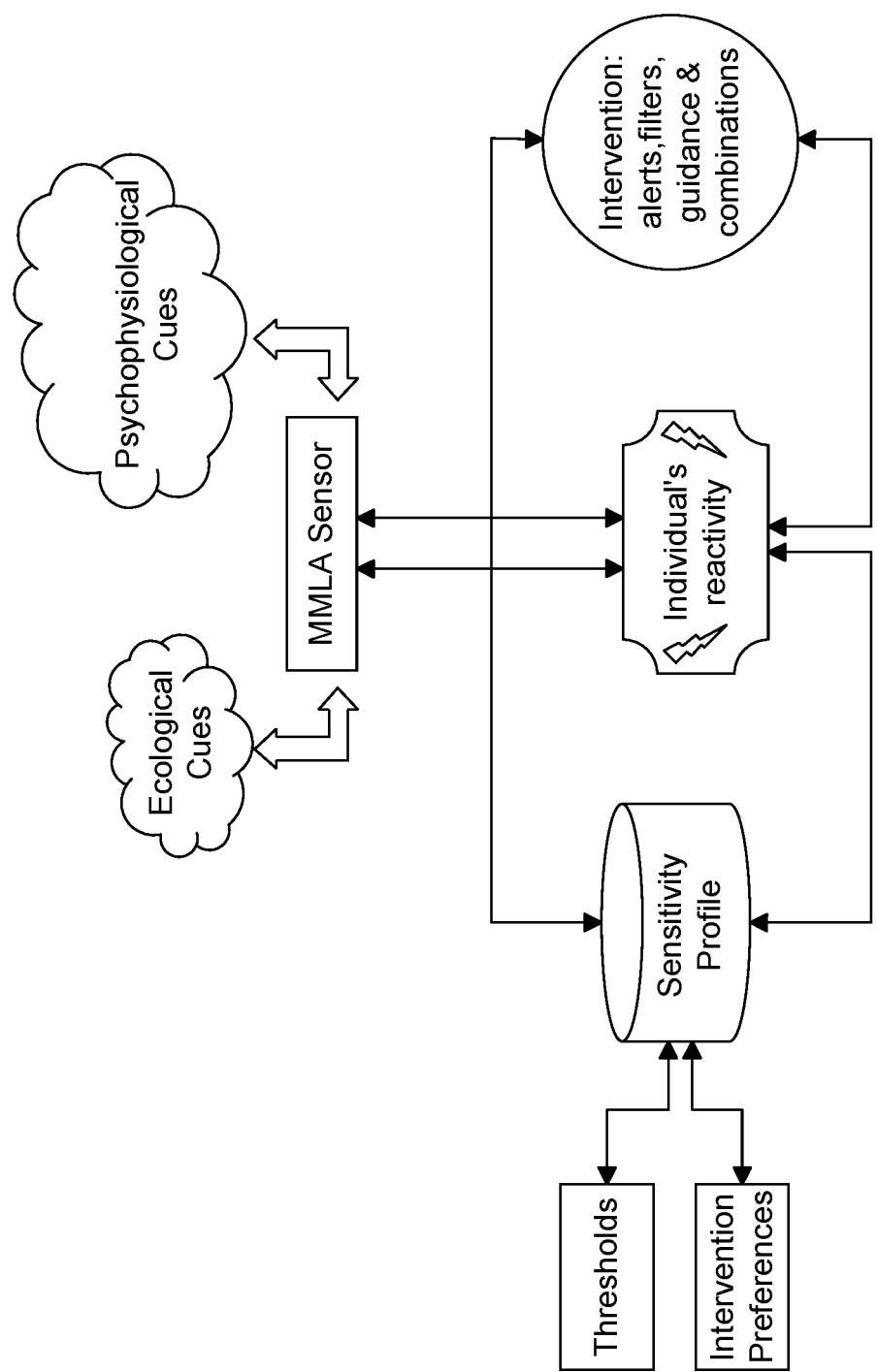
FIG. 48 is a high level flow diagram conceptually illustrating the operation of a multi-sensory assistive wearable system, in accordance with some implementations of the disclosure.

FIG. 48 is a high level flow diagram conceptually illustrating the operation of a multi-sensory assistive wearable system, in accordance with some implementations of the disclosure. An individual/wearer reacts to the environment. MMLA sensors (e.g., as incorporated in the wearable device and/or some other device in the user's environment) collect data corresponding to ecological cues (e.g., temperature data, image data, etc.) and psychophysiological cues (e.g., pupillary data, GSR data, heart rate data, etc.). The user's sensitivity profile, which can include thresholds and intervention/mediation preferences, is used to determine an intervention/media that is an alert, filter, guidance, or combination thereof. The user's reaction continues to be measured after the mediation. As such, a feedback loop can enable a constant and consistent pathway to unfold, whereby the individual's responses are weighed against ecological and psychophysiological responses. Once a personalization threshold is exceeded, an assistive or mediative event occurs, and the system again monitors the individual's response—weighing this against the current sensory input.

In some implementations, as long as the system determines that there is a mismatch in signals that align to personalization aims that can be accommodated through assistive means, and that these address sensory, attention, and/or mental health markers, the individual can receive a mediation. In some implementations, if mediations are no longer effective or not enhancing a user's experience, they can be disabled by the individual (e.g., via a user interface of the wearable device or mobile device) or any of the stakeholders.

In some implementations, cues that are no longer distracting can be removed from the identification process.

Tables 47A-47B show some example design specifications, including latency parameters, for implementing audiometric sensing, physiological/psychophysiological sensing, and transmission in accordance with some implementations of the disclosure. It should be appreciated that system specifications can vary depending on the available hardware.

TABLE 47A (design specifications for low performance)

| Protocol | Description | Range | Latency | Bitrate |
|---|---|---|---|---|
| Audiometric sensing | Omnidirectional dynamic or moving coil microphone | 50 Hz-20 kHz response; −42 to −30 dBv sensitivity, S/N 60 dBA, and 2 KΩ output | 11.61-23.22 ms | 512-1024 samples @ 44.1 kHz sampling rate |
| Physiological/ Psychophysiological sensing | GSR conductance and triaxial accelerometer | SCL 2-20 µS; Change in SCL 1-3 µS; Amplitude 0.2-1 µS; | SCR 1-3 s; SCR rise time 1-3 s; SCR half recovery time 2-10 s | Frequency 1-3 pm |
| Bluetooth transmission | Headset wearable to mobile phone | 5-30 meters | 200 ms | 2.1 Mbps |
| Wireless transmission | | 32m indoors 95m outdoors | ~150 ms | 600 Mbps |

TABLE 47B (design specifications for enhanced performance)

| Protocol | Description | Range | Latency | Bitrate |
|---|---|---|---|---|
| Audiometric sensing | Omnidirectional dynamic or moving coil microphone | 20 Hz-20 kHz response; −42 dBv sensitivity, S/N 39 dBA, and 1 KΩ output | 2.9-5.8 ms | 128-256 samples @ 44.1 kHz sampling rate |
| Physiological/ Psychophysiological sensing | GSR conductance and triaxial accelerometer | SCL 2 µS; Change in SCL 1 µS; Amplitude 0.2 µS; | SCR 1 s; SCR rise time 1 s; SCR half recovery time 2 s | Frequency 3 pm |

TABLE 47B-continued (design specifications for enhanced performance)

| Protocol | Description | Range | Latency | Bitrate |
|---|---|---|---|---|
| Bluetooth transmission | Headset wearable to mobile phone or computer | 30 meters | 200 ms | 2.1 Mbps |
| Wireless transmission | Mobile or computer to router | 32m indoors 95m outdoors | ~150 ms | 600 Mbps |

Applications

The multi-sensory assistive wearable technology described herein can be utilized across a myriad of applications to supply a myriad of potential advantages. For example, in an employment application, the technology described herein can potentially reduce distractibility, improve attention and performance, lower anxiety, and/or increase employee output and/or satisfaction. Metrics that could potentially be improved in the employment application include improved onboarding and training of neurodiverse, autistic, and neurotypical applicants and new hires, reduced employee turnover, increased productivity rate, diversity and/or inclusion, increased profit per employee, lowered healthcare costs, and/or ROI, employee net promoter score, cost of HR per employee, employee referral, combinations thereof and the like.

In an academic application, the technology described herein can potentially increase concentration and/or comprehension, and reduced, minimized and/or substantially eliminated hesitation and/or increased, enhanced and/or increased comfort. Metrics that could potentially be improved in an academic application include retention rates (next term persistence versus resignation), graduation rates, time to completion, credits to degree and/or conferrals, academic performance, educational goal tracking, academic reputation, and/or underemployment of recent graduates.

In a social application, the technology described herein can potentially increase participation and/or motivation, and reduce apprehension. Metrics that could potentially be improved in a social application include primary socialization (learn attitudes, values, and/or actions appropriate to individuals and culture), secondary socialization (learn behavior of smaller groups within society), developmental socialization (learn behavior in social institution and/or developing social skills), anticipatory socialization (rehearse future positions, occupations, and/or relationships), and resocialization (discarding former behavior and/or accepting new patterns as part of transitioning one's life).

In a transportation lorry/trucking application, the technology described herein can potentially increase and/or improve attention and/or performance, reduce fatigue, and improve response times. Metrics that could potentially be improved in a transportation lorry/trucking application include logistics benefits including increased safety and/or productivity (shut down engine, recommend rest, crash data statistics and/or analysis, etc.), reduced logistical strain and/or financial burden (reduced shipping, delivery time, and/or transportation costs), effective planning, dispatch, and/or scheduling.

In a transportation aircraft application, the technology described herein can potentially increase focus and/or performance, and reduce fatigue and/or apprehension reduction. Metrics that could potentially be improved in a transportation aircraft setting include safety (e.g., fatality and/or accident rate, system risk events, runway incursions, hazard risk mitigation, commercial space launch incidents, worldwide fatalities), efficiency (taxi-in/out time, gate arrival/delay, gate-to-gate times, distance at level-flight descent, flown v. filed flight times, average distance flown, arrival and/or departure delay totals, number of operations, on-time arrivals, average fuel burned), capacity (average daily capacity and daily operations, runway pavement conditions, NAS reliability), environment (noise exposure, renewable jet fuel, NAW-wide energy efficiency, emission exposure), and/or cost effectiveness (unit per cost operation).

In an IoT application, the technology described herein can potentially integrate mechanical and digital machines, objects, animals, and/or people (each with unique identifiers) received transferred information from the wearable so that actionable commands and/or analyses can occur. Metrics that could potentially be improved in the IoT application include an increase in physiological/psychophysiological activity can provide alerts to parents, caregivers, and/or professionals (para and otherwise) in the event wearable thresholds are exceeded. Integration to environmental control units (ECU) bridge between the wearable and appliances including, but not limited to TV's, radios, lights, VCR's, motorized drapes, and/or motorized hospital beds, heating, and/or ventilation units (air-con), clothes washers and/or driers.

In a performance enhancement application, the technology described herein can potentially improve procrastination, mental health, fatigue, anxiety, and/or focus. Metrics that could potentially be improved in a performance enhancement application include testing (logic processing, advocacy, curiosity, technical acumen and/or tenacity), Leadership (mentorship, subject matter expertise, team awareness, interpersonal skills, reliability), Strategy & Planning (desire, quality, community, knowledge and functionality), Intangibles (communication, diplomacy, negotiations, self-starter, confidence, maturity and selflessness).

In telemedicine, emergency medicine, and healthcare application, the technology described herein can potentially improve the ability for medical and healthcare practitioners to share data with wearable users to help fine tune therapies, Rx, dispatch for emergency assist, surgical suite monitoring and/or optimization, work-schedule, and/or logistics strategy, pupillometry indicating unsafe conditions, unsafe warnings if thresholds are crossed (performance or physiological/psychophysiological). Metrics that could potentially be improved in a telemedicine, emergency medicine, and/or healthcare application include telemedicine metrics (e.g., consultation time, diagnoses accuracy, rate of readmission, quality of service/technology, patient and/or clinician retention, time and/or travel saved, treatment plan adherence, patient referral), surgical metrics (e.g., first case starts, turnover times, location use/time, complications, value-based purchasing, consistency of service, outcomes), emergency metrics (e.g., average patient flow by hour, length of processing/stay, Time-to-Relative Value Unit, Patients Seen, RVU produced, Current Procedural Terminology (CPTs) performance, average evaluation and management distribution percentage, total number of deficient charts.

In a parental, guardian, and/or educational monitoring application, the technology described herein can potentially abet metric parenting (and guardianship) whereby work-life balance is made possible by meeting actionable and measurable goals and deadlines to improve family dynamics, including being more present, aware, and/or tracking engagement of children (particularly those with exceptionalities, although it is not limited to gifted, neurodiverse but all children). Metrics that could potentially be improved in a parental, guardian, and/or educational monitoring application include family time, engagement, academic improvement, reduction in digital media technologies, screen time, online and console gaming, schedule adherence, nutritional faithfulness, safety and/or exposure to substance abuse, seizure and/or location monitoring.

As various changes could be made in the above systems, devices and methods without departing from the scope of the invention, it is intended that all matter contained in the above description shall be interpreted as illustrative and not in a limiting sense. Any numbers expressing quantities of ingredients, constituents, reaction conditions, and so forth used in the specification are to be interpreted as encompassing the exact numerical values identified herein, as well as being modified in all instances by the term "about." Notwithstanding that the numerical ranges and parameters setting forth, the broad scope of the subject matter presented herein are approximations, the numerical values set forth are indicated as precisely as possible. Any numerical value, however, may inherently contain certain errors or inaccuracies as evident from the standard deviation found in their respective measurement techniques. None of the features recited herein should be interpreted as invoking 35 U.S.C. § 112, paragraph 6, unless the term "means" is explicitly used.

In this document, the terms "machine readable medium," "computer readable medium," and similar terms are used to generally refer to non-transitory mediums, volatile or non-volatile, that store data and/or instructions that cause a machine to operate in a specific fashion. Common forms of machine-readable media include, for example, a hard disk, solid state drive, magnetic tape, or any other magnetic data storage medium, an optical disc or any other optical data storage medium, any physical medium with patterns of holes, a RAM, a PROM, EPROM, a FLASH-EPROM, NVRAM, any other memory chip or cartridge, and networked versions of the same.

These and other various forms of computer readable media can be involved in carrying one or more sequences of one or more instructions to a processing device for execution. Such instructions embodied on the medium, are generally referred to as "instructions" or "code." Instructions can be grouped in the form of computer programs or other groupings. When executed, such instructions can enable a processing device to perform features or functions of the present application as discussed herein.

In this document, a "processing device" can be implemented as a single processor that performs processing operations or a combination of specialized and/or general-purpose processors that perform processing operations. A processing device can include a CPU, GPU, APU, DSP, FPGA, ASIC, SOC, and/or other processing circuitry.

The various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Each of the processes, methods, and algorithms described in the preceding sections can be embodied in, and fully or partially automated by, instructions executed by one or more computer systems or computer processors comprising computer hardware. The processes and algorithms can be implemented partially or wholly in application-specific circuitry. The various features and processes described above can be used independently of one another, or can be combined in various ways. Different combinations and sub-combinations are intended to fall within the scope of this disclosure, and certain method or process blocks can be omitted in some implementations. Additionally, unless the context dictates otherwise, the methods and processes described herein are also not limited to any particular sequence, and the blocks or states relating thereto can be performed in other sequences that are appropriate, or can be performed in parallel, or in some other manner. Blocks or states may be added to or removed from the disclosed example embodiments. The performance of certain of the operations or processes can be distributed among computer systems or computers processors, not only residing within a single machine, but deployed across a number of machines.

As used herein, the term "or" can be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

I claim:

1. A system, comprising:
   a wearable device comprising one or more sensors;
   one or more processors; and
   one or more non-transitory computer-readable media having executable instructions stored thereon that, when executed by the one or more processors, cause the system to perform operations comprising:
   obtaining user sensory sensitivity data corresponding to user input indicating whether a user of the wearable device is visually sensitive, sonically sensitive, or interoceptively sensitive;
   storing a first identifier that indicates whether the user is neurodiverse or neurotypical;
   determining, using at least the first identifier and the user sensory sensitivity data, one or more sensory thresholds specific to the user and mediation data corresponding to one or more mediations specific to the user, the one or more sensory thresholds selected from auditory, visual, or physiological sensory thresholds;

storing the one or more sensory thresholds and the mediation data;

recording, using the one or more sensors, a sensory input stimulus to the user;

comparing the sensory input stimulus with the one or more sensory thresholds specific to the user;

in response to comparing the sensory input stimulus with the one or more sensory thresholds, determining, based at least on the mediation data, a mediation of the one or more mediations to be provided to the user, the mediation configured to provide the user relief from distractibility, inattention, anxiety, fatigue, or sensory issues; and providing the mediation to the user, the mediation comprising an alert mediation, a guidance mediation, or a filter mediation.

2. The system of claim 1, wherein:

the operations further comprise: receiving user demographic data corresponding to user input indicating an age, education level, or gender of the user; and determining the one or more sensory thresholds specific to the user and the mediation data corresponding to the one or more mediations specific to the user, comprises: determining, using at least the first identifier, the user sensory sensitivity data, and the user demographic data, the one or more sensory thresholds and the mediation data.

3. The system of claim 1, wherein the first identifier indicates whether or not the user is autistic.

4. The system of claim 3, wherein the first identifier indicates that the user is autistic.

5. The system of claim 4, wherein:

the mediation is configured to provide the user relief from fatigue;

the mediation comprises the filter mediation; and the filter mediation comprises filtering, in real-time, an audio signal presented to the user or an optical signal presented to the user.

6. The system of claim 4, wherein the mediation is configured to provide the user relief from a distraction by increasing a response time of the user to the distraction.

7. The system of claim 4, wherein:

obtaining the user sensory sensitivity data comprises receiving, at a graphical user interface, one or more first responses by the user to one or more first prompts indicating whether the user is visually sensitive, sonically sensitive, or interoceptively sensitive; and the operations further comprise deriving the first identifier indicating that the user is autistic by:

receiving, at the graphical user interface, one or more second responses by the user to one or more second prompts indicating an anxiety level of the user;

deriving, based on the sensory sensitivity data, one or more sensory sensitivity scores comprising a visual sensitivity score, a sonic sensitivity score, or an interoceptive sensitivity score;

deriving, based on the one or more second responses, an anxiety score; and predicting, using a model that predicts a probability of autism based at least on an anxiety level and one or more sensory sensitivity levels, based at least on the anxiety score and the one or more sensory sensitivity scores, that the user is autistic.

8. The system of claim 4, wherein:

obtaining the user sensory sensitivity data comprises receiving, at a graphical user interface, one or more first responses by the user to one or more first prompts indicating whether the user is visually sensitive, sonically sensitive, or interoceptively sensitive; and the operations further comprise deriving the first identifier indicating that the user is autistic by:

receiving, at the graphical user interface, one or more second responses by the user to one or more second prompts indicating a fatigue level of the user;

deriving, based on the sensory sensitivity data, one or more sensory sensitivity scores comprising a visual sensitivity score, a sonic sensitivity score, or an interoceptive sensitivity score;

deriving, based on the one or more second responses, a fatigue score; and predicting, using a model that predicts a probability of autism based at least on a fatigue level and one or more sensory sensitivity levels, based at least on the fatigue score and the one or more sensory sensitivity scores, that the user is autistic.

9. The system of claim 1, wherein obtaining the user sensory sensitivity data further comprises: recording, using at least the one or more sensors, a response by the user to a visual stimulus, a sonic stimulus, or a physiological stimulus.

10. The system of claim 1, wherein the mediation comprises a combination mediation of at least two mediations selected from the alert mediation, the guidance mediation, and the filter mediation.

11. The system of claim 10, wherein the combination mediation comprises the alert mediation followed by the filter mediation.

12. The system of claim 11, wherein:

the alert mediation comprises alerting the user about a distraction that is visual or auditory; and the filter mediation comprises: filtering, in real-time, an audio or optical signal presented to the user, the audio or optical signal associated with the distraction.

13. The system of claim 1, wherein the system further comprises one or more fog nodes configured to locally store sensor data collected by the one or more sensors, the sensor data including first sensor data associated with the sensory input stimulus.

14. The system of claim 13, wherein:

storing the one or more sensory thresholds and the mediation data, comprises: locally storing, using the one or more fog nodes, the one or more sensory thresholds and the mediation data; and comparing the sensory input stimulus with the one or more sensory thresholds, comprises: comparing, using the one or more fog nodes, the sensory input stimulus with the one or more sensory thresholds.

15. The system of claim 13, further comprising one or more edge nodes configured to communicatively couple to the one or more fog nodes and a cloud server remotely located from the wearable device.

16. The system of claim 15, wherein the one or more edge nodes are configured to:

encrypt the first sensor data associated with the sensory input stimulus to obtain encrypted data;

transmit the encrypted data to the cloud server; and receive a response from the cloud server.

17. The system of claim 15, wherein the one or more fog nodes and the one or more edge nodes reside on a local area network (LAN) containing the wearable device, an ad-hoc network containing the wearable device, a LAN of a mobile device directly coupled to the wearable device, or an ad-hoc network of the mobile device.

18. The system of claim 15, wherein:
the sensor data comprises second sensor data that does not trigger the mediation; and
the system is configured such that the second sensor data that does not trigger the mediation is not made available to any cloud server remotely located from the wearable device.

19. The system of claim 15, wherein:
the mediation comprises the filter mediation that comprises filtering, in real-time, an optical signal presented to the user;
the first sensor data associated with the sensory input stimulus comprises first image data;
the one or more edge nodes or the one or more fog nodes are configured to determine whether the first image data is sufficiently similar to second image data stored at the cloud server; and
determining the mediation to be provided to the user comprises in response to determining that the first image data is sufficiently similar to the second image data, determining the filter mediation.

20. The system of claim 15, wherein:
the mediation comprises the filter mediation that comprises filtering, in real-time, an audio signal presented to the user;
the first sensor data associated with the sensory input stimulus comprises first audio data;
the one or more edge nodes or the one or more fog nodes are configured to determine whether the first audio data is sufficiently similar to second audio data stored at the cloud server; and
determining the mediation to be provided to the user comprises in response to determining that the first audio data is sufficiently similar to the second audio data, determining the filter mediation.

21. The system of claim 1, wherein the operations further comprise:
presenting to the user, on a graphical user interface, one or more access controls that grant or deny access to user data to one or more other users, the user data comprising sensor data collected by the one or more sensors, the one or more sensory thresholds, the mediation data, or a record of mediations presented to the user; and
receiving data corresponding to user input selecting the one or more access controls.

22. The system of claim 1, wherein the operations further comprise:
presenting to the user, on a graphical user interface, one or more access controls that grant or deny access to one or more other users to influence mediations that are presented to the user; and
receiving data corresponding to user input actuating the one or more access controls.

23. The system of claim 1, wherein the operations further comprise: presenting to the user, on a graphical user interface, a graphical summary of progress of the user from using the wearable device, the graphical summary including a moving average of time between mediations.

24. The system of claim 1, wherein:
the one or more sensors comprise multiple sensors of different types, the multiple sensors comprising: an auditory sensor, a galvanic skin sensor, a pupillary sensor, a body temperature sensor, a head sway sensor, or an inertial movement unit;
recording the sensory input stimulus to the user comprises obtaining first sensory data corresponding to a first sensory input stimulus from a first sensor of the multiple sensors, and second sensory data corresponding to a second sensory input stimulus from a second sensor of the multiple sensors; and
determining the mediation to be provided to the user, comprises: inputting at least the first sensory data and the second sensory data into a fusion-based deep learning (FBDL) model that outputs an identification of the mediation to be provided to the user.

25. The system of claim 24 wherein determining the mediation to be provided to the user, comprises: inputting at least the first sensory data, the second sensory data, and the mediation data into the FBDL model that outputs the identification of the mediation to be provided to the user.

26. A method, comprising:
obtaining, at a wearable device system, user sensory sensitivity data corresponding to user input indicating whether a user of a wearable device of the wearable device system is visually sensitive, sonically sensitive, or interoceptively sensitive;
storing a first identifier that indicates whether the user is neurodiverse or neurotypical;
determining, at the wearable device system, using at least the first identifier and the user sensory sensitivity data, one or more sensory thresholds specific to the user and mediation data corresponding to one or more mediations specific to the user, the one or more sensory thresholds selected from auditory, visual, or physiological sensory thresholds;
storing, at a storage of the wearable device system, the one or more sensory thresholds and the mediation data;
recording, using one or more sensors of the wearable device system, a sensory input stimulus to the user;
comparing, at the wearable device system, the sensory input stimulus with the one or more sensory thresholds specific to the user;
in response to comparing the sensory input stimulus with the one or more sensory thresholds, determining, based at least on the mediation data, a mediation of the one or more mediations to be provided to the user, the mediation configured to provide the user relief from distractibility, inattention, anxiety, fatigue, or sensory issues; and
providing, using at least the wearable device, the mediation to the user, the mediation comprising an alert mediation, a guidance mediation, or a filter mediation.

27. The method of claim 26, wherein:
the method further comprises: receiving user demographic data corresponding to user input indicating an age, education level, or gender of the user; and
determining the one or more sensory thresholds specific to the user and the mediation data corresponding to the one or more mediations specific to the user, comprises: determining, using at least the first identifier, the user sensory sensitivity data, and the user demographic data, the one or more sensory thresholds and the mediation data.

28. The method of claim 26, wherein the first identifier indicates whether or not the user is autistic.

* * * * *